United States Patent
Kawano et al.

(12) 
(10) Patent No.: US 6,627,630 B1
(45) Date of Patent: Sep. 30, 2003

(54) CONDENSED PYRIDAZINE DERIVATIVES, THEIR PRODUCTION AND USE

(75) Inventors: Yasuhiko Kawano, Suita (JP); Hideaki Nagaya, Toyonaka (JP); Michiyo Gyoten, Daito (JP); Yukio Hara, Kawanishi (JP); Motoki Ikeuchi, Nishinomiya (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/807,806

(22) PCT Filed: Oct. 20, 1999

(86) PCT No.: PCT/JP99/05786
§ 371 (c)(1),
(2), (4) Date: Apr. 18, 2001

(87) PCT Pub. No.: WO00/23450
PCT Pub. Date: Apr. 27, 2000

(30) Foreign Application Priority Data

Oct. 21, 1998 (JP) .......................... 10/299424
Oct. 21, 1998 (JP) .......................... 10/299425
Oct. 28, 1998 (JP) .......................... 10/307317

(51) Int. Cl.[7] .................. A61K 31/50; A61P 11/06; C07D 487/00
(52) U.S. Cl. ........................... 514/248; 544/236
(58) Field of Search ................ 514/248; 544/236

(56) References Cited

U.S. PATENT DOCUMENTS

| 3,878,217 | A |   | 4/1975  | Carr et al. ............ 260/293.68 |
| 3,957,766 | A | * | 5/1976  | Berger et al. .............. 544/118 |
| 4,499,088 | A |   | 2/1985  | Takaya et al. .............. 514/202 |
| 4,908,365 | A |   | 3/1990  | Buzas et al. ................. 514/252 |
| 5,091,531 | A | * | 2/1992  | Hodgson ..................... 544/236 |
| 5,145,850 | A |   | 9/1992  | Miyake et al. .............. 514/248 |
| 5,155,108 | A |   | 10/1992 | Miyake et al. .............. 514/248 |
| 5,202,324 | A |   | 4/1993  | Miyake et al. .............. 514/248 |
| 5,369,104 | A |   | 11/1994 | Miyake et al. .............. 514/212 |
| 5,389,633 | A |   | 2/1995  | Miyake et al. ........... 514/233.2 |
| 5,491,145 | A |   | 2/1996  | Miyake et al. .............. 514/248 |
| 5,492,909 | A |   | 2/1996  | Miyake et al. ........... 514/233.2 |
| 5,922,712 | A |   | 7/1999  | Miyake et al. .............. 514/248 |
| 6,248,740 | B1 | * | 6/2001 | Kawano et al. ............. 514/248 |
| 6,444,666 | B1 | * | 9/2002 | Ladduwahetty et al. . 514/228.5 |
| 2002/0151713 | A1 | * | 10/2002 | Chen ....................... 544/235 |

FOREIGN PATENT DOCUMENTS

| JP | 64-13090    | 1/1989  |
| WO | WO 96/08496 | 3/1996  |
| WO | WO 96/23798 | 8/1996  |
| WO | WO 98/49167 | 11/1998 |
| WO | WO 99/14203 | 3/1999  |

OTHER PUBLICATIONS

Glanze, W. D. MOSBY's Medical & Nursing Dictionary, 2nd Edition, 1986, St. Louis, MO., p. 334, 937, 938, 1172.*

M. Abou–Gharbia et al. "New Antihistamines: Substituted Piperazine and Piperidine Derivatives as Novel $H_1$–Antagonists", Journal of Medicinal Chemistry, vol. 38 (1995), No. 20, pp. 4026–4032.

* cited by examiner

*Primary Examiner*—Mukund J. Shah
*Assistant Examiner*—Tamthom N. Truong
(74) *Attorney, Agent, or Firm*—Mark Chao; Elaine M. Ramesh

(57) ABSTRACT

A condensed pyridazine derivative which is useful as a pharmaceutical composition for preventing or treating allergic skin diseases such as contact dermatitis, pruritus, dried dermatitis, acute urticaria and prurigo.

20 Claims, No Drawings

CONDENSED PYRIDAZINE DERIVATIVES, THEIR PRODUCTION AND USE

This application is the National Stage of International Application No. PCT/JP99/05786, filed on Oct. 20, 1999.

TECHNICAL FIELD

The present invention relates to condensed pyridazine derivatives exhibiting an excellent anti-allergic, anti-histaminic, anti-inflammatory or eosinophil chemotaxis-inhibiting activity, or other activities, and useful as an agent for treating or preventing atopic dermatitis, allergic rhinitis, bronchial asthma, allergic conjunctivitis, chronic urticaria, etc., their pro-drugs, methods for producing them and use.

BACKGROUND ART

Many condensed pyridazine derivatives are currently synthesized as drugs for a variety of diseases. For example, U.S. Pat. No. 3,915,968 discloses a compound represented by the formula:

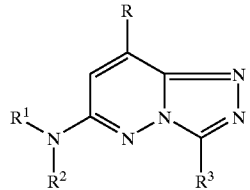

wherein R and $R^3$ independently represent a hydrogen atom or a lower alkyl group (at least one of R and $R^3$ is a lower alkyl group); $R^1$ and $R^2$ represent a heterocyclic group selected from the group consisting of pyrrolidine, piperidine, piperazine and morpholine taken together with the adjacent nitrogen atom; or a salt thereof. U.S. Pat. No. 4,136,182 is closes that a compound represented by the formula:

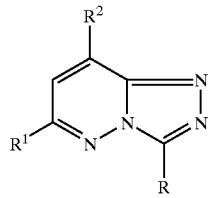

wherein R represents a hydrogen atom, a phenyl group or a lower alkylcarbonylamino group; $R^1$ represents morpholino or piperidino; $R^2$ represents a hydrogen atom or a lower alkyl group (at least one of R and $R^2$ is a group other than a hydrogen atom; when R is a phenyl group, $R^1$ is morpholino and $R^2$ is a lower alkyl group); or a salt thereof, is useful as a bronchodilator for mitigating bronchial spasms.

Also, Japanese Patent Unexamined Publication No. 279447/1995 discloses that a compound represented by the formula:

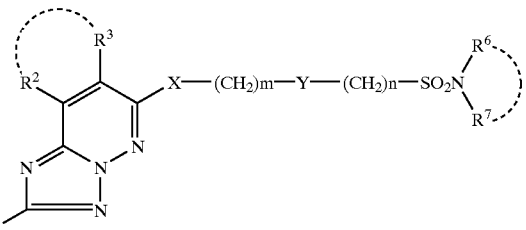

wherein $R^1$ represents a hydrogen atom, a lower alkyl group that may be substituted, or a halogen atom; $R^2$ and $R^3$ independently represent a hydrogen atom or a lower alkyl group which may be substituted, or may form a 5- to 7-membered ring with the adjacent —C=C—; X represents an oxygen atom or $S(O)_p$ (p represents an integer of 0 to 2); Y represents a group represented by the formula:

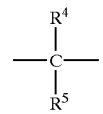

($R^4$ and $R^5$ independently represent a hydrogen atom or a lower alkyl group which may be substituted) or a divalent group derived from a 3- to 7-membered homocycle or heterocycle which may be substituted; $R^6$ and $R^7$ independently represent a hydrogen atom, a lower alkyl group which may be substituted, a cycloalkyl group which may be substituted, or an aryl group that may be substituted, or may form a nitrogen-containing heterocyclic group which may be substituted, with the adjacent nitrogen atom; m represents an integer from 0 to 4, and n represents an integer from 0 to 4; or a salt thereof; and, as an example synthetic product, a compound of the formula:

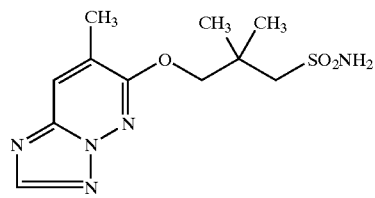

exhibits anti-asthmatic, anti-PAF, anti-inflammatory and anti-allergic activities.

Furthermore, Japanese Patent Unexamined Publication No. 279446/1995 describes a compound represented by the formula:

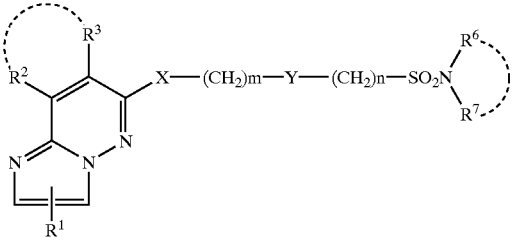

wherein $R^1$ represents a hydrogen atom, a lower alkyl group which may be substituted, or a halogen atom; $R^2$ and $R^3$ independently represent a hydrogen atom or a lower alkyl group which may be substituted (provided that either of $R^2$ and $R^3$ is a hydrogen atom, the other represents a lower alkyl group which may be substituted), or may form a 5- to 7-membered ring taken together with the adjacent —C=C—; X represents an oxygen atom or $S(O)_p$ (p represents an integer of 0 to 2): Y represents a group represented by the formula:

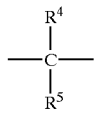

($R^4$ and $R^5$ independently represent a hydrogen atom or a lower alkyl group which may be substituted) or a divalent group derived from a 3- to 7-membered homocycle or heterocycle which may be substituted; $R^6$ and $R^7$ independently represent a hydrogen atom, a lower alkyl group which may be substituted, a cycloalkyl group which may be substituted, or an aryl group which may be substituted, or may form a nitrogen-containing heterocyclic group which may be substituted, taken together with the adjacent nitrogen atom; m represents an integer from 0 to 4, and n represents an integer from 0 to 4; or a salt thereof; and discloses that these compounds possess anti-allergic, anti-inflammatory and anti-PAF (platelet activating factor) activities to suppress bronchial spasms and bronchial contraction, therefore could be utilized as effective anti-asthmatic agents.

On the other hand, as compounds exhibiting anti-allergic or anti-histaminic activities, there may be mentioned, for example, terfenadine (The Merck Index, 12th edition, 9307) and ebastine (The Merck Index, 12th edition, 3534), which are already in clinical use.

And, EP128536 discloses anti-bacterial compounds represented by the formula:

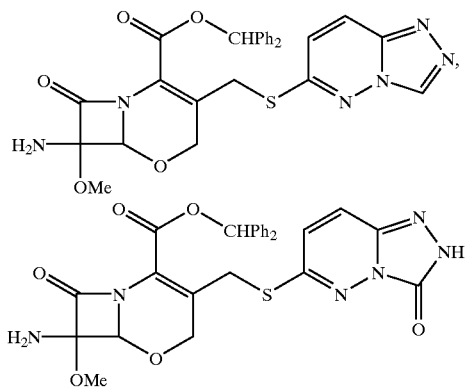

and so on, and U.S. Pat. No. 4,499,088 discloses antibacterial compounds represented by the formula:

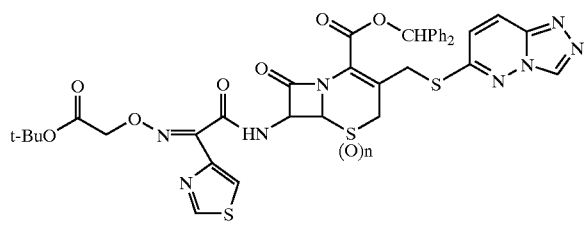

and so on. However, they never disclose about anti-allergic action, anti-histaminic action, anti-inflammatory action and so on.

There is demand for the development of novel compounds more satisfactory than conventional anti-allergic agents, anti-histaminic agents, anti-inflammatory agents in terms of action efficacy, sustained action, safety etc., their production and novel pharmaceutical composition.

DISCLOSURE OF INVENTION

Through various extensive investigations, the present inventors found that condensed pyridazine compounds represented by the formula:

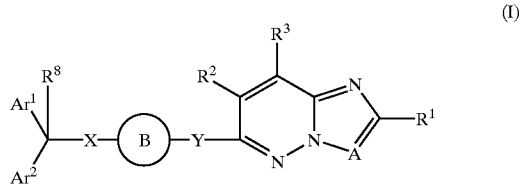

(I)

wherein $Ar^1$ and $Ar^2$ are independently an aromatic group which may be substituted, and $Ar^1$ and $Ar^2$ may form a condensed cyclic group with an adjacent carbon atom; ring B is a nitrogen-containing heterocycle may be substituted; X and Y are the same or different and are independently a bond, an oxygen atom, $S(O)_p$ (p is an integer of 0 to 2), $NR^4$ wherein $R^4$ is a hydrogen atom or a lower alkyl group, or a divalent linear lower hydrocarbon group which may contain 1 to 3 hetero atoms and the bivalent linear lower hydrocarbon group may be substituted; A is a nitrogen atom or $CR^7$ ($R^7$ is a hydrogen atom, a halogen atom, a hydrocarbon group optionally having a substituent, an acyl group or a hydroxy group optionally having a substituent; $R^1$, $R^2$ and $R^3$ are the same or different and are independently a hydrogen atom, a halogen atom, a hydrocarbon group optionally having a substituent, an acyl group or a hydroxy group which may be substituted; $R^8$ is a hydrogen atom, a hydroxy group which may be substituted by lower alkyl or a carboxyl group; provided that the nitrogen-containing heterocycle represented by ring B is not a heterocycle represented by the formula:

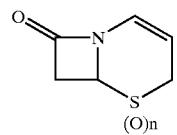

wherein n is 0 or 1, or a salt thereof, owing to their unique chemical structure characterized by the presence of substitutional piperidine or piperazine via a spacer from the 6-position of the [1,2,4]triazolo[1,5-b]pyridazine or imidazo [1,2-b]pyridazine skeleton, exhibits unexpectedly excellent activities for preventing or treating allergic skin diseases such as contact dermatitis, pruritus and so on.

And, the present inventors found that condensed pyridazine derivatives represented by the formula:

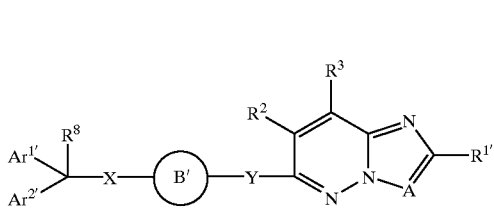

(I')

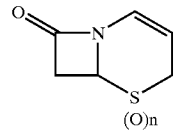

(I)

wherein Ar¹' and Ar²' are independently an aromatic group optionally having a substituent, and Ar¹' and Ar²' may form a condensed cyclic group with an adjacent carbon atom; ring B' is a nitrogen-containing heterocycle optionally having a substituent; X and Y are the same or different and are independently a bond, an oxygen atom, S(O)p (p is an integer of 0 to 2), NR⁴ wherein R⁴ is a hydrogen atom or a lower alkyl group, or a bivalent linear lower hydrocarbon group which may contain 1 to 3 hetero atoms and the bivalent linear lower hydrocarbon group may be substituted; A is a nitrogen atom or CR⁷ wherein R⁷ is a hydrogen atom, a halogen atom, a hydrocarbon optionally having a substituent, an acyl group or a hydroxy group optionally having a substituent; R¹ is a hydrocarbon group substituted with an optionally esterified carboxyl group, R² and R³ are the same or different and are independently a hydrogen atom, a halogen atom, a hydrocarbon group optionally having a substituent, an acyl group or a hydroxy group optionally having a substituent; R⁸ is a hydrogen atom, a hydroxy group which may be substituted by lower alkyl or a carboxyl group, or a salt thereof, owing to their unique chemical structure characterized by the presence of substitutional piperidine or piperazine via a spacer from the 6-position of the [1,2,4]triazolo[1,5-b]pyridazine or imidazo[1,2-b]pyridazine skeleton, can be produced in good efficiency and in a high yield.

Furthermore, the inventors found that among the above mentioned compound (I) or a salt thereof, a hydrate of a compound represented by the formula:

wherein Ar¹ and Ar² are independently an aromatic group optionally having a substituent, and Ar¹ and Ar² may form a condensed cyclic group with an adjacent carbon atom; ring B is a nitrogen-containing heterocycle optionally having a substituent; X and Y are the same or different and are independently a bond, an oxygen atom, S(O)p (p is an integer of 0 to 2), NR⁴ wherein R⁴ is a hydrogen atom or a lower alkyl group, or a bivalent linear lower hydrocarbon group which may contain 1 to 3 hetero atoms and the bivalent linear lower hydrocarbon group may be substituted; A is a nitrogen atom or CR⁷ wherein R⁷ is a hydrogen atom, a halogen atom, a hydrocarbon optionally having a substituent, an acyl group or a hydroxy group optionally having a substituent; R¹, R² and R³ are the same or different and are independently a hydrogen atom, a halogen atom, a hydrocarbon group optionally having a substituent, an acyl group or a hydroxy group optionally having a substituent; R⁸ is a hydrogen atom, a hydroxy group which may be substituted by a lower alkyl group or a carboxyl group, provided that the nitrogen-containing heterocycle represented by ring B is not a heterocycle represented by the formula:

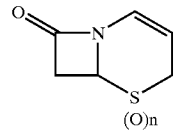

wherein n is 0 or 1, or a salt thereof, or a pro-drug thereof,

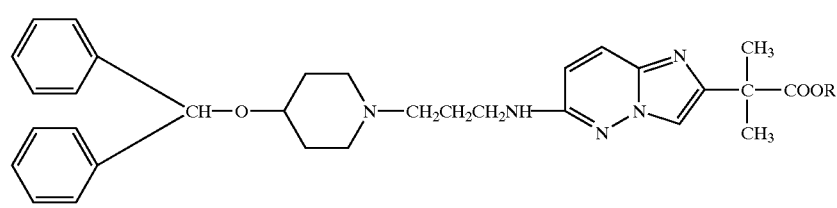

(I'')

wherein R is a hydrogen atom or an ethyl group, or a succinate or citrate of the compound (I'') and 2-[6-[3-[4-(diphenylmethoxy)piperidino]propylamino]-3-methylimidazo[1,2-b]pyridazin-2-yl]-2-methylpropionic acid or a salt thereof, which are excellent in stability, exhibit an excellent anti-allergic activity.

The inventors conducted further investigations based on these findings, and developed the present invention.

The present invention provides:

1. A pharmaceutical composition for preventing or treating allergic skin diseases which comprises a compound represented by the formula:

2. A pharmaceutical composition as defined in term 1 wherein the allergic skin disease is contact dermatitis, pritus, dried dermatitis, acute urticaria or prurigo, 3. A pharmaceutical composition as defined in term 1 wherein Ar¹ and Ar¹ are independently (1) a C₆₋₁₄ aromatic hydrocarbon group, (2) a 5 to 8 membered aromatic heterocyclic group containing 1 to 4 hetero atoms selected from a nitrogen atom, a sulfur atom and an oxygen atom other than carbon atoms or (3) a group removed a hydrogen atom from a condensed ring formed by the 5 to 8 membered aromatic heterocyclic group and the C₆₋₁₄ aromatic hydrocarbon group, and the C₆₋₁₄ aromatic hydrocarbon group, the 5 to 8 membered aromatic heterocyclic group and the group formed by the 5 to 8 membered aromatic heterocyclic group and the C₆₋₁₄ aromatic hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl, (xxvii) $C_{6-10}$ aryloxy and (xxviii) $C_{7-16}$ aralkyloxy; and $A^1$ and $Ar^2$ may form a condensed cyclic group with the adjacent carbon atom represented by the formula:

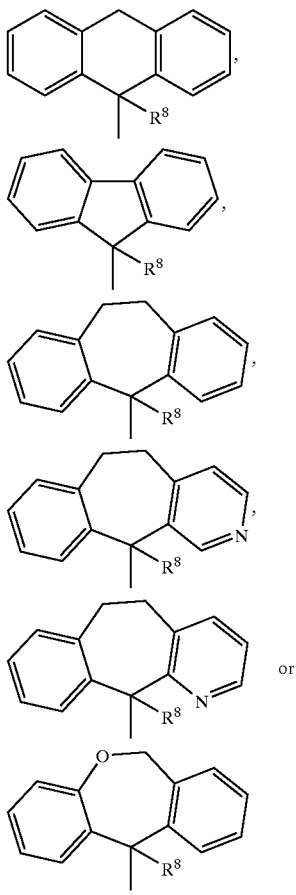

wherein $R^8$ is a hydrogen atom, a hydroxy group which may be substituted by $C_{1-6}$ alkyl or a carboxyl group, and the condensed cyclic group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino,
(xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

the ring B is a 3 to 13 membered nitrogen-containing heterocycle containing at least one nitrogen atom which may contain 1 to 3 hetero atoms selected from a nitrogen atom, an oxygen atom and a sulfur atom, and the 3 to 13 membered nitrogen-containing heterocycle may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

X and Y are same or different ① a bond, ② an oxygen atom, ③ S(O)p wherein p is an integer of 0 to 2, ④ $NR^4$ wherein $R^4$ is a hydrogen atom or a linear or branched $C_{1-6}$ alkyl group or ⑤ a bivalent linear $C_{1-6}$ hydrocarbon group which may contain 1 to 3 hetero atoms selected from an oxygen atom and a sulfur atom, and the bivalent linear $C_{1-6}$ hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

A is a nitrogen atom or $CR^7$ wherein $R^7$ is
(1) a hydrogen atom,
(2) a halogen atom,
(3) a $C_{1-6}$ alkyl group, a $C_{2-6}$ alkenyl group, a $C_{2-6}$ alkynyl group, a $C_{3-6}$ cycloalkyl group condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxycarbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy (4) an acyl group represented by the formula: $-(C=O)-R^9$, $-SO_2-R^9$, $-SO-R^9$, $-(C=O)NR^{10}R^9$, $-(C=O)O-R^9$, $-(C=S)O-R^9$ or $-(C=S)NR^{10}R^9$ wherein $R^9$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo or (c) a group represented by the formula: $-OR^{11}$ wherein $R^{11}$ is a hydrogen atom or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{716}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, $R^{10}$ is a hydrogen atom or a $C_{1-6}$ alkyl group, or (5) a group represented by the formula: $-OR^{12}$ wherein $R^{12}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo $R^1$, $R^2$ and $R^3$ are the same or different and are independently (1) a hydrogen atom, (2) a halogen atom, (3) a $C_{1-6}$ alkyl group, a $C_{2-6}$ alkenyl group, a $C_{2-6}$ alkynyl group, a $C_{3-6}$ cycloalkyl group condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv); 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxviii) oxo, (4) an acyl group represented by the formula: $-(C=O)-R^{13}$, $-SO_2-R^{13}$, $-SO-R^{13}$, $-(C=O)NR^{14}R^{13}$, $-(C=O)O-R^{13}$, $-(C=S)O-R^{13}$ or $-(C=S)NR^{14}R^{13}$ wherein $R^{13}$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo or (c) a group represented by the formula: —$OR^{15}$ wherein $R^{15}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

$R^{14}$ is a hydrogen atom or a $C_{1-6}$ alkyl group; or (5) a group represented by the formula: —$OR^{16}$ wherein $R^{16}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo:

$R^8$ is a hydrogen atom, a hydroxy group which may be substituted by $C_{1-6}$ alkyl or a carboxyl group, 4. A pharmaceutical composition as defined in term 1 wherein $Ar^1$ and $Ar^2$ are independently (1) a phenyl group which may be substituted by a halogen atom or $C_{1-6}$ alkyl or (2) a 5 to 8 membered aromatic heterocyclic group containing 1 to 4 hetero atoms selected from a nitrogen atom, a sulfur atom and an oxygen atom other than carbon atoms; the ring B is a ring represented by the formula:

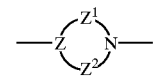

wherein Z is a nitrogen atom or a methyne group; $Z^1$ and $Z^2$ is independently a linear $C_{1-4}$ alkylene group which may be substituted by a hydroxy group, an oxo group or a $C_{1-6}$ alkyl group; X is a bond, an oxygen atom or NH; Y is (i) a $C_{1-6}$ alkylene group,
(ii) —$(CH_2)p^1O$—,
(iii) —$(CH_2)$—$p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O(CH_2)q^2NH$— or
(xiv) —$(CH_2)q^1O(CH_2)q^2S$— wherein $p^1$ is an integer of 1 to 6, $q^1$ and $q^2$ are an integer of 1 to 3; A is a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group; $R^1$ is (1) a hydrogen atom, (2) a $C_{1-6}$ alkyl group which maybe substituted by carboxyl, $C_{1-6}$ alkoxy-carbonyl, hydroxy or carbamoyl optionally having mono- or di-$C_{1-6}$ alkyl, (3) a $C_{6-14}$ aryl group, (4) a $C_{1-6}$ alkoxy group, (5) a $C_{1-6}$ alkoxy-carbonyl group, (6) a carboxyl group, (7) a carbamoyl group which may be substituted by a $C_{1-6}$ alkyl group optionally having carboxyl or $C_{1-6}$ alkoxy-carbonyl or (8) a $C_{3-6}$ cycloalkyl group which may be substituted by $C_{1-6}$ alkoxy-carbonyl; $R^2$ is a hydrogen atom, a $C_{1-6}$ alkyl group, a $C_{1-6}$ alkoxy-carbonyl group or a carboxyl group; $R^3$ is a hydrogen atom; $R^8$ is a hydrogen atom or a hydroxyl group, 5. A pharmaceutical composition as defined in term 1 wherein $Ar^1$ and $Ar^2$ are a phenyl group; the ring B is a ring represented by the formula:

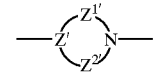

wherein $Z'$ is a methyne group; $Z^{1'}$ and $Z^{2'}$ are a methylene group or an ethylene group; X is a bond or an oxygen atom;

Y is —(CH$_2$)p$^1$NH— wherein p$^1$ is an integer of 1 to 6; A is CR$^{7"}$ wherein R$^{7"}$ is a hydrogen atom or a C$_{1-6}$ alkyl group; R$^1$ is (1) a hydrogen atom, (2) a C$_{1-6}$ alkyl group which may be substituted by carboxyl or C$_{1-6}$ alkoxycarbonyl or (3) a carbamoyl group which may be substituted by a C$_{1-6}$ alkyl group optionally having C$_{1-6}$ alkoxycarbonyl; R$^2$ is a hydrogen atom; R$^3$ is a hydrogen atom; R$^8$ is a hydrogen atom, 6. A pharmaceutical composition as defined in term 1 wherein the compound is
   2-[6-[3-[4-(diphenylmethoxy)piperidino]propylamino] imidazo[1,2-b]pyridazin-2-yl]-2-methylpropionic acid or a salt thereof,
7. A pharmaceutical composition as defined in term 1 wherein the compound is
   2-[6-[3-[4-(diphenylmethoxy)piperidino]propylamino] imidazo[1,2-b]pyridazin-2-yl]-2-methylpropionic acid dihydrate,
8. A method for preventing or treating allergic skin diseases which comprises administering an effective amount of a compound represented by the formula:

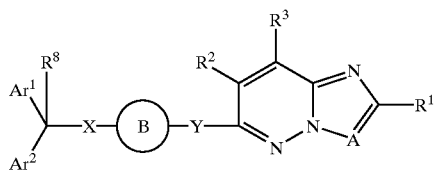

(I)

wherein Ar$^1$ and Ar$^2$ are independently an aromatic group optionally having a substituent, and Ar$^1$ and Ar$^2$ may form a condensed cyclic group with an adjacent carbon atom; ring B is a nitrogen-containing heterocycle optionally having a substituent; X and Y are the same or different and are independently a bond, an oxygen atom, S(O)p (p is an integer of 0 to 2), NR$^4$ wherein R$^4$ is a hydrogen atom or a lower alkyl group, or a bivalent linear lower hydrocarbon group which may contain 1 to 3 hetero atoms and the bivalent linear lower hydrocarbon group may be substituted; A is a nitrogen atom or CR$^7$ wherein R$^7$ is a hydrogen atom, a halogen atom, a hydrocarbon optionally having a substituent, an acyl group or a hydroxy group optionally having a substituent; R$^1$, R$^2$ and R$^3$ are the same or different and are independently a hydrogen atom, a halogen atom, a hydrocarbon group optionally having a substituent, an acyl group or a hydroxy group optionally having a substituent; R$^8$ is a hydrogen atom, a hydroxy group which may be substituted by lower alkyl or a carboxyl group, provided that the nitrogen-containing heterocycle represented by ring B is not a heterocycle represented by the formula:

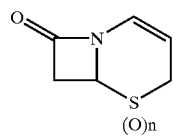

wherein n is 0 or 1, or a salt thereof, or a pro-drug thereof to mammals,

9. A method for preventing to treating as defined in term 8 wherein the allergic skin disease is contact dermatitis, pruritus, dried dermatitis, acute urticaria or prurigo, 10. Use of a compound represented by the formula:

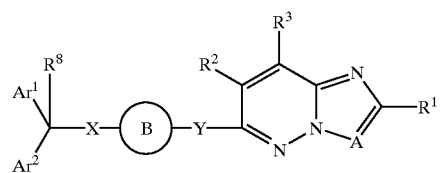

(I)

wherein Ar$^1$ and Ar$^2$ are independently an aromatic group optionally having a substituent, and Ar$^1$ and Ar$^2$ may form a condensed cyclic group with an adjacent carbon atom; ring B is a nitrogen-containing heterocycle optionally having a substituent; X and Y are the same or different and are independently a bond, an oxygen atom, S(O)p (p is an integer of 0 to 2), NR$^4$ wherein R$^4$ is a hydrogen atom or a lower alkyl group, or a bivalent linear lower hydrocarbon group which may contain 1 to 3 hetero atoms and the bivalent linear lower hydrocarbon group may be substituted; A is a nitrogen atom or CR$^1$ wherein R$^7$ is a hydrogen atom, a halogen atom, a hydrocarbon optionally having a substituent, an acyl group or a hydroxy group optionally having a substituent; R$^1$, R$^2$ and R$^3$ are the same or different and are independently a hydrogen atom, a halogen atom, a hydrocarbon group optionally having a substituent, an acyl group or a hydroxy group optionally having a substituent; R$^8$ is a hydrogen atom, a hydroxy group which may be substituted by a lower alkyl group or a carboxyl group, provided that the nitrogen-containing heterocycle represented by ring B is not a heterocycle represented by the formula:

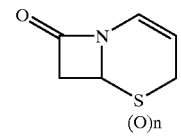

wherein n is 0 or 1, or a salt thereof, or a pro-drug thereof for preparing a pharmaceutical composition for preventing or treating allergic skin diseases, 11. Use as defined in term 10 wherein the allergic skin disease is contact dermatitis, pruritus, dried dermatitis, acute urticaria or prurigo, 12. A method for producing a compound represented by the formula:

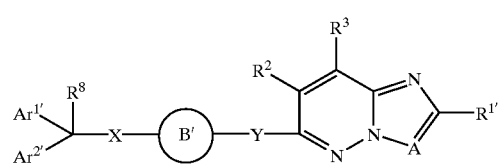

(I')

wherein Ar$^{1'}$ and Ar$^{2'}$ are independently an aromatic group optionally having a substituent, and Ar$^{1'}$ and Ar$^{2'}$ may form a condensed cyclic group with an adjacent carbon atom; ring B' is a nitrogen-containing heterocycle optionally having a substituent; X and Y are the same or different and are independently a bond, an oxygen atom, S(O)p (p is an integer of 0 to 2), NR$^4$ wherein R$^4$ is a hydrogen atom or a lower alkyl group, or a bivalent linear lower hydrocarbon group which may contain 1 to 3 hetero atoms and the bivalent linear lower hydrocarbon group may be substituted;

A is a nitrogen atom or $CR^7$ wherein $R^7$ is a hydrogen atom, a halogen atom, a hydrocarbon optionally having a substituent, an acyl group or a hydroxy group optionally having a substituent; $R^{1'}$ is a hydrocarbon group substituted by an optionally esterified carboxyl group; $R^2$ and $R^3$ are the same or different and are independently a hydrogen atom, a halogen atom, a hydrocarbon group optionally having a substituent, an acyl group or a hydroxy group optionally having a substituent; $R^8$ is a hydrogen atom, a hydroxy group which may be substituted by a lower alkyl group or a carboxyl group, or a salt thereof, which comprises reacting a compound represented by the formula:

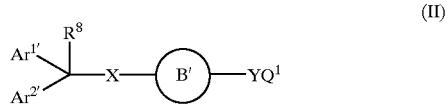

(II)

wherein $Q^1$ represents a leaving group; the other symbols are same as defined in the above, or a salt thereof, with a compound represented by the formula:

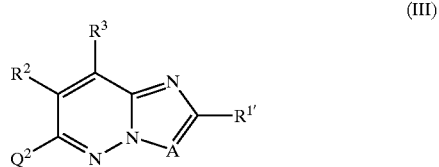

(III)

wherein $Q^2$ represents a leaving group; the other symbols are same as defined above, or a salt thereof in a solvent or/and in the presence of a base, and if necessary in an atmosphere of inert gas, 13. A method as defined in term 12 wherein the solvent is a non-protic solvent having a high boiling point,
14. A method as defined in term 12 wherein the solvent is sulfoxides,
15. A method as defined in term 12 wherein the solvent is a dimethyl sulfoxide,
16. A method as defined in term 12 wherein the base is an alkali metal carbonate,
17. A method as defined in term 12 wherein the base is a sodium carbonate,
18. A method as defined in term 12 wherein the reaction is conducted in the solvent and in the presence of a base,
19. A method as defined in term 12 wherein the reaction is further conducted in the presence of halogenated alkali metals,
20. A method as defined in term 19 wherein halogenated alkali metal is a sodium bromide,
21. A method as defined in term 12 wherein $Ar^{1'}$ and $Ar^{2'}$ are a $C_{6-14}$ single cyclic or condensed cyclic aromatic hydrocarbon group which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy and (xxviii) $C_{7-16}$ aralkyloxy; and $Ar^{1'}$, $Ar^{2'}$ and the adjacent carbon atom may form a condensed cyclic group represented by the formula:

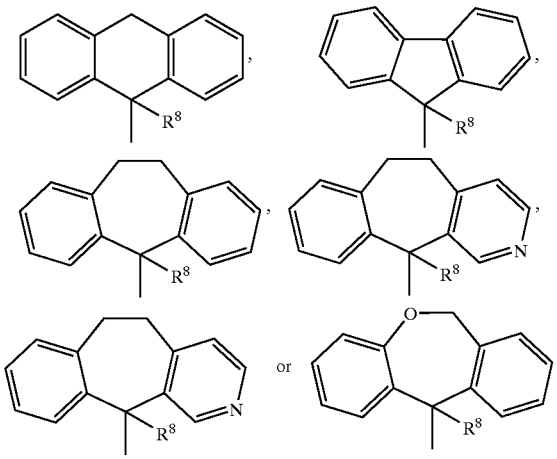

wherein $R^8$ is a hydrogen atom, a hydroxy group which may be substituted by $C_{1-6}$ alkyl or a carboxyl group, and the condensed cyclic group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

the ring B' is a 6-membered: nitrogen-containing heterocycle which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

X and Y are same or different and are independently ① a bond, ② an oxygen atom, ③ $S(O)p$ wherein p is an integer of 0 to 2, ④ $NR^4$ wherein $R^4$ is a hydrogen atom or a linear or branched $C_{1-6}$ alkyl group or (5) a bivalent linear $C_{1-6}$ hydrocarbon group which may contain 1 to 3 hetero atoms selected from an oxygen atom and a sulfur atom, and the bivalent linear $C_{1-6}$ hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-4}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

A is a nitrogen atom or $CR^7$ wherein $R^7$ is
  (1) a hydrogen atom,
  (2) a halogen atom,
  (3) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo,
  (4) an acyl group represented by the formula: —(C=O)—$R^9$, —$SO_2$—$R^9$, —SO—$R^9$, —(C=O)$NR^{10}R^9$, —(C=O)O—$R^9$, —(C=S)O—$R^9$ or —(C=S)$NR^{10}R^9$ wherein $R^9$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo or (c) a group represented by the formula: —$OR^{11}$ wherein $R^{11}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, $R^{10}$ is a hydrogen atom or a $C_{1-6}$ alkyl group, or
  (5) a group represented by the formula: —$OR^{12}$ wherein $R^{12}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

$R^{1'}$ is a $C_{1-6}$ alkyl group, a $C_{2-6}$ alkenyl group, a $C_{2-6}$ alkynyl group, a $C_{3-6}$ cycloalkyl group, condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group which is substituted by a group represented by the formula: —COOR$^{11}$ wherein R$^{11}$ is (1) a hydrogen atom or (2) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group e and a $C_{7-16}$ aralkyl group which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino (v) and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl, (xxvii) $C_{6-10}$ aryloxy, (xxviii) $C_{7-16}$ aralkyloxy and (xxix) oxo;

R$^2$ and R$^3$ are the same or different and are independently
  (1) a hydrogen atom,
  (2) a halogen atom,
  (3) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo,
  (4) an acyl group represented by the formula: —(C=O)—R$^{13}$, —SO$_2$—R$^{13}$, —SO—R$^{13}$, —(C=O)NR$^{14}$R$^{13}$, —(C=O)O—R$^{13}$, —(C=S)O—R$^{13}$ or —(C=S)NR$^{14}$R$^{13}$ wherein R$^{13}$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy; (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) or (c) a group represented by the formula: —OR$^{15}$ wherein R$^{15}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, R$^{14}$ is a hydrogen atom or a $C_{1-6}$ alkyl group; or
  (4) a group represented by the formula: —OR$^{16}$ wherein R$^{16}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix)

carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

$R^8$ is a hydrogen atom, a hydroxy group which may be substituted by a $C_{1-6}$ alkyl group or a carboxyl group, 22. A method for producing a compound as defined in term 12 wherein (1) $Ar^{1'}$ and $Ar^{2'}$ are independently a phenyl group; ring B' is

X is an oxygen atom; Y is a propylamino group; $R^8$ is a hydrogen atom; A is CH; $R^{1'}$ is a carboxyl dimethylmethyl group; and $R^2$ and $R^3$ are a hydrogen atom, (2) $Ar^{1'}$ and $Ar^{2'}$ are independently a phenyl group; ring B' is

X is an oxygen atom; Y is a propylamino group; $R^8$ is a hydrogen atom; A is CH; $R^{1'}$ is an ethoxycarbonyl dimethylmethyl group; and $R^2$ and $R^3$ are a hydrogen atom, (3) $Ar^{1'}$ and $Ar^{2'}$ are independently a phenyl group; ring B' is

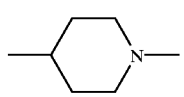

X is an oxygen atom; Y is a propylamino group; $R^8$ is a hydrogen atom; A is CH; $R^{1'}$ is a carboxyl dimethylmethyl group; $R^2$ and $R^3$ are a hydrogen atom; the solvent is a dimethylsulfoxide and the base is a sodium carbonate, or (4) $Ar^{1'}$ and $Ar^{2'}$ are independently a phenyl group; ring B' is X is an oxygen atom; Y is a propylamino group; $R^8$ is a hydrogen atom; A is CH; $R^{1'}$ is an ethoxycarbonyl dimethylmethyl group; $R^2$ and $R^3$ are a hydrogen atom; the solvent is a 1-methyl-2-pyrrolidone and the base is a sodium carbonate, 23. A method for producing a compound as defined in term 12 wherein the leaving group represented by $Q^1$ is a hydrogen atom or an alkali metal, 24. A method for producing a compound as defined in term 12 wherein the leaving group represented by $Q^2$ is a halogen atom, $C_{6-10}$ arylsulfonyloxy group or a $C_{1-4}$ alkylsulfonyloxy group, 25. A hydrate of a compound represented by the formula:

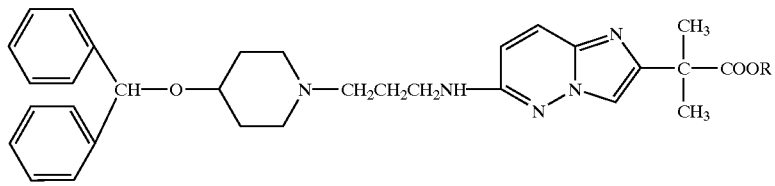

(I'')

wherein R is a hydrogen atom or an ethyl group, or a succinate or citrate of the compound (I''), 26. 2-[6-[3-[4-(diphenylmethoxy)piperidino]propylamino]imidazo[1,2-b]pyridazin-2-yl]-2-methylpropionic acid dehydrate, 27. A compound as defined in term 26 which shows the following Powder X-ray diffraction analysis result:

| D-Space, angstrom | Intensity $I/I_0$ (%) |
|---|---|
| 6.94 | 84 |
| 12.88 | 41 |
| 13.72 | 62 |
| 15.10 | 53 |
| 17.56 | 84 |
| 18.70 | 39 |
| 19.24 | 62 |
| 20.66 | 60 |
| 21.06 | 100 |
| 21.76 | 54 |
| 26.42 | 43 |
| 28.24 | 37, |

28. A compound as defined in term 25 which is ① ethyl 2-[6-[3-[4-(diphenylmethoxy)piperidino]propylamino]imidazo[1,2-b]pyridazin-2-yl]-2-methylpropionate disuccinate or ② ethyl 2-[6-[3-[4-(diphenylmethoxy)piperidino]propylamino]imidazo[1,2-b]pyridazin-2-yl]-2-methylpropionate citrate, 29. 2-[6-[3-[4-(diphenylmethoxy)piperidino]propylamino)-3-methylimidazo[1,2-b]pyridazin-2-yl)-2-methylpropionic acid or a salt thereof, 30. A pro-drug of a compound as claimed in any one of claims 13 to 11, 31. A method for producing a compound as defined in term which comprises (1) contacting a compound which is obtained by reacting a compound represented by the formula:

(II″)

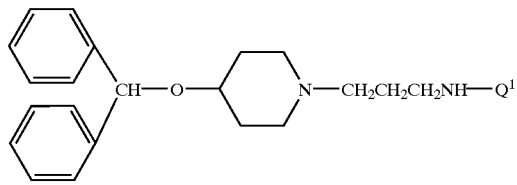

wherein $Q^1$ is a leaving group, or a salt thereof with a compound represented by the formula:

(III″)

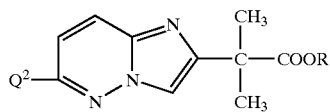

wherein $Q^2$ is a leaving group, R is same as defined in claim 13, or a salt thereof with a water, or (2) reacting a free form of the compound (I″) as defined in claim 13 with a succinic acid or citric acid, 32. A pharmaceutical composition which comprises any one of compounds as defined in terms 25 to 29 or a pro-drug as defined in term 30,
33. A pharmaceutical composition as defined in term 32 which is an anti-histaminic agent and/or an eosinophil chemotaxis-inhibiting agent,
34. A pharmaceutical composition as defined in term 32 which is an anti-allergic agent,
35. A pharmaceutical composition as defined in term 32 which is an agent for treating or preventing asthma, allergic conjunctivitis, allergic rhinitis, chronic urticaria or atopic dermatitis,
36. A method for suppressing a histamine and/or an eosinophil chemotaxis comprising administering an effective amount of any one of compounds as defined in terms 25 to 29 or a pro-drug as defined in term 30 to mammals,
37. A method for treating or preventing allergic diseases comprising administering an effective amount of any one of compounds as defined in terms 25 to 29 or a pro-drug as defined in term 30 to mammals,
38. A method for treating or preventing asthma, allergic conjunctivitis, allergic rhinitis, chronic urticaria or atopic dermatitis which comprises administering any one of compounds as defined in terms 25 to 29 or a pro-drug as defined in term 30 to mammals,
39. Use of any one of compounds as defined in terms 25 to 29 or a pro-drug as defined in term 30 for preparing a pharmaceutical composition for suppressing a histamine and/or an eosinophil chemotaxis,
40. Use of any one of compounds as defined in terms 25 to 29 or a pro-drug as defined in term 30 for preparing a pharmaceutical composition for treating or preventing allergic diseases, and
41. Use of any one of compounds as defined in terms 25 to 29 or a pro-drug as defined in term 30 for preparing a pharmaceutical composition for treating or preventing asthma, allergic conjunctivitis, allergic rhinitis, chronic urticaria or atopic dermatitis.

And, the present invention provides:

42. An agent for treating or preventing as defined in term 1 wherein $Ar^1$ and $Ar^2$ are independently an aromatic hydrocarbon group which may be substituted,
43. An agent for treating or preventing as defined in term 1 wherein $Ar^1$ and $Ar^2$ are independently a phenyl group which may be substituted,
44. An agent for treating or preventing as defined in term 1 wherein $Ar^1$ and $Ar^2$ are independently (i) a phenyl group which may be substituted by a halogen atom or $C_{1-6}$ alkyl or (ii) a 5 to 8 membered aromatic heterocyclic group containing 1 to 4 hetero atoms selected from a nitrogen atom, a sulfur atom and an oxygen atom other than carbon atoms,
45. An agent for treating or preventing as defined in term 1 wherein the ring B is a ring represented by the formula:

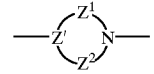

wherein Z is a nitrogen atom or a methyne group; $Z^1$ and $Z^2$ are independently a linear $C_{1-4}$ alkylene group which may be substituted by hydroxy, oxo or $C_{1-6}$ alkyl, 46. An agent for treating or preventing as defined in term 45 wherein $Z^1$ and $Z^2$ are independently a linear $C_{1-2}$ alkylene group,
47. An agent for treating or preventing as defined in term 1 wherein X is a bond, an oxygen atom or NH,
48. An agent for treating or preventing as defined in term 1 wherein X is a bond or an oxygen atom,
49. An agent for treating or preventing as defined in term 1 wherein Y is a group represented by the formula:

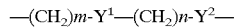

wherein $Y^1$ and $Y^2$ are the same or different and are independently a bond, an oxygen atom, S(O)p wherein p is an integer of 0 to 2, $NR^4$ wherein $R^4$ is a hydrogen atom or a lower alkyl group, a carbonyl group, a carbonyloxy group or a group represented by the formula:

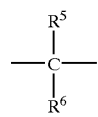

wherein $R^5$ and $R^6$ are the same or different and are independently a hydroxy group or a $C_{1-4}$ alkyl group; m and n are an integer of 0 to 4, and sum of m and n is not more than 6, 50. An agent for treating or preventing as defined in term 1 wherein Y is
   (i) a $C_{1-6}$ alkylene group, (ii) —(CH₂)p¹O—,
(iii) —(CH₂)p¹NH—,
(iv) —(CH₂)p¹S—,
(v) —(CH₂)q¹CH(OH)(CH₂)q²O—,
(vi) —(CH₂)q¹CH(OH)(CH₂)q²NH—,
(vii) —(CH₂)q¹CH(OH)(CH₂)q²S—,
(viii) —(CH₂)p¹CONH—,
(ix) —COO(CH₂)p¹O—,
(x) —COO(CH₂)p¹NH—,
(xi) —COO(CH₂)p¹S—,
(xii) —(CH₂)q¹O(CH₂)q²O—,
(xiii) —(CH₂)q¹O(CH₂)q²NH— or
(xiv) —(CH₂)q¹O(CH₂)q²S— wherein $p^1$ is an integer of 1 to 6, $q^1$ and $q^2$ are an integer of 1 to 3, 51. An agent for treating or preventing as defined in term 1 wherein $R^1$, $R^2$, $R^3$ and $R^7$ are the same or different and are independently (i) a hydrogen atom, (ii) a $C_{1-6}$ alkyl group which may be substituted by carboxyl or $C_{1-6}$ alkoxy-carbonyl, (iii) a $C_{1-6}$ alkoxy group, (iv) a $C_{1-6}$ alkoxy-carbonyl group or (v) a carboxyl group, 52. An agent for treating or preventing as defined in term 1 wherein $R^1$ is, (i) a hydrogen atom, (ii) a $C_{1-6}$ alkyl group which may be substituted by carboxyl, $C_{1-6}$ alkoxy-carbonyl, hydroxy or carbamoyl optionally having mono- or di-$C_{1-6}$ alkyl, (iii) a $C_{6-14}$ aryl group, (iv) a $C_{1-6}$ alkoxy group, (v) a $C_{1-6}$ alkoxy-carbonyl group, (vi) a carboxyl group, (vii) a carbamoyl group which may be substituted by a $C_{1-6}$ alkyl group optionally having carboxyl or $C_{1-6}$ alkoxy-carbonyl or (viii) a $C_{3-6}$ cycloalkyl group which may be substituted by $C_{1-6}$ alkoxy-carbonyl, 53. An agent for treating or preventing as defined in term 1 wherein $R^2$ is a hydrogen atom, a $C_{1-6}$ alkyl group, a $C_{1-6}$ alkoxy-carbonyl group or a carboxyl group, 54. An agent for treating or preventing as defined in term 1 wherein $R^3$ is a hydrogen atom, 55. An agent for treating or preventing as defined in term 1 wherein $R^7$ is a hydrogen atom, a halogen atom, a $C_{1-6}$ alkyl group, a $C_{1-6}$ alkoxy-carbonyl group or a carboxyl group, 56. An agent for treating or preventing as defined in term 1 wherein $R^8$ is a hydrogen atom or a hydroxy group, 57. An agent for treating or preventing as defined in term 1 wherein A is a nitrogen atom, 58. An agent for treating or preventing as defined in term 1 wherein A is $CR^{7'}$ wherein $R^{7'}$ is a hydrogen atom, a halogen atom, a $C_{1-6}$ alkyl group, a $C_{1-6}$ alkoxy-carbonyl group or a carboxyl group, 59. An agent for treating or preventing as defined in term 1 wherein A is CH, 60. An agent for treating or preventing as defined in term 1 wherein the compound is Ethyl 2-[6-[3-[4-(diphenylmethoxy)piperidino]propylamino]imidazo[1,2-b]pyridazin-2-yl]-2-methylpropionate or a salt thereof, 61. An agent for treating or preventing as defined in term 1 wherein the compound is 2-[6-[3-[4-(diphenylmethoxy)piperidino]propylamino]imidazo[1,2-b]pyridazin-2-yl]-2-methylpropionic acid or a salt thereof, 62. An agent for treating or preventing as defined in term 1 wherein the compound is Ethyl N-[6-[3-[4-(diphenylmethoxy)piperidino]propylamino]imidazo[1,2-b]pyridazine-2-carbonyl]glycinate or a salt thereof, 63. An agent for treating or preventing as defined in term 1 wherein the compound is Ethyl 2-[6-[3-[4-(diphenylmethoxy)piperidino)propylamino]-3-methylimidazo[1,2-b]pyridazin-2-yl]-2-methylpropionate or a salt thereof, 64. An agent for treating or preventing as defined in term 1 wherein the compound is Ethyl 2-[6-[3-[4-(diphenylmethylamino)piperidino]propylamino]imidazo[1,2-b]pyridazin-2-yl]-2-methylpropionate or a salt thereof, 65. An agent for treating or preventing as defined in term 1 wherein the compound is 2-[6-[3-[4-(diphenylmethoxy)piperidino]propylamino]-3-methylimidazo[1,2-b]pyridazin-2-yl]-2-methylpropionic acid or a salt thereof, 66. An agent for treating or preventing as defined in term 1 wherein the compound is a hydrate of a compound represented by the formula:

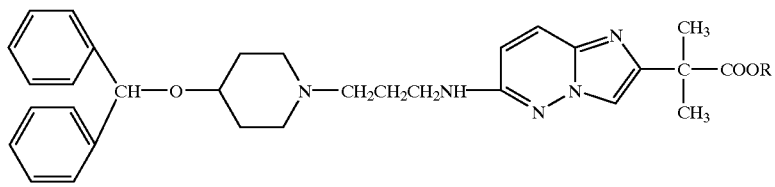

(I″)

wherein R is a hydrogen atom or an ethyl group, or a succinate or citrate of the compound (I″), 67. An agent for treating or preventing as defined in term 1 wherein the compound is ethyl 2-[6-[3-[4-(diphenylmethoxy)piperidino]propylamino]imidazo[1,2-b]pyridazin-2-yl]-2-methylpropionate disuccinate, 68. An agent for treating or preventing as defined in term 1 wherein the compound is ethyl 2-[6-[3-[4-(diphenylmethoxy)piperidino]propylamino]imidazo[1,2-b]pyridazin-2-yl]-2-methylpropionate citrate, 69. A method as defined in term 13 where in the boiling point of the solvent is about 90° C. to about 220° C., 70. A method as defined in term 12 wherein the solvent is ethers, aromatic hydrocarbons, nitriles, cyclic amides, sulfoxides, cyclic sulfones, halogenated hydrocarbons or azoles, 71. A method as defined in term 12 wherein the solvent is dioxane, tetrahydrofuran, benzene, toluene, xylene, acetonitrile, N,N-dimethylformamide, N,N-dimethylacetamide, 1-methyl-2-pyrolidone, dimethyl sulfoxide, sulforane, dichloroethane, chloroform, imidazole, 2-methylimidazole or pyridine, 72. A method as defined in term 12 wherein the solvent is cyclic amides or sulfoxides, 73. A method as defined in term 12 wherein the solvent is 1-methyl-2-pyrolidone, dimethyl sulfoxide or sulforane, 74. A method as defined in term 12 wherein the base is alkali metal hydrides, alkali metal alkoxide, alkali metal hydroxides, alkali metal carbonates, alkali earth metal hydrides, alkali earth metal alkoxide, alkali earth metal hydroxides or alkali earth metal carbonates, 75. A method as defined in term 12 wherein the base is sodium hydride, potassium hydride, sodium methoxide, sodium ethoxide, sodium t-butoxide, sodium hydroxide, potassium hydroxide, lithium carbonate, sodium carbonate or potassium carbonate, 76. A method as defined in term 12 wherein the reaction temperature is about 100° C. to about 180° C., 77. A method as defined in term 12 wherein the reaction time is about 30 minutes to about 30 hours, 78. A method as defined in term 12 wherein the reaction is conducted in the presence of magnesium sulfate, zinc chloride, cuprous chloride (CuCl), potassium fluoride or lithium chloride, 79. A method as defined in term 12 wherein an amount of the compound (II) or a salt thereof is at about 1 to about 5 mol to 1 mol of the compound (III) or a salt thereof, 80. A method as defined in term 12 wherein an amount of the compound (II) or a salt thereof is at about 1.0 to about 1.7 mol to 1 mol of the compound (III) or a salt thereof in the presence of the base, 81. A method as defined in term 12 wherein an amount of the compound (II) or a salt thereof is at about 1.5 mol to 1 mol of the compound (III) or a salt thereof in the presence of the base, 82. A method as defined in term 12 wherein the reaction is conducted in an atmosphere of inert gas, 83. A method as defined in term 12 wherein the inert gas is $N_2$ gas or argon gas, 84. A method as defined in term 12 wherein $R^{1'}$ is a hydrocarbon group substituted by a group represented by the formula: —$COOR^{11}$ wherein $R^{11}$ is a hydrogen atom or a hydrocarbon group which may be substituted, 85. A method as defined in term 12 wherein $R^{1'}$ is a $C_{1-6}$ alkyl group which may be substituted by carboxyl or $C_{1-6}$ alkoxy-carbonyl, 86. A method as defined in term 12 wherein $R^{1'}$ is a carboxyl dimethylmethyl group or $C_{1-6}$ alkoxy-carbonyl dimethyl-methyl group, 87. A method as defined in term 12 wherein $R^{1'}$ is carboxyl or ethoxycarbonyl, 88. A method as defined in term 12 wherein $Ar^{1'}$ and $Ar^{2'}$ are independently a phenyl group which may be substituted by a halogen atom or $C_{1-6}$ alkyl; the ring B' is a ring represented by the formula:

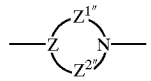

wherein Z is a nitrogen atom or a methyne group; $Z^{1''}$ and $Z^{2''}$ is independently an ethylene group which may be substituted by hydroxy, oxo or $C_{1-6}$ alkyl; X is a bond, an oxygen atom or NH; Y is (i) a $C_{1-6}$ alkylene group,
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O(CH_2)q^2NH$— or
(xiv) —$(CH_2)q^1O(CH_2)q^2S$— wherein $p^1$ is an integer of 1 to 6, $q^1$ and $q^2$ are an integer of 1 to 3; A is a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group; $R^{1'}$ is a $C_{1-6}$ alkyl group which may be substituted by carboxyl or $C_{1-6}$ alkoxy-carbonyl; $R^2$ is a hydrogen atom, a $C_{1-6}$ alkyl group, a $C_{1-6}$ alkoxy-carbonyl group or a carboxyl group; $R^3$ is a hydrogen atom; $R^8$ is a hydrogen atom or a hydroxyl group, 89. A method as defined in term 12 wherein $Ar^{1'}$ and $Ar^{2'}$ are independently a phenyl group; the ring B' is a ring represented by the formula:

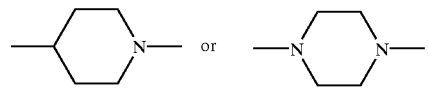

X is an oxygen atom or a bond; Y is —$(CH_2)p^1NH$— wherein $p^1$ is an integer of 1 to 6; A is $CR^{7''}$ wherein $R^{7''}$ is a hydrogen atom or a $C_{1-6}$ alkyl group; $R^{1'}$ is a $C_{1-6}$ alkyl group which may be substituted by carboxyl or $C_{1-6}$ alkoxy-carbonyl; $R^2$ is a hydrogen atom; $R^3$ is a hydrogen atom; $R^8$ is a hydrogen atom, 90. A method as defined in term 23 wherein the alkali metal is lithium, sodium or potassium, and 91. N-[6-[3-[4-(diphenylmethoxy)piperidino]propylamino]-3-methylimidazo[1,2-b]pyridazine-2-carbonyl]glycine (thereinafter referred to as compound (Ib)) oa a salt thereof.

And, when the compound (I), (I'), (I") or a salt thereof has asymmetric carbons, the present invention includes stereoisomers or racemates. The compound (I) or a salt thereof may be hydrate or anhydride.

MODE FOR CARRYING OUT THE INVENTION

1. Explanation of Compound (I)

In the above mentioned formula (I), $Ar^1$ and $Ar^2$ are independently an aromatic group which may be substituted, and $Ar^1$ and $Ar^2$ may form a condensed cyclic ring with an adjacent carbon atom.

As the "aromatic group" represented by $Ar^1$ and $Ar^2$, for example, ① a single cyclic or condensed cyclic aromatic hydrocarbon group, preferably $C_{6-14}$ single cyclic or condensed cyclic aromatic hydrocarbon group such as $C_{6-14}$ aryl group (e.g. phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl, 9-phenanthryl, etc.), more preferably phenyl, tolyl, xylyl, biphenyl, 1-naphthyl, 2-naphthyl, particularly phenyl, etc., ② a group removed a hydrogen atom from a single cyclic group (preferably 5 to 8 membered single cyclic group) containing more than 1 (for example 1 to 4, preferably 1 to 3) and one or more than two kinds of hetero atoms selected from a nitrogen atom, a sulfur atom and an oxygen atom other than carbon atoms, or a condensed aromatic heterocyclic group thereof, preferably an aromatic hetero ring removed a hydrogen atom, more specifically an aromatic heterocycle such as thiophene, benzo[b]thiophene, benzo[b]furan, benzimidazole, benzoxazole, benzothiazole, benzisothiazole, naphtho[2,3-b]thiophene, thianthrene, furan, indolylzine, xanthene, phenoxathlin, pyrrole, imidazole, triazole, thiazole, oxazole, pyrazole, pyridine, pyrazine, pyrimidine, pyridazine, indole, isoindole, 1H-indazole, purine, 4H-quinolizine, isoquinoline, quinoline, phthalazine, naphthylidine, quinoxaline, quinazoline, cinnoline, carbazole, β-carboline, phenanthridine, acridine, phenazine, isothiazole, phenothiazine, isoxazole, furaxan, phenoxazine or isochroman, preferably pyridine, thiophene, furan, more preferably pyridine, or a condensed ring formed by these rings (preferably the single ring as mentioned above) and one or few (preferably 1 or 2, more preferably 1) aromatic ring (for example the above mentioned aromatic hydrocarbon group, more preferably benzene ring, etc.), etc. are used.

As the "aromatic group of the aromatic group optionally having a substituent" represented by $Ar^1$ and $Ar^2$ for example, phenyl, etc. are preferable.

As the "substituents" of the "aromatic group" represented by $Ar^1$ and $Ar^2$, for example, (i) a halogen atom (e.g. fluorine, chlorine, bromine, iodine), (ii) a lower alkylenedioxy group (e.g. $C_{1-3}$ alkylenedioxy such as methylenedioxy, ethylenedioxy), (iii) a nitro group, (iv) a cyano group, (v) an optionally halogenated lower alkyl group, (vi) an optionally halogenated lower alkenyl group, (vii) an optionally halogenated lower alkynyl group, (viii) a lower cycloalkyl group (e.g. $C_{3-6}$ cycloalkyl such as cyclopropyl, cyclobutyl, cyclopenthyl, cyclohexyl), (ix) an optionally substituted lower alkoxy group, (x) an optionally halogenated lower alkylthio group, (xi) a hydroxy group, (xii) an amino group, (xiii) a mono-lower alkylamino group (e.g. mono-$C_{1-6}$ alkylamino such as methylamino, ethylamino, propylamino, isopropylamino, butylamino), (xiv) a di-lower alkylamino group (e.g. di-$C_{1-6}$ alkylamino such as dimethylamino, diethylamino, dipropylamino, dibutylamino), (xv) a 5 or 6 membered cyclic amino group (e.g. morpholino, piperazin-1-yl, piperidino, pyrrolidin-1-yl), (xvi) a lower alkylcarbonyl group (e.g. $C_{1-6}$ alkylcarbonyl such as acetyl, propionyl), (xvii) a carboxyl group, (xviii) a lower alkoxy-carbonyl group (e.g. $C_{1-6}$ alkoxy-carbonyl such as methoxycarbonyl, ethoxycarbonyl, propoxycarbonyl, butoxycarbonyl), (xix) a carbamoyl group, (xx) a thiocarbamoyl group, (xxi) a mono-lower alkyl-carbamoyl group (e.g. N-mono-$C_{1-6}$ alkyl-carbamoyl such as methylcarbamoyl, ethylcarbamoyl), (xxii) a di-lower alkyl-carbamoyl group (e.g. di-$C_{1-6}$ alkyl-carbamoyl such as dimethylcarbamoyl, diethylcarbamoyl), (xxiii) aryl-carbamoyl (e.g. $C_{6-10}$ aryl-carbamoyl such as phenylcarbamoyl, naphthylcarbamoyl), (xxiv) a sulfo group, (xxv) a lower alkyl sulfonyl group (e.g. $C_{1-6}$ alkyl sulfonyl such as methylsulfonyl, ethylsulfonyl), (xxvi) an aryl group (e.g. $C_{6-10}$ aryl such as phenyl, naphthyl) or (xxvii) an aryloxy group (e.g. $C_{6-10}$ aryloxy such as phenyloxy, naphthyloxy), (xxviii) an aralkyloxy group (e.g. $C_{7-16}$ aralkyloxy such as benzyloxy), etc. are used.

As the "optionally halogenated lower alkyl group", for example, a lower alkyl group (e.g. $C_{1-6}$ alkyl such as methyl, ethyl, propyl, isopropyl, butyl, isobutyl, sec-butyl, tert-butyl, pentyl, hexyl) optionally substituted by 1 to 3 halogen atoms (e.g. fluorine, chlorine, bromine, iodine), etc. are exemplified. As specific examples, for example, methyl, fluoromethyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. are used.

As the "optionally halogenated lower alkenyl group", for example, a lower alkenyl group and the "optionally halogenated lower alkynyl group", for example, a lower alkenyl group (e.g., a $C_{2-6}$ alkenyl group such as vinyl, propenyl, isopropenyl, 2-buten-1-yl, 4-penten-1-yl, 5-hexen-1-yl, etc.) optionally substituted by 1 to 3 halogen atoms (e.g. fluorine, chlorine, bromine, iodine) and a lower alkynyl group (e.g., a $C_{2-6}$ alkynyl group such as 2-butyn-1-yl, 4-pentyn-1-yl, 5-hexyn-1-yl, etc.) optionally substituted by 1 to 3 halogen atoms (e.g. fluorine, chlorine, bromine, iodine), etc. are used.

As the "optionally substituted lower alkoxy group", for example, a lower alkoxy group (e.g. a $C_{1-6}$ alkoxy group such as methoxy, ethoxy, propoxy, isopropoxy, n-butoxy, isobutoxy, sec-butoxy, tert-butoxy, etc.) optionally substituted by 1 to 3 halogen atoms (e.g. fluorine, chlorine, bromine, iodine), mono- or di-lower alkylamino groups (e.g. mono- or di-$C_{1-6}$ alkylamino such as methylamino, dimethylamino, ethylamino, dimethylamino) or lower alkoxy-carbonyl groups (e.g. $C_{1-6}$ alkoxy-carbonyl such as methoxycarbonyl, ethoxycarbonyl), etc. are used.

As the "optionally halogenated lower alkylthio group", for example, a lower alkylthio group (e.g. a $C_{1-6}$ alkylthio group such as methylthio, ethylthio, n-propylthio, isopropylthio, n-butylthio, isobutylthio, sec-butylthio, tert-butylthio) optionally substituted by 1 to 3 halogen atoms (e.g. fluorine, chlorine, bromine, iodine), etc. are used, and as specific examples, methylthio, difluoromethylthio, trifluoromethylthio, ethylthio, propylthio, isopropylthio, butylthio, 4,4,4-trifluorobutylthio, pentylthio, hexylthio, etc. are used.

As specific examples of the condensed ring formed by $Ar^1$, $Ar^2$ and the adjacent carbon atom, for example, a condensed ring represented by the formula:

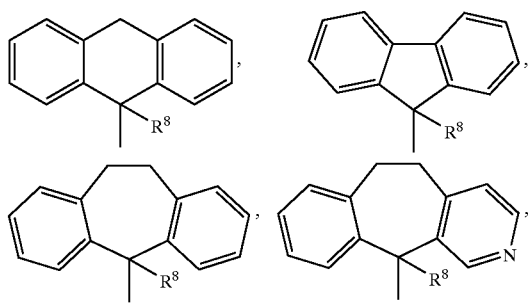

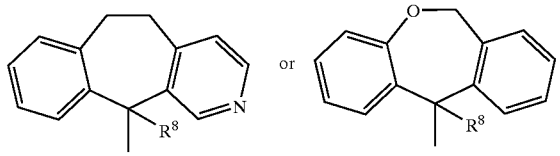

wherein R⁸ is same as defined above, etc. are used.

As $Ar^1$ and $Ar^2$, same or different and independently, an aromatic hydrocarbon group (preferably $C_{6-14}$ aromatic hydrocarbon group) which may be substituted is preferable, and a benzene ring which may be substituted is more preferable. More specifically, as $Ar^1$ and $Ar^2$, independently, (1) a phenyl group which may be substituted by a halogen atom or $C_{1-6}$ alkyl or (2) a 5 to 8 membered aromatic heterocyclic group containing 1 to 4 hetero atoms selected from a nitrogen atom, a sulfur atom and an oxygen atom other than carbon atoms, etc. are preferable.

In the above mentioned formula (I), the ring B represents a "nitrogen-containing heterocycle optionally having a substituent", provided that the ring B is not a heterocycle represented by the formula:

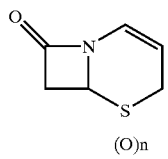

wherein n is 0 or 1.

As the "nitrogen-containing heterocycle" represented by the ring B, for example, a 3 to 13 membered nitrogen-containing heterocycle containing at least one nitrogen atom which may contain 1 to 3 hetero atoms selected w from a nitrogen atom, an oxygen atom and a sulfur atom, etc. are used. In the above mentioned formula (I), it is preferable that a bivalent group removed one hydrogen atom from the nitrogen atom and others atom of the ring B, respectively, is formed. Specifically, a 3 to 9 membered (preferably 3 to 6 membered) nitrogen atom-containing heterocyclic group such as

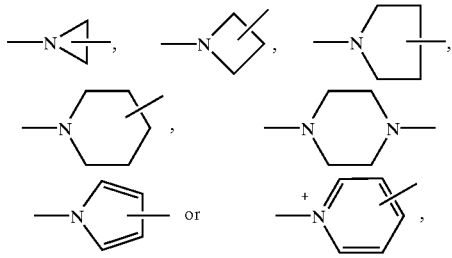

etc. are preferable.

As the substituents of the nitrogen atom-containing heterocycle represented by the ring B, for example, an oxo group as well as the "substituents" of the "aromatic group optionally having a substituent" represented by $Ar^1$ and $Ar^2$, etc. are used.

As preferable specific examples of the ring B, for example, a ring represented by the formula:

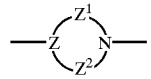

wherein Z is a nitrogen atom or a methyne group, $Z^1$ and $Z^2$ are independently a linear $C_{1-4}$ alkylene group which may be substituted by a hydroxy group, an oxo group or a $C_{1-6}$ alkyl group, etc. are used.

As the "$C_{1-6}$ alkyl group", for example, a linear or branched $C_{1-6}$ alkyl group such as methyl, ethyl, propyl, isopropyl, butyl, isobutyl, sec-butyl, tert-butyl, pentyl, hexyl, etc. are used.

As the "linear $C_{1-4}$ alkylene group", for example, a linear $C_{1-4}$ alkylene group such as methylene, ethylene, propylene, butylene, etc. are used.

As the "linear $C_{1-4}$ alkylene group which may be substituted by a hydroxy group, an oxo group or a $C_{1-6}$ alkyl group" represented by $Z^1$ and $Z^2$, an unsubstituted linear $C_{1-4}$ alkylene group, etc. are used, and particularly, an unsubstituted linear $C_{1-2}$ alkylene group is preferable.

As more preferable ring B, piperidine, piperazine, etc. are exemplified.

In the above mentioned formula (I), X and Y are the same or different and are independently ① a bond, ② an oxygen atom, ③ S(O)p (p is an integer of 0 to 2), ④ $NR^4$ wherein $R^4$ is a hydrogen atom or a lower alkyl group or ⑤ a bivalent linear lower hydrocarbon group which may contain 1 to 3 hetero atoms and the bivalent linear lower hydrocarbon group may have substituents.

As the lower alkyl group represented by $R^4$, for example, a linear or branched $C_{1-6}$ alkyl group such as methyl, ethyl, propyl, isopropyl, butyl, isobutyl, sec-butyl, tert-butyl, pentyl, hexyl, etc. are used.

As the "bivalent linear lower hydrocarbon group which may contain 1 to 3 hetero atoms" represented by X and Y, for example, a group which is formed by removing each one hydrogen atom (sum two hydrogen atoms) bonded to same or different carbon atom from a lower ($C_{1-6}$)hydrocarbon, and which may optionally contain hetero atoms selected from an oxygen atom and a sulfur atom in the hydrocarbon chain is exemplified.

As specific examples of the "bivalent linear lower hydrocarbon group", for example, (i) a $C_{1-6}$ alkylene group (e.g., —$CH_2$—, —$(CH_2)_2$—, —$(CH_2)_3$—, —$(CH_2)_4$—, —$(CH_2)_5$—, —$(CH_2)_6$—, etc.)

(ii) a $C_{2-6}$ alkenylene group (e.g., —CH=CH—, —CH=CH—$CH_2$—, —$CH_2$—CH=CH—$CH_2$—, —$(CH_2)_2$—CH=CH—$CH_2$—, —$(CH_2)_2$—CH=CH—$(CH_2)_2$—, —$(CH_2)_3$—CH=CH—$CH_2$—, etc.), (iii) a $C_{2-6}$ alkynylene group (e.g., —C≡C—, —C≡C—$CH_2$—, —CH—C≡C—$CH_2$—, —$(CH_2)_2$—C≡C—$CH_2$—, —$(CH_2)_2$—C≡C—$(CH_2)_2$—, —$(CH_2)_3$—C≡C—$CH_2$—, etc.), etc. are used.

As the "substituents" of the "bivalent linear lower hydrocarbon group which may contain 1 to 3 hetero atoms" represented by X and Y, an oxo group as well as the "substituents" of the "aromatic group optionally having a substituent" represented by the above mentioned $Ar^1$ and $Ar^2$, etc. are used, and a hydroxy group or an oxo group is preferable.

As X, a bond, an oxygen atom or NH is preferable, and particularly, a bond or an oxygen atom is preferable.

As Y, for example, a group represented by the formula:

—(CH$_2$)$m$-Y$^1$—(CH$_2$)$n$-Y$^2$— wherein Y$^1$ and Y$^2$ are the same or different and are independently a bond, an oxygen atom, S(O)p wherein p is same as defined above, NR$^4$ wherein R$^4$ is same as defined above, a carbonyl group, a carbonyloxy group or a group represented by the formula:

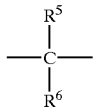

wherein R$^5$ and R$^6$ are the same or different and are independently a hydroxy group or a C$_{1-4}$ alkyl group; m and n are independently an integer of 0 to 4, (provised that, sum of m and n is not more than 6), etc. are used.

As the "C$_{1-4}$ alkyl group" represented by R$^5$ and R$^6$, for example, a linear or branched C$_{1-4}$ alkyl group such as methyl, ethyl, propyl, isopropyl, butyl, isobutyl, sec-butyl, tert-butyl, etc. are used.

As Y, for example, a group represented by
(i) a C$_{1-6}$ alkylene group,
(ii) —(CH$_2$)p$^1$O—,
(iii) —(CH$_2$)p$^1$NH—,
(iv) —(CH$_2$)p$^1$S—,
(v) —(CH$_2$)q$^1$CH(OH)(CH$_2$)q$^2$O—,
(vi) —(CH$_2$)q$^1$CH(OH)(CH$_2$)q$^2$NH—,
(vii) —(CH$_2$)q$^1$CH(OH)(CH$_2$)q$^2$S—,
(viii) —(CH$_2$)p$^1$CONH—,
(ix) —COO(CH$_2$)p$^1$O—,
(x) —COO(CH$_2$)p$^1$NH—,
(xi) —COO(CH$_2$)p$^1$S—,
(xii) —(CH$_2$)q$^1$O(CH$_2$)q$^2$O—,
(xiii) —(CH$_2$)q$^1$O(CH$_2$)q$^2$NH— or
(xiv) —(CH$_2$)q$^1$O(CH$_2$)q$^2$S— wherein p$^1$ is an integer of 1 to 6, q$^1$ and q$^2$ are an integer of 1 to 3, etc. are preferable.

Of them, as Y, a bond, —(CH$_2$)$_2$—O—, —(CH$_2$)$_3$—O—, —(CH$_2$)$_4$—O—, —(CH$_2$)$_6$—O—, —(CH$_2$)$_2$—NH—, —(CH$_2$)$_3$—NH—, —(CH$_2$)$_4$—NH—, —(CH$_2$)$_3$—S—, —CH$_2$—CH(OH)—CH$_2$—O—, —(CH$_2$)$_2$—CO—NH—, —CH$_2$—CO—NH—, —CO—O—(CH$_2$)$_2$—O—, —CO—O—(CH$_2$)$_3$—O—, —(CH$_2$)$_6$—NH—, —(CH$_2$)$_6$—S—, —(CH$_2$)$_2$—O—(CH$_2$)$_2$—O—, —(CH$_2$)$_2$—O—(CH$_2$)$_2$—S—, etc. are preferable.

In the above mentioned formula (I) A is a nitrogen atom or CR$^7$ wherein R$^7$ is a hydrogen atom, a halogen atom, a hydrocarbon group which may be substituted, an acyl group or a hydroxy group which may be substituted.

As the "halogen atom" represented by R$^7$, fluorine, chlorine, bromine, iodine are exemplified.

As the "hydrocarbon group" represented by R$^7$, for example, a group removed one hydrogen atom from the hydrocarbon compound is exemplified, and as the specific examples, a linear and cyclic hydrocarbon group such as alkyl group, alkenyl group, alkynyl group, cycloalkyl group, aryl group, aralkyl group, etc. are exemplified. Of them, a C$_{1-16}$ chain (linear or branched) or cyclic hydrocarbon group, etc. are preferable, and (a) an alkyl group, preferably lower alkyl group (e.g. a C$_{1-6}$ alkyl group such as methyl, ethyl, propyl, isopropyl, butyl, isobutyl, sec-butyl, tert-butyl, pentyl, hexyl, etc.), (b) an alkenyl group, preferably lower alkenyl group (e.g. a C$_{2-6}$ alkenyl such as vinyl, allyl, isopropenyl, butenyl, isobutenyl, sec-butenyl, etc.), (c) an alkynyl group, preferably lower alkynyl (e.g. a C$_{2-6}$ alkynyl such as propargyl, ethynyl, butynyl, 1-hexynyl, etc.), (d) a cycloalkyl group, preferably lower cycloalkyl (e.g. a C$_{3-6}$ cycloalkyl such as cyclopropyl, cyclobutyl, cyclopentyl, cyclohexyl which may condense with a benzene ring optionally having 1 to 3 lower alkoxys (e.g. a C$_{1-6}$ alkoxy group such as methoxy), etc.), (e) an aryl group (e.g. C$_{6-14}$ aryl group such as phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl or 9-phenanthryl, etc., preferably phenyl), (f) an aralkyl group (e.g. a C$_{7-16}$ aralkyl group such as benzyl, phenethyl, diphenylmethyl, 1-naphthylmethyl, 2-naphthylmethyl, 2-phenylethyl, 2-diphenylethyl, 1-phenylpropyl, 2-phenylpropyl, 3-phenylpropyl, 4-phenylbutyl or 5-phenylpentyl, etc., preferably benzyl).

As the "substituents" of the "hydrocarbon group" represented by R$^7$, for example, an oxo group as well as the "substituents" of the "aromatic group optionally having a substituent" represented by the above mentioned Ar$^1$ and Ar$^2$, etc. are used.

As the "acyl group" represented by R$^7$, for example, —(C=O)—R$^9$, —SO$_2$—R$^9$, —SO—R$^9$, —(C=O)NR$^{10}$R$^9$, —(C=O)O—R$^9$, —(C=S)O—R$^9$ or —(C=S)NR$^{10}$OR$^9$ wherein R$^9$ is a hydrogen atom, a hydrocarbon group optionally having a substituent or a hydroxy group optionally having a substituent; and R$^{10}$ is a hydrogen atom or a lower alkyl group (e.g., a C$_{1-6}$ alkyl group such as methyl, ethyl, propyl, isopropyl, butyl, isobutyl, sec-butyl, tert-butyl, pentyl, hexyl, etc. and preferably a C$_{1-3}$ alkyl such as methyl, ethyl, propyl, isopropyl, etc.), etc. are exemplified.

Of them, —(C=O)—R$^9$, —SO$_2$—R$^9$, —SO—R$^9$, —(C=O)NR$^{10}$OR$^9$, —(C=O)O—R$^{9^2}$ are preferred, and —(C=O)—R$^9$ is more preferred.

The "hydrocarbon group" represented by R$^9$ represents a group having one hydrogen atom removed from the hydrocarbon compound, and as the example, for example, a chained (linear or branched) or cyclic hydrocarbon group such as alkyl group, alkenyl group, alkynyl group, cycloalkyl group, aryl group, aralkyl group, etc. are exemplified, and specifically, the "hydrocarbon group" represented by the above mentioned R$^7$, etc. are exemplified, and of them, a C$_{1-6}$ linear or cyclic hydrocarbon group, etc. are preferable, and particularly a lower (C$_{1-6}$)alkyl group, etc. are preferable.

As the "substituents" of the "hydrocarbon group" represented by R$^9$, for example, an oxo group as well as the "substituents" of the "aromatic group optionally having a substituent" represented by the above mentioned Ar$^1$ and Ar$^2$, etc. are used.

As the "hydroxy group optionally having a substituent" represented by R$^9$, for example, same those as the "hydroxy group optionally having a substituent" represented by R$^7$ as mentioned below, etc. are used.

The "hydroxy group optionally having a substituent" represented by R$^7$ represents (1) a hydroxy group or (2) a hydroxy group having one group such as the above mentioned "hydrocarbon group optionally having a substituent" instead of a hydrogen atom of the hydroxy group.

As $R^7$, for example, (1) a hydrogen atom, (2) a $C_{1-6}$ alkyl group which may be substituted by a carboxyl group or $C_{1-6}$ alkoxy-carbonyl, (3) a $C_{1-6}$ alkoxy group, (4) a $C_{1-6}$ alkoxy-carbonyl group, (5) a carboxyl group, etc. are preferable, and particularly a hydrogen atom, a halogen atom, a $C_{1-6}$ alkyl group, a $C_{1-6}$ alkoxy-carbonyl group and a carboxyl group are preferable.

As A, a nitrogen atom, $CR^{7'}$ wherein $R^{7'}$ is a hydrogen atom, a halogen atom, a $C_{1-6}$ alkyl group, a $C_{1-6}$ alkoxy-carbonyl group or a carboxyl group is preferable, and of them, a nitrogen atom, CH or C—$CH_3$ is preferable, particularly a nitrogen atom or CH is preferable.

In the above mentioned formula (I), $R^1$, $R^2$ and $R^3$ are the same or different and are independently a hydrogen atom, a halogen atom, a hydrocarbon group optionally having a substituent, an acyl group or a hydroxy group optionally having a substituent.

As the "halogen atom" represented by $R^1$, $R^2$ and $R^3$, fluorine, chlorine, bromine, iodine are exemplified.

As the "hydrocarbon group optionally having a substituent" represented by $R^1$, $R^2$ and $R^3$, for example, the "hydrocarbon, group optionally having a substituent" represented by the above mentioned $R^1$, etc. are used.

As the "acyl group" represented by $R^1$, $R^2$ and $R^3$, for example, the "acyl group" represented by the above mentioned $R^7$, etc. are used.

As the "hydroxy group optionally having a substituent" represented by $R^1$, $R^2$ and $R^3$, for example, the "hydroxy group optionally having a substituent" represented by $R^7$, etc. may be used.

As $R^1$, $R^2$ and $R^3$, same or different and independently, (1) a hydrogen atom, (2) a $C_{1-6}$ alkyl group which may be substituted by carboxyl or $C_{1-6}$ alkoxy-carbonyl, (3) a $C_{1-6}$ alkoxy group, (4) a $C_{1-6}$ alkoxy-carbonyl group, (5) a carboxyl group or (6) a $C_{6-14}$ aryl group (preferably phenyl) is preferable, and (1) a hydrogen atom, (2) a $C_{1-6}$ alkyl group which may be substituted by carboxyl or $C_{1-6}$ alkoxy-carbonyl, (3) a $C_{1-6}$ alkoxy group, (4) a $C_{1-6}$ alkoxy-carbonyl group or (5) a carboxyl group is more preferable.

And, as $R^1$, (1) a hydrogen atom, (2) a $C_{1-6}$ alkyl group which may be substituted by a group selected from the group consisting of carboxyl, $C_{1-6}$ alkoxy-carbonyl, hydroxy or carbamoyl optionally having mono- or di-$C_{1-6}$ alkyl, (3) a $C_{6-14}$ aryl group, (4) a $C_{1-6}$ alkoxy group, (5) a $C_{1-6}$ alkoxy-carbonyl group, (6) a carboxyl group, (7) a carbamoyl group optionally having $C_{1-6}$ alkyl which may be substituted by carboxyl or $C_{1-6}$ alkoxy-carbonyl or (8) a $C_{3-6}$ cycloalkyl group which may be substituted by $C_{1-6}$ alkoxy-carbonyl, etc. are also preferable.

As $R^2$, a hydrogen atom, a $C_{1-6}$ alkyl group, a $C_{1-6}$ alkoxy-carbonyl group or a carboxyl group is preferable.

As $R^3$, a hydrogen atom is preferable.

In the above mentioned formula (I), $R^8$ represents a hydrogen atom or a hydroxy group which may be substituted by lower alkyl.

In the above mentioned formula (I), as the "lower alkyl group" of the "hydroxy group which may be substituted by a lower alkyl group" represented by $R^8$, for example, a $C_{1-6}$ alkyl group such as methyl, ethyl, propyl, isopropyl, butyl, isobutyl, sec-butyl, tert-butyl, pentyl, hexyl, etc. are used.

As $R^8$, a hydrogen atom or a hydroxyl group is preferable, and particularly a hydrogen atom is preferable.

As the compound (I) of the present invention, a compound wherein $Ar^1$ and $Ar^2$ are independently (1) a phenyl group which may be substituted by a halogen atom or $C_{1-6}$ alkyl or (2) a 5 to 8 membered aromatic heterocyclic group containing 1 to 4 hetero atoms selected from a nitrogen atom, a sulfur atom and an oxygen atom other than carbon atoms; the ring B is a ring represented by the formula:

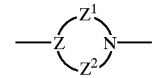

wherein Z is a nitrogen atom or a methyne group; $Z^1$ and $Z^2$ is independently a linear $C_{1-4}$ alkylene group which may be substituted by a hydroxy group, an oxo group or a $C_{1-6}$ alkyl group; X is a bond, an oxygen atom or NH; Y is a group represented by (i) a $C_{1-6}$ alkylene group,
(ii) —$(CH_2)p^1O$—,
(iii) —$(CH_2)p^1NH$—,
(iv) —$(CH_2)p^1S$—,
(v) —$(CH_2)q^1CH(OH)(CH_2)q^2O$—,
(vi) —$(CH_2)q^1CH(OH)(CH_2)q^2NH$—,
(vii) —$(CH_2)q^1CH(OH)(CH_2)q^2S$—,
(viii) —$(CH_2)p^1CONH$—,
(ix) —$COO(CH_2)p^1O$—,
(x) —$COO(CH_2)p^1NH$—,
(xi) —$COO(CH_2)p^1S$—,
(xii) —$(CH_2)q^1O(CH_2)q^2O$—,
(xiii) —$(CH_2)q^1O(CH_2)q^2NH$— or
(xiv) —$(CH_2)q^1O(CH_2)q^2S$— wherein $p^1$ is an integer of 1 to 6, $q^1$ and $q^2$ are an integer of 1 to 3; A is a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group; $R^1$ is (1) a hydrogen atom, (2) a $C_{1-6}$ alkyl group which maybe substituted by (i) carboxyl, (ii) $C_{1-6}$ alkoxy-carbonyl, (iii) hydroxy or (iv) carbamoyl optionally having mono- or di-$C_{1-6}$ alkyl, (3) a $C_{6-14}$ aryl group, (4) a $C_{1-6}$ alkoxy group, (5) a $C_{1-6}$ alkoxy-carbonyl group, (6) a carboxyl group, (7) a carbamoyl group optionally having $C_{1-6}$ alkyl which may be substituted by carboxyl or $C_{1-6}$ alkoxy-carbonyl or (8) a $C_{3-6}$ cycloalkyl group which may be substituted by $C_{1-6}$ alkoxy-carbonyl; $R^2$ is a hydrogen atom, a $C_{1-6}$ alkyl group, a $C_{1-6}$ alkoxy-carbonyl group or a carboxyl group; $R^3$ is a hydrogen atom; $R^8$ is a hydrogen atom or a hydroxyl group, is preferable.

Particularly, a compound wherein $Ar^1$ and $Ar^2$ are a phenyl group; the ring B is a ring represented by the formula:

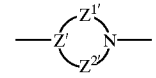

wherein Z is a methyne group; $Z^{1'}$ and $Z^{2'}$ are a methylene group or an ethylene group (preferably, an ethylene group); X is a bond, an oxygen atom or NH (preferably, a bond or an oxygen atom); Y is —$(CH_2)p^1NH$— wherein p is an integer of 1 to 6; A is $CR^{7''}$ wherein $R^{7''}$ is a hydrogen atom or a $C_{1-6}$ alkyl group; $R^1$ is (1) a hydrogen atom, (2) a $C_{1-6}$ alkyl group which may be substituted by carboxyl or $C_{1-6}$ alkoxy-carbonyl or (3) a carbamoyl group optionally having $C_{1-6}$ alkyl which may be substituted by $C_{1-6}$ alkoxy-carbonyl; $R^2$ is a hydrogen atom; $R^3$ is a hydrogen atom; $R^8$ is a hydrogen atom, is more preferable.

More specifically,
(i) Ethyl 2-[6-[3-[4-(diphenylmethoxy)piperidino] propylamino]imidazo[1,2-b]pyridazin-2-yl]-2- methylpropionate or a salt thereof (particularly, a difumarate thereof, a disuccinate thereof or a citrate thereof),
(ii) 2-[6-[3-[4-(diphenylmethoxy)piperidino] propylamino]imidazo[1,2-b]pyridazin-2-yl]-2-methylpropionic acid or a salt thereof (particularly, a dehydrate thereof),
(iii) Ethyl N-[6-[3-[4-(diphenylmethoxy)piperidino] propylamino]imidazo[1,2-b]pyridazine-2-carbonyl] glycinate or a salt thereof,
(iv) Ethyl 2-[6-[3-[4-(diphenylmethoxy)piperidino] propylamino]-3-methylimidazo,[1,2-b]pyridazin-2-yl]-2-methylpropionate or a salt thereof (particularly, a dihydrochloride thereof),
(v) Ethyl 2-[6-[3-[4-(diphenylmethylamino)piperidino] propylamino]imidazo[1,2-b]pyridazin-2-yl]-2-methylpropionate or a salt thereof,
(vi) 2-[6-[3-[4-(diphenylmethoxy)piperidino] propylamino]-3-methylimidazo[1,2-b]pyridazin-2-yl]-2-methylpropionic acid or a salt thereof, and
(vii) N-[6-[3-[4-(diphenylmethoxy)piperidino] propylamino)-3-methylimidazo[1,2-b]pyridazine-2-carbonyl]glycine or a salt thereof, etc. are preferable.

2. Explanation of Compound (I')

In the above mentioned formula, $Ar^{1'}$ and $Ar^{2'}$ represents an aromatic group optionally having a substituent, and $Ar^{1'}$ and $Ar^{2'}$ may form a condensed cyclic ring with an adjacent carbon atom.

As the aromatic group represented by $Ar^{1'}$ and $Ar^2$, for example, a single cyclic or condensed cyclic aromatic hydrocarbon group is used. Specifically, a $C_{6-14}$ single cyclic or condensed cyclic aromatic hydrocarbon group such as a $C_{6-14}$ aryl group such as phenyl, tolyl, xylyl, biphenyl, 1-naphthyl, 2-naphthyl, 2-indenyl, 1-anthryl, 2-anthryl, 9-anthryl, 1-phenanthryl, 2-phenanthryl, 3-phenanthryl, 4-phenanthryl, 9-phenanthryl, etc. (more preferably phenyl, tolyl, xylyl, biphenyl, 1-naphthyl, 2-naphthyl, particularly phenyl, etc.), etc. are used.

As the aromatic ring represented by $Ar^{1'}$ and $Ar^{2'}$, for example, a $C_{6-14}$ aryl group such as phenyl, etc. are preferable.

As the substituents of the aromatic ring represented by $Ar^{1'}$ and $Ar^{2'}$, for example,
(i) a halogen atom (e.g. fluorine, chlorine, bromine, iodine),
(ii) a lower alkylenedioxy group (e.g. $C_{1-3}$ alkylenedioxy such as methylenedioxy, ethylenedioxy),
(iii) a nitro group,
(iv) a cyano group,
(v) an optionally halogenated lower alkyl group,
(vi) an optionally halogenated lower alkenyl group,
(vii) an optionally halogenated lower alkynyl group,
(viii) a lower cycloalkyl group (e.g. $C_{3-6}$ cycloalkyl such as cyclopropyl, cyclobutyl, cyclopentyl, cyclohexyl),
(ix) an optionally substituted lower alkoxy group,
(x) an optionally halogenated lower alkylthio group,
(xi) a hydroxy group,
(xii) an amino group,
(xiii) a mono-lower alkylamino group (e.g. mono-$C_{1-6}$ alkylamino such as methylamino, ethylamino, propylamino, isopropylamino, butylamino),
(xiv) a di-lower alkylamino group (e.g. di-$C_{1-4}$ alkylamino such as dimethylamino, diethylamino, dipropylamino, dibutylamino),
(xv) a 5 or 6 membered cyclic amino group (e.g. morpholino, piperazin-1-yl, piperidino, pyrrolidin-1-yl),
(xvi) a lower alkylcarbonyl group (e.g. $C_{1-6}$ alkylcarbonyl such as acetyl, propionyl),
(xvii) a carboxyl group,
(xviii) a lower alkoxy-carbonyl group (e.g. $C_{1-6}$ alkoxy-carbonyl such as methoxycarbonyl, ethoxycarbonyl, propoxycarbonyl, butoxycarbonyl),
(xix) a carbamoyl group,
(xx) a thiocarbamoyl group,
(xxi) a mono-lower alkyl-carbamoyl group (e.g. mono-$C_{1-6}$ alkyl-carbamoyl such as methylcarbamoyl, ethylcarbamoyl),
(xxii) a di-lower alkyl-carbamoyl group (e.g. di-$C_{1-6}$ alkyl-carbamoyl such as dimethylcarbamoyl, diethylcarbamoyl),
(xxiii) aryl-carbamoyl (e.g. $C_{6-10}$ aryl-carbamoyl such as phenylcarbamoyl, naphthylcarbamoyl),
(xxiv) a sulfo group,
(xxv) a lower alkyl sulfonyl group (e.g. $C_{1-6}$ alkyl sulfonyl such as methylsulfonyl, ethylsulfonyl),
(xxvi) an aryl group (e.g. $C_{6-10}$ aryl such as phenyl, naphthyl),
(xxvii) an aryloxy group (e.g. $C_{6-10}$ aryloxy such as phenyloxy, naphthyloxy),
(xxviii) an aralkyloxy group (e.g. $C_{7-16}$ aralkyloxy such as benzyloxy),
(xxviv) an oxo group, etc. are used.

As the "optionally halogenated lower alkyl group", for example, a lower alkyl group (e.g. a $C_{1-6}$ alkyl group such as methyl, ethyl, propyl, isopropyl, butyl, isobutyl, sec-butyl, tert-butyl, pentyl, hexyl) optionally substituted by 1 to 3 halogen atoms (e.g. fluorine, chlorine, bromine, iodine), etc. are exemplified, and as specific examples, methyl, fluoromethyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc. are used.

As the "optionally halogenated lower alkenyl group" and "optionally halogenated lower alkynyl group", for example, a lower alkenyl group (e.g. a $C_{2-6}$ alkenyl group such as vinyl, propenyl, isopropenyl, 2-buten-1-yl, 4-penten-1-yl, 5-hexen-1-yl) optionally substituted by 1 to 3 halogen atoms (e.g. fluorine, chlorine, bromine, iodine) and a lower alkynyl group (e.g. a $C_{2-6}$ alkynyl group such as 2-butyn-1-yl, 4-pentyn-1-yl, 5-hexyn-1-yl) optionally substituted by 1 to 3 halogen atoms (e.g. fluorine, chlorine, bromine, iodine), etc. are used.

As the "optionally substituted lower alkoxy group", for example, a lower alkoxy group (e.g. a $C_{1-6}$ alkoxy group such as methoxy, ethoxy, propoxy, isopropoxy, n-butoxy, isobutoxy, sec-butoxy, tert-butoxy) optionally having 1 to 3 halogen atoms (e.g. fluorine, chlorine, bromine, iodine), mono- or di-lower alkylamino groups (e.g. mono- or di-$C_{1-6}$ alkylamino such as methylamino, dimethylamino, ethylamino, dimethylamino) or lower alkoxy-carbonyl groups (e.g. a $C_{1-6}$ alkoxy-carbonyl group such as methoxycarbonyl, ethoxycarbonyl), etc. are used.

As the "optionally halogenated lower alkylthio group", for example, a lower alkylthio group (e.g. a $C_{1-6}$ alkylthio group such as methylthio, fluoromethylthio, ethylthio, n-propylthio, isopropylthio, n-butylthio, isobutylthio, sec-butylthio, tert-butylthio) optionally having 1 to 3 halogen atoms (e.g. fluorine, chlorine, bromine, iodine), etc. exemplified, and as specific examples, for example, methylthio, difluoromethylthio, trifluoromethylthio, ethylthio, propylthio, isopropylthio, butylthio, 4,4,4-trifluorobutylthio, pentylthio, hexylthio, etc. are used.

As specific examples of the condensed ring formed by $Ar^{1'}$, $Ar^{2'}$ and the adjacent carbon atom, for example, a condensed ring represented by the formula:

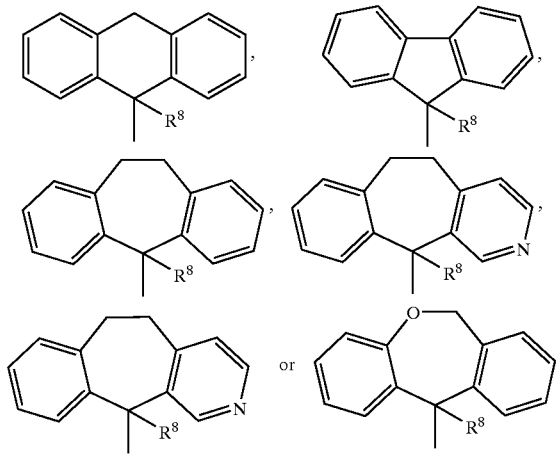

wherein $R^8$ is same as defined above, etc. are used.

As $Ar^{1'}$ and $Ar^2$, same or different and are independently, a $C_{6-14}$ aromatic hydrocarbon group optionally having a substituent is preferable and a phenyl group optionally having a substituent is more preferable. More specifically, as $Ar^{1'}$ and $Ar^{2'}$, independently, (1) a phenyl group which may be substituted by a halogen atom or $C_{1-6}$ alkyl, etc. are preferable and particularly an unsubstituted phenyl group is preferable.

In the above mentioned formula, the ring B' represents a 6-membered nitrogen-containing heterocycle optionally having a substituent.

As the 6-membered nitrogen-containing heterocycle represented by the ring B', for example, a 6-membered nitrogen-containing heterocycle containing at least one nitrogen atom and further optionally containing 1 to 3 hetero atoms selected from, e.g., by a nitrogen atom, an oxygen atom and a sulfur atom, etc. are used. In the above mentioned formula (I), it is preferable that a bivalent group removed one hydrogen atom from the nitrogen atom and others atom of the ring B', respectively, is formed. Specifically, a 6 membered nitrogen atom-containing heterocyclic group such as

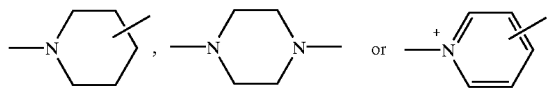

etc. are preferable.

As the substituents of the 6-membered nitrogen atom-containing heterocycle represented by the ring B', for example, the same substituents of the "aromatic group optionally having a substituent" represented by $Ar^{1'}$ and $Ar^{2'}$ as mentioned above, etc. are used.

As specific preferable examples of the ring B', for example, a ring represented by the formula:

wherein Z is a nitrogen atom or a methine group, $Z^{1''}$ and $Z^{2''}$ are independently an ethylene group which may be substituted by a hydroxy group, an oxo group or a $C_{1-6}$ alkyl group, etc. are used.

As the $C_{1-6}$ alkyl group which is a substituent for the ethylene group represented by $Z^{1''}$ and $Z^{2''}$, for example, a linear or branched $C_{1-3}$ alkyl group such as methyl, ethyl, propyl, isopropyl, butyl, isobutyl, sec-butyl, tert-butyl, pentyl, hexyl, etc. are used.

Preferable examples of the "ethylene group which may be substituted by a hydroxy group, an oxo group or a $C_{1-6}$ alkyl group" are an unsubstituted methylene group and an unsubstituted ethylene group, and particularly an unsubstituted ethylene group is preferable.

As more preferable examples of the ring B', a 6-membered ring represented by the formula:

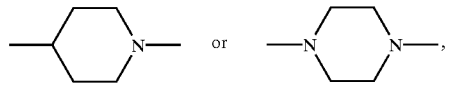

particularly

etc. are preferable.

In the above mentioned formula, X and Y represent the same meanings as mentioned above, and the same preferable groups as mentioned above are used.

In the above mentioned formula, A represents the same meaning as mentioned above, and the same preferable groups as mentioned above are used. Among them, as A, a nitrogen atom or $CR^{7'}$ wherein $R^{7'}$ is a hydrogen atom, a halogen atom, a $C_{1-6}$ alkyl group, a $C_{1-6}$ alkoxy-carbonyl group or a carboxyl group is preferable and particularly a nitrogen atom or CH is preferable.

$R^{1'}$ represents a hydrocarbon group substituted by an optionally esterified carboxyl group.

As the hydrocarbon group represented by $R^{1'}$, for example, the same those as the hydrocarbon group represented by $R^7$ are used. Among them, a $C_{1-6}$ alkyl group such as methyl, ethyl, propyl, isopropyl, butyl, sec-butyl, tert-butyl, etc. are preferable, and particularly an isopropyl group is preferable.

As the "optionally esterified carboxyl group" which is a substituent for the hydrocarbon group represented by $R^{1'}$, a group represented by the formula: $-COOR^{11}$ wherein $R^{11}$ is a hydrogen atom or a hydrocarbon group which may be substituted, etc. are used.

As the hydrocarbon group which may be substituted represented by $R^{11}$, for example, the same those as the hydrocarbon group optionally having a substituent represented by $R^7$ are used. Among them, a $C_{1-6}$ alkyl group such as methyl, ethyl, propyl, isopropyl, butyl, sec-butyl, tert-butyl, etc. are preferable, and particularly an ethyl group is preferable.

As the "optionally esterified carboxyl group", for example, a carboxyl group optionally esterified with a $C_{1-6}$ alkyl group, etc. are preferable.

As R$^{1'}$, for example, a C$_{1-6}$ alkyl group which may be substituted by carboxyl or C$_{1-6}$ alkoxy-carbonyl (particularly, ethoxycarbonyl, etc.), etc. are preferable and particularly a carboxyl dimethylmethyl group or an ethoxycarbonyl dimethylmethyl group are preferred.

In the above mentioned formula, R$^2$ and R$^3$ represent the same meanings as mentioned above, and the same preferable groups as mentioned above are used.

In the above mentioned formula, R$^8$ represents the same meaning as mentioned above and the same preferable groups mentioned above are use.

As the subjected compound (I') of the method for producing of the present invention, a compound wherein Ar$^{1'}$ and Ar$^{2'}$ are, independently a phenyl group which may be substituted by a halogen atom or C$_{1-6}$ alkyl; the ring B' is a ring represented by the formula:

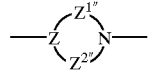

wherein Z is a nitrogen atom or a methyne group, Z$^{1''}$ and Z$^{2''}$ are independently an ethylene group which may be substituted by a hydroxy group, an oxo group or a C$_{1-6}$ alkyl group;

X is a bond, an oxygen atom or NH;

Y is a group represented by
(i) a C$_{1-6}$ alkylene group,
(ii) —(CH$_2$)p$^1$O—,
(iii) —(CH$_2$)p$^1$NH—,
(iv) —(CH$_2$)p$^1$S—,
(v) —(CH$_2$)q$^1$CH(OH)(CH$_2$)q$^2$O—,
(vi) —(CH$_2$)q$^1$CH(OH)(CH$_2$)q$^2$NH—,
(vii) —(CH$_2$)q$^1$CH(OH)(CH$_2$)q$^2$S—,
(viii) —(CH$_2$)p$^1$CONH—,
(ix) —COO(CH$_2$)p$^1$O—,
(x) —COO(CH$_2$)p$^1$NH—,
(xi) —COO(CH$_2$)p$^1$S—,
(xii) —(CH$_2$)q$^1$O(CH$_2$)q$^2$O—,
(xiii) —(CH$_2$)q$^1$O(CH$_2$)q$^2$NH— or
(xiv) —(CH$_2$)q$^1$O(CH$_2$)q$^2$S— wherein p$^1$ is an integer of 1 to 6, q$^1$ and q$^2$ are an integer of 1 to 3, respectively;

A is a nitrogen atom or CR$^{7'}$ wherein R$^{7'}$ is a hydrogen atom, a halogen atom, a C$_{1-6}$ alkyl group, a C$_{1-6}$ alkoxy-carbonyl group or a carboxyl group;

R$^{1'}$ is a C$_{1-6}$ alkyl group which may be substituted by carboxyl, C$_{1-6}$ alkoxy-carbonyl;

R$^2$ is a hydrogen atom, a C$_{1-6}$ alkyl group, a C$_{1-6}$ alkoxy-carbonyl group or a carboxyl group;

R$^3$ is a hydrogen atom;

R$^8$ is a hydrogen atom or a hydroxyl group, is preferable.

Particularly, a compound wherein Ar$^{1'}$ and Ar$^{2'}$ are independently a phenyl group; ring B' is a group represented by the formula:

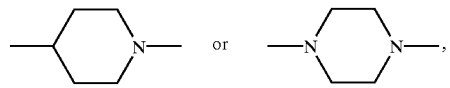

X is a bond or an oxygen atom; Y is a group represented by the formula: —(CH$_2$)p$^1$NH— wherein p$^1$ is an integer of 1 to 6; A is CR$^{7'''}$ wherein R$^{7'''}$ is a hydrogen atom or a C$_{1-6}$ alkyl group; R$^1$ is a C$_{1-6}$ alkyl group which may be substituted by carboxyl or C$_{1-6}$ alkoxy-carbonyl; R$^2$ is a hydrogen atom; R$^3$ is a hydrogen atom; and R$^8$ is a hydrogen atom, is preferable.

Moreover, a compound wherein Ar$^1$ and Ar$^2$ are independently a phenyl group; ring B is

X is an oxygen atom; Y is a trimethyleneamino group; R$^8$ is a hydrogen atom; A is CH; R$^1$ is a carboxyl dimethylmethyl group; and R$^2$ and R$^3$ are a hydrogen atom (particularly a hydrate such as dihydrate of the compound), and a compound wherein Ar$^1$ and Ar$^2$ are independently a phenyl group; ring B is

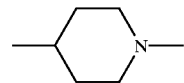

X is an oxygen atom; Y is a propyl group; R$^8$ is a hydrogen atom; A is CH; R$^1$ is an ethoxycarbonyl dimethylmethyl group;

and R$^2$ and R$^3$ are a hydrogen atom (particularly fumarate such as difumarate of the compound), are preferable.

3. Explanation of Compound (I'')

In the above mentioned formula (I''), R represents a hydrogen atom or an ethyl group. As R, a hydrogen atom is preferable.

As the hydrate of compound (I''), for example, a hydrate containing 1 to 5 H$_2$O is used, and of them dihydrate is preferable.

As the succinate of compound (I''), for example, a salt with 1 to 2 succinic acids is used, and of them a salt with disuccinic acids is preferable.

As the citrate of compound (I''), for example, a salt with 1 to 2 citric acids is used, and of them a salt with one citric acid is preferable.

The succinate or citrate of the compound (I'') may be a hydrate or anhydride. As the hydrates of the succinate or citrate of the compound (I''), for example, a hydrate containing 1 to 5 H$_2$O is used.

As the succinate or citrate of the compound (I''), an anhydride is preferable.

Preferable example of the compound (I'') is a hydrate when R is a hydrogen atom, and is a salt with disuccinic acids or a salt with one citric acid when R is an ethyl group.

As the compound of the present invention, particularly,
① 2-[6-[3-[4-(diphenylmethoxy)piperidino]propylamino]imidazo[1,2-b]pyridazin-2-yl]-2-methylpropionic acid dihydrate,
② Ethyl 2-[6-[3-[4-(diphenylmethoxy)piperidino]propylamino]imidazo[1,2-b]pyridazin-2-yl]-2-methylpropionate disuccinate, and
③ Ethyl 2-[6-[3-[4-(diphenylmethoxy)piperidino]propylamino]imidazo[1,2-b]pyridazin-2-yl]-2-methylpropionate citrate are preferable.

And,
① 2-[6-[3-[4-(diphenylmethoxy)piperidino]propylamino]-3-methylimidazo[1,2-b]pyridazin-2-yl]-2-methylpropionic acid (compound (Ia)) or a salt thereof,
② N-[6-[3-[4-(diphenylmethoxy)piperidino]propylamino]-3-methylimidazo[1,2-b]pyridazin-2- carbonyl]glycine (compound (Ib)) or a salt thereof, etc. are preferably used.

Salts of the compound (Ia), or (Ib) include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, methane sulfonic acid, benzene sulfonic acid). Provided that these compounds have an acidic group such as that of a carboxylic acid, as a substituent thereof, the acidic group may form a salt with an inorganic base (e.g., an alkali metal or alkaline earth metal such as sodium, potassium, calcium or magnesium, or ammonia) or an organic base (e.g., a tri-$C_{1-3}$ alkylamine such as triethylamine).

The compound (Ia), (Ib) or a salt thereof may be an anhydride or a hydrate. Examples of the hydrates of the compound (Ia), (Ib) or a salt thereof are a hydrate containing 1 to 5 $H_2O$, particularly dihydrate.

4. About Pro-drug

A pro-drug of the above mentioned compound (I), (I'), (I"), (Ia), (Ib) or a salt thereof (hereinafter referred to as the compound of the present invention) means a compound which is converted to the compound of the present invention under the physiological condition or with a reaction due to an enzyme, an gastric acid, etc. in vivo, that is, a compound which is converted to the compound of the present invention with oxidation, reduction, hydrolysis, etc. according to an enzyme; a compound which is converted to the compound of the present invention with gastric acid, etc.

Examples of the pro-drug of the compound of the present invention include a compound wherein an amino group of the compound of the present invention is substituted with acyl, alkyl and phosphoryl group, etc. (e.g. a compound wherein an amino group of the compound of the present invention is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl group, etc.); a compound wherein an hydroxy group of the compound of the present invention is substituted with acyl, alkyl, phosphoryl, boryl group, etc. (e.g. a compound wherein an hydroxy group of the compound of the present invention is substituted with acetyl, palmitoyl, propanoyl, pivaloyl, succinyl, fumaryl, alanyl, dimethylaminomethylcarbonyl, etc.); a compound wherein a carboxyl group of the compound of the present invention is modified with ester, amide, etc. (e.g. a compound wherein a carboxyl group of the compound of the present invention is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drug can be produced by per se known method from the compound of the present invention.

The pro-drug of the compound of the present invention may be a compound which is converted into the compound of the present invention under the physiological conditions as described in "Pharmaceutical Research and Development", Vol. 7 (Drug Design), pages 163–198 published in 1990 by Hirokawa Publishing Co. (Tokyo, Japan).

5. About Method for the Production of the Compound (I), (I"), (Ia), (Ib) or a Salt Thereof Methods for producing the compound (I) including the compound. (I"), (Ia) and (Ib) are mentioned below.

(A) The compound (I) of the present invention or a salt thereof can be produced by reacting a compound represented by the formula:

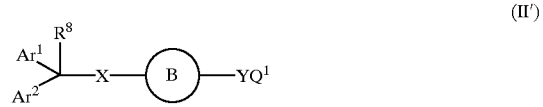

(II')

wherein $Q^1$ represents a leaving group; the other symbols have the same definitions as those shown above, or a salt thereof, with a compound represented by the formula:

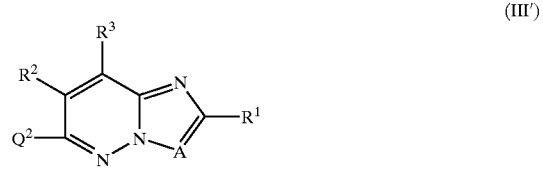

(III')

wherein $Q^2$ represents a leaving group; the other symbols have the same definitions as those shown above, or a salt thereof.

As the leaving group represented by $Q^1$, for example, alkali metals such as sodium and potassium, etc. are used. And, $Q^1$ may be a hydrogen atom.

As the leaving group represented by $Q^2$, a halogen group (e.g., chloro, bromo, iodo), a $C_{6-10}$ arylsulfonyloxy group (e.g., benzenesulfonyloxy, p-tolylsulfonyloxy), a $C_{1-4}$ alkylsulfonyloxy group (e.g., methanesulfonyloxy), etc. are used.

In this reaction, the compound (II') or a salt thereof is normally used at 1 to 5 mol, preferably 1 to 2 mol, per mol of the compound (III') or a salt thereof. This condensation reaction is preferably carried out in the presence of a base. As the base, for example, alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate, etc. are used.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(B) Also, the compound (I) of the present invention or a salt thereof can be produced by reacting a compound represented by the formula:

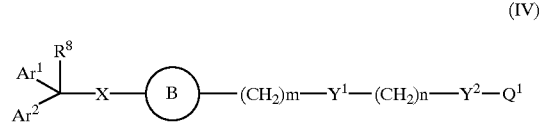

(IV)

wherein the symbols have the same definitions as those shown above, or a salt thereof, with a compound represented by the formula:

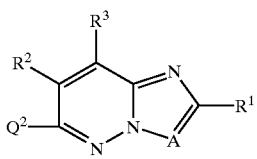
(III')

wherein the symbols have the same definitions as those shown above, or a salt thereof.

In this reaction, the compound (IV) or a salt thereof is normally used at 1 to 5 mol, preferably 1 to 2 10 mol, per mol of the compound (III') or a salt thereof. This condensation reaction is preferably carried out in the presence of a base. As the base, for example, alkali metal hydrides such as sodium hydride and potassium hydride; alkali metal alkoxides such as sodium methoxide and sodium ethoxide; alkali metal hydroxides such as sodium hydroxide and potassium hydroxide; and alkali, metal, carbonates, such as sodium carbonate and potassium carbonate, etc, are used.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(C) Also, compound (I) of the present invention or a salt thereof can be produced by reacting a compound represented by the formula:

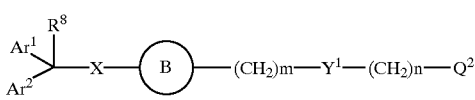
(V)

wherein the symbols have the same definitions as those shown above, or a salt thereof, with a compound represented by the formula:

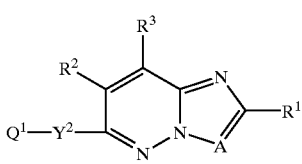
(VI')

wherein the symbols have the same definitions as those shown above, or a salt thereof.

In this reaction, the compound (V) or a salt thereof is normally used at 1 to 5 mol, preferably 1 to 2 mol, per mol of the compound (VI') or a salt thereof. This condensation-;reaction is preferably carried out in the presence of a base. As the base, alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate, etc. are used.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(D) Also, compound (I) of the present invention or a salt thereof can be produced by reacting a compound represented by the formula:

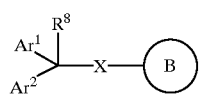
(VII)

wherein the symbols have the same definitions as those shown above, or a salt thereof, with a compound represented by the formula:

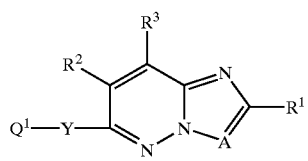
(VI)

wherein the symbols have the same definitions as those shown above, or a salt thereof.

In this reaction, the compound (VII) or a salt thereof is normally used at 1 to 5 mol, preferably 1 to 2 mol, per mol of the compound (VI) or a salt thereof. This condensation reaction is preferably carried out in the presence of abase. As the base, alkali metal hydrides such as sodium hydride and potassium hydride; alkali metal alkoxides such as sodium methoxide and sodium ethoxide; alkali metal hydroxides such as sodium hydroxide and potassium hydroxide; and alkali metal carbonates such as sodium carbonate and potassium carbonate, etc. are used.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 50 to 100° C.

Reaction time is normally 30 minutes to 24 hours, preferably 1 to 6 hours.

(E) Also, compound (I) of the present invention or a salt thereof can be produced by reacting a compound represented by the formula:

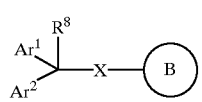
(VII)

wherein the symbols have the same definitions as those shown above, or a salt thereof, with a compound represented by the formula:

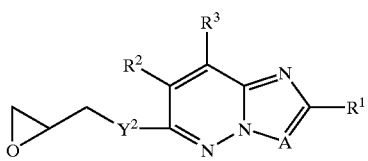

(VIII)

wherein the symbols have the same definitions as those shown above, or a salt thereof.

In this reaction, the compound (VII) or a salt thereof is normally used at 1 to 5 mol, preferably 1 to 2 mol, per mol of the compound (VIII) or a salt thereof.

In addition, this reaction can also be carried out in an inert solvent exemplified by alcohols such as methanol and ethanol; ethers such as dioxane and tetrahydrofuran; aromatic hydrocarbons such as benzene, toluene and xylene; nitriles such as acetonitrile; amides such as N,N-dimethylformamide and N,N-dimethylacetamide; and sulfoxides such as dimethyl sulfoxide.

Reaction temperature is normally 10 to 200° C., preferably 5.0 to 100° C.

Reaction time is normally 30 minutes to 24 hours, preferably 1 to 6 hours.

When the compound (I) is obtained in free form, it can be converted into a salt by a conventional method. When the compound (I) is obtained as a salt, it can be converted into a free form or another salt by a conventional method. When the compound (I) is obtained as an anhydride, it can be converted into a hydrate by contacting it with a water.

The hydrate of the compound (I") and succinate or citrate of the compound (I") of the present invention included in the compound (I) are obtained by (1) reacting a compound represented by the formula:

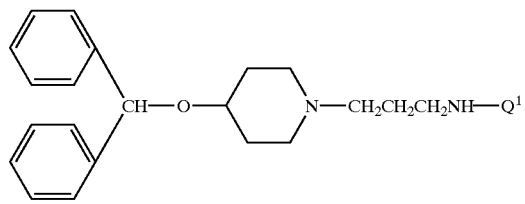

(II")

wherein $Q^2$ is a leaving group, or a salt thereof with a compound represented by the formula:

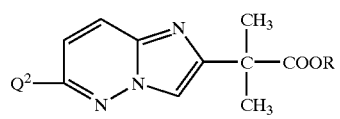

(III")

wherein $Q^2$ is a leaving group, R is same as defined in above, or a salt thereof, then adding a water, or (2) reacting a free form of the compound (I") with a succinic acid or citric acid. The conditions of the reaction are same those with the method for producing for the above mentioned compound (I).

The compound of the invention or a salt thereof thus obtained can be isolated and purified by known means such as solvent extraction, pH adjustment, liquid-liquid transformation, salting out, crystallization, recrystallization and chromatography. When the compound of the invention or a salt thereof contains optical isomers, they can be resolved into the R- and S-configurations by an ordinary means of optical resolution.

Salts of the compound (I), (Ia) or (Ib) includes, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, methanesulfonic acid, benzenesulfonic acid). Provided that the compound (I), (Ia) or (Ib) has an acidic group such as that of a carboxylic acid, as a substituent thereof, the acidic group may form a salt with an inorganic base (e.g., an alkali metal or alkaline earth metal such as sodium, potassium, calcium or magnesium, or ammonia) or an organic base (e.g., a tri-$C_{1-3}$ alkylamine such as triethylamine).

Hereinafter described are methods of producing staring compounds (II'), (II"), (III'), (III"), (VI'), (IV) to (VIII) or salts thereof which are used to produce the compound (I) or a salt thereof. Salts of these starting compounds are same those as salts of the compound (I).

The starting compounds (II'), (II") and (IV) or salts thereof can, for example, be synthesized by the method described in the Journal of Medicinal Chemistry, Vol. 32, p. 583 (1989), or a modification thereof.

The starting compounds (III'), (III") or salts thereof can, for example, be synthesized by the method described in the Journal of Organic Chemistry, Vol. 39, p. 2143 (1974) or a modification thereof.

The starting compound (V) or a salt thereof can, for example, be synthesized by the methods described in Japanese Patent Unexamined Publication No. 2739/1987 etc., or modifications thereof.

The starting compounds (VI) and (VIII) or salts thereof can, for example, be synthesized by the methods described in Japanese Patent Unexamined Publication No. 223287/1991, or modifications thereof.

The starting compound (VII) or a salt thereof can, for example, be synthesized by the method described in the Journal of Medicinal Chemistry, Vol. 38, p. 2472 (1995), or a modification thereof.

Although these starting compounds or salts thereof thus obtained can be isolated and purified by known means such as solvent extraction, pH adjustment, liquid-liquid transformation, salting-out, crystallization, recrystallization and chromatography, they may be used as starting materials for the next process, in the form of reaction mixture without purification.

Also, when the starting compound used in each of the reactions for synthesizing the above-described desired compounds and starting compounds has an amino group, a carboxyl group or a hydroxyl group as a substituent, these substituents may have a protective group in common use in peptide chemistry etc.; the desired compound can be obtained by removing, as appropriate, the protective group after completion of the reaction.

The amino group-protecting groups include, for example, formyl, $C_{1-6}$ alkylcarbonyls that may have a substituent (e.g., acetyl, ethylcarbonyl), phenylcarbonyl, $C_{1-6}$ alkyl-oxycarbonyls (e.g., methoxycarbonyl, ethoxycarbonyl), phenyloxycarbonyl, $C_{7-10}$ aralkyl-carbonyls (e.g., benzylcarbonyl), trityl, phthaloyl and N,N-dimethylaminomethylene. Substituents for these groups include halogen atoms (e.g., fluoro, chloro, bromine, iodine), $C_{1-6}$ alkyl-carbonyls (e.g., methylcarbonyl, ethylcarbonyl, butylcarbonyl) and nitro groups, the number of substituents being about 1 to 3.

The carboxyl group-protecting groups include, for example, $C_{1-6}$ alkyls that may have a substituent (e.g., methyl, ethyl, n-propyl, isopropyl, n-butyl, tert-butyl), phenyl, trityl and silyl. Substituents for these groups include halogen atoms (e.g., fluoro-, chloro, bromine, iodine), formyl, $C_{1-6}$ alkyl-carbonyls (e.g., acetyl, ethylcarbonyl, butylcarbonyl) and nitro groups, the number of substituents being about 1 to 3.

The hydroxyl group-protecting groups include, for example, $C_{1-6}$ alkyls that may have a substituent (e.g. methyl, ethyl, n-propyl, isopropyl, n-butyl, tert-butyl), phenyl, $C_{7-10}$ aralkyls (e.g., benzyl), formyl, $C_{1-6}$ alkyl-carbonyls (e.g., acetyl, ethylcarbonyl), phenyloxycarbonyl, benzoyl, $C_{7-10}$ aralkyl-carbonyls (e.g., benzylcarbonyl), pyranyl, furanyl and silyl. Substituents for these groups include halogen atoms. (e.g., fluoro, chloro, bromine, iodine), $C_{1-6}$ alkyls (e.g., methyl, ethyl, n-propyl), phenyl, $C_{7-10}$ aralkyls (e.g., benzyl) and nitro groups, the number of substituents being about 1 to 4.

The protecting groups can be removed by commonly known methods or modifications thereof, including treatments with acids, bases, reducing agents, ultraviolet rays, hydrazine, phenylhydrazine, sodium N-methyldithiocarbamate, tetrabutylammonium fluoride, palladium acetate etc.

6. About Method for Producing for the Compound (I')

According to the method of the present invention, the compound (I') or a salt thereof can be produced by reacting a compound represented by the formula:

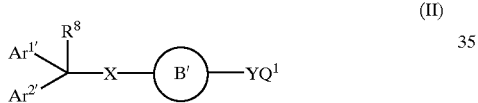

(II)

wherein $Q^1$ represents a leaving group; the other symbols have the same definitions as those shown above, or a salt thereof, with a compound represented by the formula:

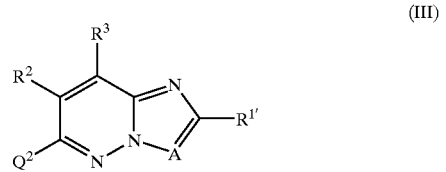

(III)

wherein $Q^2$ represents a leaving group; the other symbols have the same definitions as those shown above, or a salt thereof, in a solvent or/and in the presence of a base.

As the leaving group represented by $Q^1$, alkali metals such as lithium, sodium and potassium, etc. are used. And, $Q^1$ may be a hydrogen atom.

As the leaving group represented by $Q^2$, a halogen atom (e.g., chloro, bromine, iodine), a $C_{6-10}$ arylsulfonyloxy group (e.g., benzenesulfonyloxy, p-tolylsulfonyloxy), a $C_{1-4}$ alkyl-sulfonyloxy group (e.g., methanesulfonyloxy), etc. are used.

As the solvent used in the method of the present invention, for example, a non-proton solvent having a high boiling point, etc. are used. The boiling point of the solvent are, for example, about 90 to about 220° C., preferably about 110 to about 160° C.

As the solvent,
(1) ethers such as dioxane and tetrahydrofuran,
(2) aromatic hydrocarbons such as benzene, toluene and xylene,
(3) nitriles such as acetonitrile,
(4) straight chained or cyclic amides such as N,N-dimethylformamide, N,N-dimethylacetamide and 1-methyl-2-pyrrolidone,
(5) sulfoxides such as dimethyl sulfoxide,
(6) cyclic sulfones such as sulfolane,
(7) halogenated hydrocarbons such as dichloroethane and chloroform,
(8) azoles such as imidazole, 2-methylimidazole and pyridine, etc. are used. Of them, cyclic amides such as 1-methyl-2-pyrrolidone, sulfoxides such as dimethyl sulfoxide, cyclic sulfones such as sulfolane, etc. are preferred, and cyclic amides such as 1-methyl-2-pyrrolidone, sulfoxides such as dimethylsulfoxide, etc. are more preferred, and particularly sulfoxides such as dimethyl sulfoxide, etc. are preferred. And, alcohols such as methanol, ethanol, etc. may be used as the solvent.

As the base used in the method of the present invention, for example,
(1) alkali metal hydrides such as sodium hydride and potassium hydride,
(2) alkali metal alkoxides such as sodium methoxide, sodium ethoxide and sodium t-butoxide,
(3) alkali metal hydroxides such as sodium hydroxide and potassium hydroxide,
(4) alkali metal carbonates such as lithium carbonate, sodium carbonate and potassium carbonate, etc. are used. Of them, alkali metal carbonates such as sodium carbonate and potassium carbonate, etc. are preferred, particularly sodium carbonate is more preferred.

The reaction of the present invention is preferably conducted in the solvent and in the presence of the base.

And, additives for promoting the reaction can be used in the method of the present invention. Examples of the additives are magnesium sulfate, zinc chloride, cuprous chloride (CuCl), potassium fluoride, lithium chloride and so on.

In this reaction, the compound (II) or a salt thereof is normally used at about 1 to about 5 mol, preferably about 1 to about 2 mol, per mol of the compound (III) or a salt thereof.

And, a volume of the compound (II) or a salt thereof can be reduced by conducting the reaction of the present invention in the presence of a base, particularly alkali metal carbonate such as sodium carbonate, comparing the reaction in the presence of no base. When the reaction is conducted in the presence of a base, the compound (II) or a salt thereof is normally used at about 1.0 to about 1.7 mol, preferably about 1.5 mol, per mol of the compound (III) or a salt thereof.

Reaction temperature is normally about 10 to 200° C., preferably about 100 to about 180° C., more preferably about 110 to 160° C.

Reaction time is normally about 30 minutes to about 30 hours, preferably about 30 minutes to about 24 hours, more preferably about 1 hour to about 6 hours.

And, the reaction of the present invention can be conducted in an atmosphere of inert gas such as $N_2$ gas, argon gas, etc.

Particularly, when the compound (I') wherein $Ar^{1'}$ and $Ar^{2'}$ are independently a phenyl group; ring B' is

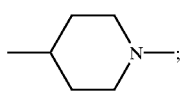

X is an oxygen atom; Y is a propylamino group; $R^8$ is a hydrogen atom; A is CH; $R^{1'}$ is a carboxyl dimethylmethyl group; and $R^2$ and $R^3$ are a hydrogen atom, or a salt thereof is produced, as the solvent, a dimethylsulfoxide, etc. are preferable and as the base, a sodium carbonate, etc. are preferable.

And, when the compound (I') wherein $Ar^{1'}$ and $Ar^{2'}$ are independently a phenyl group; ring B' is

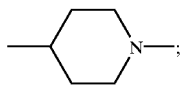

X is an oxygen atom; Y is a propylamino group; $R^8$ is a hydrogen atom; A is CH; $R^{1'}$ is an ethoxycarbonyl dimethylmethyl group; and $R^2$ and $R^3$ are a hydrogen atom, or a salt thereof is produced, as the solvent, a 1-methyl-2-pyrolidone, dimethylsulfoxide, etc. are preferable and as the base, a sodium carbonate, etc. are preferable.

Furthermore, this reaction can be conducted in the presence of halogenated alkali metals. As the halogenated alkali metals, a sodium chloride, a sodium fluoride, a sodium bromide, etc. are used, and particularly a sodium bromide is preferable. Thus by adding the halogenated alkali metals, amounts of the subjected compound can increase.

Particularly, when the compound (I') wherein $Ar^{1'}$ and $Ar^{2'}$ are independently a phenyl group; ring B' is

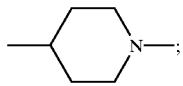

X is an oxygen atom; Y is a propylamino group; $R^8$ is a hydrogen atom; A is CH; $R^{1'}$ is a carboxyl dimethylmethyl group; and $R^2$ and $R^3$ are a hydrogen atom, or a salt thereof is produced, as the solvent, a dimethylsulfoxide, etc. are preferable and as the base, a sodium carbonate, etc. are used and as the halogenated alkali metals, a sodium bromide, etc. are used.

When the halogenated alkali metals are used, the halogenated alkali metals are normally used at about 0.05 to about 0.25 mol, preferably about 0.1 to about 0.15 mol, per mol of the compound (II) or a salt thereof.

When the compound (I') is obtained in free form, it can be converted into a salt by a conventional method. When the compound (I') is obtained as a salt, it can be converted into a free form or another salt by a conventional method. The compound (I) or a salt thereof thus obtained can be isolated and purified by known means such as solvent extraction, pH adjustment, liquid-liquid transformation, salting out, crystallization, recrystallization and chromatography. When the compound (I') or a salt thereof contains optical isomers, it can be resoluted into the R- and S-configurations by an ordinary means of optical resolution.

Hereinafter described are methods of producing staring compounds (II) and (III) or salts thereof which are used to produce the compound (I') or a salt thereof.

Salts of the compounds (I'), (II) and (III) include, for example, salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, methanesulfonic acid, benzenesulfonic acid). Provided that these compounds have an acidic group such as that of a carboxylic acid, as a substituent thereof, the acidic group may form a salt with an inorganic base (e.g., an alkali metal or alkaline earth metal such as sodium, potassium, calcium or magnesium, or ammonia) or an organic base (e.g., a tri-$C_{1-3}$ alkylamine such as triethylamine).

When the compound (I') has an ester group in the molecule, it can be converted to a carboxylic acid thereof by a conventional hydrolysis. And, When the compound (I') has a carboxylic acid group in the molecule, it can be converted to an esther thereof by a conventional estherification.

The starting compounds (II) or salts thereof can, for example, be synthesized by the method described in the Journal of Medicinal Chemistry, Vol. 32, p. 583 (1989), or a modification thereof.

The starting compound (III) or a salt thereof can, for example, be synthesized by the method described in the Journal of Organic Chemistry, Vol. 39, p. 2143 (1974) or a modification thereof.

Although these starting compounds or salts thereof thus obtained can be isolated and purified by known means such as solvent extraction, pH ajustment, liquid-liquid transformation, salting-out, crystallization, recrystallization and chromatography, they may be used as starting materials for the next process, in the form of reaction mixture without purification.

Also, when the starting compound used in each of the reactions for synthesizing the above-described desired compounds and starting compounds has an amino group, a carboxyl group or a hydroxyl group as a substituent, these substituents may have a protective group in common use in peptide chemistry etc.; the desired compound can be obtained by removing, as appropriate, the protective group after completion of the reaction.

Examples of the amino group-protecting groups, the carboxyl group-protecting groups, the hydroxyl group-protecting groups are same those mentioned above.

The protecting groups can be removed by commonly known methods or modifications thereof, including treatments with acids, bases, reducing agents, ultraviolet rays, hydrazine, phenylhydrazine, sodium N-methyldithiocarbamate, tetrabutylammonium fluoride, palladium acetate, etc.

The compound (I) of the present invention, a salt thereof or a pro-drug thereof can be safely used as an anti-allergic agent in mammals (e.g., human, mice, dogs, rats, bovines), because it exhibits excellent anti-allergic, anti-histaminic, anti-inflammatory, anti-PAF (platelet activating factor) or eosinophil chemotaxis inhibiting activity, etc., with low toxicity (acute toxicity: $LD_{50}$>2 g/kg). The compound (I), a salt thereof or a pro-drug thereof exhibits an eosinophil chemotaxis inhibiting activity as well as an anti-histaminic activity, and can be used to prevent or treat allergic skin diseases such as eczematous dermatitis, contact dermatitis, pruritus, dried dermatitis, acute urticaria, prurigo, etc., and inflammatory dermatosis such as atopic dermatitis, etc.

The hydrate of the compound (I″) has an excellent stability exceeding that of an anhydride of the compound (I″).

The succinate or citrate of the compound (I″) has an excellent stability exceeding that of a fumarate of the compound (I″).

The compound (I') or a salt thereof, the hydrate of the compound (I″), the succinate or citrate of the compound (I″), compound (Ia), (Ib) or a salt thereof, or a pro-drug thereof can be safely used as an anti-allergic agent in mammals (e.g., human, mice, dogs, rats, bovines), because it exhibits excellent anti-allergic, anti-histaminic, anti-inflammatory, anti-PAF (platelet activating factor) or eosinophil chemotaxis inhibiting activity, etc., with low toxicity (acute toxicity: $LD_{50}>2$ g/kg). The compound (I') or a salt thereof, the hydrate of the compound (I"), the succinate or citrate of the compound (I"), compound (Ia), (Ib) or a salt thereof, or a pro-drug thereof exhibits an eosinophil chemotaxis inhibiting activity as well as an anti-histaminic activity, and can be used to prevent or treat allergic diseases such as chronic urticaria, atopic dermatitis, allergic rhinitis, allergic conjunctivitis and hypersensitive pneumonitis; dermal diseases (particularly, allergic skin diseases) such as eczema, herpetic dermatitis and psoriasis; and respiratory diseases such as eosinophilic pneumonia (PIE syndrome), chronic obstructive pulmonary disease (COPD) and asthma, etc., in the above-mentioned mammals. Preferably, these compounds can be used to prevent or treat asthma, allergic conjunctivitis, allergic rhinitis, chronic urticaria and atopic dermatitis.

Furthermore, the compound (I) or a salt thereof, the compound (I') or a salt thereof, the hydrate of the compound (I"), the succinate or citrate of the compound (I"), preventing increase of intranasal pressure, sneezing frequency, nasal secretion, pollinosis, hypersensitivity of upper respiratory tract, etc.

Route of administration may be oral or another route.

Also, the preparation for the present invention may contain as active ingredients pharmaceutical components other than the compound (I) or a salt thereof, the compound (I') or a salt thereof, the hydrate of the compound (I"), the succinate or citrate of the compound (I"), or a pro-drug thereof (thereinafter referred to as the compound of the resent invention).

Such pharmaceutically active components include, for example, anti-asthmatics (e.g., theophylline, procaterol, ketotifen, azelastine, seratrodast), anti-allergic agents (e.g., ketotifen, terfenadine, azelastine, epinastine), anti-inflammatory agents (e.g., diclofenac sodium, ibuprofen, indomethacin), antibacterial agents (e.g., cefixime, cefdinir, ofloxacin, tosufloxacin) and antifungal agents (e.g., fluconazole, itraconazole). These components are not subject to limitation, as long as the object of the present invention is accomplished, and may be used in appropriate mixing ratios. Useful dosage forms include, for example, tablets (including sugar-coated tablets and film-coated tablets), pills, capsules (including microcapsules), granules, fine granules, powders, syrups, emulsions, suspensions, injectable preparations, inhalants and ointments. These preparations are prepared by conventional methods (e.g., methods described in the Pharmacopoeia of Japan).

In the preparation of the present invention, the content of the compound (I) or a salt thereof is normally about 0.01 to about 100% by weight, preferably about 0.1 to about 50% by weight, and more preferably about 0.5 to about 20% by weight, relative to the entire preparation, depending on the form of the preparation.

Specifically, tablets can be produced by granulating a pharmaceutical as-is, or in a uniform mixture with excipients, binders, disintegrating agents and other appropriate additives, by an appropriate method, then adding lubricants etc., and subjecting the mixture to compressive shaping, or by subjecting to direct compressive shaping a pharmaceutical as-is, or in a uniform mixture with excipients, binders, disintegrating agents and other appropriate additives, or subjecting to compressive shaping previously prepared granules as-is, or in a uniform mixture with appropriate additives. These tablets may incorporate coloring agents, correctives etc. as necessary, and may be coated with appropriate coating agents.

Injectable preparations can be produced by dissolving, suspending or emulsifying a given amount of a pharmaceutical in an aqueous solvent such as water for injection, physiological saline or Ringer's solution, or a non-aqueous solvent such as a vegetable oil, and diluting to a given amount, or transferring a given amount of a pharmaceutical into a container for injection and sealing the container.

Examples of the carriers for oral preparations are substances in common use in pharmaceutical production, such as starch, mannitol, crystalline cellulose and carboxymethyl cellulose sodium. Examples of the carriers for injectable preparations are distilled water, physiological saline, glucose solutions and transfusions. Other additives in common use for pharmaceutical production can also be added,as appropriate.

Depending on patient age, body weight, symptoms, route and frequency of administration and other factors, the daily dose of these preparations is normally about 0.1 to about 100 mg/kg, preferably about 1 to about 50 mg/kg, and more preferably about 1 to about 10 mg/kg, based on daily dose of active ingredient (the compound (I) or a salt thereof), once or in two portions daily for each asthmatic adult.

The present invention is hereinafter described in more detail by means of the following examples, reference examples, formulation examples and experimental examples, which are not to be construed as limitative.

In the examples and reference examples below, the fraction containing the desired product was detected by observation via TLC (thin-layer chromatography). In the TLC observation, $60F_{254}$, produced by Merck, was used as a TLC plate, with a UV detector as a means of detection.

X-Ray Powder Diffraction analyses were performed as follows:

RINT1100 (Rikagaku) measurement model was used.

The samples were loaded into a quartz (zero scatter) sample holder for the XRPD pattern measurement. A powder diffractometer equipped with a Cu X-ray tube source, primary beam monochromator, and position sensitive detector (PSD) were used. The incident beam was collimated using a 1° divergence slit. The source was operated at 40 KV and 40 mA and the sample was illuminated with Cu $K_{\alpha 1}$ radiation. The XRPD patterns were measured from 3 to 35θ at the rate of 6.0000°/minute. The most prominent peak was determined as 100%, and X-ray peaks with greater than 30% were listed.

EXAMPLE A: COMPOUND (I)

EXAMPLE 1A

Production of 6-[3-[4-(Diphenylmethyl)-1-piperazinyl]propoxy][1,2,4]triazolo[1, 5-b] pyridazine Dihydrochloride 4-(Diphenylmethyl)-1-piperazinepropanol (466 mg) was dissolved in dried tetrahydrofuran (10 ml), followed by addition of sodium t-butoxide (173 mg). The mixture was refluxed under, heating for 30 minutes. After the mixture was cooled, 6-chloro[1,2,4]triazolo[1,5-b ]pyridazine (268 mg) was added to the mixture. The resulting mixture was refluxed under heating for 3 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and methanol (10:1). Fractions containing the objective compound were collected and dissolved in ethyl acetate (10 ml), followed by addition of 4N HCl in ethyl acetate solution (0.7 ml). The resulting crystals were recrystallized from 95% aqueous ethanol to yield the title compound (413 mg).

m.p. 251–253° C.; Elemental Analysis for $C_{25}H_{30}N_6OCl_2$; Calculated (%): C, 59.88; H, 6.03; N, 16.76; Found (%): C, 59.76; H, 6.09; N, 16.80.

EXAMPLE 2A

Production of 6-[3-[4-(Diphenylmethoxy) piperidino]propoxy][1,2,4]triazolo[1,5-b]pyridazine Fumarate 4-(Diphenylmethoxy)-1-Piperidinepropanol (390 mg) was dissolved in dried tetrahydrofuran (10 ml), followed by addition of sodium t-butoxide (127 mg). The mixture was refluxed under heating for 30 minutes. After the mixture was cooled, 6-chloro[1,2,4]triazolo[1,5-b]pyridazine (215 mg) was added thereto. The resulting mixture was refluxed for 3 hours under heating. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (95:5:1). Fractions containing the objective compound were collected and dissolved in ethanol (10 ml). Fumaric acid (93 mg) was added to the solution to precipitate crystals. The resulting crystals were recrystallized from ethanol to yield the title compound (218 mg).

m.p. 157–159° C.; Elemental Analysis for $C_{30}H_{33}N_5O_6$; Calculated (%): C, 64.39; H, 5.94; N, 12.51; Found (%): C, 64.16; H, 5.71; N, 12.32.

EXAMPLE 3A

Production of 6-[3-[4-(Diphenylmethyl)-1-piperazinyl]propoxy]-7-isopropyl[1,2,4]triazolo[1,5-b]pyridazine Dihydrochloride 4-(Diphenylmethyl)-1-piperazinepropanol (466 mg) was dissolved in dried tetrahydrofuran (10 ml), followed by addition of sodium t-butoxide (173 mg). The mixture was refluxed under heating for 30 minutes. After the mixture was cooled, 6-chloro-7-isopropyl[1,2,4]triazolo[1,5-b]pyridazine (295 mg) was added thereto. The resulting mixture was refluxed for 3 hours under heating. After cooling, ice-water was added to the mixture, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and methanol (10:1). Fractions containing the objective compound were collected and dissolved in ethanol (10 ml), followed by addition of 1N-HCl (3 ml). The mixture was concentrated under reduced pressure. The resulting crystals were recrystallized from ethyl acetate to yield the title compound (582 mg).

m.p. 177° C.; Elemental Analysis for $C_{28}H_{36}N_6OCl_2$; Calculated (%): C, 59.89; H, 6.82; N, 14.97; Found (%): C, 59.47; H, 6.89; N, 14.45.

EXAMPLE 4A

Production of 6-[3-[4-(Diphenylmethoxy) piperidino]propoxy]-7-isopropyl[1,2,4]triazolo[1,5-b]pyridazine Fumarate 4-(Diphenylmethoxy)-1-piperidinepropanol (488 mg) was dissolved in dried tetrahydrofuran (10 ml), followed by addition of sodium t-butoxide (173 mg). The mixture was refluxed under heating for 30 minutes. After the mixture was cooled, 6-chloro-7-isopropyl[1,2,4]triazolo[1,5-b]pyridazine (295 mg) was added thereto. The resulting mixture was refluxed for 3 hours under heating. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (95:5:1). Fractions containing the objective compound were collected and dissolved in ethanol (10 ml). Fumaric acid (98 mg) was added to the solution to precipitate crystals. The resulting crystals were recrystallized from ethyl acetate to yield the title compound (385 mg).

m.p. 163–165° C.; Elemental Analysis for $C_{33}H_{39}N_5O_6$; Calculated (%): C, 65.87; H, 6.53; N, 11.64; Found (%): C, 65.77; H, 6.46; N, 11.71.

EXAMPLE 5A

Production of 6-[3-[4-(Diphenylmethyl)-1-piperazinyl]propylamino][1,2,4]triazolo[1,5-b]pyridazine Process A:

6-(3-Hydroxypropylamino)[1,2,4]triazolo[1,5-b]pyridazine

6-Chloro[1,2,4]triazolo[1,5-b]pyridazine (928 mg) was dissolved in ethanol (10 ml). 3-Amino-1-propanol (1.23 g) was added to the solution. The mixture was refluxed under heating for 20 hours. After being cooled, the mixture was concentrated under reduced pressure to an half of its volume. The resulting precipitates were washed with ethanol and dried to yield the title compound (835 mg).

m.p. 193–194° C.; Elemental Analysis for $C_8H_{11}N_5O$; Calculated (%): C, 49.73; H, 5.74; N, 36.25; Found (%): C, 49.70; H, 5.53; N, 36.28.

Process B:

6-(3-Hydroxypropylamino)[1,2,4]triazolo[1,5-b]pyridazine (450 mg) was suspended in tetrahydrofuran (15 ml). N-Ethyldiisopropylamine (582 mg) and methanesulfonyl chloride (533 mg) were added to the suspension. The resulting mixture was stirred at room temperature for one hour. Ice-water and sodium chloride were added to the mixture, followed by extraction with ethyl acetate. The extract was washed with an aqueous sodium chloride saturated solution, dried over magnesium sulfate and concentrated under reduced pressure. The residue was dissolved in N, N-dimethylformamide (10 ml), followed by addition of 1-(diphenylmethyl)piperazine (504 mg), sodium iodide (298 mg) and potassium carbonate (276 mg). The mixture was stirred at 60° C. for two hours. After the mixture was cooled, ice-water was added to the mixture, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (90:10:1). Fractions containing the objective compound were collected and concentrated. The resulting crystals were washed with ethyl ether and dried to yield the title compound (281 mg).

m.p. 139–140° C.; Elemental Analysis for $C_{25}H_{29}N_7.0.5H_2O$; Calculated (%): C, 68.78; H, 6.93; N, 22.46; Found (%): C, 68.72; H, 6.86; N, 22.16.

EXAMPLE 6A

Production of 6-[3-[4-(Diphenylmethoxy) piperidino]propylamino][1,2,4]triazolo[1,5-b] pyridazine 6-(3-Hydroxypropylamino)[1,2,4]triazolo[1,5-b] pyridazine (290 mg) was suspended in tetrahydrofuran (10 ml). N-ethyldiisopropylamine (388 mg) and methanesulfonyl chloride (344 mg) were added to the suspension, and the mixture was stirred at room temperature for one hour. Ice-water and sodium chloride were added to the mixture, followed by extraction with ethyl acetate. The extract was washed with an aqueous sodium chloride saturated solution, dried over magnesium sulfate and concentrated under reduced pressure. The residue was dissolved in N,N-dimethylformamide (5 ml), followed by addition of 4-(dipheylmethoxy)piperidine (352 mg), sodium iodide (208 mg) and potassium carbonate (193 mg). The mixture was stirred at room temperature for 15 hours and at 60° C. for 3 hours. After the mixture was cooled, ice-water was added thereto, followed by extraction with ethyl acetate. The extract was washed with an aqueous sodium chloride saturated solution, dried over magnesium chloride and concentrated under reduced pressure. The residue was subjected to silica gel column chromatography and eluted with a mixture of ethyl acetate, methanol and triethylamine (90:10:1). Fractions containing the objective compound were concentrated. The resulting crystals were washed with ethyl ether and dried to yield the title compound (209 mg).

m.p. 136–138° C.; Elemental Analysis for $C_{26}H_{30}N_6O$; Calculated (%): C, 70.56; H, 6.83; N, 18.99; Found (%): C, 70.43; H, 6.83; N, 19.04.

EXAMPLE 7A

Production of 6-[3-[4-(Dipheylmethyl)-1-piperazinyl]-propylthio][1,2,4]triazolo[1,5-b] pyridazine Process A:
6-(3-Bromopropylthio)[1,2,4]triazolo[1,5-b]pyridazine Methyl 3-mercaptopropionate (3.9 ml) was dissolved in methanol (40 ml), followed by addition of a 2N sodium methoxide solution in methanol (15 ml) and 6-chloro[1,2,4]triazolo[1,5-b]pyridazine (1.55 g). The mixture was refluxed under heating for one hour. After being cooled, the mixture was concentrated under reduced pressure. Ethyl acetate was added to the residue. The resulting crystals were collected, washed with ethyl acetate and suspended in terahydrofuran (40 ml), followed by addition of 1,3-dibromopropane (3.06 ml). The mixture was refluxed under heating for two hours. After the mixture was cooled, ice-water was added thereto. The mixture was extracted with ethyl acetate. The extract was washed with an aqueous sodium chloride saturated solution, dried over magnesium sulfate and concentrated under reduced pressure. A mixed solvent of ethyl acetate-hexane (1:1) was added to the residue. The resulting crystals were collected and dried to yield the title compound (1.97 g).

m.p. 133–135° C.; Elemental Analysis for $C_8H_9N_4SBr$; Calculated (%): C, 35.18; H, 3.32; N, 20.51; Found (%): C, 35.11; H, 3.13; N, 20.43.

Process B:
6-(3-Bromopropylthio)[1,2,4]triazolo[1,5-b]pyridazine (546 mg) and 1-(diphenylmethyl)piperazine (505 mg) were dissolved in acetonitrile (15 ml), followed by addition of sodium iodide (373 mg) and potassium carbonate (277 mg). The mixture was stirred at 50–60° C. for 15 hours, followed by addition of ice-water and extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and methanol (95:5). Fractions containing the objective compound were collected and concentrated. The resulting crystals were collected, washed with ethyl ether and dried to yield the title compound (507 mg).

m.p. 128–130° C.; Elemental Analysis for $C_{25}H_{28}N_6S$; Calculated (%): C, 67.54; H, 6.35; N, 18.90; Found (%): C, 67.25; H, 6.29; N, 18.78.

EXAMPLE 8A

Production of 6-[3-[4-(Diphenylmethoxy) piperidino]propylthio][1,2,4]triazolo[1,5-b] pyridazine Fumarate 6-(3-Bromopropylthio)[1,2,4]triazolo[1,5-b]pyridazine (546 mg) and 4-(diphenylmethoxy)piperidine (535 mg) were dissolved in acetonitrile (15 ml), followed by addition of sodium iodide (373 mg) and potassium carbonate (277 mg). The mixture was stirred at 50–60° C. for 15 hours, followed by addition of ice-water after cooled and extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (95:5:1). Fractions containing the objective compound were collected and concentrated. The residue was dissolved in ethanol (20 ml), followed by addition of fumaric acid (159 mg). The resulting crystals were collected, washed with ethyl ether and dried to yield the title compound (435 mg).

m.p. 185–187° C.; Elemental Analysis for $C_{30}H_{33}N_5OS.0.5H_2O$; Calculated (%): C, 61.63; H, 5.86; N, 11.98; Found (%): C, 61.98; H, 5.83; N, 11.95.

EXAMPLE 9A

Production of 6-[3-[4-(Diphenylmethyl)-1-piperazinyl]propylthio]-7-isopropyl[1,2,4]triazolo[1,5-b]pyridazine Process A:
6-(3-Chloropropylthio)-7-isopropyl[1,2,4]triazolo[1,5-b]pyridazine Methyl 3-mercaptopropionate (3.9 ml) was dissolved in methanol (40 ml), followed by addition of 2N sodium methoxide in methanol solution (15 ml) and 6-chloro-7-isopropyl[1,2,4]triazolo[1,5-b]pyridazine (1.97 g). The mixture was refluxed under heating for 40 minutes. After being cooled, the mixture was concentrated under reduced pressure. Ethyl acetate was added to the residue. The resulting crystals were collected, washed with ethyl acetate and suspended in tetrahydrofuran (40 ml), followed by addition of 1-bromo-3-chloropropane (2 ml). The mixture was refluxed under heating for two hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of hexane and ethyl acetate (2:3). Fractions containing the objective compound were collected and concentrated under reduced pressure. The resulting crystals were collected and dried to yield the title compound (2.39 g).

m.p. 82–83° C.; Elemental Analysis for $C_{11}H_{15}N_4SCl$; Calculated (%): C, 48.79; H, 5.58; N, 20.69; Found (%): C, 48.79; H, 5.53; N, 20.87.

Process B:

6-(3-Chloropropylthio)-7-isopropyl[1,2,4]triazolo[1,5-b]pyridazine (542 mg) and 1-(diphenylmethyl)piperazine (555 mg) were dissolved in acetonitrile (15 ml), followed by addition of sodium iodide (447 mg) and potassium carbonate (277 mg). The mixture was refluxed under heating for 20 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography followed by elution with ethyl acetate. Fractions containing the objective compound were collected and concentrated. The resulting crystals were recrystallized from a mixture of ethyl acetate and ethyl ether (1:1) and dried to yield the title compound (607 mg).

m.p. 137–139° C.; Elemental Analysis for $C_{28}H_{34}N_6S$; Calculated (%): C, 69.10; H, 7.04; N, 17.27; Found (%): C, 69.04; H, 7.06; N, 17.33.

EXAMPLE 10A

Production of 6-[3-[4-(Diphenylmethoxy)piperidino]propylthio]-7-isopropyl[1,2,4]triazolo[1,5-b]pyridazine Fumarate 6-(3-Chloropropylthio)-7-isopropyl[1,2,4]triazolo[1,5-b]pyridazine (542 mg) and 4-(diphenylmethoxy)piperidine (535 mg) were dissolved in acetonitrile (15 ml), followed by addition of sodium iodide (447 mg) and potassium carbonate (277 mg). The mixture was refluxed under heating for 15 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography, followed by elution with a mixture of ethyl acetate and methanol (95:5). Fractions containing the objective compound were collected and concentrated. The residue was dissolved in ethanol (20 ml), followed by addition of fumaric acid (196 mg). The resulting crystals were collected, washed with ethanol and dried to yield the title compound (780 mg).

m.p. 164–165° C.; Elemental Analysis for $C_{33}H_{39}N_5O_5S$; Calculated (%): C, 64.16; H, 6.36; N, 11.34; Found (%): C, 64.45; H, 6.49; N, 11.67.

EXAMPLE 11A

Production of 6-[4-(Diphenylmethoxy)piperidino][1,2,4]triazolo[1,5-b]pyridazine 4-(Diphenylmethoxy)piperidine (1.12 g) and 6-chloro[1,2,4]triazolo[1,5-b]pyridazine (558 mg) were dissolved in 1-butanol (25 ml), followed by addition of N-ethyldiisopropylamine (700 mg). The mixture was refluxed under heating for 17 hours. After being cooled, the mixture was concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of hexane and ethyl acetate (1:3). Fractions containing the objective compound were collected and recrystallized from ethanol to yield the title compound (757 mg).

m.p. 137–139° C.; Elemental Analysis for $C_{23}H_{23}N_5O$; Calculated (%): C, 71.67; H, 6.01; N, 18.17; Found (%): C, 71.75; H, 5.90; N, 18.34.

EXAMPLE 12A

Production of 6-[4-[4-(Diphenylmethoxy)piperidino]butylamino][1,2,4]triazolo[1,5-b]pyridazine 4-(Diphenylmethoxy)-1-piperidinebutanamine (1.83 g) and 6-chloro[1,2,4]triazolo[1,5-b]pyridazine (557 mg) were dissolved in 1-butanol (30 ml), followed by addition of N-ethyldiisopropylamine (931 mg). The mixture was refluxed under heating for 14 hours. After being cooled, the mixture was concentrated under reduced pressure, followed by addition of ice-water and extraction with ethyl acetate. The extract was washed with an aqueous sodium chloride saturated solution, dried over magnesium sulfate and concentrated under reduced pressure. The residue was subjected to a silica gel column chromatography and eluted with a mixture of ethyl acetate, methanol and triethylamine (45:5:1). Fractions containing the objective compound were collected and concentrated. The resulting crystals were collected, washed with ethyl ether and dried to yield the title compound (149 mg).

m.p. 102–104° C.; Elemental Analysis for $C_{27}H_{32}N_6O$; Calculated (%): C, 71.03; H, 7.06; N, 18.41; Found (%): C, 70.78; H, 6.77; N, 18.40.

EXAMPLE 13A

Production of 6-[2-[4-(Diphenylmethoxy)piperidino]ethylamino][1,2,4]triazolo[1,5-b]pyridazine Process A:

Production of 6-(2-Hydroxyethylamino)[1,2,4]triazolo[1,5-b]pyridazine

2-Aminoethanol (2.01 g) and 6-chloro[1,2,4]triazolo[1,5-b]pyridazine (2.03 g) were dissolved in ethanol (22 ml). The mixture was refluxed under heating for 20 hours. After being cooled, the mixture was concentrated under reduced pressure. The resulting crystals were collected and dried to yield the title compound (1.48 g).

m.p. 219–221° C.; Elemental Analysis for $C_7H_9N_5O$; Calculated (%): C, 46.92; H, 5.06; N, 39.09; Found (%): C, 46.67; H, 5.00; N, 38.93.

Process B:

6-(2-Hydroxyethylamino)[1,2,4]triazolo[1,5-b]pyridazine (1.25 g) was suspended in tetrahydrofurane (40 ml), followed by addition of N-ethyldiisopropylamine (1.81 g) and methanesulfonyl chloride (1.60 g). The mixture was stirred at room temperature for 45 minutes, followed by addition of ice-water and sodium chloride to be saturated therewith. The mixture was extracted with ethyl acetate. The extract was washed with an aqueous sodium chloride saturated solution, dried over magnesium sulfate and concentrated under reduced pressure. The residue was dissolved in N,N-dimethylformamide (21 ml), followed by addition of 4-(diphenylmethoxy)piperidine (1.79 g), sodium iodide (1.00 g) and potassium carbonate (927 mg). The mixture was stirred at room temperature for 15 hours and at 60° C. for 1.5 hours, followed by addition of ice-water and extraction with ethyl ether. The extract was washed with an aqueous sodium chloride saturated solution dried over magnesium sulfate and concentrated under reduced pressure. The resulting crystals were collected, washed with ethyl ether and dried to yield the title compound (1.13 g).

m.p. 152–154° C.; Elemental Analysis for $C_{25}H_{28}N_6O$; Calculated (%): C, 70.07; H, 6.59; N, 19.61; Found (%): C, 69.66; H, 6.40; N, 20.03.

EXAMPLE 14A

Production of 6-[2-[4-(Diphenylmethoxy) piperidino]ethoxy][1,2,4]triazolo[1,5-b]pyridazine Fumarate 4-(Diphenylmethoxy)-1-piperidineethanol (774 mg) was dissolved in dried tetrahydrofuran (20 ml), followed by addition of sodium t-butoxide (263 mg). The mixture was refluxed under heating for 30 minutes. After the mixture was cooled, 6-chloro[1,2,4]triazolo[1,5-b]pyridazine (385 mg) was added thereto. The mixture was refluxed under heating for 6 hours. After the mixture was cooled, ice-water was added to the mixture, followed by extraction with ethyl acetate. The extract was washed with an aqueous sodium chloride saturated solution, dried over magnesium sulfate and concentrated under reduced pressure. The residue was subjected silica gel column chromatography and eluted with a mixture of ethyl acetate and methanol (10:1). Fractions containing the objective compound were collected, dissolved in ethanol and crystallized with the addition of fumaric acid (216 mg). The resulting crystals were recrystallized from ethanol to yield the title compound (420 mg).

m.p. 176–177° C.; Elemental Analysis for $C_{29}H_{31}N_5O_6 \cdot H_2O$; Calculated (%): C, 61.80; H, 5.90; N, 12.43; Found (%): C, 61.72; H, 5.65; N, 12.03.

EXAMPLE 15A

Production of 7-t-Butyl-6-[2-[4-(Diphenylmethoxy) piperidino]ethoxy][1,2,4]triazolo[1,5-b]pyridazine 4-(Diphenylmethoxy)-1-piperidineethanol (740 mg) was dissolved in dried tetrahydrofuran (18 ml), followed by addition of sodium t-butoxide (251 mg). The mixture was refluxed under heating for 25 minutes. After the mixture was cooled, 7-tert-butyl-6-chloro[1,2,4]triazolo[1,5-b] pyridazine (501 mg) was added thereto. The mixture was refluxed under heating for 2 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with ethyl acetate. Fractions containing the objective compound were collected and recrystallized from ethyl acetate to yield the title compound (380 mg).

m.p. 133–135° C.; Elemental Analysis for $C_{29}H_{35}N_5O_2$; Calculated (%): C, 71.73; H, 7.26; N, 14.42; Found (%): C, 71.47; H, 7.06; N, 14.19.

EXAMPLE 16A

Production of 1-[4-(Diphenylmethoxy)piperidino]-3-([1,2,4]triazolo[1,5-b]pyridazin-6-yloxy)-2-propanol Process A:

Production of 6-(2-Oxiranylmethoxy)[1,2,4]triazolo[1,5-b]pyridazine

Glycidol (0.13 ml) and suspended in N,N-dimethylformamide (5 ml), followed by addition of 60% oily sodium hydride (80 mg) at room temperature. The mixture was stirred for 3 hours, followed by addition of an aqueous sodium chloride solution and extraction with ethyl acetate. The extract was dried over magnesium sulfate and concentrated under reduced pressure. The residue was subjected to silica gel column chromatography and eluted with ethyl acetate. Fractions containing the objective compound were collected and dried to give the title compound (170 mg).

$^1$H-NMR (CDCl$_3$) δ ppm: 2.7–2.9 (1H, m), 2.9–3.1 (1H, m), 3.3–3.4 (1H, m), 4.1–4.4 (1H, m), 4.7–4.9 (1H, m), 7.11 (1H, d, J=9 Hz), 8.02 (1H, d, J=9 Hz), 8.34 (1H, s).

Process B:

6-(2-Oxiranylmethoxy)[1,2,4]triazolo[1,5-b]pyridazine (171 mg) and 4-(diphenylmethoxy)piperidine (238 mg) were suspended in ethanol (8 ml). The suspension was stirred at 60° C. for 5 hours and concentrated under reduced pressure. Ethyl acetate was added to the residue. The resulting crystals were collected, washed with ethyl ether and dried to yield the title compound (327 mg).

m.p. 133–135° C.; Elemental Analysis for $C_{26}H_{29}N_5O_3$; Calculated (%): C, 67.96; H, 6.36; N, 15.24; Found (%): C, 67.84; H, 6.13; N, 15.34.

EXAMPLE 17A

Production of 1-[4-(Diphenylmethyl)-1-piperazinyl]-3-([1,2,4]triazolo[1,5-b]pyridazin-6-yloxy)-2-propanol Dihydrochloride 6-(2-Oxiranylmethoxy)(1,2,4)triazolo[1,5-b]pyridazine (485 mg) and 1-(diphenylmethyl)piperazine (764 mg) were suspended in ethanol (30 ml). The mixture was stirred at 60° C. for 15 hours and concentrated under reduced pressure. Ethyl acetate was added to the residue. The resulting crystals were collected, washed with diethyl ether and dissolved in ethyl acetate (20 ml). 4N HCl in ethyl acetate solution (5 ml) was added thereto, followed by concentration under reduced pressure. The resulting crystals were recrystallized from ethanol to yield the title compound (392 mg).

m.p. 242° C. (decomp.); Elemental Analysis for $C_{25}H_{30}N_6O_2Cl_2 \cdot H_2O$; Calculated (%): C, 56.08; H, 6.02; N, 15.69; Found (%): C, 56.44; H, 6.03; N, 15.84.

EXAMPLE 18A

Production of 6-[3-[4-(Diphenylmethoxy) piperidino]-N-([1,2,4]triazolo[1,5-b]pyridazin-6-yl) propionamide Process A:

3-Chloro-N-([1,2,4]triazolo[1,5-b]pyridazin-6-yl) propionamide

6-Amino[1,2,4]triazolo[1,5-b]pyridazine (0.80 g) was dissolved in N,N-dimethylacetamide (7 ml), followed by addition of 3-chloropropionyl chloride (0.68 ml) under ice-cooling. The mixture was stirred at room temperature for 1 hour and poured into ice-water, followed by extraction with a mixture of ethyl acetate and tetrahydrofuran (1:1).

The extract was washed with an aqueous sodium chloride saturated solution, dried over magnesium sulfate and concentrated under reduced pressure. Ethyl ether was added to the residue. The resulting crystals were collected by filtration and dried to yield the title compound (0.875 g).

$^1$H-NMR (DMSO-d$_6$) δ ppm: 2.99 (2H, t, J=7 Hz), 3.91 (2H, t, J=7 Hz), 8.36, 8.43 (each 1H, d, J=10 Hz), 8.57 (1H,s), 11.37 (1H, s).

Process B:

3-Chloro-N-([1,2,4]triazolo[1,5-b]pyridazin-6-yl) propionamide (339 mg) and 4-(diphenylmethoxy)piperidine (401 mg) were dissolved in acetonitrile (15 ml), followed by addition of sodium iodide (447 mg) and potassium carbonate (249 mg). The mixture was stirred at room temperature for 15 hours, followed by addition of ice-water and extraction with ethyl acetate. The extract was washed with an aqueous sodium chloride saturated solution, dried over magnesium sulfate and concentrated under reduced pressure. The residue was subjected to a silica gel column chromatography and eluted with a mixture of ethyl acetate and methanol (85:15). Fractions containing the objective compound were collected and concentrated. The resulting crystals were recrystallized from ethanol to yield the title compound (495 mg).

m.p. 176–177° C.; Elemental Analysis for $C_{26}H_{28}N_6O_2$; Calculated (%): C, 68.40; H, 6.18; N, 18.41; Found (%): C, 68.20; H, 6.00; N, 18.36.

EXAMPLE 19A

Production of 3-[4-(Diphenylmethyl)-1-piperazinyl]-N-([1,2,4]triazolo[1,5-b]pyridazin-6-yl) propionamide 3-Chloro-N-([1,2,4]triazolo[1,5-b]pyridazin-6-yl) propionamide (339 mg) and 1-(diphenylmethyl)piperazine (379 mg) were dissolved in acetonitrile (15 ml), followed by addition of sodium iodide (447 mg) and potassium carbonate (249 mg). The mixture was stirred at room temperature for 15 hours and refluxed under heating for 8 hours. After the mixture was cooled, ice-water was added thereto, followed by extraction with ethyl acetate. The extract was washed with an aqueous sodium chloride saturated solution, dried over magnesium sulfate and concentrated under reduced pressure. The resulting crystals were recrystallized from ethanol to yield the title compound (408 mg).

m.p. 176–177° C.;

Elemental Analysis for $C_{25}H_{27}N_7O$; Calculated (%): C, 66.65; H, 6.26; N, 21.76; Found (%): C, 66.36; H, 6.16; N, 21.95.

EXAMPLE 20A

Production of 6-[3-[4-(Diphenylmethoxy) piperidino]propylamino]-2-methyl[1,2,4]triazolo[1, 5-b]pyridazine 6-Chloro-2-methyl[1,2,4]triazolo[1,5-b]pyridazine (655 mg) and 4-(diphenylmethoxy)-1-piperidinepropanamine (1.26 g) was suspended in 1-butanol (20 ml), followed by addition of N-ethyldiisopropylamine (1.94 ml). The mixture was refluxed under heating for 22 hours, followed by addition of ice-water and sodium hydrogen carbonate and extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (50:5:1). Fractions containing the objective compound were collected and concentrated. The resulting crystals were washed with hexane and dried to yield the title compound (547 mg).

m.p. 119–120° C.; Elemental Analysis for $C_{27}H_{32}N_6O$; Calculated (%): C, 71.03; H, 7.06; N, 18.41; Found (%): C, 70.91; H, 6.95; N, 18.18.

EXAMPLE 21A

Production of 6-[3-[4-(Diphenylmethoxy) piperidino]propoxy]-2-methyl[1,2,4]triazolo[1,5-b] pyridazine 4-(Diphenylmethoxy)-1-piperidinepropanol (743 mg) was dissolved in dried tetrahydrofuran (17 ml), followed by addition of sodium t-butoxide (241 mg). The mixture was heated to 60° C. and stirred for 30 minutes. After the mixture was cooled, 6-chloro-2-methyl[1,2,4]triazolo[1,5-b] pyridazine (384 mg) was added thereto, followed by reflux under heating for 21 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (50:5:1). Fractions containing the objective compound were collected. The resulting crystals were washed with ethyl ether and dried to yield the title compound (700 mg).

m.p. 134–136° C.; Elemental Analysis for $C_{27}H_{31}N_5O_2$; Calculated (%): C, 70.87; H, 6.83; N, 15.31; Found (%): C, 70.67; H, 6.94; N, 15.34.

EXAMPLE 22A

Production of 6-[4-[4-(Diphenylmethoxy) piperidino)butoxy][1,2,4]triazolo[1,5-b]pyridazine Fumarate 4-(Diphenylmethoxy)-1-piperidinebutanol (2.04 g) was dissolved in dried tetrahydrofuran (60 ml), followed by addition of 60% oily sodium hydride (480 mg). The mixture was refluxed under heating for 70 minutes. After the mixture was cooled, 6-chloro[1,2,4]triazolo[1,5-b]pyridazine (927 mg) and N,N-dimethylformamide (30 ml) were added thereto, followed by reflux under heating for 18 hours. After the mixture was cooled, ice-water was added thereto, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate, methanol and triethylamine (50.:5:1). The fractions containing the objective compound were collected. The obtained oily mixture was dissolved in ethanol, followed by addition of fumaric acid (80 mg). This mixture was concentrated under reduced pressure, and the residue was recrystallized from methanol to yield the title compound (266 mg).

m.p. 159–161° C.; Elemental Analysis for $C_{31}H_{35}N_5O_6$; Calculated (%): C, 64.91; H, 6.15; N, 12.21; Found (%): C, 64.72; H, 6.10; N, 12.06.

EXAMPLE 23A

Production of 2-[4-(Diphenylmethoxy)piperidino]-
N-([1,2,4]triazolo[1,5-b]pyridazin-6-yl)acetamide Process A:

Production of 2-Bromo-N-([1,2,4]triazolo[1,5-b]
pyridazin-6-yl)acetamide

6-Amino[1,2,4]triazolo[1,5-b]pyridazine (1.32 g) was dissolved in N,N-dimethylacetamide (12 ml), followed by addition of bromoacetyl bromide (1.02 ml) under ice-cooling. The mixture was stirred at room temperature for 30 minutes and poured into ice-water. The resulting crystals were washed with water and ethyl acetate and dried to yield the title compound (2.37 g).

m.p. 210° C. (decomp.); Elemental Analysis for $C_7H_6N_5OBr$; Calculated (%): C, 32.83; H. 2.36; N, 27.35; Found (%): C, 33.04; H, 2.50; N, 26.84.

Process B:

2-Bromo-N-([1,2,4]triazolo[1,5-b]pyridazin-6-yl) acetamide (605 mg) and 4-(diphenylmethoxy)piperidine (632 mg) were dissolved in acetonitrile (20 ml), followed by addition of potassium carbonate (391 mg). The mixture was stirred at room temperature for 3 hours, followed by addition of ice-water and extraction with ethyl acetate. The extract was washed with an aqueous sodium chloride saturated solution, dried over magnesium sulfate and concentrated under reduced pressure. The resulting crystals were collected, recrystallized from ethanol and dried to yield the title compound (769 mg).

m.p. 158–160° C.; Elemental Analysis for $C_{25}H_{26}N_6O_2$; Calculated (%): C, 67.86; H, 5.92; N, 18.99; Found (%): C, 67.59; H, 5.91; N, 18.76.

EXAMPLE 24A

Production of 2-[4-(Diphenylmethyl)-1-
piperazinyl]-N-([1,2,4]triazolo[1,5-b]pyridazin-6-yl)
acetamide 2-Bromo-N-([1,2,4]triazolo[1,5-b]pyridazin-6-yl) acetamide (636 mg) and 1-(diphenylmethyl)piperazine (627 mg) were dissolved in acetonitrile (20 ml), followed by addition of potassium carbonate (411 mg). The mixture was stirred at room temperature for 2 hours, followed by addition of ice-water and extraction with ethyl acetate. The extract was washed with aqueous sodium chloride saturated solution, dried over magnesium sulfate and concentrated under reduced pressure. The resulting crystals were collected by filtration and recrystallized from methanol to yield the title compound (525 mg).

m.p. 203–204° C.; Elemental Analysis for $C_{24}H_{25}N_7O$; Calculated (%): C, 67.43; H, 5.89; N, 22.93; Found (%): C, 67.22; H, 5.87; N, 22.97.

EXAMPLE 25A

Production of 6-[2-[4-(Diphenylmethoxy)
piperidinocarbonyloxy]ethoxy][1,2,4]triazolo[1,5-b]
pyridazine Process A:

2-([1,2,4]Triazolo[1,5-b]pyridazin-6-yloxy)ethanol

60% Oily sodium hydride (510 mg) was suspended in N,N-dimethylformamide (70 ml), followed by addition of 2-(t-butyldiphenylsilyloxy)ethanol (3.83 g). The mixture was stirred at room temperature for 1 hour, followed by addition of 6-chloro[1,2,4]triazolo[1,5-b]pyridazine (1.98 g). The mixture was stirred at room temperature for 5 hours and poured into ice-water, followed by extraction with ethyl ether. The extract was washed with an aqueous sodium chloride solution, dried over magnesium sulfate and concentrated under reduced pressure. The residue was dissolved in tetrahydrofuran (40 ml), followed by addition of tetra-n-butylammoniumfluoride trihydrate (2.02 g). The mixture was stirred at room temperature for 10 minutes and concentrated under reduced pressure. The residue was subjected to silica gel column chromatography and eluted with a mixture of ethyl acetate and hexane (1:1). Fractions containing the objective compound were collected and concentrated to yield the title compound (0.875 g).

$^1$H-NMR (CDCl$_3$) δ ppm: 4.06 (2H, t, J=5 Hz), 4.5–4.7 (2H, m), 7.10, 8.01 (each 1H, d, J=10 Hz), 8.34 (1 H, s).

Process B:

2-([1,2,4]triazolo[1,5-b]pyridazin-6-yloxy)ethanol (275 mg) was dissolved in tetrahydrofuran (12 ml), followed by addition of N,N'-carbonyldiimidazole (544 mg). The mixture was stirred at room temperature for 3 hours, followed by addition of 4-(diphenylmethoxy)piperidine (900 mg) and N-ethyldiisopropylamine (0.53 ml). The mixture was further stirred at room temperature for 13 hours and concentrated under reduced pressure. The residue was subjected to silica gel column chromatography and eluted with ethyl acetate. Fractions containing the objective compound were collected and concentrated to yield the title compound (490 mg).

m.p. 75–76° C.; Elemental Analysis for $C_{26}H_{27}N_5O_4$; Calculated (%): C, 65.95; H, 5.75; N, 14.79; Found (%): C, 65.88; H, 5.84; N, 14.88.

EXAMPLE 26A

Production of 6-[2-[4-(Diphenylmethyl)-1-
piperazinyl-carbonyloxy]ethoxy][1,2,4]triazolo[1,5-
b]pyridazine 2-([1,2,4]triazolo[1,5-b]pyridazin-6-yloxy)ethanol (450 mg) was dissolved in tetrahydrofuran (20 ml), followed by addition of N,N'-carbonyldiimidazole (649 mg). The mixture was stirred at room temperature for 3 hours, followed by addition of 1-(diphenylmethyl)piperazine (1.07 g) and N-ethyldiisopropylamine (0.73 ml). The mixture was stirred at 60° C. for 17 hours and concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and hexane (1:1). Fractions containing the objective compound were collected a and concentrated. The resulting crystals were recrystallized from ethyl acetate to yield the title compound (464 mg).

m.p. 157–159° C.; Elemental Analysis for $C_{25}H_{26}N_6O_3 \cdot 0.5H_2O$; Calculated (%): C, 64.23; H, 5.82; N, 17.98; Found (%): C, 64.32; H. 5.50; N, 17.56.

EXAMPLE 27A

Production of 6-[3-[4-(Diphenylmethoxy)
piperidino-carbonyloxy]propoxy][1,2,4]triazolo[1,5-
b]pyridazine Process A:

1-[(3-t-Butyldiphenylsilyloxy)propoxycarbonyl]-4-
(diphenylmethoxy)piperidine 3-(t-butyldiphenylsilyloxy)propanol (2.12 g) was dissolved in tetrahydrofuran (20 ml), followed by addition of N,N'-carbonyldiimidazole (1.20 g). The mixture was stirred at room temperature for 20 minutes, followed by addition of 4-(diphenylmethoxy)piperidine (1.98 g) and N-ethyldiisopropylamine (1.28 ml). The mixture was stirred at room temperature for 23 hours and concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and hexane (1:10). Fractions containing the objective compound were collected and concentrated to yield the title compound (3.95 g).

$^1$H-NMR (CDCl$_3$), δ ppm: 1.04 (9H, s), 1.50–1.90 (6H, m), 3.05–3.25 (2H, m), 3.50–3.80 (5H, m), 4.21 (2H, t, J=7 Hz), 5.51 (1H, s), 7.2–7.8 (20H, m).

Process B:

Production of 3-[4-(Diphenylmethoxy) piperidinocarbonyloxy]-1-propanol

1-[(3-t-butyldiphenylsilyloxy)propoxycarbonyl]-4-(diphenylmethoxy)piperidine (1.95 g) was dissolved in tetrahydrofuran (15 ml), followed by addition of tetra-n-butylammoniumfluoride trihydride (2.02 g). The mixture was stirred at room temperature for 3 hours and concentrated under reduced pressure. The residue was subjected to silica gel column chromatography and eluted with ethyl acetate. Fractions containing the objective compound were collected and concentrated to yield the title compound (1.33 g).

$^1$H-NMR (CDCl$_3$) δ ppm: 1.5–2.0 (6H, m), 3.1–3.4 (2H, m), 3.5–3.9 (5H, m), 4.26 (2H, t, J=6 Hz), 5.52 (1H, s), 7.1–7.5 (10H, m).

Process C:

3-[4-(Diphenylmethoxy)piperidinocarbonyloxy]-1-propanol (1.33 g) was dissolved in tetrahydrofuran (30 ml), followed by addition of sodium t-butoxide (339 mg). The mixture was stirred at 60° C. for 1.5 hours. After the mixture was cooled, 6-chloro[1,2,4]triazolo[1,5-b]pyridazine (496 mg) was added thereto. The mixture was refluxed under heating for two hours, followed by addition of ice-water and extraction with ethyl acetate. The extract was washed with an aqueous sodium chloride solution, dried over magnesium sulfate and concentrated under reduced pressure. The residue was subjected to silica gel column chromatography and eluted with ethyl acetate. Fractions containing the objective compound were collected and concentrated to yield the title compound (0.730 g).

m.p. 119–120° C.; Elemental Analysis for $C_{27}H_{29}N_5O_4$; Calculated (%): C, 66.51; H, 6.00; N, 14.36; Found (%): C, 66.65; H, 5.78; N, 14.64.

EXAMPLE 28A

Production of 6-[3-[4-(Diphenylmethyl)-1-piperazinyl-carbonyloxy]propoxy][1,2,4]triazolo[1,5-b]pyridazine Hydrochloride Process A:

Production of 1-[3-(t-Butyldiphenylsilyloxy) propoxycarbonyl]-4-(diphenylmethyl)piperazine 3-(t-butyldiphenylsilyloxy)propanol (1.71 g) was dissolved in tetrahydrofuran (16 ml), followed by addition of N,N'-carbonyldiimidazole (0.97 g). The mixture was stirred at room temperature for 20 minutes, followed by addition of 1-(diphenylmethyl)piperazine (1.51 g) and N-ethyldiisopropylamine (1.03 ml). The mixture was stirred at 60° C. for 16 hours. After being cooled, the mixture was concentrated under reduced pressure. Ice-water was added to the residue, followed by extraction with ethyl acetate. The extract was washed with an aqueous sodium chloride saturated solution, dried over magnesium sulfate and concentrated under reduced pressure. The residue was subjected to silica gel column chromatography and eluted with a mixture of ethyl acetate and hexane (1:10). Fractions containing the objective compound were collected and concentrated to yield the title compound (2.53 g).

$^1$H-NMR (CDCl$_3$) δ ppm: 1.03 (9H, s), 1.7–2.0 (2H, m), 2.2–3.6 (8H, m), 3.71 (2H, t, J=6 Hz), 4.21 (2H, t, J=6 Hz), 4.21 (1H, s), 7.1–7.7 (20H, m).

Process B:

Production of 4-(Diphenymethyl)-1-(3-hydroxypropoxy) carbonyl)piperazine

1-[3-(t-butyldiphenylsilyloxy)propoxycarbonyl]-1-(diphenylmethyl)piperazine (2.50 g) was dissolved in tetrahydrofuran (12 ml), followed by addition of tetra-n-butylammoniumfluoride trihydrate (1.46 g). The mixture was stirred at room temperature for 3 hours and concentrated under reduced pressure. The residue was subjected to silica gel column chromatography and eluted with a mixture of ethyl acetate and hexane (1:1). Fractions containing the objective compound were collected and concentrated to yield the title compound (1.51 g).

$^1$H-NMR (CDCl$_3$) δ ppm: 1.7–2.0 (6H, m), 2.2–3.6 (8H, m), 3.64 (2H, t, J=6 Hz), 4.25 (2H, t, J=6 Hz), 4.24 (1H, s), 7.1–7.5 (10H, m).

Process C:

3-[4-(Diphenylmethyl)-1-piperazinylcarbonyloxy]-1-propanol piperazine (1.44 g) was dissolved in tetrahydrofuran (30 ml), followed by addition of sodium t-butoxide (429 mg). The mixture was stirred at 60° C. for 0.5 hour. After the mixture was cooled, 6-chloro[1,2,4]triazolo[1,5-b]pyridazine (627 mg) was added thereto. This mixture was refluxed under heating for three hours, followed by addition of ice-water and extraction with ethyl acetate. The extract was washed with an aqueous sodium chloride solution, dried over magnesium sulfate and concentrated under reduced pressure. The residue was subjected to silica gel column chromatography and eluted with a mixture of ethyl acetate and hexane (3:1). Fractions containing the objective compound were collected and concentrated. The residue was dissolved in ethyl acetate (10 ml), followed by addition of an ethyl acetate solution of 4N HCl (0.32 ml). The mixture was concentrated under reduced pressure. The resulting crystals were recrystallized from ethanol to yield the title compound (0.450 g).

m.p. 167–169° C.; Elemental Analysis for $C_{26}H_{29}N_6O_3Cl.0.5H_2O$; Calculated (%): C, 60.29; H, 5.84; N, 16.22; Found (%): C, 60.52; H, 5.96; N, 16.05.

EXAMPLE 29A

Production of 6-[6-[4-(Diphenylmethoxy)piperidino]hexyloxy][1,2,4]triazolo[1,5-b]pyridazine Fumarate 4-(Diphenylmethoxy)-1-piperidinehexanol (0.905 g) was dissolved in tetrahydrofuran (15 ml), followed by addition of 60% oily sodium hydride (118 mg). The mixture was refluxed under heating for 1 hour. After the mixture was cooled, 6-chloro[1,2,4]triazolo[1,5-b]pyridazine (381 mg) was added thereto. This mixture was refluxed under heating for hours, followed by addition of addition of ice-water and extraction with ethyl acetate. The extract was washed with an aqueous sodium chloride solution, dried over magnesium sulfate and concentrated under reduced pressure. The residue was subjected to silica gel column chromatography and eluted with a mixture of ethyl acetate, methanol and triethylamine (50:5:1). Fractions containing the objective compound were collected and concentrated. The residue was dissolved in ethyl acetate (10 ml), followed by addition of a solution of fumaric acid (263 mg) in methanol (10 ml). The mixture was concentrated, and the residue was recrystallized from ethyl acetate to yield the title compound (0.979 g).

m.p. 136–138° C.; Elemental Analysis for $C_{33}H_{39}N_5O_6$; Calculated (%): C, 65.87; H, 6.53; N, 11.64; Found (%): C, 65.79; H. 6.54; N, 11.62.

EXAMPLE 30A

6-[6-[4-(Diphenylmethyl)-1-piperazinyl]hexyloxy][1,2,4]triazolo[1,5-b]pyridazine Fumarate 4-(Diphenylmethyl)-1-piperazinehexanol (0.640 g) was dissolved in tetrahydrofuran (10 ml), followed by addition of 60% oily sodium hydride (145 mg). The mixture was refluxed under heating for 1 hour. After the mixture was cooled, 6-chloro[1,2,4]triazolo[1,5-b]pyridazine (281 mg) was added thereto. This mixture was refluxed under heating for 1.5 hours. Ice-water was added to the mixture, followed by extraction with ethyl acetate. The extract was washed with an aqueous sodium chloride solution, dried over magnesium sulfate and concentrated under reduced pressure. The residue was subjected to silica gel column chromatography and eluted with ethyl acetate. Fractions containing the objective compound were collected and dissolved in ethyl acetate (10 ml), followed by addition of a solution of fumaric acid (140 mg) in methanol (10 ml). The mixture was concentration, and the residue was recrystallized from ethanol to yield the title compound (189 mg).

m.p. 149–151° C.; Elemental Analysis for $C_{32}H_{38}N_6O_5.0.5H_2O$; Calculated (%): C, 64.52; H, 6.60; N, 14.11; Found (%): C, 64.95; H, 6.64; N, 13.91.

EXAMPLE 31A

Production of 6-[3-[4-(Diphenylmethoxy)piperidino]propoxy]-2-phenyl[1,2,4]triazolo[1,5-b]pyridazine Hydrochloride 4-(Diphenylmethoxy)-1-piperidinepropanol (487 mg) was dissolved in dried tetrahydrofuran (10 ml), followed by addition of sodium t-butoxide (144 mg). The mixture was refluxed under heating for 40 minutes. After the mixture was cooled, 6-chloro-2-phenyl[1,2,4]triazolo[1,5-b]pyridazine (315 mg) was added thereto. This mixture was refluxed under heating for 4 hours. After the mixture was cooled, ice-water was added thereto, followed by extraction with a mixture of ethyl acetate and tetrahydrofuran (2:1). The extract was washed with an aqueous sodium chloride saturated solution, dried over magnesium sulfate and concentrated under reduced pressure. The residue was subjected to silica gel column chromatography and eluted with a mixture of ethyl acetate and methanol (10:1). Fractions containing the objective compound were collected, concentrated and dissolved in ethyl acetate (10 ml), followed by addition of 4N HCl in ethyl acetate solution (0.25 ml) and concentrated under reduced pressure. The resulting crystals were recrystallized from ethanol to yield the title compound (0.334 g).

m.p. 127–129° C.; Elemental Analysis for $C_{32}H_{34}N_5O_2Cl.H_2O$; Calculated (%): C, 66.95; H, 6.32; N, 12.20; Found (%): C, 67.01; H, 6.46; N, 12.27.

EXAMPLE 32A

Production of 6-[3-[4-(Diphenylmethoxy)piperidino]propylamino]-2-phenyl[1,2,4]triazolo[1,5-b]pyridazine 365 mg of 6-chloro-2-phenyl[1,2,4]triazolo[1,5-b]pyridazine and 0.513 g of 4-(diphenylmethoxy)-1-piperidinepropanamine were suspended in 8 ml of 1-butanol; 0.54 ml of N-ethyldiisopropylamine was added, followed by heating and refluxing for 19 hours. Ice water and sodium hydrogen carbonate were added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; the resulting crystal was recrystallized from ethyl acetate to yield 308 mg of the title compound.

Melting point: 170–172° C.; Elemental analysis (for $C_{32}H_{34}N_6O.0.5H_2O$): Calculated (%): C, 72.84; H, 7.69; N, 15.93; Found (%): C, 73.08; H, 7.61; N, 16.03.

EXAMPLE 33A

Production of 2-t-Butyl-6-[3-[4-(Diphenylmethoxy)piperidino]propoxy][1,2,4]triazolo[1,5-b]pyridazine Fumarate 911 mg of 4-(diphenylmethoxy)-1-piperidinepropanol was dissolved in 20 ml of dry tetrahydrofuran; 296 mg of sodium t-butoxide was added, followed by heating and refluxing for 30 minutes. After cooling, 589 mg of 2-t-butyl-6-chloro[1,2,4]triazolo[1,5-b]pyridazine was added, followed by heating and refluxing for 6 hours. After cooling ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; the residue was dissolved in 10 ml of ethyl acetate; a solution of 102 mg of fumaric acid in 10 ml of methanol was added, followed by concentration. The residue was recrystallized from ethyl acetate to yield 382 mg of the title compound.

Melting point: 170–172° C.; Elemental analysis (for $C_{34}H_{41}N_5O_6$): Calculated (%): C, 66.32; H, 6.71; N, 11.37; Found (%): C, 66.15; H, 6.74; N, 11.28.

EXAMPLE 34A

Production of 2-t-Butyl-6-[3-[4-(Diphenylmethoxy)piperidino]propylamino][1,2,4]triazolo[1,5-b]pyridazine Fumarate 276 mg of 2-t-butyl-6-chloro[1,2,4]triazolo[1,5-b]pyridazine and 0.425 g of 4-(diphenylmethoxy)-1-piperidinepropanamine were suspended in 8 ml of 1-butanol; 0.45 ml of N-ethyldiisopropylamine was added, followed by heating and refluxing for 40 hours. Ice water and sodium hydrogen carbonate were added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; the residue was dissolved in 10 ml of ethyl acetate; a solution of 40 mg of fumaric acid in 5 ml of methanol was added, followed by concentration. The residue was powdered by the addition of ethyl ether, filtered and collected to yield 164 mg of the title compound.

Melting point: Softened from 80° C.; Elemental analysis (for $C_{34}H_{42}N_6H_2O.0.5Et_2O$): Calculated (%): C, 64.55; H, 7.37; N, 12.55; Found (%): C, 64.79; H, 7.76; N, 12.44.

EXAMPLE 35A

Production of 6-[6-[4-(Diphenylmethoxy) piperidino]hexylamino][1,2,4]triazolo[1,5-b] pyridazine Process A:
6-[([1,2,4]triazolo[1,5-b]pyridazin-6-yl)amino]-1-hexanol 2.03 g of 6-chloro[1,2,4]triazolo[1,5-b]pyridazine was dissolved in 20 ml of ethanol; 3.85 g of 6-amino-1-hexanol was added, followed by heating and refluxing for 19 hours. After cooling, the crystal obtained was collected by filtration, washed with ethanol and dried to yield 3.64 g of the title compound.

$^1$H-NMR (CDCl$_3$) δ ppm: 1.3–1.8 (8H, m), 3.46 (2H, t, J=6 Hz), 3.67 (2H, q, J=6 Hz), 4.58 (1H, broad s), 6.71, 7.78 (each 1H, d, J=10 Hz), 8.19 (1H, s).

Process B:

1.64 g of 6-[([1,2,4]triazolo[1,5-b]pyridazin-6-yl)amino]-1-hexanol was suspended in 40 ml of tetrahydrofuran; 2.25 g of N-ethyldiisopropylamine and 2.0 g of methanesulfonyl chloride were added, followed by stirring at room temperature for 5.5 hours. Ice water and sodium chloride were added, followed by extraction with ethyl acetate-tetrahydrofuran (2:1); the extract was washed with saturated saline, dried over magnesium sulfate and concentrated under reduced pressure. The residue was dissolved in 14 ml of acetonitrile; 743 mg of 4-(diphenylmethoxy)piperidine, 457 mg of potassium iodide and 380 mg of potassium carbonate were added, followed by stirring at 50° C. for 16 hours. After cooling, ice water was added, followed by extraction with ethyl acetate; the extract was washed with saturated saline and dried over magnesium sulfate and concentrated under reduced pressure. The residue was subjected to silica gel column chromatography and eluted with ethyl acetate-:methanol:triethylamine (50:5:1). The desired fraction was collected and concentrated; the crystal obtained was recrystallized from ethyl acetate-ethyl ether (1:1) to yield 597 mg of the title compound.

Melting point: 97–98° C.; Elemental analysis (for C$_{29}$H$_{36}$NO): Calculated (%): C, 71.87; H, 7.49; N, 17.34; Found (%): C, 71.77; H, 7.37; N, 17.36.

EXAMPLE 36A

Production of Methyl 6-[3-[4-(Diphenylmethoxy) piperidino]propylamino][1,2,4]triazolo[1,5-b] pyridazine-2-carboxylate 0.92 g of methyl 6-chloro[1,2,4]triazolo[1,5-b] pyridazine-2-carboxylate and 1.40 g of 4-(diphenylmethoxy)-1-piperidinepropanamine were suspended in 20 ml of N,N-dimethylformamide; 1.49 ml of N-ethyldiisopropylamine was added, followed by heating and refluxing at 80° C. for 15 hours. After cooling, ice water and sodium chloride were added, followed by extraction with ethyl acetate-tetrahydrofuran (1:2); the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; the residue was recrystallized from ethanol-ethyl acetate (1:2) to yield 639 mg of the title compound.

Melting point: 93–96° C.; Elemental analysis (for C$_{28}$H$_{32}$N$_6$O$_3$.0.5H$_2$O): Calculated (%): C, 65.99; H, 6.53; N, 16.49; Found (%): C, 65.69; H, 6.28; N, 16.58.

EXAMPLE 37A

Production of 6-[6-[4-(Diphenylmethyl)-1-piperazinyl]hexylamino][1,2,4]triazolo[1,5-b] pyridazine 1.64 g of 6-(6-hydroxyhexylamino)[1,2,4]triazolo[1,5-b]pyridazine was suspended in 40 ml of tetrahydrofuran; 2.25 g of N-ethyldiisopropylamine and 2.0 g of methanesulfonyl chloride were added, followed by stirring at room temperature for 1 hour. Ice water and sodium chloride were added, followed by extraction with ethyl acetate; the extract was washed with saturated saline, dried over magnesium sulfate and concentrated under reduced pressure. The residue was dissolved in 13 ml of N,N-dimethylformamide; 694 mg of 1-(diphenylmethyl)piperazine, 456 mg of potassium iodide and 379 mg of potassium carbonate were added, followed by stirring at room temperature for 2 hours and at 60° C. for 4 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; the crystal obtained was recrystallized from ethyl acetate and dried to yield 702 mg of the title compound.

Melting point: 130–132° C.; Elemental analysis (for C$_{28}$H$_{35}$N$_7$): Calculated (%): C, 71.61; H, 7.51; N, 20.88; Found (%): C, 71.39; H, 7.39; N, 21.04.

EXAMPLE 38A

Production of 6-[3-[4-(Diphenylmethoxy) piperidino]propoxy]imidazo[1,2-b]pyridazine Fumarate 159 mg of sodium t-butoxide was dissolved in 15 ml of N,N-dimethylformamide; 4.89 mg of 4-(diphenylmethoxy)-1-piperidinepropanol was added, followed by stirring at 60° C. for 30 minutes. After cooling, 253 mg of 6-chloroimidazo [1,2-b]pyridazine was added, followed by stirring at 80–90° C. for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (90:10:1). The desired fraction was collected, dissolved in 10 ml of ethyl acetate; a solution of 93 mg of fumaric acid in 10 ml of methanol was added, followed by concentration. The crystal precipitated was collected by filtration, washed with ethyl acetate and dried to yield 288 mg of the title compound.

Melting point: 155–157° C.; Elemental analysis (for C$_{31}$H$_{34}$N$_4$O$_6$.H$_2$O): Calculated (%): C, 64.57; H, 6.29; N, 9.72; Found (%): C, 64.24; H, 5.98; N, 9.28.

EXAMPLE 39A

Production of 6-[3-[4-(Diphenylmethoxy) piperidino]propylamino]imidazo[1,2-b]pyridazine Fumarate [2:3]

325 mg of 4-(diphenylmethoxy)-1-piperidinepropanamine and 184 mg of 6-chloroimidazo[1,2-b]pyridazine were stirred at 180° C. for 1 hour. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (90:10:1). The desired fraction was collected, dissolved in 10 ml of ethyl acetate; a solution of 193 mg of fumaric acid in 10 ml of methanol was added, followed by concentration. Acetone was added to the residue; the crystal precipitated was collected by filtration, washed with acetone and dried to yield 246 mg of the title compound.

Melting point: 137–139° C.; Elemental analysis (for $C_{33}H_{31}N_5O_7.0.5H_2O$): Calculated (%): C, 63.45; H, 6.13; N, 11.21; Found (%): C, 63.66; H, 6.00; N, 11.12.

EXAMPLE 40A

Production of Ethyl 2-[6-[3-[4-(Diphenylmethoxy) piperidino]propylamino]imidazo[1,2-b]pyridazin-2-yl]-2-methylpropionate Difumarate 4.2 g of 4-(diphenylmethoxy)-1-piperidinepropanamine and 1.76 g of ethyl 2-(6-chloroimidazo[1,2-b]pyridazin-2-yl)-2-methylpropionate were stirred at 190–200° C. for 3.5 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (100:5:1). The desired fraction was collected, dissolved in 16 ml of ethyl acetate; a solution of 867 mg of fumaric acid in 16 ml of methanol was added, followed by concentration. Acetone was added to the residue; the crystal precipitated was collected by filtration, washed with acetone and dried to yield 2.30 g of the title compound.

Melting point:126–128° C.; Elemental analysis (for $C_{41}H_{49}N_5O_{11}$): Calculated (%): C, 62.50; H. 6.27; N, 8.89; Found (%): C, 62.28; H, 6.15; N, 8.97.

EXAMPLE 41A

Production of 6-[3-[4-(Diphenylmethoxy) piperidino]propoxy]-2-methoxyimidazo[1,2-b] pyridazine 758 mg of 4-(diphenylmethoxy)-1-piperidinepropanol was dissolved in 40 ml of N,N-dimethylformamide; 102 mg of a 60% sodium hydride dispersion in mineral oil was added, followed by stirring at 60° C. for 40 minutes. After cooling, 428 mg of 6-chloro-2-methoxyimidazo[1,2-b] pyridazine was added, followed by stirring at 100° C. for 2.5 hours. After cooling, ice water and sodium chloride were added, followed by extraction with ethyl acetate-tetrahydrofuran (1:2); the extract was washed with saturated saline, dried over magnesium sulfate and concentrated under reduced pressure. The residue was subjected to silica gel column chromatography and eluted with ethyl acetate-:methanol:triethylamine (50:5:1). The desired fraction was collected and concentrated; the crystal precipitated was recrystallized from ethanol to yield 499 mg of the title compound.

Melting point: 133–135° C.; Elemental analysis (for $C_{28}H_{32}N_4O_3$): Calculated (%): C, 71.16; H, 6.83; N, 11.86; Found (%): C, 71.23; H, 6.83; N, 11.94.

EXAMPLE 42A

Production of 6-[3-[4-(Diphenylmethyl)-1-piperazinyl]propoxy]-2-methoxyimidazo[1,2-b] pyridazine 251 mg of 4-(diphenylmethyl)-1-piperazinepropanol was dissolved in 14 ml of N,N-dimethylformamide; 36 mg of a 60% sodium hydride dispersion in mineral oil was added, followed by stirring at 60° C. for 30 minutes. After cooling, 149 mg of 6-chloro-2-methoxyimidazo[1,2-b]pyridazine was added, followed by stirring at 90° C. for 4.5 hours. After cooling, ice water and sodium chloride were added, followed by extraction with ethyl acetate-tetrahydrofuran (1:2); the extract was washed with saturated saline, dried over magnesium sulfate and concentrated under reduced pressure. The residue was subjected to silica gel column chromatography and eluted with ethyl acetate. The desired fraction was collected; the crystal precipitated was recrystallized from ethyl acetate to yield 99 mg of the title compound.

Melting point: 144–146° C.; Elemental analysis (for $C_{27}H_{31}N_5O_2$): Calculated (%): C, 70.87; H, 6.83; N, 15.31; Found (%): C, 70.79; H, 6.82; N, 13.39.

EXAMPLE 43A

Production of 2-[6-[3-[4-(Diphenylmethoxy) piperidino]propylamino]imidazo[1,2-b]pyridazin-2-yl]-2-methylpropionic Acid 468 mg of ethyl 2-[6-[3-[4-(diphenylmethoxy)piperidino]propylamino]imidazo[1,2-b]pyridazin-2-yl]-2-methylpropionate was dissolved in 3 ml of ethanol; 2 ml of a 1 N aqueous solution of sodium hydroxide was added, followed by stirring at room temperature for 15 hours. After the mixture was concentrated under reduced pressure. The residue was diluted with water and washed with ethyl acetate; the water layer was adjusted to pH 7 by the addition of 1 N hydrochloric acid, followed by extraction with ethyl acetate-tetrahydrofuran (1:1); the extract was washed with saturated saline, dried over magnesium sulfate and concentrated under reduced pressure. Ethyl acetate was added to the residue; the crystal precipitated was collected by filtration, washed with ethyl acetate and dried to yield 267 mg of the title compound.

Melting point: 205–206° C.; Elemental analysis (for $C_{31}H_{37}N_5O_3$): Calculated (%): C, 70.56; H, 7.07; N, 13.27; Found (%): C, 70.46; H, 7.06; N, 13.36.

EXAMPLE 44A

Production of t-Butyl 2-[6-[3-[4-(Diphenylmethoxy) piperidino]propoxy]imidazo[1,2-b]pyridazin-2-yl]-2-methylpropionate Difumarate 70 mg of 60% sodium hydride dispersion in mineral oil was dissolved in 5 ml of N,N-dimethylformamide; 570 mg of 4-(diphenylmethoxy)-1-piperidinepropanol was added, followed by stirring at room temperature under reduced pressure for 30 minutes. After 520 mg of t-butyl 2-(6-chloroimidazo[1,2-b]pyridazin-2-yl)-2-methylpropionate was added, followed by stirring at room temperature for 8 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate-:methanol:triethylamine (195:5:1). The desired fraction was collected and dissolved in 5 ml of ethyl acetate; a solution of 233 mg of fumaric acid in 10 ml of methanol was added, followed by concentration. The crystal precipitated was collected by filtration, washed with acetone and dried to yield 631 mg of the title compound.

Melting point: 162–164° C.; Elemental analysis (for $C_{43}H_{52}N_4O_{12}$): Calculated (%): C, 63.22; H, 6.42; N, 6.86; Found (%): C, 62.91; H, 6.36; N, 6.90.

EXAMPLE 45A

Production of 2-[6-[3-[4-(Diphenylmethoxy) piperidino]propoxylimidazo[1,2-b]pyridazin-2-yl]2-methylpropionic Acid 818 mg of t-butyl 2-[6-[3-[4-(diphenylmethoxy) piperidino]propoxy]imidazo[1,2-b]pyridazin-2-yl]-2- methylpropionate was dissolved in 8 ml of 1-butanol; 393 mg of potassium hydroxide was added, followed by stirring at 90° C. for 14 hours. After cooling, the water layer was added to 7 ml of 1 N hydrochloric acid, followed by extraction with ethyl acetate; the extract was washed with saturated saline, dried over magnesium sulfate and concentrated under reduced pressure. Ethyl acetate was added to the residue; the crystal precipitated was collected by filtration, washed with ethyl acetate and dried to yield 465 mg of the title compound.

Melting point: 183–185° C.; Elemental analysis (for $C_{31}H_{36}N_4O_4 \cdot 2.5H_2O$): Calculated (%): C, 64.90; H, 7.20; N, 9.77; Found (%): C, 65.15; H, 6.73; N, 9.52.

EXAMPLE 46A

Production of Ethyl 2-[6-[3-[4-(Diphenylmethoxy) piperidino]propoxy]imidazo[1,2-b]pyridazin-2-yl]-2-methylpropionate Difumarate 529 mg of 2-[6-[3-[4-(diphenylmethoxy)piperidino] propoxy]imidazo[1,2-b]pyridazin-2-yl]-2-methylpropionic acid was dissolved in 3 ml of N,N-dimethylformamide; 0.207 ml of N-ethyldiisopropylamine and 0.135 ml of ethyl iodide were added, followed by stirring at room temperature for 15 hours. Ice water was added to the reaction mixture, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (100:5:1). The desired fraction was collected and dissolved in 3 ml of ethyl acetate: a solution of 153 mg of fumaric acid in 3 ml of methanol was added, followed by concentration. The crystal precipitated was collected by filtration, washed with ethyl acetate and dried to yield 406 mg of the title compound.

Melting point: 116–122° C.; Elemental analysis (for $C_{41}H_{48}N_4O_{12} \cdot 0.5H_2O$): Calculated (%): C, 61.72; H, 6.19; N, 7.02; Found (%): C, 61.61; H, 6.11; N, 6.85.

EXAMPLE 47A

Production of 6-[2-[2-[4-(Diphenylmethyl)-1-piperazinyl]ethoxy]ethoxy]-7-methyl[1,2,4]triazolo [1,5-b]pyridazine 260 mg of 60% sodium hydride dispersion in mineral oil was suspended in 20 ml of tetrahydrofuran; 1.15 g of 2-[2-[4-(diphenylmethyl)-1-piperazinyl]ethoxy]ethanol was added, followed by heating and refluxing for 1 hour. After cooling, 540 mg of 6-chloro-7-methyl[1,2,4]triazolo[1,5-b] pyridazine was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with dichloromethane-ethyl acetate-methanol (10:10:1). The desired fraction was collected; the crystal precipitated was collected by filtration, washed with ethyl ether and dried to yield 730 mg of the title compound.

Melting point: 71–72° C.; Elemental analysis (for $C_{27}H_{32}N_6O_2$): Calculated (%): C, 68.62; H, 6.82; N, 17.78; Found (%): C, 68.35; H, 6.71; N, 17.79.

EXAMPLE 48A

Production of 6-[2-[2-[4-(Diphenylmethyl)-1-piperazinyl]ethoxy]ethoxy][1,2,4]triazolo[1,5-b] pyridazine Dihydrochloride 100 mg of 60% sodium hydride in oil was suspended in 20 ml of tetrahydrofuran; 470 mg of 2-[2-[4-(diphenylmethyl)-1-piperazinyl]ethoxy]ethanol was added, followed by heating and refluxing for 1 hour. After cooling, 200 mg of 6-chloro[1,2,4]triazolo[1,5-b]pyridazine was added, followed by heating and refluxing for 4.5 hours. After cooling, ice water was added, followed by extraction with ethyl acetate; the extract was washed with saturated saline, dried over magnesium sulfate and concentrated under reduced pressure. The residue was subjected to silica gel column chromatography and eluted with dichloromethane-ethyl acetate-methanol (10:10:1). The desired fraction was collected and dissolved in 5 ml of ethyl acetate; 0.83 ml of a 4 N hydrogen chloride solution in ethyl acetate was added; the crystal precipitated was collected by filtration, washed with ethyl ether and dried to yield 0.54 g of the title compound.

Melting point: 182–184° C.; Elemental analysis (for $C_{26}H_{32}N_6O_2Cl_2 \cdot H_2O$): Calculated (%): C, 56.83; H, 6.24; N, 15.29; Found (%): C, 56.98; H, 6.10; N, 15.39.

EXAMPLE 49A

Production of 6-[4-[4-(Diphenylmethyl)-1-piperazinyl]butoxy]-7-methyl[1,2,4]triazolo[1,5-b] pyridazine Dihydrochloride 240 mg of a 60% sodium hydride dispersion in mineral oil was suspended in 20 ml of tetrahydrofuran; 0.99 g of 4-(diphenylmethyl)-1-piperazinebutanol was added, followed by heating and refluxing for 1 hour. After cooling, 510 mg of 6-chloro-7-methyl[1,2,4]triazolo[1,5-b]pyridazine was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with dichloromethane-ethyl acetate-methanol (20:20:1). The desired fraction was collected and dissolved in 5 ml of ethyl acetate; 0.64 ml of a 4 N hydrogen chloride solution in ethyl acetate was added; the crystal precipitated was collected by filtration, washed with ethyl ether and dried to yield 470 mg of the title compound.

Melting point: 190–192° C.; Elemental analysis (for $C_{27}H_{34}N_6OCl_2 \cdot 0.5AcOEt \cdot H_2O$): Calculated (%): C, 58.88; H, 6.82; N, 14.21; Found (%): C, 59.11; H, 6.82; N, 14.03.

EXAMPLE 50A

Production of 6-[2-[2-[4-(Diphenylmethyl)-1-piperazinyl]-ethoxy]ethylthio][1,2,4]triazolo[1,5-b] pyridazine Dihydrochloride Process A:

6-[2-(2-Bromoethoxy)ethylthio][1,2,4]triazolo[1,5-b] pyridazine 2.8 ml of methyl 3-mercaptopropionate was dissolved in 10 ml of methanol; 19.4 ml of a 2 N sodium methoxide solution in methanol and 1.0 g of 6-chloro[1,2,4]triazolo[1, 5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 20 ml of tetrahydrofuran; 1.63 ml of 2-bromoethyl ether was added, followed by heating and refluxing for 2 hours. After cooling, ice water was added, followed by extraction with ethyl acetate; the extract was washed with saturated saline, dried over magnesium sulfate and concentrated under reduced pressure. The residue was subjected to silica gel column chromatography and eluted with dichloromethane:ethyl acetate:methanol (20:20:1). The desired fraction was collected to yield 0.60 g of the title compound as an oily substance.

$^1$H-NMR (CDCl$_3$): δ ppm: 3.49 (2H, t, J=6 Hz), 3.55 (2H, t, J=6 Hz), 3.86 (2H, t, J=6 Hz), 3.90 (2H, t, J=6 Hz), 7.22, 7.93 (each 1H, d, J=9 Hz), 8.37 (1H, s).

Process B:

890 mg of 6-[2-(2-bromoethoxy)ethylthio[1,2,4]triazolo [1,5-b]pyridazine and 740 mg of 1-(diphenylmethyl) piperazine were dissolved in 10 ml of N,N-dimethylformamide; 490 mg of potassium carbonate was added, followed by stirring at room temperature for 24 hours. Ice water was added, followed by extraction with ethyl acetate; the extract was washed with saturated saline, dried over magnesium sulfate and concentrated under reduced pressure. The residue was subjected to silica gel column chromatography and eluted with dichloromethane:methanol (10:1). The desired fraction was collected and concentrated; the residue was dissolved in 5 ml of ethyl acetate; 1. 64 ml of a 4 N hydrogen chloride solution in ethyl acetate was added; the crystal precipitated was collected by filtration, washed with ethyl ether and dried to yield 1.13 g of the title compound.

Melting point: 188–189° C.; Elemental analysis (for C$_{26}$H$_{32}$N$_6$OSCl$_2$.H$_2$O): Calculated (%): C, 55.22; H, 6.06; N, 14.86; Found (%): C, 55.49; H, 6.02; N, 15.08.

EXAMPLE 51A

Production of 6-[6-[4-(Diphenylmethyl)-1-piperazinyl]hexyloxy]-7-methyl[1,2,4]triazolo[1,5-b] pyridazine Dihydrochloride 210 mg of 60% sodium hydride in oil was suspended in 15 ml of tetrahydrofuran; 0.91 g of 4-(diphenylmethyl)-1-piperazinehexanol was added, followed by heating and refluxing for 1 hour. After cooling, 6-chloro-7-methyl[1,2, 4]triazolo[1,5-b]pyridazine was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with dichloromethane-ethyl acetate-methanol (1.0:10:1). The desired fraction was collected and dissolved in 5 ml of ethyl acetate; 1.44 ml of a 4 N hydrogen chloride solution in ethyl acetate was added; the crystal precipitated was collected by filtration, washed with ethyl ether and dried to yield 1.06 g of the title compound, which was then recrystallized from ethanol.

Melting point 170–172° C.; Elemental analysis (for C$_{29}$H$_{38}$N$_6$OCl$_2$.0.5EtOH): Calculated (%): C, 62.06; H, 7.11; N, 14.47; Found (%): C, 61.77; H, 6.94; N, 14.33.

EXAMPLE 52A

Production of 6-[6-[4-(Diphenylmethoxy) piperidino]hexyloxy]-7-methyl[1,2,4]triazolo[1,5-b] pyridazine Hydrochloride 160 mg of 60% sodium hydride in oil was suspended in 20 ml of tetrahydrofuran; 1.24 g of 4-(diphenylmethoxy)-1-piperidinehexanol was added, followed by heating and refluxing for 1 hour. After cooling, 570 mg of 6-chloro-7-methyl[1,2,4]triazolo[1,5-b]pyridazine was added, followed by heating and refluxing for 1 hour. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate-methanol (10:1). The desired fraction was collected and dissolved in 5 ml of ethyl acetate; 0.54 ml of a 4 N hydrogen chloride solution in ethyl acetate was added; the crystal precipitated was collected by filtration, washed with ethyl ether and dried to yield 0.70 g of the title compound.

Melting point: 208–209° C.; Elemental analysis (for C$_{30}$H$_{38}$N$_5$O$_2$Cl.0.8H$_2$O): Calculated (%): C, 65.45; H, 7.25; N, 12.72; Found (%): C, 65.47; H, 7.21; N, 12.60.

EXAMPLE 53A

Production of 6-[2-[2-[4-(Diphenylmethoxy) piperidino]ethoxy]ethoxy]-7-methyl[1,2,4]triazolo[1, 5-b]pyridazine 190 mg of 60% sodium hydride in oil was suspended in 15 ml of tetrahydrofuran; 1.47 g of 2-[2-[4-(diphenylmethoxy)piperidino]ethoxy]ethanol was added, followed by heating and refluxing for 1 hour. After cooling, 660 mg of 6-chloro-7-methyl[1,2,4]triazolo[1,5-b] pyridazine was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate-methanol a (10:1). The desired fraction was collected; the crystal precipitated was collected by filtration, washed with ethyl ether and dried to yield 1.23 g of the title compound.

Melting point: 80–82° C.; Elemental analysis (for C$_{28}$H$_{33}$N$_5$O$_3$): Calculated (%): C, 68.97; H, 6.82; N, 14.36; Found (%): C, 68.75; H, 6.70; N, 14.57.

EXAMPLE 54A

Production of 6-[6-[4-(Diphenylmethyl)-1-piperazinyl]hexylthio]-7-methyl[1,2,4]triazolo[1,5-b]pyridazine Dihytochloride Process A:

6-(6-Bromohexylthio)-7-methyl[1,2,4]triazolo[1,5-b] pyridazine 5.57 g of methyl 3-mercaptopropionate was dissolved in 20 ml of methanol; 35.6 ml of a 2 N sodium methoxide solution in methanol and 2.0 g of 6-chloro-7-methyl[1,2,4] triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 30 ml of tetrahydrofuran; 3.65 ml of 1,6-dibromohexane was added, followed by heating and refluxing for 3 hours. After cooling, ice water was added, followed by extraction with ethyl acetate; the extract was washed with saturated saline, dried over magnesium sulfate and concentrated under reduced pressure. Ethyl ether was added to the residue; the crystal precipitated was collected by filtration to yield 2.42 g of the title compound.

$^1$H-NMR (CDCl$_3$) δ ppm: 1.49–1.54 (4H, m), 1.75–1.95 (4H, m), 2.40 (3H, s), 3.31 (2H, t, J=7 Hz), 3.43 (2H, t, J=7 Hz), 7.72 (1H, s), 8.30 (1H, s).

Process B:

1.0 g of 6-(6-bromohexylthio)-7-methyl[1,2,4]triazolo[1, 5-b]pyridazine and 770 mg of 1-(diphenylmethyl)piperazine were dissolved in 10 ml of N,N-dimethylformamide; 500 mg of potassium carbonate was added, followed by stirring at room temperature for 18 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (20:1). The desired fraction was collected and concentrated; the residue was dissolved in 5 ml of ethyl acetate; 1.96 ml of a 4 N hydrogen chloride solution in ethyl acetate was added; the crystal precipitated was collected by filtration, washed with ethyl ether and dried to yield 0.98 g of the title compound.

Melting point: 180–182° C.; Elemental analysis (for $C_{29}H_{38}N_6SCl_2.0.4H_2O$): Calculated (%): C, 59.97; H, 6.73; N, 14.47; Found (%): C, 60.17; H, 6.55; N, 14.62.

EXAMPLE 55A

Production of 6-[2-[2-[4-(Diphenylmethyl)-1-piperazinyl]ethoxy]ethylthio]-7-methyl[1,2,4]triazolo[1,5-b]pyridazine Dihydrochloride Process A:

6-[2-(2-Bromoethoxy)ethylthio]-7-methyl[1,2,4]triazolo[1,5-b]pyridazine 5.57 g of methyl 3-mercaptopropionate was dissolved in 20 ml of methanol; 35.6 ml of a 2 N sodium methoxide solution in methanol and 2.0 g of 6-chloro-7-methyl[1,2,4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 30 ml of tetrahydrofuran; 2.98 ml of 2-bromoethyl ether was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with dichloromethane:ethyl acetate:methanol (30:30:1). The desired fraction was collected to yield 2.06 g of the title compound as an oily substance.

$^1$H-NMR (CDCl$_3$) δ ppm: 2.42 (3H, s), 3.50 (2H, t, J=6 Hz), 3.56 (2H, t, J=6 Hz), 3.86 (2H, t, J=6 Hz), 3.91 (2H, t, J=6 Hz), 7.74 (1H, s), 8.30 (1H, s).

Process B:

1.0 g of 6-[2-(2-bromoethoxy)ethylthio]-7-methyl[1,2,4]triazolo[1,5-b]pyridazine and 790 mg of 1-(diphenylmethyl)piperazine were dissolved in 10 ml of N,N-dimethylformamide; 520 mg of potassium carbonate was added, followed by stirring at room temperature for 23 hours. Ice water was added, followed by extraction with ethyl acetate; the extract was washed with saturated saline, dried over magnesium sulfate and concentrated under reduced pressure. The residue was subjected to silica gel column chromatography and eluted with dichloromethane:ethyl acetate:methanol (5:5:1). The desired fraction was collected and concentrated; the residue was dissolved in 5 ml of ethyl acetate; 1.55 ml of a 4 N hydrogen chloride solution in ethyl acetate was added; the crystal precipitated was collected by filtration, washed with ethyl ether and dried to yield 0.85 g of the title compound, which was then recrystallized from ethanol.

Melting point: 198–200° C.; Elemental analysis (for $C_{27}H_{34}N_6OSCl_2$): Calculated (%): C, 57.75; H, 6.10; N, 14.97; Found (%): C, 57.53; H, 6.00; N, 14.93.

EXAMPLE 56A

Production of 6-[6-[4-(Diphenylmethoxy)piperidino]hexylthio]-7-methyl[1,2,4]triazolo[1,5-b]pyridazine Fumarate 1.0 g of 6-(6-bromohexylthio)-7-methyl[1,2,4]triazolo[1,5-b]pyridazine and 810 mg of 4-(diphenylmethoxy)piperidine were dissolved in 10 ml of N,N-dimethylformamide; 500 mg of potassium carbonate was added, followed by stirring at room temperature for 24 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected and concentrated; the residue was dissolved in 10 ml of ethanol; 290 mg of fumaric acid was added, followed by concentration. Ethyl ether was added to the residue; the crystal precipitated was collected by filtration, washed with ethyl ether and dried to yield 1.43 g of the title compound.

Melting point 137–138° C.; Elemental analysis (for $C_{34}H_{41}N_5O_5S.0.5H_2O$): Calculated (%): C, 63.73; H, 6.61; N, 10.93; Found (%): C, 63.97; H, 6.44; N, 11.00.

EXAMPLE 57A

Production of 6-[2-[2-[4-(Diphenylmethoxy)piperidino]ethoxy]ethylthio]-7-methyl[1,2,4]triazolo[1,5-b]pyridazine Fumarate 1.09 g of 6-[2-(2-bromoethoxy)ethylthio]-7-methyl[1,2,4]triazolo[1,5-b]pyridazine and 840 mg of 4-(diphenylmethoxy)piperidine were dissolved in 10 ml of N,N-dimethylformamide; 520 mg of potassium carbonate was added, followed by stirring at room temperature for 23 hours. Ice water was added, followed by extraction with ethyl acetate; the extract was washed with saturated saline, dried over magnesium sulfate and concentrated under reduced pressure. The residue was subjected to silica gel column chromatography and eluted with dichloromethane:ethyl acetate:methanol (5:5:1). The desired fraction was collected; the residue was dissolved in 10 ml of ethanol; 200 mg of fumaric acid was added, followed by concentration. Ethyl ether was added to the residue; the crystal precipitated was collected by filtration, washed with ethyl ether and dried to yield 0.78 g of the title compound.

Melting point: 119–122° C.; Elemental analysis (for $C_{32}H_{31}N_5O_6S.0.5H_2O$): Calculated (%): C, 61.13; H, 6.09; N, 11.14; Found (%): C, 61.12; H, 5.82; N, 11.40.

EXAMPLE 58A

Production of 6-[2-[2-[4-(Diphenylmethoxy)piperidino]ethoxy]ethylthio][1,2,4]triazolo[1,5-b]pyridazine Fumarate 1.35 g of 6-[2-(2-bromoethoxy)ethylthio][1,2,4]triazolo[1,5-b]pyridazine and 1.19 g of 4-(diphenylmethoxy)piperidine were dissolved in 15 ml of N,N-dimethylformamide, 740 mg of potassium carbonate was added, followed by stirring at room temperature for 17 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected; the residue was dissolved in 10 ml of ethanol; 360 mg of fumaric acid was added, followed by concentration. Ethyl ether was added to the residue; the crystal precipitated was collected by filtration, washed with ethyl ether and dried to yield 1.64 g of the title compound.

Melting point: 110–111° C.; Elemental analysis (for $C_{31}H_{35}N_5O_6S.0.5H_2O$): Calculated (%): C, 60.57; H, 5.90; N, 11.39; Found (%): C, 60.35; H, 5.73; N, 11.16.

EXAMPLE 59A

Production of 6-[2-[2-[4-(Diphenylmethyl)-1-piperazinyl]ethoxy]ethylthio]-7-isopropyl[1,2,4]triazolo[1,5-b]pyridazine Dihydrochloride Process A:

6-[2-(2-Bromoethoxy)ethylthio]-7-isopropyl[1,2,4]triazolo[1,5-b]pyridazine 2.05 g of methyl 3-mercaptopropionate was dissolved in 10 ml of methanol; 7.64 ml of a 2 N sodium methoxide solution in methanol and 1.0 g of 6-chloro-7-isopropyl[1,2,4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 15 ml of tetrahydrofuran; 1.28 ml of 2-bromoethyl ether was added, followed by heating and refluxing for 2 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (20:1). The desired fraction was collected to yield 0.98 g of the title compound.

$^1$H-NMR (CDCl$_3$) δ ppm: 1.35 (6H, s), 3.15–3.30 (1H, m), 3.50 (2H, t, J=6 Hz), 3.55 (2H, t, J=6 Hz), 3.86 (2H, t, J=6 Hz), 3.91 (2H, t, J=6 Hz), 7.80 (1H, s), 8.31 (1H, s).

Process B:

0.98 g of 6-[2-(2-bromoethoxy)ethylthio]-7-isopropyl[1,2,4]triazolo[1,5-b]pyridazine and 720 mg of 1-(diphenylmethyl)piperazine were dissolved in 10 ml of N,N-dimethylformamide; 470 mg of potassium carbonate was added, followed by stirring at room temperature for 15 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected and concentrated; the residue was dissolved in 5 ml of ethyl acetate; 1.45 ml of a 4 N hydrogen chloride solution in ethyl acetate was added; the crystal precipitated was collected by filtration, washed with ethyl ether and dried to yield 1.04 g of the title compound, which was then recrystallized from ethanol.

Melting point: 143–145° C.; Elemental analysis (for C$_{29}$H$_{38}$N$_6$OSCl$_2$.H$_2$O): Calculated (%): C, 57.32; H, 6.64; N, 13.83; Found (%): C, 57.20; H, 6.43; N, 13.89.

EXAMPLE 60A

Production of 6-[2-[2-[4-(Diphenylmethyl)-1-piperazinyl]ethoxy]ethylthio]-7-t-butyl[1,2,4]triazolo[1,5-b]pyridazine Process A:

6-[2-(2-Bromoethoxy)ethylthio]-7-t-butyl[1,2,4]triazolo[1,5-b]pyridazine 2.23 g of methyl 3-mercaptopropionate was dissolved in 10 ml of methanol; 7.2 ml of a 2N sodium methoxide solution in methanol and 1.0 g of 6-chloro-7-t-butyl[1,2,4]triazolo[1,5-b]pyridazine were added, followed by heating and refluxing for 1 hour. After cooling, the mixture was concentrated under reduced pressure; ethyl acetate was added to the residue; the crystal precipitated was collected, washed with ethyl acetate and suspended in 20 ml of tetrahydrofuran; 1.19 ml of 2-bromoethyl ether was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:hexane (2:1). The desired fraction was collected to yield 1.06 g of the title compound.

$^1$H-NMR (CDCl$_3$) δ ppm: 1.56 (9H, s), 3.50 (2H, t, J=6 Hz), 3.58 (2H, t, J=6 Hz), 3.86 (2H, t, J=6 Hz), 3.92 (2H, t, J=6 Hz), 7.94. (1H, s), 8.32 (1H, s).

Process B:

1.06 g of 6-[2-(2-bromoethoxy)ethylthio]-7-t-butyl[1,2,4]triazolo[1,5-b]pyridazine and 740 mg of 1-(diphenylmethyl)piperazine were dissolved in 10 ml of N,N-dimethylformamide; 480 mg of potassium carbonate was added, followed by stirring at room temperature for 18 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (20:1). The desired fraction was collected and. concentrated; the crystal precipitated was collected by filtration, washed with ethyl ether and dried to yield 0.85 g of the title compound.

Melting point: 106–108° C.; Elemental analysis (for C$_{30}$H$_{38}$N$_6$OS): Calculated (%): C, 67.89; H, 7.22; N, 15.83; Found (%): C, 67.65; H, 7.33; N, 15.98.

EXAMPLE 61A

Production of 6-[2-[2-[4-(Diphenylmethyl)-1-piperazinyl]ethoxy]ethoxy]-7-isopropyl[1,2,4]triazolo[1,5-b]pyridazine 160 mg of 60% sodium hydride in oil was suspended in 20 ml of tetrahydrofuran; 1.20 g of [2-[4-(diphenylmethyl)-1-piperazinyl]ethoxy]ethanol was added, followed by heating and refluxing for 1 hour. After cooling, 610 mg of 6-chloro-7-isopropyl[1,2,4]triazolo[1,5-b]pyridazine was added, followed by heating and refluxing for 1 hour. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected; the crystal precipitated was collected by filtration, washed with ethyl ether and dried to yield 790 mg of the title compound.

Melting point: 119–120° C.; Elemental analysis (for C$_{29}$H$_{36}$N$_6$O$_2$.0.5H$_2$O): Calculated (%): C, 68.34; H, 7.32; N, 16.49; Found (%): C, 68.64; H, 7.31; N, 16.54.

EXAMPLE 62A

Production of 7-t-Butyl-6-[2-[2-[4-(Diphenylmethyl)-1-piperazinyl]ethoxy]ethoxy][1,2,4]triazolo[1,5-b]pyridazine Dihydrochloride 150 mg of 60% sodium hydride in oil was suspended in 20 ml of tetrahydrofuran; 1.05 g of [2-[4-(diphenylmethyl)-1-piperazinyl]ethoxy]ethanol was added, followed by heating and refluxing for 1 hour. After cooling, 650 mg of 7-t-butyl-6-chloro[1,2,4]triazolo[1,5-b]pyridazine was added, followed by heating and refluxing for 2 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate-:methanol (10:1). The desired fraction was collected; the residue was dissolved in 5 ml of ethyl acetate; 2.1 ml of a 4N hydrogen chloride solution in ethyl acetate was added; the crystal precipitated was collected by filtration, washed with ethyl ether and dried to yield 1.55 g of the title compound.

Melting point: 150–152° C.; Elemental analysis (for $C_{30}H_{40}N_6O_2Cl_2.0.5H_2O$): Calculated (%): C, 60.39; H, 6.92; N, 14.09; Found (%): C, 60.20; H, 6.64; N, 14.09.

EXAMPLE 63A

Production of 7-t-Butyl-6-[2-[2-[4-(Diphenylmethoxy)piperidino]ethoxy]ethoxy][1,2,4]triazolo[1,5-b]pyridazine Fumarate 120 mg of 60% sodium hydride in oil was suspended in 20 ml of tetrahydrofuran; 0.94 g of 2-[2-[4-(diphenylmethoxy)piperidino]ethoxy]ethanol was added, followed by heating and refluxing for 1 hour. After cooling, 530 mg of 7-t-butyl-6-chloro[1,2,4]triazolo[1,5-b]pyridazine was added, followed by heating and refluxing for 3 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected; the residue was dissolved in 10 ml of ethanol; 250 mg of fumaric acid a was added, followed by concentration. Ethyl ether was added to the residue; the crystal precipitated was collected by filtration, washed with ethyl ether and dried to yield 1.17 g of the title compound.

Melting point: 80–82° C.; Elemental analysis (for $C_{35}H_{43}N_5O_7.1.3H_2O$): Calculated (%): C, 62.82; H, 6.87; N, 10.46; Found (%): C, 62.89; H, 6.69; N, 10.22.

EXAMPLE 64A

Production of Ethyl 2-[6-[5-[4-(Diphenylmethoxy)piperidino]pentylamino]imidazo[1,2-b]pyridazin-2-yl]-2-methylpropionate Difumarate 1.41 g of 4-(diphenylmethoxy)-1-piperidinepentanamine and 0.536 g of ethyl 2-(6-chloroimidazo[1,2-b]pyridazin-2-yl)-2-methylpropionate were stirred at 190–200° C. for 3.5 hours. After cooling, ethyl acetate tetrahydrofuran (2:1) was added; the mixture was washed with aqueous sodium bicarbonate and saturated saline, dried over sodium sulfate and concentrated under reduced pressure. The residue was subjected to silica gel column chromatography and eluted with ethyl acetate:methanol:triethylamine (185:15:2). The desired fraction was collected, dissolved in 5 ml of ethanol; a solution of 235 mg of fumaric acid in 5 ml of methanol was added, followed by concentration. Ethyl ether was added to the residue; the resulting powder was collected by filtration, washed with ethyl ether and dried to yield 0.629 g of the title compound.

Melting point: 138° C.; Elemental analysis (for $C_{43}H_{53}N_5O_{11}$): Calculated (%): C, 63.30; H, 6.55; N, 8.58; Found (%): C, 64.24; H, 6.92; N, 8.42.

EXAMPLE 65A

Production of Ethyl 2-[6-[3-[4-(Diphenylmethoxy)piperidino]-2-hydroxypropylamino]imidazo[1,2-b]pyridazin-2-yl]-2-methylpropionate Difumarate 0.511 g of 1-amino-3-[4-(diphenylmethoxy)piperidino]-2-propanol and 0.268 g of ethyl 2-(6-chloroimidazo[1,2-b]pyridazin-2-yl)-2-methylpropionate were stirred at 190–200° C. for 3 hours. After cooling, ethyl acetate-tetrahydrofuran (2:1) was added; the mixture was washed with aqueous sodium bicarbonate and saturated saline, dried over magnesium sulfate and concentrated under reduced pressure. The residue was subjected to silica gel column chromatography and eluted with ethyl acetate:methanol:triethylamine (90:10:1). The desired fraction was collected, dissolved in 5 ml of ethyl acetate; a solution of 82 mg of fumaric acid in 5 ml of methanol was added, followed by concentration. Ethyl ether was added to the residue; the resulting powder was collected by filtration, washed with ethyl ether and dried to yield 0.223 g of the title compound.

Melting point: 145° C.; Elemental analysis (for $C_{41}H_{49}N_5O_{12}.Et_2O$): Calculated (%): C, 61.56; H, 6.77; N, 7.98; Found (%): C, 61.39; H, 6.49; N, 7.91.

EXAMPLE 66A

Production of Ethyl 2-[6-[3-[4-[bis(4-Fluorophenyl)methoxy)piperidino]propylamino]imidazo[1,2-b]pyridazin-2-yl]-2-methylpropionate Difumarate 1.62 g of 4-[bis(4-fluorophenyl)methoxyl-1-piperidinepropanamine and 0.803 g of ethyl 2-(6-chloroimidazo[1,2-b]pyridazin-2-yl)-2-methylpropionate were stirred at 190–200° C. for 3 hours. After cooling, aqueous sodium bicarbonate and saline were added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (90:10:1). The desired fraction was collected, dissolved in 20 ml of ethyl acetate; a solution of 301 mg of fumaric acid in 10 ml of methanol was added, followed by concentration. Acetone was added to the residue; the crystal precipitate was collected by filtration, washed with acetone and dried to yield 0.966 g of the title compound.

Melting point: 159–161° C.; Elemental analysis (for $C_{41}H_{47}N_5O_{11}F_2.0.5H_2O$): Calculated (%): C, 59.13; H, 5.81; N, 8.41; Found (%): C, 58.94; H, 5.84; N, 8.34.

EXAMPLE 67A

Production of Ethyl 6-[3-[4-(Diphenylmethoxy)piperidino]propylamino]imidazo[1,2-b]pyridazine-2-carboxylate Difumarate 686 mg of 4-(diphenylmethoxy)-1-piperidinepropanamine and 477 mg of ethyl 6-chloroimidazo[1,2-b]pyridazine-2-carboxylate were dissolved in 7 ml of N,N-dimethylformamide; 0.73 ml of N-ethyldiisopropylamine was added, followed by stirring in an oil bath (80° C.) for 18.5 hours. After cooling, ice water and sodium chloride were added, followed by extraction with ethyl acetate-tetrahydrofuran (1:1); the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected, dissolved in 5 ml of ethyl acetate; a solution of 95 mg of fumaric acid in 5 ml of ethanol was added, followed by concentration. Acetone-ethyl ether (1:2) was added to the residue to cause recrystallization; the crystal precipitate was collected by filtration and washed with ethyl ether to yield 211 mg of the title compound.

Melting point: 176–179° C.; Elemental analysis (for $C_{38}H_{43}N_5O_{11}$): Calculated (%): C, 61.20; H, 5.81; N, 9.39; Found (%): C, 61.17; H, 5.98; N, 9.80.

EXAMPLE 68A

Production of Isopropyl 2-[6-[3-[4-(Diphenylmethoxy)piperidino]propoxy]imidazo[1,2-b]pyridazin-2-yl]-2-methylpropionate Difumarate 8.10 g of 4-(diphenylmethoxy)-1-piperidinepropanol was dissolved in 60 ml of N,N-dimethylformamide; 1.11 g of 60% sodium hydride in oil was added, followed by stirring at room temperature under reduced pressure for 1 hour. While the solution was ice cooled, 7.79 g of isopropyl 2-(6-chloroimidazo[1,2-b]pyridazin-2-yl]-2-methylpropionate was added, followed by stirring at constant temperature for 4 hours. Ice water was added, followed by extraction with ethyl acetate-tetrahydrofuran (1:1); the extract was washed with saturated saline, dried over magnesium sulfate and concentrated under reduced pressure. The residue was subjected to silica gel column chromatography and eluted with ethyl acetate. The desired fraction was collected and concentrated under reduced pressure. The residue was dissolved in 10 ml of ethanol; 476 mg of fumaric acid was added, followed by concentration again. The residue was crystallized by the addition of ethyl acetate, collected by filtration, washed with ethyl acetate and dried to yield 1.05 g of the title compound.

Melting point: 145–147° C.; Elemental analysis (for $C_{42}H_{50}N_4O_{12}$): Calculated (%): C, 62.83; H, 6.28; N, 6.98; Found (%): C, 62.50; H, 6.10; N. 7.04.

EXAMPLE 69A

Production of Ethyl 2-[6-[3-[4-[bis(4-Methylphenyl)methoxy]piperidino]propylamino]imidazo[1,2-b]pyridazin-2-yl]-2-methylpropionate Difumarate 2.11 g of 4-[bis(4-methylphenyl)methoxy]-1-piperidinepropanamine and 0.803 g of ethyl 2-[6-chloroimidazo[1,2-b]pyridazin-2-yl]-2-methylpropionate were stirred at 190–200° C. for 3 hours. After cooling, aqueous sodium bicarbonate was added, followed by extraction with ethyl acetate; the extract was washed with saturated saline, dried over sodium sulfate and concentrated under reduced pressure. The residue was subjected to silica gel column chromatography and eluted with ethyl acetate-:methanol:triethylamine (95:5:1). The desired fraction was collected, dissolved in 20 ml of ethyl acetate; a solution of 358 mg of fumaric acid in 20 ml of methanol was added, followed by concentration. Acetone was added to the residue; the crystal precipitated was collected by filtration, washed with acetone and dried to yield 0.901 g of the title compound.

Melting point: 159–161° C.; Elemental analysis (for $C_{43}H_{38}N_5O_{11}$): Calculated (%): C, 63.30; H, 6.55; N, 8.56; Found (%): C, 63.29; H, 6.32; N, 8.67.

EXAMPLE 70A

Production of N-[6-[3-[4-(Diphenylmethoxy)piperidino]propylamino]imidazo[1,2-b]pyridazine-2-carbonyl]glycine Ethyl Ester 1.90 g of 4-(diphenylmethoxy)-1-piperidinepropanamine and 1.38 g of N-(6-chloroimidazo[1,2-b]pyridazine-2-carbonyl)glycine ethyl ester were dissolved in 15 ml of 1-methyl-2-pyrrolidone; 0.841 ml of N-ethyldiisopropylamine was added, followed by stirring in an oil bath (90–100° C.) for 24 hours. After cooling, ice water were added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (95:5:1). The desired fraction was collected and recrystallized from ethyl acetate to yield 1.28 g of the title compound.

Melting point: 172–174° C.; Elemental analysis (for $C_{32}H_{38}N_6O_4 \cdot 0.5H_2O$): Calculated (%): C, 66.30; H, 6.78; N, 14.50; Found (%): C, 66.42; H, 6.68; N, 14.55.

EXAMPLE 71A

Production of N-[6-[3-[4-(Diphenylmethoxy)piperidino]propylamino]imidazo[1,2-b]pyridazine-2-carbonyl]glycine Ethyl Ester Dihydrochloride 0.628 g of N-[6-[3-[4-(diphenylmethoxy)piperidino]propylamino]imidazo[1,2-b]pyridazine-2-carbonyl]glycine ethyl ester was dissolved in 10 ml of tetrahydrofuran; 1.5 ml of a 4 N hydrogen chloride solution in ethyl acetate was added, followed by concentration under reduced pressure. To the residue, 10 ml of methanol was added, followed by concentration under reduced pressure. The crystal obtained was collected and washed with ethyl acetate to yield 0.658 g of the title compound.

Melting point: 205° C.; Elemental analysis (for $C_{32}H_{40}N_6O_4Cl_2$): Calculated (%): C, 59.72; H, 6.26; N, 13.06; Found (%): C, 59.74; H, 6.41; N, 12.63.

EXAMPLE 72A

Production of N-[6-[3-[4-(Diphenylmethoxy)piperidino]propylamino]imidazo[1,2-b]pyridazine-2-carbonyl]glycine 0.810 g of N-[6-[3-[4-(diphenylmethoxy)piperidino]propylamino]imidazo[1,2-b]pyridazine-2-carbonyl]glycine ethyl ester was dissolved in 4 ml of ethanol; 2 ml of a 1 N aqueous solution of sodium hydroxide was added, followed by stirring at room temperature for 3 hours. The mixture was concentrated under reduced pressure; ice water and 2.1 ml of 1 N hydrochloric acid were added to the residue, followed by extraction with ethyl acetate-tetrahydrofuran (1:2); the extract was washed with saturated saline, dried over magnesium sulfate and concentrated under reduced pressure. The residue was powdered by the addition of ethyl acetate, collected by filtration and washed with ethyl acetate to yield 0.183 g of the title compound.

Melting point: 171° C.; Elemental analysis (for $C_{30}H_{34}N_6O_4 \cdot 2H_2O \cdot AcOEt$): Calculated (%): C, 61.25; H, 6.95; N, 12.60; Found (%): C, 61.30; H, 6.74; N, 12.45.

EXAMPLE 73A

Production of 2-[6-[3-[4-(Diphenylmethoxy)piperidino]propylamino]imidazo[1,2-b]pyridazin-2-yl]-2-methylpropionamide Dihydrochloride 1.29 g of 4-(diphenylmethoxy)-1-piperidinepropanamine and 0.478 g of 2-(6-chloroimidazo[1,2-b]pyridazin-2-yl)-2-methylpropionamide were stirred at 190–200° C. for 70 minutes. After cooling, aqueous sodium bicarbonate was added, followed by extraction with ethyl acetate. The extract was washed with saline, dried over magnesium sulfate and concentrated under reduced pressure. The residue was subjected to silica gel column chromatography and eluted with ethyl acetate:methanol:triethylamine (90:10:1). The desired fraction was collected; the residue was dissolved in 10 ml of ethyl acetate; 1.5 ml of a 4 N hydrogen chloride solution in ethyl acetate was added, followed by concentration under reduced pressure. Ethyl acetate was added to the residue; the resulting powder was collected by filtration, washed with ethyl acetate and dried to yield 0.823 g of the title compound.

Melting point: 191° C.; Elemental analysis (for $C_{31}H_{40}N_6O_2Cl_2$.AcOEt): Calculated (%): C, 64.11; H, 7.38; N, 12.82; Found (%): C, 63.70; H, 7.27; N, 12.34.

EXAMPLE 74A

Production of 2-[6-[3-[4-(Diphenylmethoxy) piperidino]propylamino]imidazo[1,2-b]pyridazin-2-yl]-N,N,2-trimethylpropionamide Dihydrochloride 1.04 g of 4-(diphenylmethoxy)-1-piperidinepropanamine and 0.426 g of 2-(6-chloroimidazo[1,2-b]pyridazin-2-yl)-N,N,2-trimethylpropionamide were stirred at 190–200° C. for 60 minutes. After cooling, aqueous sodium bicarbonate was added, followed by extraction with ethyl acetate. The extract was washed with saline, dried over magnesium sulfate and concentrated under reduced pressure. The residue was subjected to silica gel column chromatography and eluted with ethyl acetate:methanol:triethylamine (85:15:1). The desired fraction was collected; the residue was dissolved in 10 ml of ethyl acetate; 1.5 ml of a 4 N hydrogen chloride solution in ethyl acetate was added, followed by concentration under reduced pressure. The residue was recrystallized from acetone to yield 0.823 g of the title compound.

Melting point: 183° C.; Elemental analysis (for $C_{33}H_{44}N_6O_2Cl_2$.1.5H$_2$O): Calculated (%): C, 60.54; H, 7.24; N, 11.84; Found (%): C, 60.48; H, 7.28; N, 11.90.

EXAMPLE 75A

Production of 2-[6-[3-[4-(Diphenylmethoxy) piperidino]propylamino]imidazo[1,2-b]pyridazin-2-yl)-2-methylpropanol 1.29 g of 4-(diphenylmethoxy)-1-piperidinepropanamine and 0.451 g of 2-(6-chloroimidazo[1,2-b]pyridazin-2-yl]-2-methylpropanol were stirred at 190–200° C. for 90 minutes. After cooling, aqueous sodium bicarbonate was added, followed by extraction with ethyl acetate. The extract was washed with saline, dried over magnesium sulfate and concentrated under reduced pressure. The residue was subjected to silica gel column chromatography and eluted with ethyl acetate:methanol:triethylamine (90:10:1). The desired fraction was collected; the residue was recrystallized from ethyl ether to yield 0.465 g of the title compound.

Melting point: 105–108° C.; Elemental analysis (for $C_{31}H_{39}N_5O_2$.0.5H$_2$O): Calculated (%): C, 71.24; H, 7.71; N, 13.40; Found (%): C, 71.22; H, 7.87; N, 13.32.

EXAMPLE 76A

Production of N-[6-[3-[4-(Diphenylmethoxy) piperidino]propylamino]imidazo[1,2-b]pyridazine-2-carbonyl]-2,2-dimethylglycine Ethyl Ester Dihydrochloride 1.23 g of 4-(diphenylmethoxy)-1-piperidinepropanamine and 1.18 g of N-(6-chloroimidazo[1,2-b]pyridazine-2-carbonyl]-2,2-dimethylglycine ethyl ester were dissolved in 15 ml of N,N-dimethylformamide; 1.31 ml of N-ethyldiisopropylamine was added, followed by stirring at 70° C. for 9.5 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected, concentrated under reduced pressure and dissolved in 5 ml of ethyl acetate; 0.28 ml of a 4 N hydrogen chloride solution in ethyl acetate was added, followed by concentration again. Ethyl acetate was added to the residue; the crystal precipitated was collected by filtration, washed with ethyl ether and dried to yield 284 mg of the title compound.

Melting point: 194–196° C.; Elemental analysis (for $C_{34}H_{44}N_6O_4Cl_2$): Calculated (%): C, 60.80; H, 6.60; N, 12.51; Found (%): C, 60.82; H, 6.67; N, 12.77.

EXAMPLE 77A

Production of Ethyl 2-[6-[3-[4-(Diphenylmethyl) piperazino]propylamino]imidazo[1,2-b]pyridazin-2-yl]-2-methylpropionate Trihydrochloride 1.31 g of 4-(diphenylmethyl)-1-piperazinepropanamine and 567 mg of ethyl 2-(6-chloroimidazo[1,2-b]pyridazin-2-yl]-2-methylpropionate were stirred at 185° C. for 3 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected, concentrated under reduced pressure and dissolved in 5 ml of ethyl acetate; 0.80 ml of a 4 N hydrogen chloride solution in ethyl acetate was added, followed by concentration again. Ethanol was added to the residue; the crystal precipitated was collected by filtration, washed with ethanol-ethyl acetate (1:3) and dried to yield 502 mg of the title compound.

Melting point: 190–193° C.; Elemental analysis (for $C_{32}H_{43}N_6O_2Cl_3$.H$_2$O): Calculated (%): C, 57.53; H, 6.79; N, 12.58; Found (%): C, 57.27; H, 6.52; N, 12.55.

EXAMPLE 78A

Production of 2-[6-[4-[4-(Diphenylmethoxy) piperidino]butylamino]imidazo[1,2-b]pyridazin-2-yl]-2-methylpropionic Acid 1.56 g of 4-(diphenylmethoxy)-1-piperidinebutanamine and 617 mg of ethyl 2-(6-chloroimidazo[1,2-b]pyridazin-2-yl)-2-methylpropionate were stirred at 185° C. for 3 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected, concentrated under reduced pressure and dissolved in 5 ml of ethyl acetate; 0.52 ml of a 4 N hydrogen chloride solution in ethyl acetate was added, followed by concentration. The residue was dissolved in 4 ml of ethanol; 4 ml of a 1 N aqueous solution of sodium hydroxide was added, followed by stirring at room temperature for 4 hours; 1 ml of a 2 N aqueous solution of sodium hydroxide was added, followed by stirring at 50° C. for 16 hours. The mixture was concentrated under reduced pressure. The residue was diluted with water and washed with ethyl acetate; the water layer was adjusted to pH 4.5 by the addition of 4 N hydrochloric acid and extracted with ethyl acetate-tetrahydrofuran (1:1); the extract was washed with saturated saline, dried over magnesium sulfate and concentrated under reduced pressure. The residue was powdered by the addition of ethyl acetate, collected by filtration and dried to yield 271 mg of the title compound.

Amorphous; Elemental analysis (for $C_{32}H_{39}N_5O_3 \cdot 2.1H_2O$, 0.5AcOEt): Calculated (%): C, 65.49; H, 7.63; N, 11.23; Found (%): C, 65.23; H, 7.29; N, 11.19.

EXAMPLE 79A

Production of 2-[6-[2-[4-(Diphenylmethoxy) piperidino]ethylamino]imidazo[1,2-b]pyridazin-2-yl]-2-methylpropionic Acid Process A:

Production of Isopropyl 2-[6-(2-Hydroxyethylamino] imidazo[1,2-b]pyridazin-2-yl]-2-methylpropionate 130 mg of 2-aminoethanol and 300 mg of isopropyl 2-(6-chloroimidazo[1,2-b]pyridazin-2-yl]-2-methylpropionate were stirred at 170° C. for 4 hours. After cooling, 260 mg of 2-aminoethanol was added, followed by stirring at 170° C. for 45 minutes. After cooling, water was added, followed by extraction with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected and concentrated under reduced pressure; the crystal precipitated was collected by filtration and dried to yield 145 mg of the title compound.

$^1$H-NMR (CDCl$_3$) δ ppm: 1.29 (3H, s), 1.32 (3H, s), 1.64 (6H, s), 3.44 (2H, td, J=4.6, 6.1 Hz), 3.88 (2H, t, J=4.6 Hz), 4.96–5.15 (1H, m), 5.43 (1H, t, J=6.2 Hz), 5.72 (1H, d, J=9.7 Hz), 6.98 (1H, d, J=9.7 Hz), 7.45 (1H, s).

Process B:

Production of Isopropyl 2-[6-[(2-Methanesulfonyloxy) ethylamino]imidazo[1,2-b]pyridazin-2-yl]-2-methylpropionate 2.18 g of isopropyl 2-[6-(2-hydroxyethylamino)imidazo[1,2-b]pyridazin-2-yl]-2-methylpropionate was suspended in 20 ml of tetrahydrofuran; 2.45 ml of N-ethyldiisopropylamine and 1.10 ml of methanesulfonyl chloride were added, followed by stirring at room temperature for 1 hour. Ice water was added, followed by extraction with ethyl acetate; the extract was washed with saturated saline, dried over magnesium sulfate and concentrated under reduced pressure and dried to yield 2.37 g of the title compound.

$^1$H-NMR (CDCl$_3$) δ ppm: 1.19 (3H, s), 1.22 (3H, s), 1.63 (6H, s), 3.40 (3H, s), 3.74 (2H, td, J=5.1, 5.4 Hz), 4.48 (2H, t, 5.1 Hz), 4.76 (1H, t, J=5.4 Hz), 4.95–5.12 (1H, m), 6.39 (1H, d, J=9.6 Hz), 7.54 (1H, s), 7.62 (1H, d, J=9.6 Hz).

Process C:

Production of Isopropyl 2-[6-[2-[4-(Diphenylmethoxy) piperidino]ethylamino]imidazo[1,2-b]pyridazin-2-yl]-2-methylpropionate 1.13 g of isopropyl 2-[6-[2-(methanesulfonyloxy) ethylamino]imidazo[1,2-b]pyridazin-2-yl]-2-methylpropionate was dissolved in 15 ml of N,N-dimethylformamide; 943 mg of 4-(diphenylmethoxy) piperidine, 586 mg of potassium iodide and 488 mg of potassium carbonate were added, followed by stirring at 60° C. for 2 hours. Ice water was added; the mixture was saturated with sodium chloride and extracted with ethyl acetate; the extract was washed with saturated saline, dried over magnesium sulfate and concentrated under reduced pressure. The residue was subjected to silica gel column chromatography and eluted with ethyl acetate:methanol (10:1). The desired fraction was collected, concentrated under reduced pressure and dried to yield 571 mg of the title compound.

$^1$H-NMR (CDCl$_3$). δ ppm: 1.18 (3H, s), 1.21 (3H, s), 1.60–1.20 (4H, m), 1.62.(6H, s), 2.10–2.30 (2H, m), 2.59 (2H, t, J=5.6 Hz), 2.70–2.85 (2H, m), 3.35 (2H, dt, J=5.3, 5.6 Hz), 3.35–3.55 (1H, m), 4.90–5.10 (1H, m), 5.05 (1H), 5.53 (1H, s), 6.39 (1H, d, J=9.4 Hz), 7.16–7.39 (10H, m), 7.54 (1H, s), 7.57 (1H, d, J=9.4 Hz).

Process D:

565 mg of isopropyl 2-[6-[2-[4-(diphenylmethoxy) piperidino]ethylamino]imidazo[1,2-b]pyridazin-2-yl]-2-methylpropionate was dissolved in 4 ml of ethanol; 2.04 ml of a 1N aqueous sodium hydroxide solution was added, followed by refluxing for 20 hours. After cooling, the mixture was concentrated under reduced pressure. The residue was diluted with water and adjusted to pH 5.5 by the addition of 1 N hydrochloric acid. Ethyl acetate was added; the crystal precipitated was collected by filtration, washed with water and ethyl acetate and dried to yield 443 mg of the title compound.

Melting point: 194–198° C.; Elemental analysis (for $C_{30}H_{35}N_5O_3 \cdot 2.5H_2O$): Calculated (%): C, 64.50; H, 7.22; N, 12.54; Found (%): C, 64.57; H, 7.03; N, 12.58.

EXAMPLE 80A

Production of [6-[3-[4-(Diphenylmethoxy) piperidino]propylamino]imidazo[1,2-b]pyridazin-2-yl]-2-carboxylic Acid 876 mg of ethyl [6-[3-[4-(diphenylmethoxy)piperidino] propylamino]imidazo[1,2-b]pyridazin-2-yl]-2-carboxylate was dissolved in 5 ml of ethanol; 1.9 ml of a 1 N aqueous sodium hydroxide solution was added, followed by stirring at room temperature for 3 hours. After the mixture was concentrated under reduced pressure. The residue was diluted with water and washed with ethyl acetate; the water layer was adjusted to pH 5 by the addition of 1 N hydrochloric acid. The crystal precipitated was collected by filtration, washed with water and ethyl acetate and dried to yield 256 mg of the title compound.

Melting point: 152–155° C.; Elemental analysis (for $C_{28}H_{31}N_5O_3 \cdot 1.5H_2O$): Calculated (%): C, 65.61; H, 6.69; N, 13.66; Found (%): C, 65.52; H. 6.61; N, 13.61.

EXAMPLE 81A

Production of Ethyl 2-[3-Chloro-6-[3-[4-(diphenylmethoxy)piperidino]propoxy]imidazo[1,2-b]pyridazin-2-yl]-2-methylpropionate 0.5 Fumarate 334 mg of 4-(diphenylmethoxy)-1-piperidinepropanol was dissolved in 20 ml of N,N-dimethylformamide; 45 mg of a 60% dispersion of sodium hydride in mineral oil was added, followed by stirring at room temperature under reduced pressure for 35 minutes. 310:mg of ethyl 2-[3,6-dichloroimidazo[1,2-b]pyridazin-2-yl]-2-methylpropionate was then added, followed by stirring at 0° C. for 2 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate. The desired fraction was collected; the crystal precipitated was dissolved in 5 ml of ethanol; 160 mg of fumaric acid was added, followed by concentration under reduced pressure. Ethyl acetate was added to the residue; the mixture was washed with aqueous sodium bicarbonate and saturated saline, dried over magnesium sulfate and concentrated under reduced pressure. Ethyl acetate was added to the residue to cause crystallization; the crystal precipitated was collected by filtration, washed with ethyl ether and dried to yield 168 mg of the title compound.

Melting point: 186–188° C.; Elemental analysis (for $C_{35}H_{41}N_4O_6Cl.0.5H_2O$): Calculated (%): C, 63.87; H, 6.43; N, 8.51; Found (%): C, 63.33; H, 6.34; N, 8.85.

EXAMPLE 82A

Production of Ethyl 2-[3-Chloro-6-[3-[4-(diphenylmethyl)-1-piperazinyl]propoxylimidazo[1,2-b]pyridazin-2-yl]-2-methylpropionate Dihydrochloride 1.0 g of 4-(diphenylmethyl)-1-piperazinepropanol was dissolved in 10 ml of N,N-dimethylformamide; 142 mg of a 60% dispersion of sodium hydride in mineral oil was added, followed by stirring at room temperature under reduced pressure for 40 minutes. To the reaction mixture, 973 mg of ethyl 2-(3,6-dichloroimidazo[1,2-b]pyridazin-2-yl)-2-methylpropionate was added, followed by stirring at 0° C. for 2 hours. Ice water was added, followed by extraction with ethyl acetate; the extract was washed with saturated saline, dried over magnesium sulfate and concentrated under reduced pressure. The residue was subjected to silica gel column chromatography and eluted with hexane:ethyl acetate:triethylamine (50:50:1). The desired fraction was collected and concentrated under reduced pressure; the crystal precipitated was dissolved in 5 ml of ethyl acetate; 1.01 ml of a 4 N hydrogen chloride solution in ethyl acetate acid was added, followed by concentration again. The residue was recrystallized from methanol, collected by filtration, washed with ethyl acetate and dried to yield 424 mg of the title compound.

Melting point: 203–205° C.; Elemental analysis (for $C_{32}H_{40}N_5OCl_3.H_2O$): Calculated (%): C, 57.62; H, 6.35; N, 10.50; Found (%): C, 57.60; H, 6.37; N, 10.15.

EXAMPLE 83A

Production of Ethyl 2-[3-Chloro-6-[3-[4-(diphenylmethoxy)piperidino]propylamino]imidazo[1,2-b]pyridazin-2-yl]-2-methylpropionate Dihydrochloride 2.56 g of 4-(diphenylmethoxy)-1-piperidinepropanamine and 1.19 g of ethyl 2-[3,6-dichloroimidazo[1,2-b]pyridazin-2-yl]-2-methylpropionate were stirred at 160° for 3 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and dissolved in 5 ml of ethyl acetate; 0.80 ml of a 4 N hydrogen chloride solution in ethyl acetate was added, followed by concentration. The residue was powdered by the addition of ether and dried to yield 1.33 g of the title compound.

Amorphous;

Elemental analysis (for $C_{33}H_{42}N_5O_3Cl_3.0.5H_2O$): Calculated (%): C, 58.97; H, 6.45; N, 10.42; Found (%): C, 58.98; H, 6.64; N, 10.42.

EXAMPLE 84A

Production of Ethyl 2-[3-Chloro-6-[3-[4-(diphenylmethyl)-1-piperazinyl]propylamino]imidazo[1,2-b]pyridazin-2-yl]-2-methylpropionate Trihydrochloride 1.75 g of 4-(diphenylmethyl)-1-piperazinepropanamine and 854 mg of ethyl 2-[3,6-dichloroimidazo[1,2-b]pyridazin-2-yl]-2-methylpropionate were stirred at 160° C. for 4 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol (30:1). The desired fraction was collected, concentrated under reduced pressure and dissolved in 5 ml of ethyl acetate; 1.55 ml of a 4 N solution of hydrogen chloride in ethyl acetate was added, followed by concentration again. The crystal precipitated was washed by the addition of ethanol-ethyl acetate (1:3), collected by filtration and dried to yield 628 mg of the title compound.

Melting point: 203–205° C.; Elemental analysis (for $C_{32}H_{42}N_6O_2Cl_4.H_2O$): Calculated (%): C, 54.71; H, 6.31; N, 11.96; Found (%): C, 54.88; H, 6.07; N, 11.97.

EXAMPLE 85A

Production of 2-[3-Chloro-6-[3-[4-(diphenylmethyl)-1-piperazinyl]propylamino]imidazo[1,2-b]pyridazin-2-yl]-2-methylpropionic Acid 633 mg of ethyl 2-[3-chloro-6-[3-[4-(diphenylmethyl)-1-piperazinyl]propylamino]imidazo[1,2-b]pyridazin-2-yl]-2-methylpropionate trihydrochloride was dissolved in 6 ml of ethanol; 2.31 ml of a 2 N aqueous solution of sodium hydroxide was added, followed by thermal refluxing for 1.5 hours. After cooling, the mixture was concentrated under reduced pressure. The residue was diluted with water and washed with ethyl acetate; the water layer was adjusted to pH 5 by the addition of 1 N hydrochloric acid. Methanol was added; the crystal precipitated was collected by filtration, washed with water-ethyl acetate and dried to yield 462 mg of the title compound.

Melting point: 184–186° C.; Elemental analysis (for $C_{30}H_{35}N_6O_2Cl.H_2O$): Calculated (%): C, 63.76; H, 6.60; N, 14.87; Found (%): C, 63.49; H, 6.52; N, 14.81.

EXAMPLE 86A

Production of 2-[6-[2-[4-(Diphenylmethyl)-1-piperazinyl]ethylamino]imidazo[1,2-b]pyridazin-2-yl]-2-methylpropionic Acid Process A:

Production of Isopropyl 2-[6-[2-[4-Diphenylmethyl)-1-piperazinyl]ethylamino]imidazo[1,2-b]pyridazin-2-yl]-2-methylpropionate 1.24 g of isopropyl 2-[6-[2-(methanesulfonyloxy)ethylamino]imidazo[1,2-b]pyridazin-2-yl]-2-methylpropionate was dissolved in 15 ml of N,N-dimethylformamide; 977 mg of 1-(diphenylmethyl)piperazine, 642 mg of potassium iodide and 535 mg of potassium carbonate were added, followed by stirring at room temperature for 1 hour and at 60° C. for 1.5 hours. Ice water and sodium chloride were added, followed by extraction with ethyl acetate; the extract was washed with saturated saline, dried over magnesium sulfate and concentrated under reduced pressure. The residue was subjected to silica gel column chromatography and eluted with ethyl acetate. The desired fraction was collected, concentrated under reduced pressure and dried to yield 570 mg of the title compound.

$^1$H-NMR (CDCl$_3$) δ ppm: 1.17 (3H, s), 1.20 (3H, s), 1.62 (6H, s), 2.36–2.60 (8H, m), 2.63 (2H, t, J=5.8 Hz), 3.37 (2H, dt, J=5.6, 5.8 Hz), 4.24 (1H, s), 4.37 (1H), 4.90–5.10 (1H, m), 6.38 (1H, d, J=9.6 Hz), 7.13–7.44 (10H, m), 7.52 (1H, s), 7.55 (1H, d, J=9.4 Hz).

Process B:

565 mg of isopropyl 2-[6-[2-[4-(diphenylmethyl)-1-piperazinyl]ethylamino]imidazo[1,2-b]pyridazin-2-yl]-2-methylpropionate was dissolved in 4 ml of ethanol; 2.09 ml of a 1N aqueous solution of sodium hydroxide was added, followed by thermal refluxing for 19 hours. After cooling, the mixture was concentrated under reduced pressure. The residue was diluted with water and adjusted to pH 5 by the addition of 1 N hydrochloric acid. Ethyl acetate was added; the crystal precipitated was collected, washed with water and methanol and recrystallized from N,N-dimethylformamide-ethyl acetate (5:1), collected by filtration, washed with ethyl acetate and dried to yield 249 mg of the title compound.

Melting point: 192–194° C.; Elemental analysis (for C$_{29}$H$_{34}$N$_6$)$_2$.3.0H$_2$O): Calculated (%): C, 63.02; H, 7.30; N, 15.21; Found (%): C, 62.99; H, 6.72; N, 15.01.

EXAMPLE 87A

Production of 2-[3-Chloro-6-[3-[4-(diphenylmethoxy)piperidino]propylamino]imidazo [1,2-b]pyridazin-2-yl]-2-methylpropionic Acid 653 mg of ethyl 2-[3-chloro-6-[3-[4-(diphenylmethoxy)piperidino]propylamino]imidazo[1,2-b]pyridazin-2-yl]-2-methylpropionate dihydrochloride was dissolved in 6 ml of ethanol; 1.97 ml of a 2 N aqueous solution of sodium hydroxide was added, followed by thermal refluxing for 2.5 hours. After cooling, the mixture was concentrated under reduced pressure. The residue was diluted with water and washed with ethyl acetate; the water layer was adjusted to pH 4.5 by the addition of 1 N hydrochloric acid. Acetone was added; the crystal precipitated was collected by filtration, washed with water-acetone (5:1) and dried to yield 465 mg of the title compound.

Melting point: 133–135° C.; Elemental analysis (for C$_{31}$H$_{36}$N$_6$O$_3$Cl.H$_2$O): Calculated (%): C, 64.18; H, 6.60; N, 12.07; Found (%): C, 64.16; H, 6.64; N, 12.33.

EXAMPLE 88A

Production of 2-[3-Chloro-6-[3-[4-(diphenylmethyl)-1-piperazinyl]propoxy]imidazo[1,2-b]pyridazin-2-yl]-2-methylpropionic Acid 458 mg of ethyl 2-[3-chloro-6-[3-[4-(diphenylmethyl)-1-piperazinyl]propoxy]imidazo[1,2-b]pyridazin-2-yl]-2-methylpropionate trihydrochloride was dissolved in 4 ml of 2-propanol; 1.34 ml of a 2 N aqueous solution of sodium hydroxide was added, followed by stirring at 80° C. for 1.5 hours, after which 0.3 ml of a 2 N aqueous solution of sodium hydroxide was added, followed by thermal refluxing for 2 hours. After cooling, the mixture was concentrated under reduced pressure. The residue was diluted with water and washed with ethyl acetate; the water layer was adjusted to pH 4 by the addition of 1 N hydrochloric acid, followed by extraction with ethyl acetate; the extract was dried over sodium sulfate and concentrated under reduced pressure and crystallized by the addition of ethyl acetate-ethyl ether-hexane (2:5:1), collected by filtration, washed with ethyl ether and dried to yield 125 mg of the title compound.

Melting point: 118–121° C.; Elemental analysis (for C$_{30}$H$_{34}$N$_5$O$_3$Cl.1.5H$_2$O): Calculated (%): C, 62.65; H, 6.48; N, 12.18; Found (%): C, 62.95; H, 6.47; N, 11.76.

EXAMPLE 89A

Production of 2-[6-[3-[4-(Diphenylmethoxy) piperidino]propoxy]-7-methylimidazo[1,2-b] pyridazin-2-yl]-2-methylpropionic Acid To 10 ml of N,N-dimethylformamide, 0.16 g of a 60% dispersion of sodium hydride in mineral oil and 1.30 g of 4-(diphenylmethoxy)-1-piperidinepropanol were added, followed by stirring at room temperature under reduced pressure for 1 hour. While the reaction mixture was cooled with ice water, 1.31 g of isopropyl 2-(6-chloro-7-methylimidazo [1,2-b]pyridazin-2-yl)-2-methylpropionate was added, followed by stirring at room temperature for 1.5 hours. To the reaction mixture, ice water was added, followed by extraction with ethyl acetate; the extract was washed with saline, dried over magnesium sulfate and concentrated under reduced pressure. The residue was subjected to silica gel column chromatography and eluted with hexane:ethyl acetate (1:5). The desired fraction was collected to yield 582 mg of isopropyl 2-[6-[3-[4-(diphenylmethoxy)piperidino] propoxy)-7-methylimidazo[1,2-b]pyridazin-2-yl]-2-methylpropionate as an oily substance. This oily substance was dissolved in 4 ml of ethanol; 2 ml of a 1 N aqueous solution of sodium hydroxide was added and reaction mixture was heated under reflux for 7 hours. After cooling, reaction mixture was concentrated under reduced pressure followed by extraction with ethyl acetate-tetrahydrofuran (1:1); the extract was washed with saturated saline, dried over magnesium sulfate and concentrated under reduced pressure. The residue was crystallized by the addition of a small amount of water and ethyl ether, collected by filtration, washed with ethyl ether and dried to yield 0.413 g of the title compound.

Melting point: 122° C.; Elemental analysis (for C$_{32}$H$_{38}$N$_4$O$_4$.1.5H$_2$O): Calculated (%): C, 67.47; H. 7.25; N, 9.83; Found (%): C, 67.61; H, 7.13; N, 9.68.

EXAMPLE 90A

Production of 2-[6-[3-[4-(Diphenylmethoxy) piperidino]propylamino]-7-methylimidazo[1,2-b] pyridazin-2-yl]-2-methylpropionic Acid Dihydrochloride 1.40 g of 4-(diphenylmethoxy)-1-piperidinepropanamine and 0.636 g of isopropyl 2-(6-chloro-7-methylimidazo[1,2-b]pyridazin-2-yl)-2-methylpropionate were stirred at 190–200° C. for 3 hours. After cooling, aqueous sodium bicarbonate was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (185:15:2). The desired fraction was collected to yield 0.737 g of isopropyl 2-[6-[3-[4-(diphenylmethoxy) piperidino]propylamino]-7-methylimidazo[1,2-b]pyridazin-2-yl]-2-methylpropionate as an oily substance. This oily substance was dissolved in 6 ml of ethanol; 3.15 ml of a 1 N aqueous solution of sodium hydroxide was added, followed by thermal refluxing for 7 hours. After cooling, the mixture was concentrated under reduced pressure; under ice cooling conditions, 1.89 ml of 1 N hydrochloric acid was added; the residue was washed with ethyl acetate. To the water layer, 1.89 ml of 1 N hydrochloric acid was added to saturate with sodium chloride, followed by extraction with ethyl acetate-tetrahydrofuran (1:1); the extract was washed with saturated saline, dried over magnesium sulfate and concentrated under reduced pressure; 1.89 ml of 1 N hydrochloric acid was added to the residue, followed by concentration to dryness under reduced pressure. The residue was crystallized by the addition of ethyl ether, collected by filtration, washed with ethyl ether and dried to yield 0.445 g of the title compound.

Melting point: 202° C. (decomposed); Elemental analysis (for $C_{32}H_{41}N_5O_3Cl_2.0.5H_2O$): Calculated (%): C, 61.63; H, 6.79; N, 11.23; Found (%): C, 61.66; H, 6.83; N, 11.11.

EXAMPLE 91A

Production of Pivaloyloxymethyl 2-[6-[3-(4-Diphenylmethoxy)piperidino]propylamino]imidazo[1,2-b]pyridazin-2-yl]-2-methylpropionate Difumarate 1.36 g of ethyl 2-[6-[3-(4-diphenylmethoxy)piperidino]propylamino]imidazo[1,2-b]pyridazin-2-yl]-2-methylpropionate difumarate was suspended in 20 ml of ethyl acetate and washed with aqueous sodium bicarbonate; the ethyl acetate layer was dried over magnesium sulfate and concentrated under reduced pressure. The residue was dissolved in 8 ml of ethanol; 4.3 ml of a 1 N aqueous solution of sodium hydroxide was added, followed by stirring at room temperature for 40 hours. The mixture was concentrated under reduced pressure; while the residue was cooled with ice, 4.3 ml of 1 N hydrochloric acid and saline were added, followed by extraction with ethyl acetate-tetrahydrofuran (1:1); the extract was washed with saturated saline, dried over magnesium sulfate and concentrated under reduced pressure. The residue was dissolved in 5 ml of N,N-dimethylformamide; 0.374 ml of chloromethyl pivalate and 0.357 g of potassium carbonate were added, followed by stirring at room temperature for 20 hours. Ice water was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (185:15:2). The desired fraction was collected, dissolved in 10 ml of ethyl acetate; a solution of 227 mg of fumaric acid in 5 ml of methanol was added, followed by concentration. The residue was recrystallized from ethyl acetate to yield 0.772 g of the title compound.

Melting point: 164–167° C.; Elemental analysis (for $C_{45}H_{55}N_5O_{13}$): Calculated (%): C, 61.84; H, 6.34; N, 8.01; Found (%): C, 61.83; H, 6.30; N, 8.10.

EXAMPLE 92A

Production of Ethyl 2-[6-[4-[4-(Diphenylmethoxy)piperidino]butyl]imidazo[1,2-b]pyridazin-2-yl]-2-methylpropionate Dihydrochloride Process A:
Production of Ethyl 2-[6-(4-Chlorobutyl)imidazo[1,2-b]pyridazin-2-yl]-2-methylpropionate 5.0 g of 1-chloro-4-iodobutane was dissolved in 50–5 ml of toluene-N,N-dimethylacetamide; 2.24 g of copper-activated zinc was added, followed by stirring at 80° C. in a nitrogen atmosphere for 3.5 hours. After cooling, 3.06 g of ethyl 2-(6-chloroimidazo[1,2-b]pyridazin-2-yl)-2-methylpropionate and 160 mg of dichlorobis(triphenylphosphine)palladium(II) were added, followed by stirring at 80° C. for 4 hours. After cooling, water and ethyl acetate were added; the insoluble substances were filtered off through Celite; after the water layer was separated, the organic layer was washed with saturated saline, dried over magnesium sulfate and concentrated under reduced pressure. The residue was subjected to silica gel column chromatography and eluted with hexane:ethyl acetate (1:1). The desired fraction was collected, concentrated under reduced pressure and dried to yield 1.74 g of the title compound.

$^1$H-NMR (CDCl$_3$) δ ppm: 1.23 (3H, t, J=6.8 Hz), 1.68 (6H, s), 1.80–2.00 (4H, m), 2.84 (2H, t, J=7.2 Hz), 3.59 (2H, t, J=6.0 Hz), 4.17 (2H, q, J=7.1 Hz), 6.89 (1H, d, J=9.5 Hz), 7.80 (1H, s), 7.82 (1H, d, J=9.2 Hz).

Process B:
828 mg of ethyl 2-[6-(4-chlorobutyl)imidazo[1,2-b]pyridazin-2-yl]-2-methylpropionate was dissolved in 10 ml of acetonitrile; 752 mg of 4-(diphenylmethoxy)piperidine, 552 mg of potassium iodide and 460 mg of potassium carbonate were added, followed by stirring at 60° C. for 4 hours, after which the mixture was thermally refluxed for 18 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (100:5:2). The desired fraction was collected, concentrated under reduced pressure, dissolved in 5 ml of ethyl acetate; 1.01 ml of a 4 N solution of hydrogen chloride in ethyl acetate was added, followed by concentration under reduced pressure. The residue was powdered from ethyl ether, collected by filtration and dried to yield 1.18 g of the title compound.

Amorphous; Elemental analysis (for $C_{34}H_{44}N_4O_3Cl_2.H_2O$): Calculated (%): C, 63.25; H, 7.18; N, 8.68; Found (%): C, 63.10; H, 7.43; N, 8.64.

EXAMPLE 93A

Production of Sodium 2-[6-[4-[4-(Diphenylmethoxy)piperidino]butyl]imidazo[1,2-b]pyridazin-2-yl]-2-methylpropionate 631 mg of ethyl 2-[6-[4-[4-(diphenylmethoxy)piperidino]butyl]imidazo[1,2-b]pyridazin-2-yl]-2-methylpropionate dihydrochloride was dissolved in 4 ml of ethanol; 5.5 ml of a 1 N aqueous solution of sodium hydroxide was added, followed by thermal refluxing for 3 hours. After cooling, the mixture was concentrated under reduced pressure. The residue was diluted with water and adjusted to pH 5.5 by the addition of 1 N hydrochloric acid. Acetone was added to cause crystallization; the crystal precipitated was washed with water-acetone (2:1) and dried to yield 345 mg of the title compound.

Melting point: 177–179° C.; Elemental analysis (for $C_{32}H_{31}N_4O_3Na.1.75H_2O$): Calculated (%): C, 66.25; H, 7.04; N, 9.66; Found (%): C, 66.13; H, 6.93; N, 9.81.

EXAMPLE 94A

Production of Ethyl 2-[6-[4-[4-(Diphenylmethyl)-1-piperazinyl]butyl]imidazo[1,2-b]pyridazin-2-yl]-2-methylpropionate 921 mg of ethyl 2-[6-(4-chlorobutyl)imidazo[1,2-b]pyridazin-2-yl]-2-methylpropionate was dissolved in 10 ml of N,N-dimethylformamide; 789 mg of 1-(diphenylmethyl) piperazine, 433 mg of potassium iodide and 520 mg of potassium carbonate were added, followed by stirring at 60° C. for 5 hours. After cooling, ethyl acetate was added; the mixture was washed with saturated saline, dried over magnesium sulfate and concentrated under reduced pressure. The residue was subjected to silica gel column chromatography and eluted with ethyl acetate:triethylamine (50:1). The desired fraction was collected, concentrated under reduced pressure and crystallized from ethyl ether-hexane (1:1), collected by filtration, washed with hexane and dried to yield 554 mg of the title compound.

Melting point: 105–106° C.; Elemental analysis (for $C_{33}H_{41}N_5O_2.0.5H_2O$): Calculated (%): C, 72.23; H, 7.71; N, 12.76; Found (%): C, 72.48; H, 7.73; N, 12.95.

EXAMPLE 95A

Production of 2-[6-[4-[4-(Diphenylmethyl)-1-piperazinyl]butyl]imidazo[1,2-b]pyridazin-2-yl]-2-methylpropionic Acid 482 mg of ethyl 2-[6-[4-[4-(diphenylmethyl)-1-piperazinyl]butyl]imidazo[1,2-b]pyridazin-2-yl]-2-methylpropionate was dissolved in 2 ml of ethanol; 1.8 ml of a 1 N aqueous solution of sodium hydroxide was added, followed by thermal refluxing for 1 hour. After cooling, the mixture was concentrated under reduced pressure. The residue was diluted with water and adjusted to pH 5 by the addition of 1 N hydrochloric acid. Ethyl acetate was added to cause crystallization; the crystal precipitated was washed with water-acetone (2:1) and dried to yield 386 mg of the title compound.

Melting point: 108–110° C.; Elemental analysis (for $C_{31}H_{37}N_5O_2.H_2O$): Calculated (%): C, 70.30; H, 7.42; N, 13.22; Found (%): C, 70.22; H, 7.73; N, 13.32.

EXAMPLE 96A

Production of Isopropyl 1-[6-[3-[4-(Diphenylmethoxy)piperidino]propylamino]imidazo[1,2-b]pyridazin-2-yl]cyclopentanecarboxylate Dihydrochloride 1.67 g of 4-(diphenylmethoxy)-1-piperidinepropaneamine and 793 mg of isopropyl 1-(6-chloroimidazo[1,2-b]pyridazin-2-yl)cyclopentanecarboxylate were stirred at 165° C. for 5.5 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (100:5:2). The desired fraction was collected, concentrated under reduced pressure and dissolved in 5 ml of ethyl acetate; 0.84 ml of a 4 N solution of hydrogen chloride in ethyl acetate was added, followed by concentration. The residue was powdered by the addition of ethyl ether; the resulting powder was collected by filtration, washed with ethyl ether and dried to yield 999 mg of the title compound.

Amorphous; Elemental analysis (for $C_{36}H_{47}N_5O_3Cl_2.0.5H_2O.0.5Et_2O$): Calculated (%): C, 63.85; H, 7.47; N, 9.80; Found (%): C, 63.83; H, 7.54; N, 9.83.

EXAMPLE 97A

Production of 1-[6-[3-[4-(Diphenylmethoxy)piperidino]propylamino]imidazo[1,2-b]pyridazin-2-yl]cyclopentanecarboxylic Acid 598 mg of isopropyl 1-[6-[3-[4-(diphenylmethoxy)piperidino]propylamino]imidazo[1,2-b]pyridazin-2-yl] cyclopentanecarboxylate dihydrochloride was dissolved in 3 ml of ethanol; 2.24 ml of a 2 N aqueous solution of sodium hydroxide was added, followed by thermal refluxing for 7 hours. After cooling, the mixture was concentrated under reduced pressure. The residue was diluted with water, washed with ethyl acetate and adjusted to pH 4.5 by the addition of 1 N hydrochloric acid. The mixture was saturated with sodium chloride and extracted with ethyl acetate-tetrahydrofuran (1:2); the extract was dried over magnesium sulfate and concentrated under reduced pressure, powdered by the addition of ethyl acetate-ethyl ether (1:1), washed with ethyl ether and dried to yield 349 mg of the title compound.

Amorphous; Elemental analysis (for $C_{33}H_{39}N_5O_3.3.0H_2O$): Calculated (%): C, 65.22; H, 7.46; N, 11.52; Found (%): C, 65.19; H, 7.17; N, 11.29.

EXAMPLE 98A

Production of 1-[6-[3-[4-(Diphenylmethoxy)piperidino]propoxy]imidazo[1,2-b]pyridazin-2-yl] cyclopropanecarboxylic Acid Process A:

Production of Isopropyl 1-[6-[3-[4-(Diphenylmethoxy)piperidino]propoxy]imidazo[1,2-b]pyridazin-2-yl] cyclopropanecarboxylate 1.14 g of 4-(diphenylmethoxy)-1-piperidinepropanol was dissolved in 15 ml of N,N-dimethylacetamide; 140 mg of a 60% dispersion of sodium hydride in mineral oil was added, followed by stirring at room temperature under reduced pressure for 30 minutes. To the reaction mixture, 980 mg of isopropyl 1-(6-chloroimidazo[1,2-b]pyridazin-2-yl) cyclopropanecarboxylate was added under ice cooling conditions, followed by stirring at constant temperature for 4 hours. Ice water was added, followed by saturation with sodium chloride and subsequent extraction with ethyl acetate-tetrahydrofuran (1:1); the extract was dried over magnesium sulfate and concentrated under reduced pressure. The residue was subjected to silica gel column chromatography and eluted with ethyl acetate. The desired fraction was collected and concentrated under reduced pressure to yield 496 mg of the title compound.

$^1$H-NMR (CDCl$_3$). δ ppm: 1.25 (3H, s), 1.28 (3H, s), 1.40–2.25 (12H, m), 2.43–2.55 (2H, m), 2.70–2.88 (2H, s), 3.36–3.55 (1H, m), 4.33 (2H, t, J=6.3 Hz), 4.98–5.18 (1H, m), 5.52 (1H, s), 6.58 (1H, d, J=9.8 Hz), 7.15–7.40 (10H, m), 7.64 (1H, d, J=9.4 Hz), 8.03 (1H, s).

Process B:

490 mg of isopropyl 1-[6-[3-[4-(diphenylmethoxy)piperidino]propoxy]imidazo[1,2-b]pyridazin-2-yl] cyclopropanecarboxylate was dissolved in 2 ml of ethanol; 0.86 ml of a 2 N aqueous solution of sodium hydroxide was added, followed by thermal refluxing for 2 hours. After cooling, the mixture was concentrated under reduced pressure. The residue was diluted with water and adjusted to pH 5 by the addition of 1 N hydrochloric acid. The mixture was extracted with ethyl acetate-tetrahydrofuran (1:3); the extract was washed with saline, dried over magnesium sulfate and concentrated under reduced pressure, powdered by the addition of ethyl ether, washed with ethyl ether and dried to yield 382 mg of the title compound.

Amorphous; Elemental analysis (for $C_{31}H_{34}N_4O_4.2.0H_2O$): Calculated (%): C, 66.17; H, 6.81; N, 9.96; Found (%): C, 66.27; H, 7.00; N, 9.75.

EXAMPLE 99A

Production of Isopropyl 1-[6-[3-[4-(Diphenylmethoxy)piperidino]propylamino]imidazo[1,2-b]pyridazin-2-yl]cyclopropanecarboxylate Dihydrochloride 2.72 g of 4-(diphenylmethoxy)-1-piperidinepropanamine and 1.27 g of isopropyl 1-(6-chloroimidazo[1,2-b]pyridazin- 2-yl]cyclopropanecarboxylate were stirred at 165° C. for 4.5 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methahol:triethylamine (50:5:1). The desired fraction was collected, concentrated under reduced pressure and dissolved in 5 ml of ethyl acetate; 0.72 ml of a 4 N solution of hydrogen chloride in ethyl acetate was added, followed by concentration again. The residue was crystallized by the addition of ethyl acetate-acetone (2:1), collected by filtration, washed with ethyl acetate and dried to yield 714 mg of the title compound.

Melting point: 206–208° C.; Elemental analysis (for $C_{34}H_{43}N_5O_3Cl_2.0.5H_2O$): Calculated (%): C, 62.86; H, 6.83; N, 10.78; Found (%): C, 63.10; H, 6.88; N, 10.83.

EXAMPLE 100A

Production of 1-[6-[3-[4-(Diphenylmethoxy) piperidino]propylamino]imidazo[1,2-b]pyridazin-2-yl]cyclopropanecarboxylic Acid 554 mg of isopropyl 1-[6-[3-[4-(diphenylmethoxy) piperidino]propylamino]imidazo[1,2-b]pyridazin-2-yl]cyclopropanecarboxylate dihydrochloride was dissolved in 3 ml of ethanol; 1.73 ml of a 2 N aqueous solution of sodium hydroxide was added, followed by thermal refluxing for 1.5 hours. After cooling, the mixture was concentrated under reduced pressure. The residue was diluted with water, washed with ethyl acetate and adjusted to pH 5.5 by the addition of 1 N hydrochloric acid. The mixture was crystallized by the addition of acetone, washed with acetone and dried to yield 321 mg of the title compound.

Melting point: 115–117° C.; Elemental analysis (for $C_{31}H_{35}N_5O_3 \cdot H_2O$): Calculated (%): C, 68.49; H, 6.86; N, 12.88; Found (%): C, 68.24; H, 6.89; N, 12.93.

EXAMPLE 101A

Production of Ethyl 2-[6-[3-[4-(Diphenylmethoxy) piperidino]propyl]imidazo[1,2-b]pyridazin-2-yl]-2-methylpropionate Dihydrochloride Process A: Production of Ethyl 2-[6-[3-(Tetrahydropyranyl-2-oxy)propyl]imidazo[1,2-b]pyridazin-2-yl]-2-methylpropionate 10.6 g of 2-(3-iodopropoxy)tetrahydropyrane was dissolved in 106–10.6 ml of toluene-N,N-dimethylacetamide; 3.87 g of copper-activated zinc was added, followed by stirring at 80° C. in a nitrogen atmosphere for 3 hours. After cooling, 5.28 g of ethyl 2-(6-chloroimidazo[1,2-b]pyridazin-2-yl]-2-methylpropionate and 277 mg of dichlorobis(triphenylphosphine)palladium(II) were added, followed by stirring at 80° C. for 14 hours. After cooling, ice water and ethyl acetate were added; the insoluble substances were filtered off through Celite; after the filtrate was extracted with ethyl acetate, the extract was washed with saturated saline, dried over magnesium sulfate and concentrated under reduced pressure. The residue was subjected to silica gel column chromatography and eluted with hexane:ethyl acetate (1:1). The desired fraction was collected, concentrated under reduced pressure and dried to yield 2.64 g of the title compound.

$^1$H-NMR (CDCl$_3$) δ ppm: 1.23 (3H, t, J=7.0 Hz), 1.68 (6H, s), 1.40–1.95 (6H, m), 1.98–2.15 (2H, m), 2.87–2.96 (2H, m), 3.40–3.56 (2H, m), 3.75–3.94 (2H, m), 4.17 (2H, q, J=7.1 Hz), 4.54–4.62 (1H, broad t), 6.91 (1H, d, J=9.2 Hz), 7.79 (1H, s), 7.80 (1H, d, J=9.0 Hz).

Process B:

Production of Ethyl 2-[6-(3-Hydroxypropyl)imidazo[1,2-b]pyridazin-2-yl]-2-methylpropionate 3.67 g of ethyl 2-[6-[3-(tetrahydropyranyl-2-oxy)propyl] imidazo[1,2-b]pyridazin-2-yl]-2-methylpropionate was dissolved in 38 ml of ethanol; 2.40 g of p-toluenesulfonic acid monohydrate was added, followed by stirring at room temperature for 24 hours. After the ethanol was distilled off under reduced pressure. The residue was diluted with water and extracted with ethyl acetate and tetrahydrofuran. The extract was washed with saturated saline, dried over magnesium sulfate and concentrated under reduced pressure. The residue was subjected to silica gel column chromatography and eluted with ethyl acetate. The desired fraction was collected, concentrated under reduced pressure and dried to yield 2.05 g of the title compound.

$^1$H-NMR (CDCl$_3$) δ ppm: 1.23 (3H, t, J=7.2 Hz), 1.68 (6H, s), 1.95–2.10 (2H, m), 2.94 (2H, t, J=7.5 Hz), 3.74 (2H, q, J=7.1 Hz), 4.17 (2H, q, J=7.1 Hz), 6.91 (1H, d, J=9.0 Hz), 7.80 (1H, s), 7.82 (1H, d, J=9.2 Hz).

Process C:

Production of Ethyl 2-[6-[3-(Methanesulfonyloxy) propyl]imidazo[1,2-b]pyridazin-2-yl]-2-methylpropionate 2.04 g of ethyl 2-[6-(3-hydrbxypropyl)imidazo[1,2-b]pyridazin-2-yl]-2-methylpropionate was suspended in 40 ml of tetrahydrofuran; under ice cooling conditions, 2.41 ml of N-ethyldiisopropylamine and 0.83 ml of methanesulfonyl chloride were added, followed by stirring at room temperature for 15 minutes. Ice water was added, followed by extraction with ethyl acetate; the extract was washed with saturated saline, dried over magnesium sulfate and concentrated under reduced pressure and dried to yield 2.78 g of the title compound.

$^1$H-NMR (CDCl$_3$) δ ppm: 1.23 (3H, t, J=7.1 Hz), 1.68 (6H, s), 2.15–2.35 (2H, m), 2.97 (2H, t, J=7.5 Hz), 3.03 (3H, s), 4.17 (2H, q, J=7.4 Hz), 4.34 (2H, t, J=6.2 Hz), 6.89 (1H, d, J=9.2 Hz), 7.80 (1H, s), 7.84 (1H, d, J=10 Hz).

Process D:

1.32 g of ethyl 2-[6-[3-(methanesulfonyloxy)propyl] imidazo[1,2-b]pyridazin-2-yl]-2-methylpropionate was dissolved in 15 ml of N,N-dimethylformamide; 1.15 g of 4-(diphenylmethoxy)piperidine, 712 mg of potassium iodide and 593 mg of potassium carbonate were added, followed by stirring at 60° C. for 2 hours. After cooling, ice water was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1); the desired fraction was collected, concentrated under reduced pressure, dissolved in 5 ml of ethyl acetate; 1.6 ml of a 4 N solution of hydrogen chloride in ethyl acetate was added, followed by concentration under reduced pressure. The concentrate was powdered from ethyl ether, collected by filtration and dried to yield 1.55 g of the title compound.

Amorphous; Elemental analysis (for $C_{33}H_{42}N_4O_3Cl_2.0.5H_2O$): Calculated (%): C, 63.66; H, 6.96; N. 9.00; Found (%): C, 63.61; H, 6.94; N, 9.07.

EXAMPLE 102A

Production of 2-[6-[3-[4-(Diphenylmethoxy) piperidino]propyl]imidazo[1,2-b]pyridazin-2-yl]-2-methylpropionic Acid 905 mg of ethyl 2-[6-[3-[4-(diphenylmethoxy)piperidino] propyl]imidazo[1,2-b]pyridazin-2-yl]-2-methylpropionate dihydrochloride was dissolved in 6 ml of ethanol; 5.9 ml of a 1 N aqueous solution of sodium hydroxide was added, followed by thermal refluxing for 2 hours. After cooling, the mixture was concentrated under reduced pressure. The residue was diluted with water and adjusted to pH 4.5 by the addition of 1 N hydrochloric acid. The mixture was crystallized by the addition of acetone, washed with acetone and dried to yield 476 mg of the title compound.

Melting point: 195–205° C.; Elemental analysis (for $C_{31}H_{36}N_4O_3.0.3H_2O$): Calculated (%): C, 71.87; H, 7.12; N, 10.81; Found (%): C, 71.95; H, 6.94; N, 10.73.

EXAMPLE 103A

Production of Ethyl 2-[6-[3-[4-(Diphenylmethyl)-1-piperazinyl]propyl]imidazo[1,2-b]pyridazin-2-yl]-2-methylpropionate Trihydrochloride 1.41 g of ethyl 2-[6-[3-(methanesulfonyloxy)propyl]imidazo[1,2-b]pyridazin-2-yl]-2-methylpropionate was dissolved in 15 ml of N,N-dimethylformamide; 1.16 g of 1-(diphenylmethyl)piperazine, 760 mg of potassium iodide and 633 mg of potassium carbonate were added, followed by stirring at 60° C. for 2 hours. Ice water was added, followed by extraction with ethyl acetate; the extract was washed with saturated saline, dried over magnesium sulfate and concentrated under reduced pressure. The residue was subjected to silica gel column chromatography and eluted with ethyl acetate:triethylamine (50:1). The desired fraction was collected, concentrated under reduced pressure, dissolved in 5 ml of ethyl acetate; 2.4 ml of a 4 N solution of hydrogen chloride in ethyl acetate was added, followed by concentration again. The concentrate was recrystallized from acetone-:ethyl acetate (1:1), collected by filtration and dried to yield 1.39 g of the title compound.

Melting point: 183–185° C.; Elemental analysis (for $C_{32}H_{42}N_5O_2Cl_3.H_2O$): Calculated (%): C, 58.85; H, 6.79; N, 10.72; Found (%): C, 58.82; H, 6.52; N, 10.67.

EXAMPLE 104A

Production of 2-[6-[3-[4-(Diphenylmethyl)-1-piperazinyl]propyl]imidazo[1,2-b]pyridazin-2-yl]-2-methylpropionic Acid 1.08 g of ethyl 2-[6-[3-[4-(diphenylmethyl)-1-piperazinyl]propyl]imidazo[1,2-b]pyridazin-2-yl]-2-methylpropionate trihydrochloride was dissolved in 8 ml of ethanol; 8.5 ml of a 1 N aqueous solution of sodium hydroxide was added, followed by thermal refluxing for 2 hours. After cooling, the mixture was concentrated under reduced pressure. The residue was diluted with water and adjusted to pH 4.5 by the addition of 1 N hydrochloric acid. The mixture was crystallized by the addition of acetone, washed with water-acetone (2:1) and dried to yield 435 mg of the title compound.

Melting point: 176–178° C.; Elemental analysis (for $C_{30}H_{35}N_5O_2.0.5H_2O$): Calculated (%): C, 71.12; H, 7.16; N, 13.82; Found (%): C, 70.79; H, 6.86; N, 13.87.

EXAMPLE 105A

Production of Ethyl 2-[6-[3-[4-(Diphenylmethoxy)piperidino]propylamino]-3-methylimidazo[1,2-b]pyridazin-2-yl]-2-methylpropionate Dihydrochloride 2.38 g of 4 4-(diphenylmethoxy)-1-piperidinepropanamine and 1.03 g of ethyl 2-(6-chloro-3-methylimidazo[1,2-b]pyridazin-2-yl)-2-methylpropionate were stirred at 160° C. for 7.5 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate-:methanol:triethylamine (50:5:1). The desired fraction was collected, concentrated under reduced pressure and dissolved in 5 ml of ethyl acetate; 0.96 ml of a 4 N solution of hydrogen chloride in ethyl acetate was added, followed by concentration again. The residue was powdered by the addition of ethyl ether, collected by filtration and dried to yield 666 mg of the title compound.

Amorphous; Elemental analysis (for $C_{34}H_{45}N_5O_3Cl_2.1.5H_2O$): Calculated (%): C, 60.98; H, 7.22; N, 10.46; Found (%): C, 60.70; H. 6.95; N, 10.34.

EXAMPLE 106A

Production of Ethyl[6-[3-[4-(Diphenylmethoxy)piperidino]propylaminol-2-methylimidazo[1,2-b]pyridazin-3-yl]carboxylate 1.98 g of 4-(diphenylmethoxy)-1-piperidinepropanamine and 1.46 g of ethyl(6-chloro-2-methylimidazo[1,2-b]pyridazin-3-yl]carboxylate were dissolved in 15 ml of 1-methyl-2-pyrrolidone; 1.05 ml of N-ethyldiisopropylamine was added, followed by stirring at 120° C. for 40 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; ethyl ether-hexane (1:2) was added to the residue; the crystal precipitated was collected by filtration, washed with hexane and dried to yield 412 mg of the title compound.

Melting point: 117–119° C.; Elemental analysis (for $C_{31}H_{37}N_5O_3$): Calculated (%): C, 70.56; H, 7.07; N, 13.27; Found (%): C, 70.16; H, 6.93; N, 13.01.

EXAMPLE 107A

Production of [6-[3-[4-(Diphenylmethoxy)piperidino]propylamino]-2-methylimidazo[1,2-b]pyridazin-3-yl]carboxylic Acid 770 mg of ethyl [6-[3-[4-(diphenylmethoxy)piperidino]propylamino]-2-methylimidazo[1,2-b]pyridazin-3-yl]carboxylate was dissolved in 5 ml of ethanol; 3.2 ml of a 1 N aqueous solution of sodium hydroxide was added, followed by stirring at room temperature for 3.5 hours. After cooling, the mixture was concentrated under reduced pressure. The residue was diluted with water, washed with ethyl acetate and adjusted to pH 4.5 by the addition of 1 N hydrochloric acid. The crystal precipitated was collected by filtration, washed with water and ethyl acetate and dried to yield 265 mg of the title compound.

Melting point: 101–103° C.; Elemental analysis (for $C_{29}H_{33}N_5O_3.0.5H_2O$): Calculated (%): C, 68.48; H, 6.74; N, 13.77; Found (%): C, 68.63; H, 6.77; N, 13.91.

EXAMPLE 108A

Production of Ethyl 2-[6-[3-[4-(Diphenylmethylamino)piperidino]propylamino]imidazo[1,2-b]pyridazin-2-yl]-2-methylpropionate 3.12 g of 4-(diphenylmethylamino)-1-piperidinepropanamine and 1.72 g of ethyl 2-(6- chloroimidazo[1,2-b]pyridazin-2-yl)-2-methylpropionate were stirred at 180° C. for 3 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated under reduced pressure. The residue was crystallized by the addition of ethyl ether-hexane (1:3), collected by filtration, washed with hexane and dried to yield 1.83 g of the title compound.

Melting point 115–117° C.; Elemental analysis (for $C_{33}H_{42}N_6O_2$): Calculated (%): C, 71.45; H, 7.63; N, 15.15; Found (%): C, 71.40; H, 7.70; N, 14.94.

EXAMPLE 109A

Production of 2-[6-[3-[4-(Diphenylmethylamino)piperidino]propylamino]imidazo[1,2-b]pyridazin-2-yl]-2-methylpropionic Acid 612 mg of ethyl 2-[6-[3-[4-(diphenylmethylamino)piperidino]propylamino]imidazo[1,2-b]pyridazin-2-yl]-2-methylpropionate was dissolved in 5 ml of ethanol; 2.2 ml of a 1 N aqueous solution of sodium hydroxide was added, followed by thermal refluxing for 6 hours. After cooling, the mixture was concentrated under reduced pressure. The residue was diluted with water, washed with ethyl acetate and adjusted to pH 5 by the addition of 1 N hydrochloric acid. The mixture was saturated with sodium chloride and extracted with tetrahydrofuran; the extract was dried over magnesium sulfate and concentrated under reduced pressure, powdered by the addition of ethyl ether, collected by filtration and dried to yield 503 mg of the title compound.

Amorphous; Elemental analysis (for $C_{31}H_{38}N_6O_2 \cdot 2.7H_2O \cdot 0.8Et_2O$): Calculated (%): C, 64.93; H, 7.87; N, 13.28; Found (%): C, 64.99; H, 7.72; N, 12.85.

EXAMPLE 110A

Production of Ethyl 2-[6-[3-[4-(Diphenylmethoxy)piperidino]propylamino]imidazo[1,2-b]pyridazin-2-yl]-2-ethylbutyrate Dihydrochloride 3.03 g of 4-(diphenylmethoxy)-1-piperidinepropanamine and 1.38 g of ethyl 2-(6-chloroimidazo[1,2-b]pyridazin-2-yl)-2-ethylbutyrate were stirred at 160° C. for 1.5 hours, then at 180° C. for 2 hours. After the mixture was cooled to 90° C., ethanol and aqueous sodium bicarbonate were added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (100:5:2). The desired fraction was collected, concentrated under reduced pressure and dissolved in 5 ml of ethyl acetate; 1.4 ml of a 4 N solution of hydrogen chloride in ethyl acetate was added, followed by concentration again. The residue was powdered by the addition of ethyl ether and dried to yield 893 mg of the title compound.

Amorphous; Elemental analysis (for $C_{35}H_{41}NO_3Cl_2 \cdot Et_2O$): Calculated (%): C, 64.10; H, 7.86; N, 9.58; Found (%): C, 63.78; H, 7.57; N, 9.96.

EXAMPLE 111A

Production of N-[3-Chloro-6-[3-[4-(diphenylmethoxy)piperidino]propylamino]imidazo[1,2-b]pyridazine-2-carbonyl]glycine Ethyl Ester 0.649 g of 4-(diphenylmethoxy)-1-piperidinepropanamine and 0.53 g of N-(3,6-dichloroimidazo[1,2-b]pyridazine-2-carbonyl)glycine ethyl ester were dissolved in 7 ml of 1-methyl-2-pyrrolidone; 0.345 ml of N-ethyldiisopropylamine was added, followed by stirring in an oil bath (90–100° C.) for 24 hours. After cooling, ice water was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (185:15:2). The desired fraction was collected and recrystallized from ethyl acetate to yield 0.711 g of the title compound.

Melting point: 178–180° C.; Elemental analysis (for $C_{32}H_{37}N_6O_4Cl$): Calculated (%): C, 63.51; H, 6.16; N, 13.89; Found (%): C, 63.56; H, 6.21; N, 13.78.

EXAMPLE 112A

Production of N-[6-[3-[4-(Diphenylmethoxy)piperidino]propylamino]imidazo[1,2-b]pyridazine-2-carbonyl]-β-alanine Ethyl Ester 0.649 g of 4-(diphenylmethoxy)-1-piperidinepropanamine and 0.594 g of N-(6-chloroimidazo[1,2-b]pyridazine-2-carbonyl)-β-alanine ethyl ester were dissolved in 7 ml of 1-methyl-2-pyrrolidone; 0.345 ml of N-ethyldiisopropylamine was added, followed by stirring in an oil bath (90–100° C.) for 24 hours. After cooling, ice water was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (370:30:4). The desired fraction was collected and recrystallized from ethyl ether to yield 0.347 g of the title compound.

Melting point: 83–86° C.; Elemental analysis (for $C_{33}H_{40}N_6O_4$): Calculated (%): C, 67.79; H, 6.90; N, 14.37; Found (%): C, 68.05; H, 6.87; N, 14.38.

EXAMPLE 113A

Production of Sodium 2-[6-[3-[4-(Diphenylmethoxy)piperidino]propylamino]imidazo[1,2-b]pyridazin-2-yl]-2-methylpropionate To a solution of 2-[6-[3-[4-(diphenylmethoxy)piperidino]propylamino]imidazo[1,2-b]pyridazin-2-yl]-2-methylpropionic acid (528 mg) in methanol (2 ml), a 2N aqueous solution of sodium hydroxide (0.47 ml) was added, followed by stirring at room temperature for 5 minutes. This solution was diluted with 2-propanol and concentrated under reduced pressure. The residue was dissolved in 2-propanol and again concentrated under reduced pressure. To this residue, 2-propanol and ethyl ether were added; the resulting powder was collected by filtration to yield the title compound (474 mg).

Amorphous; Elemental analysis (for $C_{31}H_{36}N_5O_3Na \cdot 0.5H_2O$): Calculated (%): C, 66.65; H, 6.68; N, 12.54; Found (%): C, 66.45; H, 6.54; N, 12.53.

EXAMPLE 114A

Production of 6-[5-[4-(Diphenylmethoxy)piperidino]pentylamino][1,2,4]triazolo[1,5-b]pyridazine 0.705 g of 4-(diphenylmethoxy)-1-piperidinepentanamine and 0.309 g of 6-chloro[1,2,4]triazolo[1,5-b]pyridazine were stirred at 135–140° C. for 1.5 hours. After cooling, aqueous sodium bicarbonate was added, followed by extraction with ethyl acetate; the extract was washed with saline, dried over sodium sulfate and concentrated under reduced pressure. The residue was subjected to silica gel column chromatography and eluted with ethyl acetate:methanol:triethylamine (95:5:1). The desired fraction was collected, recrystallized from ethyl ether and dried to yield 0.629 g of the title compound.

Melting point: 96–98° C.; Elemental analysis (for $C_{28}H_{34}N_6O.H_2O$): Calculated (%): C, 70.12; H, 7.36; N, 17.52; Found (%): C, 70.29; H, 7.19; N, 17.62.

EXAMPLE 115A

Production of 1-[4-(Diphenylmethoxy)piperidino]-3-[([1,2,4]triazolo[1,5-b]pyridazin-6-yl)amino]-2-propanol 0.675 g of 1-amino-3-[4-(diphenylmethoxy)piperidino]-2-propanol and 0.335 g of 6-chloro[1,2,4]triazolo[1,5-b]pyridazine were stirred at 135–140° C. for 3 hours. After cooling, aqueous sodium bicarbonate was added, followed by extraction with ethyl acetate-tetrahydrofuran (2:1); the extract was washed with saline, dried over sodium sulfate and concentrated under reduced pressure. The residue was subjected to silica gel column chromatography and eluted with ethyl acetate:methanol:triethylamine (90:10:1). The desired fraction was collected, recrystallized from ethyl acetate and dried to yield 0.509 g of the title compound.

Melting point: 82–87° C.; Elemental analysis (for $C_{26}H_{30}N_6O_2.H_2O$) Calculated (%): C, 65.53; H, 6.77; N, 17.63; Found (%): C, 65.36; H, 6.50; N, 17.25.

EXAMPLE 116A

Production of tert-Butyl[6-[3-[4-(Diphenylmethoxy) piperidino]propylamino][1,2,4]triazolo[1,5-b] pyridazin-2-yl]carboxylate 563 mg of 4-(diphenylmethoxy)-1-piperidinepropanamine and 442 mg of tert-butyl (6-chloro [1,2,4]triazolo[1,5-b]pyridazin-2-yl)carboxylate were dissolved in 5 ml of pyridine, followed by stirring at 80° C. for 13.5 hours. After cooling, water was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated under reduced pressure. The residue was crystallized by the addition of ethyl acetate, collected by filtration, washed with ethyl ether and dried to yield 365 mg of the title compound.

Melting point: 133–135° C.; Elemental analysis (for $C_{31}H_{38}N_6O_3$): Calculated (%): C, 68.61; H, 7.06; N, 15.49; Found (%): C, 68.18; H, 6.81; N, 15.46.

EXAMPLE 117A

Production of [6-[3-[4-(Diphenylmethoxy) piperidino]propylamino][1,2,4]triazolo[1,5-b] pyridazin-2-yl]carboxylic Acid 2.33 g of 4-(diphenylmethoxy)-1-piperidinepropaneamine and 714 mg of (6-chloro[1,2,4] triazolo[1,5-b]pyridazin-2-yl)carboxylic acid were stirred at 175° C. for 30 minutes. After cooling, the reaction mixture was crystallized by the addition of water-ethyl acetate-ethanol (2:2:1), collected by filtration, washed with water-ethyl acetate-ethyl ether (2:1:2) and dried to yield 598 mg of the title compound.

Melting point: 135–138° C.; Elemental analysis (for $C_{27}H_{30}N_6O_3.0.5H_2O$): Calculated (%): C, 65.44; H, 6.31; N, 16.96; Found (%): C, 65.76; H, 6.13; N, 16.97.

EXAMPLE 118A

Production of Methyl[6-[3-[4-(Diphenylmethoxy) piperidino]propylamino][1,2,4]triazolo[1,5-b] pyridazin-7-yl]carboxylate 1.42 g of 4-(diphenylmethoxy)-1-piperidinepropanamine and 929 mg of methyl (6-chloro[1,2,4]triazolo[1,5-b] pyridazin-7-yl)carboxylate were dissolved in 20 ml of N,N-dimethylformamide; 1.51 ml of N-ethyldiisopropylamine was added, followed by stirring at 70° C. for 6 hours. After cooling, water was added; the mixture was saturated with sodium chloride and extracted with ethyl acetate-tetrahydrofuran (1:1); the extract was dried over magnesium sulfate and concentrated under reduced pressure. The residue was subjected to silica gel column chromatography and eluted with ethyl acetate:methanol:triethylamine (50:5:1). The desired fraction was collected and concentrated; the residue was crystallized by the addition of ethyl acetate-ethyl ether-hexane (1:2:1), collected by filtration, washed with hexane and dried to yield 905 mg of the title compound.

Melting point: 120–122° C.; Elemental analysis (for $C_{28}H_{32}N_6O_3$): Calculated (%): C, 67.18; H, 6.44; N, 16.79; Found (%): C, 67.11; H, 6.54; N, 16.87.

EXAMPLE 119A

Production of [6-[3-[4-(Diphenylmethoxy) piperidino]propylamino][1,2,4]triazolo[1,5-b] pyridazin-7-yl]carboxylic Acid 1.58 g of methyl [6-[3-[4-(diphenylmethoxy)piperidino] propylamino][1,2,4]triazolo[1,5-b]pyridazin-7-yl] carboxylate was dissolved in 10 ml of ethanol; 8.0 ml of a 1 N aqueous solution of sodium hydroxide was added, followed by stirring at room temperature for 1.5 hours. After cooling, the mixture was concentrated under reduced pressure. The residue was diluted with water and washed with ethyl acetate; 1N hydrochloric acid was added to adjust pH 4.5. The mixture was saturated with saline and extracted with tetrahydrofuran; the extract was dried over magnesium sulfate. The crystal obtained by concentration under reduced pressure was washed with ethyl ether, collected by filtration and dried to yield 788 mg of the title compound.

Melting point: 207–209° C.; Elemental analysis (for $C_{27}H_{30}N_6O_3.0.5H_2O$): Calculated (%): C, 65.44; H, 6.30; N, 16.96; Found (%): C, 65.17; H, 6.19; N, 16.90.

EXAMPLE 120A

Production of N-[6-[3-[4-(Diphenylmethoxy) piperidino]propylamino][1,2,4]triazolo[1,5-b] pyridazine-2-carbonyl]glycine Ethyl Ester 1.41 g of 4-(diphenylmethoxy)-1-piperidinepropanamine and 1.23 g of N-(6-chloro[1,2,4]triazolo[1,5-b]pyridazine-2-carbonyl)glycine ethyl ester were dissolved in 17 ml of N,N-dimethylformamide; 1.50 ml of N-ethyldiisopropylamine was added, followed by stirring at room temperature for 28 hours, then at 60° C. for 19 hours. After cooling, aqueous sodium bicarbonate was added, followed by extraction with ethyl acetate-tetrahydrofuran (1:1); the extract was dried over magnesium sulfate and concentrated under reduced pressure. The residue was subjected to silica gel column chromatography and eluted with ethyl acetate:methanol:triethylamine (50:5:1). The desired fraction was collected, concentrated, recrystallized by the addition of tetrahydrofuran, collected by filtration, washed with ethyl ether and dried to yield 987 mg of the title compound.

Melting point: 175–177° C.; Elemental analysis (for $C_{31}H_{37}N_5O_4$): Calculated (%): C, 64.12; H, 6.60; N, 16.88; Found (%): C, 63.99; H, 6.52; N, 16.85.

EXAMPLE 121A

Production of N-[6-[3-[4-(Diphenylmethoxy) piperidino]propylamino][1,2,4]triazolo[1,5-b] pyridazine-2-carbonyl]-2,2-dimethylglycine Ethyl Ester Fumarate 1.56 g of 4-(diphenylmethoxy)-1-piperidinepropanamine and 1.50 g of N-(6-chloro[1,2,4]triazolo[1,5-b]pyridazine-2-carbonyl)-2,2-dimethylglycine ethyl ester were dissolved in 20 ml of N,N-dimethylformamide; 1.65 ml of N-ethyldiisopropylamine was added, followed by stirring at 70° C. for 16 hours. After cooling, aqueous sodium bicarbonate was added, followed by extraction with ethyl acetate; the extract was washed with saturated saline, dried over magnesium sulfate and concentrated under reduced pressure. The residue was subjected to silica gel column chromatography and eluted with ethyl acetate:methanol:triethylamine (50:5:1). The desired fraction was collected and concentrated; 880 mg of the oily substance obtained was dissolved in 5 ml of ethanol, followed by the addition of 170 mg of fumaric acid and concentration; the resulting concentrate was powdered by the addition of ethyl ether, washed with ethyl ether, collected by filtration and dried to yield 931 mg of the title compound.

Amorphous; Elemental analysis (for $C_{37}H_{45}N_5O_8 \cdot 1.0H_2O$, $0.5Et_2O$): Calculated (%): C, 60.76; H, 6.80; N, 12.72; Found (%): C, 60.71; H, 6.85; N, 12.34.

EXAMPLE 122A

Production of Isopropyl[6-[3-[4-(Diphenylmethoxy) piperidino]propoxy][1,2,4]triazolo[1,5-b]pyridazin-2-yl]carboxylate 653 mg of 4-(diphenylmethoxy)-1-piperidinepropanol was dissolved in 10 ml of N,N-dimethylformamide; 88 mg of a 60% dispersion of sodium hydride in mineral oil was added, followed by stirring at room temperature under reduced pressure for 1.5 hours. To the reaction mixture, 483 mg of isopropyl(6-chloro[1,2,4]triazolo[1.,5-b]pyridazin-2-yl)carboxylate was added under ice cooling conditions, followed by stirring at constant temperature for 3.5 hours. Ice water was added, followed by extraction with ethyl acetate-tetrahydrofuran (1:1); the extract was washed with saturated saline, dried over magnesium sulfate and concentrated under reduced pressure. The residue was subjected to silica gel column chromatography and eluted with ethyl acetate:methanol (10:1). The desired fraction was collected and concentrated; the crystal precipitated was washed with ethyl ether, collected by filtration and dried to yield 462 mg of the title compound.

Melting point: 126–127° C.; Elemental analysis (for $C_{30}H_{35}N_5O_4$): Calculated (%): C, 68.03; H, 6.66; N, 13.22; Found (%): C, 68.01; H, 6.79; N, 13.42.

EXAMPLE 123A

Production of [6-[3-[4-(Diphenylmethoxy) piperidino]propoxy][1,2,4]triazolo[1,5-b]pyridazin-2-yl]carboxylic Acid 1.85 g of isopropyl[6-[3-[4-(diphenylmethoxy) piperidino]propoxy][1,2,4]triazolo[1,5-b]pyridazin-2-yl] carboxylate was dissolved in 18 ml of tetrahydrofuran; 3.8 ml of a 1 N aqueous solution of sodium hydroxide was added, followed by stirring at room temperature for 3.5 hours. After cooling, the mixture was concentrated under reduced pressure. The residue was diluted with water and washed with ethyl acetate; 1 N hydrochloric acid was added to adjust pH 4.5. The mixture was crystallized by the addition of ethanol-acetone (1:2), collected by filtration, washed with water and ethyl acetate and dried to yield 1.33 g of the title compound.

Melting point: 173–177° C.; Elemental analysis (for $C_{27}H_{29}N_5O_4 \cdot 2.5H_2O$): Calculated (%): C, 60.89; H, 6.43; N, 13.15; Found (%): C, 60.86; HI 6.21; N, 13.06.

EXAMPLE 124A

Production of N-[6-[3-[4-(Diphenylmethoxy) piperidino]propylamino][1,2,4]triazolo[1,5-b] pyridazine-2-carbonyl]-2,2-dimethylglycine 1.71 g of N-[6-[3-[4-(diphenylmethoxy)piperidino] propylamino][1,2,4]triazolo[1,5-b]pyridazine-2-carbonyl]-2,2-dimethylglycine ethyl ester was dissolved in 6 ml of ethanol; 4.5 ml of a 1 N aqueous solution of sodium hydroxide was added, followed by stirring at room temperature for 2 hours. Under ice cooling conditions, 1 N hydrochloric acid was added to bring the mixture to pH 5. The crystal obtained was collected by filtration, washed with water and ethyl acetate and dried to yield 1.24 g of the title compound.

Melting point: 247–249° C.; Elemental analysis (for $C_{31}H_{37}N_6O_4 \cdot H_2O$): Calculated (%): C, 63.14; H, 6.67; N, 16.63; Found (%): C, 63.09; H, 6.81; N, 16.70.

EXAMPLE 125A

Production of N-[6-[3-[4-(Diphenylmethoxy) piperidino]propylamino][1,2,4]triazolo[1,5-b] pyridazine-2-carbonyl]glycine 928 mg of N-[6-[3-[4-(diphenylmethoxy)piperidino] propylamino][1,2,4]triazolo[1,5-b]pyridazine-2-carbonyl] glycine ethyl ester was dissolved in 7 ml of ethanol; 2.2 ml of a 1 N aqueous solution of sodium hydroxide was added, followed by stirring at room temperature for 1.5 hours. The mixture was concentrated under reduced pressure. The residue was diluted with water; 1 N hydrochloric acid was added to bring the mixture to pH 4.5. The crystal obtained was collected by filtration, washed with water, acetone and ethyl acetate and dried to yield 443 mg of the title compound.

Melting point: 256–258° C.; Elemental analysis (for $C_{29}H_{33}N_7O_4 \cdot 1.5H_2O$): Calculated (%): C, 61.04; H, 6.36; N, 17.18; Found (%): C, 61.29; H. 6.28; N, 17.35.

EXAMPLE 126A

Production of N-[6-[3-[4-(Diphenylmethoxy) piperidino]propoxy][1,2,4]triazolo[1,5-b]pyridazine-2-carbonyl]-2,2-dimethylglycine Ethyl Ester 1.5 Fumarate 986 mg of [6-[3-[4-(diphenylmethoxy)piperidino] propoxy][1,2,4]triazolo[1,5-b]pyridazin-2-yl]carboxylic acid and 0.38 ml of N-ethyldiisopropylamine were suspended in 10 ml of N,N-dimethylformamide; 361 mg of N,N'-carbonyldiimidazole was added, followed by stirring at room temperature for 3 hours. After 372 mg of 2-aminoisobutyric acid ethyl ester hydrochloride was added, the mixture was stirred at room temperature for 43 hours, then at 60° C. for 5 hours. Ice water was added, followed by extraction with ethyl acetate-tetrahydrofuran (1:1); the extract was washed with saturated saline, dried over magnesium sulfate and concentrated under reduced pressure. The residue was subjected to silica gel column chromatography and eluted with ethyl acetate:methanol:triethylamine (50:1:1). The desired fraction was collected and concentrated under reduced pressure, after which it was dissolved in 5 ml of ethanol; 139 mg of fumaric acid was added, followed by concentration. Ethanol-ethyl acetate (1:3) was added to cause crystallization; the crystal precipitated was washed with ethyl ether, collected by filtration and dried to yield 581 mg of the title compound.

Melting point: 127–130° C.; Elemental analysis (for $C_{39}H_{46}N_6O_{11}$): Calculated (%): C, 60.45; H, 5.98; N, 10.85; Found (%): C, 60.06; H, 5.91; N, 10.80.

EXAMPLE 127A

Production of N-[6-[3-[4-(Diphenylmethoxy) piperidino]propylamino]-3-methylimidazo[1,2-b] pyridazine-2-carbonyl]glycine Ethyl Ester 1.17 g of 4-(diphenylmethoxy)-1-piperidinepropanamine and 0.891 g of N-(6-chloro-3-methylimidazo[1,2-b]pyridazine-2-carbonyl)glycine ethyl ester were dissolved in 10 ml of 1-methyl-2-pyrrolidone; 0.517 ml of N-ethyldiisopropylamine was added, followed by stirring in an oil bath (90–100° C.) for 15 hours. After cooling, ice water was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (90:10:1). The desired fraction was collected and recrystallized with ethyl acetate-ethyl ether (1:1) to yield 0.629 g of the title compound.

Melting point: 158–160° C.; Elemental analysis (for $C_{33}H_{40}N_6O_4$): Calculated (%): C, 67.79; H, 6.90; N, 14.37; Found (%): C, 67.52; H, 6.92; N, 14.13.

EXAMPLE 128A

Production of 6-[3-[4-Diphenylmethoxy)piperidino] propylamino]-2-isopropylimidazo[1,2-b]pyridazine Hydrochloride A mixture of 4-(diphenylmethoxy)-1-piperidinepropanamine (2.60 g), 6-chloro-2-isopropylimidazo[1,2-b]pyridazine (0.783 g) and potassium iodide (0.133 g) was stirred at 190° C. in a nitrogen atmosphere for 5 hours. The reaction mixture was cooled to 100° C.; ethanol (2 ml) was added drop by drop, after which the mixture was cooled to room temperature. To this mixture, an aqueous solution of sodium hydrogen carbonate (0.40 g) was added, followed by 2 extractions with ethyl acetate. The organic layers combined were washed with water, filtered and concentrated under reduced pressure. The residue was subjected to silica gel column chromatography (ethyl acetate, then ethyl acetate:methanol:triethylamine 500:25:1 and then 50:5:1). The desired fraction was collected, concentrated and dissolved in methanol; a 10% solution of hydrogen chloride/methanol (3 ml) was added, followed by concentration under reduced pressure, to yield the title compound (1.13 g).

Amorphous; Elemental analysis (for $C_{30}H_{38}N_5OCl.0.75H_2O$): Calculated (%): C, 67.52; H, 7.46; Found (%): C, 67.32; H, 7.42.

EXAMPLE 129A

Production of Ethyl 2-[6-[3-[4-[Phenyl(2-thienyl) methylamino]piperidino]propylamino]imidazo[1,2-b]pyridazin-2-yl]-2-methylpropionate Trihydrochloride 1.44 g of 4-[phenyl(2-thienyl)methylamino]-1-piperidinepropanamine and 585 mg of ethyl 2-(6-chloroimidazo[1,2-b]pyridazin-2-yl)-2-methylpropionate were dissolved in 3 ml of 1-methyl-2-pyrrolidone, followed by stirring in an oil bath (170° C.) for 4 hours. After cooling, ethanol and saturated aqueous sodium bicarbonate were added, followed by extraction with ethyl acetate; the extract was washed with saturated saline, dried over magnesium sulfate. The solution was concentrated under reduced pressure. The residue was subjected to silica gel column chromatography and eluted with ethyl acetate:methanol:triethylamine (50:5:1). The desired fraction was collected, concentrated, dissolved in 5 ml of ethyl acetate; 0.86 ml of 4N-hydrogenchloride in ethyl acetate was added, followed by concentration. Ethanol-ethyl acetate (1:4) was added to the residue; the crystal precipitated was collected by filtration and dried to yield 609 mg of the title compound.

Melting point: 175–178° C.; Elemental analysis (for $C_{31}H_{43}N_6O_2SCl_3.H_2O$): Calculated (%): C, 54.11; H, 6.59; N, 12.21; Found (%): C, 54.17; H, 6.49; N, 12.08.

EXAMPLE 130A

Production of Ethyl 2-[6-[3-[4-(Hydroxydiphenylmethyl)piperidino]propylamino] imidazo[1,2-b]pyridazin-2-yl]-2-methylpropionate Dihydrochloride 427 mg of 4-(hydroxydiphenylmethyl)-1-piperidinepropanamine and 235 mg of ethyl 2-(6-chloroimidazo[1,2-b]pyridazin-2-yl)-2-methylpropionate were stirred at 160° C. for 3.5 hours. After cooling, ethanol and saturated aqueous sodium bicarbonate were added, followed by extraction with ethyl acetate; the extract was washed with saturated saline, dried over magnesium sulfate and concentrated under reduced pressure. The residue was subjected to silica gel column chromatography and eluted with ethyl acetate:methnol:triethylamine (50:5:1). The desired fraction was collected, concentrated, dissolved in 5 ml of ethyl acetate; 0.23 ml of 4N-hydrogenchloride in ethyl acetate was added, followed by concentration. Ethyl ether was added to the residue; the powder was collected by filtration and dried to yield 216 mg of the title compound.

Aamorphous; Elemental analysis (for $C_{33}H_{43}N_5O_3Cl_2.H_2O$, 0.5$Et_2O$): Calculated (%): C, 61.49; H, 7.37; N, 10.24; Found (%): C, 61.47; H, 7.36; N, 9.87.

EXAMPLE 131A

Production of Ethyl 2-[6-[3-[3-(diphenylmethoxy) pyrrolidino]propylamino]imidazo[1,2-b]pyridazin-2-yl]-2-methylpropionate Dihydrochloride 1.53 g of 3-(diphenylmethoxy)-1-pyrrolidinepropanamine and 660 mg of ehtyl 2-(6-chloroimidazo[1,2-b]pyridazin-2-yl)-2-methylpropionate were dissolved in 3 ml of 1-methyl-2-pyrrolidone, followed by stirring in an oil bath (170° C.) for 8 hours. After cooling, saturated aqueous solution of sodium bicarbonate was added, followed by extraction with ethyl acetate; the extract was washed with water and saturated saline, dried over magnesium sulfate. The solution was concentrated under reduced pressure. The residue was subjected to silica gel column chromatography and eluted with ethyl acetate-:methanol:triethylamine (50:5:1). The desired fraction was collected, concentrated, dissolved in 5 ml of ethyl acetate; 0.81 ml of 4N-hydrogenchloride in ethyl acetate was added, followed by concentration. Ethyl ether was added to the residue; the powder was collected by filtration and dried to yield 877 mg of the title compound.

Amorphous; Elemental analysis (for $C_{32}H_{41}N_5O_3Cl_2 \cdot H_2O$): Calculated (%): C, 60.75; H, 6.85; N, 11.07; Found (%): C, 60.50; H, 6.55; N, 10.81.

EXAMPLE 132A

Production of Ethyl 2-[6-[3-[4-(10,11-Dihydro-5H-dibenzo[a,d]cyclohepten-5-oxy)piperidino] propylamino]imidazo[1,2-b]pyridazin-2-yl]-2-methylpropionate 1.69 g of 4-(10,11-dihydro-5H-dibenzo[a,d]cyclohepten-5-oxy)-1-piperidinepropanamine and 645 mg of ethyl 2-(6-chloroimidazo[1,2-b]pyridazin-2-yl)-2-methylpropionate were dissolved in 3 ml of 1-methyl-2-pyrrolidone, followed by stirring in an oil bath (170° C.) for 7 hours. After cooling, saturated aqueous sodium bicarbonate was added, followed by extraction with ethyl acetate; the extract was washed with water and saturated saline, dried over magnesium sulfate. The solution was concentrated under reduced pressure. The residue was subjected to silica gel column chromatography and eluted with ethyl acetate:methanol:triethylamine (50:5:1). The desired fraction was collected, concentrated, the residue was subjected to silica gel column chromatography again and eluted with dichloromethane:methanol:triethylamine (100:1:2). The desired fraction was collected and concentrated to yield 340 mg of the title compound.

$^1$H-NMR (CDCl$_3$) δ ppm: 1.21 (3H, t, J=7.0 Hz), 1.52–2.20 (8H, m), 1.64 (6H, s), 2.43–2.60 (2H, m), 2.70–2.92 (2H, m), 2.95–3.10 (2H, m), 3.28–3.62 (5H, m), 6.14 (2H, d, J=7.0 Hz), 6.29 (1H, d, J=9.4 Hz), 6.40–6.50 (1H, brs), 7.05–7.22 (6H, m), 7.33–7.43 (2H, m), 7.54 (1H, d, J=9.4 Hz).

REFERENCE EXAMPLE 1A

Production of 4-(Diphenylmethoxy)-1-piperidinepropanol 2.67 g of 4-(diphenylmethoxy)piperidine was dissolved in 20 ml of N,N-dimethylformamide; 1.09 ml of 3-bromopropanol and 1.66 g of potassium carbonate were added, followed by stirring at room temperature for 40 hours. Ice water was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (90:10:1). The desired fraction was collected and concentrated to yield 2.32 g of the title compound.

$^1$H-NMR (CDCl$_3$): δ ppm: 1.5–2.4 (10H, m), 2.58 (2H, t, J=5 Hz), 3.3–3.6 (1H, m), 3.78 (2H, t, J=5 Hz), 5.50 (1H, s), 7.1–7.5 (10H, m).

REFERENCE EXAMPLE 2A

Production of 4-(Diphenylmethoxy)-1-piperidinebutanol 1.05 g of 4-(diphenylmethoxy)piperidine was dissolved in 10 ml of N,N-dimethylformamide; 0.57 ml of 4-bromobutyl acetate and 652 mg of potassium carbonate were added, followed by stirring at 50 9 for 3 hours. Ice water was added, followed by extraction with ethyl ether; the extract was washed with saline, dried over magnesium sulfate and concentrated under reduced pressure. The residue was dissolved in 15 ml of ethanol; 8 ml of a 1 N aqueous solution of sodium hydroxide was added, followed by stirring at room temperature for 1 hour. After the mixture was concentrated under reduced pressure. The residue was neutralized with 1 N hydrochloric acid, followed by extraction with ethyl acetate; the extract was washed with saline, dried over magnesium sulfate and concentrated under reduced pressure, the crystal precipitate was collected, washed with ethyl ether and dried to yield 1.21 g of the title compound.

$^1$H-NMR (CDCl$_3$) δ ppm: 2.95 (2H, t, J=5 Hz), 1.6–3.4 (13H, m), 3.74 (2H, t, J=5 Hz), 5.43 (1H, s), 7.2–7.5 (10H, m).

REFERENCE EXAMPLE 3A

Production of 4-(Diphenylmethoxy)-1-piperidinehexanol 1.00 g of 4-(diphenylmethoxy)piperidine was dissolved in 10 ml of N,N-dimethylformamide; 0.49 ml of 6-bromo-1-hexanol, 0.56 g of sodium iodide and 0.62 g of potassium carbonate were added, followed by stirring at 100° C. for 1 hour. Ice water was added, followed by extraction with ethyl acetate; the extract was washed with saline, dried over magnesium sulfate and concentrated under reduced pressure. The residue was subjected to silica gel column chromatography and eluted with ethyl acetate:methanol:triethylamine (90:10:1). The desired fraction was collected and concentrated to yield 1.24 g of the title compound.

$^1$H-NMR (CDCl$_3$) δ ppm: 1.2–2.0 (12H, m), 2.0–2.2 (2H, m), 2.30 (2H, t, J=8 Hz), 2.6–2.9 (2H, m), 3.3–3.6 (1H, m), 3.63 (2H, t, J=6 Hz), 5.52 (1H, s), 7.1–7.5 (10H, m).

REFERENCE EXAMPLE 4A

Production of 2-[2-[4-(Diphenylmethoxy) piperidino]ethoxy]ethanol 1.30 g of 4-(diphenylmethoxy)piperidine was dissolved in 10 ml of N,N-dimethylformamide; 0.52 ml of 2-(2-chloroethoxy)ethanol, 0.73 g of sodium iodide and 0.81 g of potassium carbonate were added, followed by stirring at 100° C. for 1 hour. Ice water was added, followed by extraction with ethyl acetate; the extract was washed with saline, dried over magnesium sulfate and concentrated under reduced pressure. The residue was subjected to silica gel column chromatography and eluted with ethyl acetate-:methanol:triethylamine (90:10:1). The desired fraction was collected and concentrated to yield 1.47 g of the title compound.

$^1$H-NMR (CDCl$_3$) δ ppm: 1.6–2.4 (6H, m), 2.54 (2H, t, J=6 Hz), 2.6–3.0 (2H, m), 3.3–3.5 (1H, m), 3.5–3.8 (6H, m), 5.50 (1H, s), 7.1–7.5 (10H, m).

REFERENCE EXAMPLE 5A

Production of 2-[2-[4-(Diphenylmethyl)-1-piperazinyl]ethoxy]ethanol 1.00 g of 1-(diphenylmethyl)piperazine was dissolved in 10 ml of N,N-dimethylformamide; 0.42 ml of 2-(2-chloroethoxy)ethanol, 0.59 g of sodium iodide and 0.66 g of potassium carbonate were added, followed by stirring at 100° C. for 1 hour. Ice water was added, followed by extraction with ethyl acetate; the extract was washed with saline, dried over magnesium sulfate and concentrated under reduced pressure. The residue was subjected to silica gel column chromatography and eluted with dichloromethane:ethyl acetate:methanol (10:10:1). The desired fraction was collected and concentrated to yield 1.47 g of the title compound.

$^1$H-NMR (CDCl$_3$) δ ppm: 2.3–2.8 (8H, m), 2.57 (2H, t, J=6 Hz), 3.5–3.8 (6H, m), 4.21 (1H, s), 7.1–7.5 (10H, m).

REFERENCE EXAMPLE 6A

Production of 2-tert-Butyl-6-chloro[1,2,4]triazolo[1,5-b]pyridazine

Process A:
N-(6-Chloropyridazin-3-yl)pivalamidoxime
36 g of N,N-dimethylpivalamide was dissolved in 85 ml of toluene; under ice cooling conditions, 11.3 ml of phosphorus oxychloride was added drop by drop, followed by stirring at room temperature for 24 hours. To this solution, 12.0 g of 3-amino-6-chloropyridazine was added, followed by stirring at 60–70° C. for 24 hours. After cooling, ethyl acetate was added; the mixture was washed with a 2 N aqueous solution of sodium hydroxide and saline, dried over sodium a sulfate and concentrated under reduced pressure. The residue was subjected to silica gel column chromatography and eluted with hexane:ethyl acetate:triethylamine (50:50:2). The desired fraction was collected to yield 6.38 g of N$^2$-(6-chloropyridazin-3-yl)-N$^1$,N$^1$-dimethylpivalamidine. The filtrate was purified by silica gel column chromatography to yield 6.07 g of the amidine. 12.5 g of the amidine derivative obtained was dissolved in 60 ml of methanol; a solution of 4.31 g of hydroxylamine hydrochloride in 40 ml of methanol was added, followed by stirring at room temperature for 2 hours. The methanol was concentrated to half volume under reduced pressure; the crystal precipitated was collected by filtration, washed with water and ethyl ether and dried to yield 10.44 g of the title compound.

Melting point: 128–130° C.; Elemental analysis (for C$_9$H$_{13}$N$_4$OCl): Calculated (%): C, 47.27; H, 5.73; N, 24.50; Found (%): C, 47.28; H, 5.59; N, 24.34.

Process B:
4.07 g of N-(6-chloropyridazin-3-yl)pivalamidoxime was suspended in 170 ml of chloroform; 8.3 ml of phosphorus oxychloride was added drop by drop, followed by heating and refluxing for 5 hours. After cooling, ice water and a 2 N aqueous solution of sodium hydroxide were added, followed by extraction with chloroform; the extract was washed with saline, dried over magnesium sulfate and concentrated under reduced pressure. The residue was subjected to silica gel column chromatography and eluted with hexane:ethyl acetate (5:1). The desired fraction was collected and concentrated to yield 1.12 g of the title compound.

Melting point: 95–97° C.; Elemental analysis (for C$_9$H$_{11}$N$_4$Cl.0.3H$_2$O): Calculated (%): C, 50.03; H, 5.41; N, 25.93; Found (%): C, 50.23; H, 5.12; N, 25.90.

REFERENCE EXAMPLE 7A

Production of Methyl 6-Chloro[1,2,4]triazolo[1,5-b]pyridazine-2-carboxylate

Process A:
6-Chloro[1,2,4]triazolo[1,5-b]pyridazine-2-carboxylic Acid
10.0 g of 6-chloro-2-methyl[1,2,4]triazolo[1,5-b]pyridazine was added to 55 ml of concentrated sulfuric acid under ice cooling conditions; 19.4 g of sodium dichromate dihydrate was added little by little at constant temperature, followed by stirring at room temperature for 4 days. Under ice cooling conditions, about 200 ml of ice water was added; the crystal precipitated was collected by filtration, washed with water and ethyl ether and dried to yield 9.74 g of the title compound.

Melting point: 221° C. (decomp.); Elemental analysis (for C$_6$H$_3$N$_4$O$_2$Cl): Calculated (%): C, 36.29; H, 1.52; N, 28.22; Found (%): C, 35.96; H, 1.59; N, 28.12.

Process B:
3.02 g of 6-chloro[1,2,4]triazolo[1,5-b]pyridazine-2-carboxylic acid was dissolved in 50 ml of N,N-dimethylformamide; 3.15 ml of N-ethyldiisopropylamine was added, followed by the addition of 1.14 ml of methyl iodide with stirring under ice water cooling conditions. After stirring at room temperature for 19 hours, about 200 ml of ice water was added; the crystal precipitated was collected by filtration and washed with water and ethyl ether. The filtrate was purified by silica gel column chromatography; the crystal obtained was combined with the above washings and dried to yield 2.91 g of the title compound.

Melting point: 208–209° C.; Elemental analysis (for C$_7$H$_5$N$_4$O$_2$Cl): Calculated (%): C, 39.55; H, 2.37; N, 26.35; Found (%): C, 39.65; H, 2.46; N, 26.34.

REFERENCE EXAMPLE 8A

Production of Ethyl 2-(6-Chloroimidazo[1,2-b]pyridazin-2-yl)-2-methylpropionate

Method A

Process A:
Ethyl 6-Chloroimidazo[1,2-b]pyridazine-2-acetate
11.2 g of 3-amino-6-chloropyridazine was suspended in 150 ml of ethanol; 28.6 g of ethyl 4-chloroacetoacetate was added, followed by heating and refluxing for 24 hours. After cooling, the mixture was concentrated under reduced pressure. The residue was adjusted to pH 7 by the addition of an aqueous solution of sodium hydrogen carbonate, followed by extraction with ethyl acetate; the extract was washed with saline, dried over magnesium sulfate and concentrated under reduced pressure. The residue was subjected to silica gel column chromatography and eluted with hexane:ethyl acetate (2:3). The desired fraction was collected to yield 12.7 g of the title compound.

$^1$H-NMR (CDCl$_3$) δ ppm: 1.29 (3H, t, J=7 Hz), 3.89 (2H, s), 4.23 (2H, q, J=7 Hz), 7.05, 7.85 (each 1H, d, J=9 Hz), 7.95 (1H, s).

Process B:
6.8 g of ethyl 6-chloroimidazo[1,2-b]pyridazine-2-acetate was dissolved in 50 ml of N,N-dimethylformamide; while the solution was stirred under ice water cooling conditions, 2.46 g of a 60% sodium hydride dispersion in mineral oil was add little by little, followed by stirring at room temperature for 30 minutes. Under ice water cooling conditions, 4.36 ml of methyl iodide was added, followed by stirring at room temperature for 2 hours. Ice water was poured, followed by extraction with ethyl acetate; the extract was washed with saline, dried over magnesium sulfate and concentrated under reduced pressure. The residue was subjected to silica gel column chromatography and eluted with hexane:ethyl acetate (2:1). The desired fraction was collected and concentrated to yield 4.06 g of the title compound.

Melting point: 64–65° C.; Elemental analysis (for C$_{12}$H$_{14}$N$_3$O$_2$Cl): Calculated (%): C, 53.84; H, 5.27; N, 15.70; Found (%): C, 53.85; H, 5.16; N, 15.80.

Method B

The title compound may be produced according to the following method.

80.0 g of 3-amino-6-chloropyridazine, 201 g of ethyl 4-bromo-2,2-dimethyl-3-oxobutanoate and 131 g of disodium hydrogenphosphate were suspended in 300 ml of ethanol, followed by heating and refluxing for 8 hours. 300 ml of water was added to the reaction mixture, followed by two extractions with ethyl acetate. The organic layers combined was washed with 600 ml of water twice and with 300 ml of a saturated solution of sodium chloride, followed by drying on magnesium sulfate, treating with activated carbons, filtration and concentrating under reduced pressure. The residue was dissolved in 200 ml of diisopropyl ether; the insoluble substances were filtrated off and the filtrate was concentrated under reduced pressure. The residue was subjected to silica gel column chromatography (hexane:ethyl acetate 100:1, 2:1 and 1:1) and recrystallized from hexane to yield the title compound (99.3 g).

REFERENCE EXAMPLE 9A

Production of Methyl 2-(6-Chloroimidazo[1,2-b] pyridazin-2-yl)-2-methylpropionate 10.1 g of 3-amino-6-chloropyridazine was suspended in 120 ml of methanol; 23.5 g of methyl 4-chloroacetoacetate was added, followed by heating and refluxing for 20 hours. After cooling, the mixture was concentrated under reduced pressure. The residue was adjusted to pH 7 by the addition of an aqueous solution of sodium hydrogen carbonate, followed by extraction with ethyl ether; the extract was washed with saline, dried over magnesium sulfate and concentrated under reduced pressure. The residue was subjected to silica gel column chromatography and eluted with hexane:ethyl acetate (1:4). The desired fraction was collected to yield 9.15 g of methyl 6-chloroimidazo[1,2-b]pyridazine-2-acetate was dissolved in 70 ml of N,N-dimethylformamide; while the solution was stirred under ice water cooling conditions, 3.5 g of a 60% sodium hydride dispersion in mineral oil was add little by little, followed by stirring at room temperature for 30 minutes. Under ice water cooling conditions, 6.3 ml of methyl iodide was added, followed by stirring at room temperature for 5 hours. Ice water was poured, followed by extraction with ethyl acetate; the extract was washed with saline, dried over magnesium sulfate and concentrated under reduced pressure. The residue was subjected to silica gel column chromatography and eluted with hexane:ethyl acetate (1:1). The desired fraction was collected and concentrated to yield 14.1 g of the title compound.

Melting point: 92–93° C.; Elemental analysis (for $C_{11}H_{12}N_3O_2Cl$): Calculated (%): C, 52.08; H, 4.77; N, 16.56; Found (%): C, 52.01; H, 4.60; N, 16.59.

REFERENCE EXAMPLE 10A

Production of 2-(6-Chloroimidazo[1,2-b]pyridazin-2-yl)-2-methylpropionic Acid 1.40 g of methyl 2-(6-chloroimidazo[1,2-b]pyridazin-2-yl)-2-methylpropionate was dissolved in 15 ml of tetrahydrofuran; 9 ml of a 1 N aqueous solution of sodium hydroxide was added, followed by stirring at room temperature for 3 hours. After the mixture was concentrated under reduced pressure. The residue was adjusted top $H_4$ by the addition of 1N hydrochloric acid; the crystal precipitated was collected by filtration to yield 1.06 g of the title compound.

Melting point: 159–161° C.; Elemental analysis (for $C_{11}H_{10}N_3O_2Cl$): Calculated (%): C, 50.12; H, 4.21; N, 17.53; Found (%): C, 50.36; H, 4.34; N, 17.32.

REFERENCE EXAMPLE 11A

Production of tert-Butyl 2-(6-Chloroimidazo[1,2-b] pyridazin-2-yl)-2-methylpropionate 0.863 g of 2-(6-chloroimidazo[1,2-b]pyridazin-2-yl)-2-methylpropionic acid was suspended in 10 ml of toluene; 2.6 ml of N,N-dimethylformamide di-tert-butylacetal was added, followed by stirring at 80° C. for 1 hour. After cooling, the mixture was diluted with ethyl acetate, washed with an aqueous solution of sodium hydrogen carbonate and dried over magnesium sulfate and concentrated under reduced pressure, ethyl ether was added to the residue; the crystal separated was collected and dried to yield 0.52 g of the title compound.

$^1$H-NMR (CDCl$_3$) δ ppm: 1.43 (9H, s), 1.64 (6H, s), 7.02, 7.87 (each 1H, d, J=9 Hz), 7.84 (1H, s).

REFERENCE EXAMPLE 12A

Production of 6-Chloro-2-methoxyimidazo[1,2-b] pyridazine 2.69 g of 6-chloro-2-hydroxyimidazo[1,2-b]pyridazine was suspended in 30 ml of N,N-dimethylformamide; 838 mg of a 60% sodium hydride dispersion in mineral oil was added little by little, followed by stirring at room temperature for 30 minutes. Under ice water cooling conditions, 1.2 ml of methyl iodide was added, followed by stirring at room temperature for 3 days. Ice water was added, followed by extraction with ethyl acetate; the extract was washed with saline, dried over magnesium sulfate and concentrated under reduced pressure. The residue was subjected to silica gel column chromatography and eluted with hexane:ethyl acetate (5:1). The desired fraction was collected and concentrated to yield 1.05 g of the title compound.

Melting point: 134–136° C.; Elemental analysis (for $C_7H_6N_3OCl$): Calculated (%): C, 45.79; H, 3.29; N, 22.89; Found (%): C, 45.68; H, 3.27; N, 22.79.

REFERENCE EXAMPLE 13A

Production of 4-(Diphenylmethoxy)-1-piperidinepentanamine 3.70 g of potassium phthalimide was dissolved in 20 ml of N,N-dimethylformamide; 5.4 ml of 1,5-dibromopentane was added, followed by stirring at room temperature for 15 hours. Ice water was added to the reaction mixture, followed by extraction with ethyl acetate; the extract was washed with saline, dried over magnesium sulfate and concentrated under reduced pressure. The residue was subjected to silica gel column chromatography and eluted with hexane-ethyl acetate (4:1). The desired fraction was collected to yield 4.68 g of N-(5-bromopentyl)phthalimide as an oily substance. 4.68 g of N-(5-bromopentyl)phthalimide and 4.25 g of 4-(diphenylmethoxy)piperidine were dissolved in 30 ml of N,N-dimethylformamide; 2.42 g of potassium carbonate was added, followed by stirring at room temperature for 15 hours. Ice water was added to the reaction mixture, followed by extraction with ethyl acetate; the extract was washed with saline, dried over magnesium sulfate and concentrated under reduced pressure. The residue was subjected to silica gel column chromatography and eluted with hexane-ethyl acetate-triethylamine (50:50:1). The desired fraction was collected to yield 6.67 g of N-[5-[4-(diphenylmethoxy) piperidino]pentyl]phthalimide as an oily substance. 6.6 g of N-[5-[4-(diphenylmethoxy)piperidino]pentyl]phthalimide was dissolved in 30 ml of ethanol; 0.694 ml of hydrazine monohydrate was added, followed by thermal refluxing for 3 hours. After cooling, the mixture was concentrated under reduced pressure; ethyl acetate was added to the residue; the crystal precipitated was collected, dissolved in 15 ml of a 1N aqueous solution of sodium hydroxide and 20 ml of water and extracted with ethyl acetate; the extract was washed with saline, dried over sodium sulfate and concentrated under reduced pressure; the crystal obtained was collected to yield 3.29 g of the title compound.

$^1$H-NMR (CDCl$_3$) δ ppm: 1.2–2.9 (18H, m), 3.3–3.6 (1H, m), 5.52 (1H, s), 7.1–7.4 (10H, m).

REFERENCE EXAMPLE 14A

Production of 1-Amino-3-[4-(diphenylmethoxy) piperidino]-2-propanol 3.70 g of potassium phthalimide was dissolved in 20 ml of N,N-dimethylformamide; 2.58 ml of epibromohydrin was added, followed by stirring at room temperature for 15 hours. Ice water was added to the reaction mixture, followed by extraction with ethyl acetate; the extract was washed with saline, dried over magnesium sulfate and concentrated under reduced pressure; ethyl ether was added to the residue; the crystal precipitated was collected to yield 3.7 g of N-(2-oxiranylmethoxy)phthalimide. 0.61 g of N-(2-oxiranylmethoxy)phthalimide and 0.802 g of 4-(diphenylmethoxy)piperidine were dissolved n 10 ml of ethanol, followed by thermal refluxing for 2 hours. The reaction mixture was concentrated under reduced pressure. The residue was subjected to silica gel column chromatography and eluted with ethyl acetate. The desired fraction was collected to yield 1.30 g of N-[3-[4-(diphenylmethoxy) piperidino-2-hydroxypropyl]phthalimide as an oily substance. This oily substance was dissolved in 10 ml of ethanol; 0.14 ml of hydrazine monohydrate was added, followed by thermal refluxing for 3 hours. After cooling, the mixture was concentrated under reduced pressure; ethanol was added to the residue; the crystal precipitated was collected, dissolved in 3 ml of a 1 N aqueous solution of sodium hydroxide and 10 ml of water and extracted with ethyl acetate; the extract was washed with saline, dried over sodium sulfate and concentrated under reduced pressure; the crystal obtained was collected to yield 0.76 g of the title compound.

$^1$H-NMR (CDCl$_3$) δ ppm: 1.2–3.0 (12H, m), 3.3–3.55 (1H, m), 3.55–3.8 (1H, m), 5.52 (1H, s), 7.1–7.5 (10H, m).

REFERENCE EXAMPLE 15A

Production of 4-[bis(4-Fluorophenyl)methoxy)-1-piperidinepropanamine 25 g of 4,4'-difluorobenzophenone was dissolved in ethanol-tetrahydrofuran (180 ml–60 ml); 2.16 g of sodium borohydride was added under ice cooling conditions, followed by stirring at room temperature for 30 minutes. The mixture was concentrated under reduced pressure. The residue was diluted with ice water and extracted with ethyl acetate; the extract was washed with saline, dried over magnesium sulfate and concentrated under reduced pressure; the oily substance obtained was dissolved in 800 ml of toluene; 11.6 g of 4-hydroxypiperidine and 23.7 g of p-toluenesulfonic acid monohydrate were added, followed by thermal refluxing for 2 hours. After cooling, the mixture was concentrated under reduced pressure; ice water and 130 ml of a 1 N aqueous solution of sodium hydroxide were added, followed by extraction with ethyl acetate; the extract was washed with saline, dried over magnesium sulfate and concentrated under reduced pressure; the oily substance obtained (34.5 g) was dissolved in 100 ml of N,N-dimethylformamide; 16.3 g of N-(3-bromopropyl) phthalimide and 10.5 g of potassium carbonate were added, followed by stirring at room temperature for 20 hours. Ice water was added to the reaction mixture, followed by extraction with ethyl acetate; the extract was washed with saline, dried over magnesium sulfate and concentrated under reduced pressure. The residue was subjected to silica gel column chromatography and eluted with hexane-ethyl acetate (1:2). The desired fraction was collected to yield 20.5 g of N-[3-[4-[bis(4-fluorophenyl)methoxy]piperidino] propyl]phthalimide as an oily substance. 20.5 g of this oily substance was dissolved in 150 ml of ethanol; 2.02 ml of hydrazine monohydrate was added, followed by thermal refluxing for 3 hours. After cooling, the mixture was concentrated under reduced pressure; ethanol was added to the residue; the crystal precipitated was collected, dissolved in 40 ml of a 1 N aqueous solution of sodium hydroxide and extracted with ethyl acetate-tetrahydrofuran (2:1); the extract was washed with saline, dried over sodium sulfate and concentrated under reduced pressure to yield 12.07 g of the title compound as an oily substance.

$^1$H-NMR (CDCl$_3$) δ ppm: 1.5–2.2 (10H, m), 2.36 (2H, d, J=7 Hz), 2.74 (2H, d, J=7 Hz), 3.3–3.5 (1H, m), 5.47 (1H, s), 6.9–7.4 (8H, m).

REFERENCE EXAMPLE 16A

Production of 4-[bis(4-Methylphenyl)methoxy)-1-piperidinepropanamine 25 g of 4,4'-dimethylbenzophenone was dissolved in ethanol-tetrahydrofuran (180 ml–60 ml); 2.23 g of sodium borohydride was added under ice cooling conditions, followed by stirring at room temperature for 24 hours. The mixture was concentrated under reduced pressure; ice water was added to the residue; the crystal precipitated was collected and dried; the crystal obtained (30.5 g) was dissolved in 800 ml of toluene; 11.9 g of 4-hydroxypiperidine and 24.9 g of p-toluenesulfonic acid monohydrate were added, followed by thermal refluxing for 3 hours. After cooling, the mixture was concentrated under reduced pressure; 100 ml of ice water and 140 ml of a 1 N aqueous solution of sodium hydroxide were added, followed by extraction with ethyl acetate; the extract was washed with saline, dried over sodium sulfate and concentrated under reduced pressure. The residue was subjected to silica gel column chromatography and eluted with ethyl acetate-methanol-triethylamine (90:10:1). The desired fraction was collected to yield 32.8 g of 4-[bis(4-methylphenyl)methoxy] piperidine as an oily substance. 16.4 g of 4-[bis(4-methylphenyl)methoxy]piperidine was dissolved in 100 ml of N,N-dimethylformamide; 14.2 g of N-(3-bromopropyl) phthalimide and 8.15 g of potassium carbonate were added, followed by stirring at room temperature for 16 hours. Ice water was added to the reaction mixture, followed by extraction with ethyl acetate; the extract was washed with saline, dried over magnesium sulfate and concentrated under reduced pressure. The residue was subjected to silica gel column chromatography and eluted with hexane-ethyl acetate (1:2). The desired fraction was collected to yield 21.2 g of N-[3-[4-[bis(4-methylphenyl)methoxy]piperidino]

propyl]phthalimide as an oily substance. 20.5 g of this oily substance was dissolved in 150 ml of ethanol; 2.18 ml of hydrazine monohydrate was added, followed by thermal refluxing for 3 hours. After cooling, the mixture was concentrated under reduced pressure; ethanol was added to the residue; the crystal precipitated was collected, dissolved in 40 ml of a 1N aqueous solution of sodium hydroxide and extracted with ethyl acetate-tetrahydrofuran (2:1); the extract was washed with saline, dried over sodium sulfate and concentrated under reduced pressure to yield 10.5 g of the title compound as an oily substance.

$^1$H-NMR (CDCl$_3$) δ ppm: 1.4–2.9 (14H, m), 2.31 (6H, s), 3.3–3.50 (1H, m), 5.46 (1H, s), 7.11, 7.22 (each 4H, d, J=8 Hz).

REFERENCE EXAMPLE 17A

Production of N-(6-Chloroimidazo[1,2-b]pyridazine-2-carbonyl]glycine Ethyl Ester 0.593 g of 6-chloroimidazo[1,2-b]pyridazine-2-carboxylic acid was suspended in 7.5 ml of N,N-dimethylformamide; 0.535 g of N,N'-carbonyldiimidazole and 0.46 g of glycine ethyl ester hydrochloride were added, followed by stirring at room temperature for 30 minutes. To this mixture, 0.457 ml of triethylamine was added, followed by further stirring for 1 hour. Ice water was added to the reaction mixture; the crystal precipitated was collected by filtration, washed with water and dried to yield 0.749 g of the title compound.

Melting point: 190–191° C.; Elemental analysis (for C$_{11}$H$_{11}$N$_4$O$_3$Cl): Calculated (%): C, 46.74; H, 3.92; N, 19.82; Found (%): C, 46.70; H, 4.03; N, 19.75.

REFERENCE EXAMPLE 18A

Production of 2-(6-Chloroimidazo[1,2-b]pyridazin-2-yl)-2-methylpropionamide 1.20 g of 2-(6-chloroimidazo[1,2-b]pyridazin-2-yl)-2-methylpropionic acid was dissolved in 8 ml of N,N-dimethylformamide; 0.892 g of N,N'-carbonyldiimidazole was added, followed by stirring at room temperature for 30 minutes. To this mixture, 0.321 g of ammonium chloride and 0.832 ml of triethylamine were added under ice cooling conditions, followed by stirring at room temperature for 3 hours. Ice water was added to the reaction mixture; the crystal precipitated was collected by filtration, washed with water and dried to yield 0.697 g of the title compound.

Melting point: 194–195° C.; Elemental analysis (for C$_{10}$H$_{11}$N$_4$OCl): Calculated (%): C, 50.32; H, 4.65; N, 23.47; Found (%): C, 50.34; H, 4.60; N, 23.43.

REFERENCE EXAMPLE 19A

Production of 2-(6-Chloroimidazo[1,2-b]pyridazin-2-yl)-N,N,2-trimethylpropionamide 0.959 g of 2-(6-chloroimidazo[1,2-b]pyridazin-2-yl)-2-methylpropionic acid was dissolved in 6 ml of N,N-dimethylformamide; 0.714 g of N,N'-carbonyldiimidazole was added, followed by stirring at room temperature for 60 minutes. To this mixture, 0.392 g of dimethylamine hydrochloride and 0.665 ml of triethylamine were added under ice cooling conditions, followed by stirring at room temperature for 3 hours. Saline was added to the reaction mixture, followed by extraction with ethyl acetate; the extract was washed with saline, dried over magnesium sulfate and concentrated under reduced pressure. The residue was subjected to silica gel column chromatography and eluted with ethyl acetate:methanol (95:5). The desired fraction was collected and concentrated; the crystal obtained was collected by filtration to yield 0.608 g of the title compound.

Melting point: 149–151° C.; Elemental analysis (for C$_{12}$H$_{15}$N$_4$OCl): Calculated (%): C, 54.04; H, 5.67; N, 21.01; Found (%): C, 53.90; H, 5.85; N, 21.04.

REFERENCE EXAMPLE 20A

Production of 2-(6-Chloroimidazo[1,2-b]pyridazin-2-yl)-2-methylpropanol 0.719 g of 2-(6-chloroimidazo[1,2-b]pyridazin-2-yl)-2-methylpropionic acid was dissolved in 15 ml of tetrahydrofuran; 0.535 g of N,N'-carbonyldiimidazole was added, followed by stirring at room temperature for 60 minutes. To this mixture, 1.15 g of tetra-n-butylammonium borohydride was added under ice cooling conditions, followed by stirring at room temperature for 1 hour. 2 ml of 5 N hydrochloric acid was added to the reaction mixture, followed by concentration under reduced pressure. The residue was adjusted to pH 7 by the addition of aqueous sodium carbonate and extracted with ethyl acetate; the extract was washed with saline, dried over magnesium sulfate and concentrated under reduced pressure. The residue was subjected to silica gel column chromatography and eluted with ethyl acetate. The desired fraction was collected and concentrated; the crystal obtained was collected by filtration to yield 0.488 g of the title compound.

$^1$H-NMR (CDCl$_3$) δ ppm: 1.39 (6H, s), 3.72 (2H, s), 7.04, 7.82 (each 1H, d, J=9.5 Hz), 7.76 (1H, s).

REFERENCE EXAMPLE 21A

Production of N-(6-Chloroimidazo[1,2-b] pyridazine-2-carbonyl)-2,2-dimethylglycine Ethyl Ester 1.28 g of 6-chloroimidazo[1,2-b]pyridazine-2-carboxylic acid was suspended in 12 ml of N,N-dimethylformamide; 1.16 g of N,N'-carbonyldiimidazole was added, followed by stirring at room temperature for 30 minutes. To the reaction mixture, 1.20 g of 2-aminoisobutyric acid ethyl ester hydrochloride and 1.00 ml of triethylamine were added, followed by stirring at room temperature for 16 hours. Water was added, the crystal precipitated was collected by filtration; the filtrate was extracted with ethyl acetate; the extract was washed with saturated saline, dried over magnesium sulfate and concentrated under reduced pressure. The residue was combined with the above crystal collected by filtration and subjected to silica gel column chromatography and eluted with hexane:ethyl acetate (2:1). The desired fraction was collected and concentrated under reduced pressure to yield 1.20 g of the title compound.

$^1$H-NMR (CDCl$_3$) δ ppm: 1.28 (3H, t, J=7.2 Hz), 1.70 (6H, s), 4.25 (2H, q, J=7.0 Hz), 7.13 (1H, d, J=9.4 Hz), 7.87 (1H, brs), 7.89 (1H, d, J=9.6 Hz), 8.41 (1H, s).

REFERENCE EXAMPLE 22A

Production of Ethyl 2-(3,6-Dichloroimidazo[1,2-b] pyridazin-2-yl]-2-methylpropionate 4.07 g of ethyl 2-(6-chloroimidazo[1,2-b]pyridazin-2-yl)-2-methylpropionate was suspended in 60 ml of ethyl acetate; 2.13 g of N-chlorosuccinimide was added, followed by thermal refluxing for 4 hours. After cooling, water was added, followed by extraction with ethyl acetate; the extract was washed with saturated saline, dried over magnesium sulfate and concentrated under reduced pressure. The residue was subjected to silica gel column chromatography and eluted with hexane:ethyl acetate (5:1). The desired fraction was collected and concentrated under reduced pressure to yield 4.48 g of the title compound.

Melting point: 66–67° C.; Elemental analysis (for $C_{12}H_{13}N_3O_2Cl_2$): Calculated (%): C, 47.70; H, 4.34; N, 13.91; Found (%): C, 47.67; H, 4.23; N, 13.93;

REFERENCE EXAMPLE 23A

Production of Methyl 2-(6-Chloro-7-methylimidazo [1,2-b]pyridazin-2-yl)-2-methylpropionate Process A:

Production of Methyl 6-Chloro-7-methylimidazo[1,2-b]pyridazine-2-acetate 15.3 g of 6-amino-3-chloro-4-methylpyridazine was suspended in 200 ml of methanol; 25.0 ml of methyl 4-chloroacetoacetate was added, followed by thermal refluxing for 36 hours. After cooling, the mixture was concentrated under reduced pressure. The residue was adjusted to pH 7 by the addition of an aqueous solution of sodium hydrogen carbonate and extracted with ethyl acetate; the extract was washed with saline, dried over magnesium sulfate and concentrated under reduced pressure. The residue was subjected to silica gel column chromatography and eluted with hexane:ethyl acetate (1:4). The desired fraction was collected to yield 14.3 g of the title compound.

Melting point: 98–99° C.; Elemental analysis (for $C_{10}H_{10}N_3O_2Cl$): Calculated (%): C, 50.12; H, 4.21; N, 17.53; Found (%): C, 50.07; H, 4.25; N, 17.74.

Process B:

4.8 g of a 60% dispersion of sodium hydride in mineral oil was suspended in 150 ml of N,N-dimethylformamide; while this suspension was stirred under ice cooling conditions, 11.4 g of methyl 6-chloro-7-methylimidazo[1,2-b]pyridazine-2-acetate was added little by little; followed by stirring at room temperature for 30 minutes. Under ice cooling conditions, 7.5 ml of methyl iodide was added, followed by stirring at room temperature for 6 hours. Ice water was poured, followed by extraction with ethyl acetate; the extract was washed with saline, dried over magnesium sulfate and concentrated under reduced pressure. The residue was subjected to silica gel column chromatography and eluted with hexane:ethyl acetate (1:1,). The desired fraction was collected and concentrated to yield 9.17 g of the title compound.

Melting point: 109–110° C.; Elemental analysis (for $C_{12}H_{14}N_3O_2Cl$): Calculated (%): C, 53.84; H, 5.27; N, 15.70; Found (%): C, 53.96; H, 5.19; N, 15.86.

REFERENCE EXAMPLE 24A

Production of Isopropyl 1-(6-Chloroimidazo[1,2-b] pyridazin-2-yl)cyclopentanecarboxylate Process A:

Production of Methyl 1-(6-Chloroimidazo[1,2-b]pyridazin-2-yl)cyclopentanecarboxylate 5.48 g of methyl 6-chloroimidazo[1,2-b]pyridazine-2-acetate was dissolved in 42 ml of N,N-dimethylformamide; while this solution was stirred under ice cooling conditions, 1.07 g of a 60% dispersion of sodium hydride in mineral oil was added little by little; followed by stirring at room temperature for 1.5 hours. Under ice cooling conditions, 3.19 ml of 1,4-dibromobutane was added drop by drop, followed by stirring at room temperature for 18 hours. Ice water was poured, followed by extraction with ethyl acetate; the extract was washed with saturated saline, dried over magnesium sulfate and concentrated under reduced pressure. The residue was subjected to silica gel column chromatography and eluted with ethyl acetate:hexane (1:3). The desired fraction was collected and concentrated under reduced pressure to yield 1.72 g of the title compound.

$^1$H-NMR (CDCl$_3$) δ ppm: 1.63–1.85 (4H, m), 2.10–2.38 (2H, m), 2.42–2.68 (2H, m), 3.69 (3H, s), 7.02 (1H, d, J=9.4 Hz), 7.84 (1H, s), 7.86 (1H, d, J=8.6 Hz).

Process B:

In 30 ml of 2-propanol, 0.81 ml of concentrated sulfuric acid was dissolved; 1.7 of methyl 1-(6-chloroimidazo[1,2-b]pyridazin-2-yl)cyclopentanecarboxylate was added, followed by thermal refluxing for 7.5 hours. After cooling, the mixture was concentrated under reduced pressure, neutralized by the addition of aqueous sodium bicarbonate and extracted with ethyl acetate. The extract was washed with saturated saline, dried over magnesium sulfate and concentrated under reduced pressure; the crystal precipitated was collected by filtration, washed with n-hexane and dried to yield 1.30 g of the title compound. The filtrate was concentrated under reduced pressure. The residue was subjected to silica gel column chromatography and eluted with hexane:ethyl acetate (3:1). The desired fraction was collected, concentrated under reduced pressure and dried to yield 356 mg of the title compound.

$^1$H-NMR (CDCl$_3$) δ ppm: 1.18 (3H, s), 12.1 (3H, s), 1.68–1.85 (4H, m), 2.13–2.32 (2H, m), 2.45–2.60 (2H, m), 4.94–5.13 (1H, m), 7.02 (1H, d, J=9.6 Hz), 7.83 (1H, s), 7.86 (1H, d, J=9.4 Hz).

REFERENCE EXAMPLE 25A

Production of Isopropyl 1-(6-Chloroimidazo[1,2-b] pyridazin-2-yl)cyclopropanecarboxylate Process A:

Production of Methyl 1-(6-Chloroimidazo[1,2-b]pyridazin-2-yl)cyclopropanecarboxylate 5.93 g of methyl 6-chloroimidazo[1,2-b]pyridazine-2-acetate was dissolved in 45 ml of N,N-dimethylformamide; while this solution was stirred under ice cooling conditions, 2.31 g of a 60% dispersion of sodium hydride in mineral oil was added little by little; followed by stirring at room temperature for 40 minutes. Under ice cooling conditions, 2.49 ml of 1,2-dibromoethane was added drop by drop, followed by stirring at room temperature for 14 hours. Ice water was poured, followed by extraction with ethyl acetate; the extract was washed with saturated saline, dried over magnesium sulfate and concentrated under reduced pressure. The residue was subjected to silica gel column chromatography and eluted with hexane:ethyl acetate (2:1). The desired fraction was collected and concentrated under reduced pressure to yield 3.67 g of the title compound.

$^1$H-NMR (CDCl$_3$) δ ppm: 1.60–1.68 (2H, m), 1.70–1.85 (2H, m), 3.75 (3H, s), 7.00 (1H, d, J=9.6 Hz), 7.77 (1H, d, J=9.6 Hz), 8.28 (1H, s).

Process B:

In 70 ml of 2-propanol, 1.82 ml of concentrated sulfuric acid was dissolved; 3.44 g of methyl 1-(6-chloroimidazo[1,2-b]pyridazin-2-yl)cyclopropanecarboxylate was added, followed by thermal refluxing for 7.5 hours. After cooling, the mixture was concentrated under reduced pressure, neutralized by the addition of aqueous sodium bicarbonate and extracted with ethyl acetate. The extract was washed with saturated saline, dried over magnesium sulfate and concentrated under reduced pressure; the crystal precipitated was collected by filtration, washed with ether and hexane and dried to yield 1.98 g of the title compound. The filtrate was concentrated under reduced pressure. The residue was subjected to silica gel column chromatography and eluted with hexane:ethyl acetate (5:1). The desired fraction was collected, concentrated under reduced pressure and dried to yield 650 mg of the title compound.

Melting point: 112–114° C.; Elemental analysis (for $C_{13}H_{14}N_3O_2Cl$): Calculated (%): C, 55.82; H, 5.04; N, 15.02; Found (%): C, 55.75; H, 5.17; N, 14.99.

REFERENCE EXAMPLE 26A

Production of Ethyl 2-(6-Chloro-3-methylimidazo [1,2-b]pyridazin-2-yl)-2-methylpropionate Process A:

Production of Ethyl 6-Chloro-3-methylimidazo[1,2-b] pyridazine-2-acetate 2.44 g of 3-amino-6-chloropyridazine was suspended in 37 ml of ethanol; 8.40 g of ethyl 4-bromo-3-oxopentanoate was added, followed by thermal refluxing for 18 hours. After cooling, the mixture was concentrated under reduced pressure. The residue was adjusted to pH 7 by the addition of aqueous sodium bicarbonate; ethyl ether was added; the precipitate was collected by filtration and extracted with ethyl ether; the extract was washed with saturated saline, dried over magnesium sulfate and concentrated under reduced pressure. The residue was subjected to silica gel column chromatography and eluted with hexane:ethyl acetate (1:1). The desired fraction was collected to yield 2.63 g of the title compound.

$^1$H-NMR (CDCl$_3$) δ ppm: 1.27 (3H, t, J=7.1 Hz), 2.54 (3H, s), 3.85 (2H, s), 4.19 (2H, q, J=7.1 Hz), 6.99 (1H, d, J=9.6 Hz), 7.82 (1H, d, J=9.6 Hz).

Process B:

5.41 g of ethyl 6-chloro-3-methylimidazo[1,2-b] pyridazine-2-acetate was dissolved in 40 ml of N,N-dimethylformamide; while this solution was stirred under ice cooling conditions, 1.87 g of a 60% dispersion of sodium hydride in mineral oil was added little by little; followed by stirring at room temperature for 40 minutes. Under ice cooling conditions, 3.32 ml of methyl iodide was added, followed by stirring at room temperature for 15 hours. Ice water was poured, followed by extraction with ethyl acetate; the extract was washed with saturated saline, dried over magnesium sulfate and concentrated under reduced pressure. The residue was subjected to silica gel column chromatography and eluted with hexane:ethyl acetate (3:1). The desired fraction was collected and concentrated under reduced pressure to yield 2.69 g of the title compound.

$^1$H-NMR (CDCl$_3$) δ ppm: 1.21 (3H, t, J=7.2 Hz), 1.69 (6H, s), 2.48 (3H, s), 4.47 (2H, q, J=7.2 Hz), 7.21 (1H, d, J=9.6 Hz), 7.88 (1H, d, J=9.6 Hz).

REFERENCE EXAMPLE 27A

Production of Ethyl 6-Chloro-2-methylimidazo[1,2-b]pyridazine-3-carboxylate 12.9 g of 3-amino-6-chloropyridazine was suspended in 250 ml of ethanol; 18.1 g of ethyl 2-chloro-3-oxobutanoate was added, followed by thermal refluxing for 6 hours. After cooling, the mixture was concentrated under reduced pressure. The residue was adjusted to pH 7 by the addition of aqueous sodium bicarbonate; ethyl ether was added; the precipitate was collected by filtration and extracted with ethyl ether; the extract was washed with saturated saline, dried over magnesium sulfate and concentrated under reduced pressure; ethanol-1 N aqueous solution of sodium hydroxide (1:1) was added; the crystal precipitated was collected by filtration; the filtrate was concentrated again. The residue was crystallized by the addition of ethyl acetate and collected by filtration to yield 3.09 g of the title compound.

$^1$H-NMR (CDCl$_3$) δ ppm: 1.45 (3H, t, J=7.2 Hz), 2.74 (3H, s), 4.18 (2H, q, J=7.2 Hz), 6.97 (1H, d, J=9.4 Hz), 7.85 (1H, d, J=9.6 Hz).

REFERENCE EXAMPLE 28A

Production of N-(6-Chloro[1,2,4]triazolo[1,5-b] pyridazine-2-carbonyl)glycine Ethyl Ester 2.86 g of 6-chloro[1,2,4]triazolo[1,5-b]pyridazine-2-carboxylic acid and 2.72 ml of N-ethyldiisopropylamine were suspended in 30 ml of N,N-dimethylformamide; 2.63 g of N,N'-carbonyldiimidazole was added, followed by stirring at room temperature for 1 hour. To the reaction mixture, 2.21 g of glycine ethyl ester hydrochloride was added, followed by stirring at room temperature for 5 hours. Water was added; the crystal precipitated was collected by filtration, washed with water and ether and dried to yield 2.93 g of the title compound.

Melting point: 175–177° C.; Elemental analysis (for $C_{10}H_{10}N_5O_3Cl$): Calculated (%): C, 42.34; H, 3.55; N, 24.69; Found (%): C, 42.40; H, 3.56; N, 24.76.

REFERENCE EXAMPLE 29A

Production of Ethyl 2-(6-Chloroimidazo[1,2,b] pyridazin-2-yl)-2-ethylbutanoate

Process A:

Production of Ethyl 4-Bromo-2,2-diethyl-3-oxobutanoate 1.15 g of ethyl 2,2-diethyl-3-oxobutanoate was dissolved in acetic acid; 1 ml of a 25% solution of hydrobromic acid in 50 ml of acetic acid was added; a solution of 3.50 ml of bromine in 10 ml of acetic acid was added drop by drop in a water bath. After stirring at room temperature for 3 hours, the mixture was concentrated under reduced pressure. The residue was dissolved in hexane, washed with water, saturated aqueous sodium bicarbonate and saturated saline, dried over magnesium sulfate and concentrated under reduced pressure to yield 16.4 g of the title compound.

$^1$H-NMR (CDCl$_3$) δ ppm: 0.65–0.90 (6H, m), 1.28 (3H, t, J=7.2 Hz), 1.80–2.15 (4H, m), 4.09 (2H, s), 4.22 (2H, q, J=7.2 Hz).

Process B:

13.2 g of ethyl 4-bromo-2,2-diethyl-3-oxobutanoate, 5.89 g of 3-amino-6-chloropyridazine and 5.76 g of sodium bicarbonate were suspended in 33 ml of ethanol, followed by thermal refluxing for 1 day. After cooling, water was added, followed by extraction with diisopropyl ether; the extract was washed with saturated saline, dried over magnesium sulfate and concentrated under reduced pressure. The residue was subjected to silica gel column chromatography and eluted with hexane:ethyl acetate (4:1). The desired fraction was collected and concentrated under reduced pressure to yield 5.20 g of the title compound.

Melting point: 68–70° C.; Elemental analysis (for $C_{14}H_{18}N_3O_2Cl$): Calculated (%): C, 55.85; H, 6.13; N, 14.21; Found (%): C, 55.86; H, 6.07; N, 13.99.

REFERENCE EXAMPLE 30A

Production of 4-(Diphenylmethylamino)-1-piperidinepropanamine

Process A:

Production of N-[3-[4-(Diphenylaminomethyl)piperidino]propyl]phthalimide 7.38 g of N-(3-bromopropyl)phthalimide and 7.07 g of 4-(diphenylmethylamino)piperidine were dissolved in 80 ml of N,N-dimethylformamide; 4.04 g of potassium carbonate was added, followed by stirring at room temperature for 17 hours. Ice water was added to the reaction mixture, followed by extraction with ethyl acetate; the extract was washed with saline, dried over magnesium sulfate and concentrated under reduced pressure. The residue was subjected to silica gel column chromatography and eluted with hexane:ethyl acetate:triethylamine (50:50:2). The desired fraction was collected and concentrated under reduced pressure to yield 9.65 g of the title compound as an oily substance.

$^1$H-NMR (CDCl$_3$) δ ppm: 1.08–1.30 (2H, m), 1.42–1.64 (2H, m), 1.74–1.92 (4H, m), 2.25–2.42 (1H, m), 2.34 (2H, t, J=7.2 Hz), 2.65–2.83 (2H, m), 3.73 (2H, t, J=6.9 Hz), 4.96 (1H, s), 7.12–7.40 (10H, m), 7.65–7.73 (2H, m), 7.78–7.88 (2H, m).

Process B:

9.65 g of N-[3-[4-(diphenylaminomethyl)piperidino]propyl]phthalimide was dissolved in 40 ml of ethanol; 1.08 ml of hydrazine monohydrate was added, followed by thermal refluxing for 3.5 hours. After cooling, diisopropyl ether was added to the reaction mixture; the crystal precipitated was collected, washed with diisopropyl ether, dissolved in 45 ml of a 1 N aqueous solution of sodium hydroxide, 20 ml of tetrahydrofuran and 20 ml of water, and extracted with ethyl acetate. The extract was washed with water and saturated saline, dried over sodium sulfate and concentrated under reduced pressure to yield 4.02 g of the title compound.

$^1$H-NMR (CDCl$_3$) δ ppm: 1.23–1.67 (4H, m), 1.82–1.98 (4H, m), 2.29–2.36 (2H, m), 2.32–2.52 (1H, m), 3.73 (2H, t, J=7.4 Hz), 2.71 (2H, d, J=6.8 Hz), 2.73–2.9 (2H, brm), 5.02 (1H, s), 7.10–7.57 (10H, m).

REFERENCE EXAMPLE 31A

Production of N-(3,6-Dichloroimidazo[1,2-b]pyridazine-2-carbonyl)glycine Ethyl Ester 0.86 g of N-(6-Chloroimidazo[1,2-b]pyridazine-2-carbonyl)glycine ethyl ester was suspended in 30 ml of ethyl acetate; 1.2 g of N-chlorosuccinimide was added, followed by thermal refluxing for 20 hours. After cooling, 30 ml of tetrahydrofuran was added; the mixture was washed with an aqueous solution of sodium thiosulfate and saline, dried over magnesium sulfate and concentrated under reduced pressure; ethyl ether was added to the residue; the crystal precipitated was collected by filtration, washed with ethyl ether and dried to yield 0.552 g of the title compound.

$^1$H-NMR (CDCl$_3$) δ ppm: 1.32 (3H, t, J=7.2 Hz), 4.27 (2H, d, J=5.6 Hz), 4.27 (2H, q, J=7.2 Hz), 7.21, 7.91 (each 1H, d, J=9.6 Hz), 7.82 (1H, t, J=5.6 Hz).

REFERENCE EXAMPLE 32A

Production of N-(6-Chloroimidazo[1,2-b]pyridazine-2-carbonyl) β-Alanine Ethyl Ester 1.98 g of 6-chloroimidazo[1,2-b]pyridazine-2-carboxylic acid was suspended in 25 ml of N,N-dimethylformamide; 1.78 g of N,N'-carbonyldiimidazole was added, followed by stirring at room temperature for 1 hour. To this mixture, 1.69 g of β-alanine ethyl ester hydrochloride and 1.53 ml of triethylamine were added, followed by further stirring for 3 hours. Ice water was added to the reaction mixture; the crystal precipitated was collected by filtration, washed with water and dried to yield 2.57 g of the title compound.

Melting point: 132–134° C.; Elemental analysis (for C$_{12}$H$_{13}$N$_4$O$_3$Cl): Calculated (.%): C, 48.58; H, 4.42; N, 18.88; Found (%): C, 48.43; H, 4.33; N, 18.68.

REFERENCE EXAMPLE 33A

Production of Ethyl 6-Chloro-3-methylimidazo[1,2-b]pyridazine-2-carboxylate 5.83 g of 3-amino-6-chloropyridazine was suspended in 70 ml of ethanol; 9.75 g of methyl 3-bromo-2-oxobutyrate and 8.6 ml of N-ethyldiisopropylamine were added, followed by thermal refluxing for 5 hours. After cooling, the mixture was concentrated under reduced pressure. The residue was adjusted to pH 7 by the addition of an aqueous solution of sodium hydrogen carbonate and extracted with ethyl acetate-tetrahydrofuran(1:1); the extract was washed with saline, dried over magnesium sulfate and concentrated under reduced pressure; ethyl acetate was added to the residue; the crystal precipitated was collected by filtration, washed with ethyl acetate and dried to yield 3.9 g of the title compound.

Melting point: 170–171° C.; Elemental analysis (for C$_{10}$H$_{10}$N$_3$O$_2$Cl): Calculated (%): C, 50.12; H, 4.21; N, 17.53; Found (%): C, 50.28; H, 4.18; N, 17.23.

REFERENCE EXAMPLE 34A

Production of N-(6-Chloro-3-methylimidazo[1,2-b]pyridazine-2-carbonyl)glycine Ethyl Ester 3.9 g of ethyl 6-chloro-3-methylimidazo[1,2-b]pyridazine-2-carboxylate was suspended in 40 ml of tetrahydrofuran; 30 ml of a 1 N aqueous solution of sodium hydroxide was added, followed by stirring at room temperature for 3 hours. The mixture was concentrated under reduced pressure. The residue was adjusted to pH 4 by the addition of 50 ml of water and 1 N hydrochloric acid; the crystal precipitated was collected by filtration and dried to yield 2.55 g of 6-chloro-3-methylimidazo[1,2-b]pyridazine-2-carboxylic acid. 1.27 g of this carboxylic acid was dissolved in 20 ml of N,N-dimethylformamide; 1.07 g of N,N'-carbonyldiimidazole was added, followed by stirring at room temperature for 30 minutes. To this mixture, 0.922 g of glycine ethyl ester hydrochloride and 0.915 ml of triethylamine were added, followed by further stirring for 3 hours. 60 ml of ice water was added to the reaction mixture; the crystal precipitated was collected by filtration, washed with water and dried to yield 1.18 g of the title compound.

Melting point: 192–195° C.; Elemental analysis (for C$_{12}$H$_{13}$N$_4$O$_3$Cl): Calculated (%): C, 48.58; H, 4.42; N, 18.88; Found (%): C, 48.65; H. 4.13; N. 18.93.

REFERENCE EXAMPLE 35A

Production of 6-Chloro-2-isopropylimidazo[1,2-b]pyridazine

To a solution of 3-methyl-2-butanone (5.17 g) in methanol (60 ml), bromine (3.1 ml) was added under ice cooling conditions, followed by stirring for 45 minutes. To this mixture, water (30 ml) was added, followed by stirring at room temperature for 30 minutes. To this mixture, water and hexane were added; the organic layer was separated; the water layer was extracted with hexane. The organic layers combined were washed with water and a saturated aqueous solution of sodium hydrogen carbonate, dried over magnesium sulfate, filtered and concentrated under reduced pressure. The residue was dissolved in ethanol (20 ml); 3-amino-6-chloropyridazine (5.18 g) and sodium hydrogen carbonate (6.30 g) were added, followed by thermal refluxing for 3 hours. Water and ethyl acetate were added to the reaction mixture; the insoluble substances were filtered off; the organic layer was separated; the water layer was extracted with ethyl acetate. The organic layers combined were washed with water, treated with activated charcoal, filtered and concentrated under reduced pressure. The residue was dissolved in ethyl acetate; the insoluble substances were filtered and concentrated under reduced pressure. The residue was subjected to silica gel column chromatography (hexane:ethyl acetate 3:1) and recrystallized from hexane to yield the title compound (1.37 g).

Melting point: 106–108° C.; Elemental analysis (for $C_9H_{10}N_3Cl$): Calculated (%): C, 55.25; H, 5.15; N, 21.48; Cl, 18.12; Found (%): C, 55.35; H, 5.10; N, 21.50; Cl, 18.03.

REFERENCE EXAMPLE 36A

Production of Isopropyl 6-Chloro[1,2,4]triazolo[1,5-b]pyridazine-2-carboxylate 2.14 g of 6-chloro[1,2,4]triazolo[1,5-b]pyridazine-2-carboxylic acid and 5.57 ml of N-ethyldiisopropylamine were dissolved in 30 ml of N,N-dimethylformamide; 3.23 ml of isopropyl iodide was added, followed by stirring at room temperature for 10 hours and at 50° C. for 3 hours. After cooling, water was added, followed by extraction with ethyl acetate; the extract was washed with saturated saline, dried over magnesium sulfate and concentrated under reduced pressure. The residue was subjected to silica gel column chromatography and eluted with ethyl acetate. The desired fraction was collected and concentrated under reduced pressure to yield 2.21 g of the title compound.

$^1$H-NMR (CDCl$_3$) δ ppm: 1.46 (3H, s), 1.49 (3H, s), 5.33–5.53 (1H, m), 7.52 (1H, d, J=9.6 Hz), 8.19 (1H, d, J=9.6 Hz).

REFERENCE EXAMPLE 37A

Production of N-(6-Chloro[1,2,4]triazolo[1,5-b]pyridazine-2-carbonyl)-2,2-dimethylglycine Ethyl ester 1.52 g of 6-chloro[1,2,4]triazolo[1,5-b]pyridazine-2-carboxylic acid and 1.45 ml of N-ethyldiisopropylamine were suspended in 15 ml of N,N-dimethylformamide; 1.37 g of N,N'-carbonyldiimidazole was added, followed by stirring at room temperature for 3 hours. To the reaction mixture, 1.41 g of 2-aminoisobutyric acid ethyl ester hydrochloride was added, followed by stirring at room temperature for 4 hour. Water was added, followed by extraction with ethyl acetate-tetrahydrofuran (1:1); the extract was washed with saturated saline, dried over magnesium sulfate and concentrated under reduced pressure; the crystal precipitated was washed with ethyl ether, collected by filtration and dried to yield 1.48 g of the title compound. The filtrate was concentrated under reduced pressure. The residue was subjected to silica gel column chromatography and eluted with ethyl acetate. The desired fraction was collected and concentrated under reduced pressure to yield 450 mg of the title compound.

$^1$H-NMR (CDCl$_3$) δ ppm: 1.29 (3H, t, J=7.1 Hz), 1.73 (6H, s), 4.26 (2H, q, J=7.2 Hz), 7.52 (1H, d, J=9.4 Hz), 7.94 (1H, brs), 8.16 (1H, d, J=9.4 Hz).

REFERENCE EXAMPLE 38A

Production of Isopropyl 2-(6-Chloroimidazo[1,2-b]pyridazin-2-yl)-2-methylpropionate In 18 ml of isopropanol, 995 mg of concentrated sulfuric acid was dissolved; 1.0 g of methyl 2-(6-chloroimidazo[1,2-b]pyridazin-2-yl)-2-methylpropionate was added, followed by thermal refluxing for 40 hours. After cooling, the mixture was concentrated under reduced pressure, neutralized by the addition of aqueous sodium bicarbonate and extracted with ethyl acetate. The extract was washed with saturated saline, dried over magnesium sulfate and concentrated under reduced pressure; the crystal precipitated was collected, washed with hexane and dried to yield 794 mg of the title compound. The filtrate was concentrated under reduced pressure. The residue was subjected to silica gel column chromatography and eluted with hexane:ethyl acetate (5:1). The desired fraction was collected and dried to yield 215 mg of the title compound.

Melting point: 100–101° C.; Elemental analysis (for $C_{13}H_{16}N_3O_2Cl$): Calculated (%): C, 55.42; H, 5.72; N, 14.91; Found (%): C, 55.46; H. 5.53; N, 14.94.

EXAMPLE 133A

Production of Ethyl 2-[6-[3-[4-(Diphenylmethoxy)piperidino]propylamino]imidazo[1,2-b]pyridazin-2-yl]-2-methylpropionate Disuccinate In 1 mL of ethanol, 0.278 g of the ethyl 2-[6-[3-[4-(diphenylmethoxy)piperidino]propylamino]imidazo[1,2-b]pyridazin-2-yl]-2-methylpropionate synthesized in Example 40A was dissolved, and 0.118 g of succinic acid was added thereto and dissolved, followed by concentration under reduced pressure. To the residue was added 0.5 mL of tetrahydrofuran and the residue was dissolved. After addition of 2 mL of ethyl acetate, the crystals formed were collected by filtration, washed with ethyl acetate and dried to yield 0.382 g of the title compound.

Melting point 98–101° C. (decomposed); Elemental analysis: for $C_{41}H_{53}N_5O_{11}\cdot\frac{1}{3}CH_3CO_2C_2H_5$; Calculated (%): C, 61.92 ; H, 6.83 ; N, 8.53; Found (%): C, 61.54 ; H, 6.83 ; N, 8.50.

EXAMPLE 134A

Production of Ethyl 2-[6-[3-[4-(Diphenylmethoxy)piperidino]propylamino]imidazo[1,2-b]pyridazin-2-yl)-2-methylpropionate Citrate In 8 mL of ethanol, 1.667 g of the ethyl 2-[6-[3-[4-(diphenylmethoxy)piperidino]propylamino]imidazo[1,2-b]pyridazin-2-yl]-2-methylpropionate synthesized in Example 40A was dissolved, and 0.631 g of citric acid monohydrate was added thereto and dissolved under heating, followed by concentration under reduced pressure. To the residue was added 23 mL of ethyl acetate, and the crystals formed were collected by filtration and washed with 12 mL of ethyl acetate. To the crystals was added 30 mL of methanol and the crystals were dissolved under heating, followed by concentration under reduced pressure. To the residue was added 30 mL of ethanol and the residue was then dissolved. After standing, the crystals formed were collected by filtration, washed with 10 mL of ethanol and dried to yield 2.01 g of the title compound.

Melting point 176° C. (decomposed); Elemental analysis: for $C_{39}H_{49}N_5O_{10}$; Calculated (%): C, 62.64 ; H, 6.60 ; N, 9.36; Found (%): C, 62.50 ; H, 6.56 ; N, 9.43.

EXAMPLE 135A

Method for Producing 2-[6-[3-[4-(Diphenylmethoxy)piperidino]propylamino]imidazo[1,2-b]pyridazin-2-yl)-2-methylpropionic Acid Dihydrate In 600 mL of dimethyl sulfoxide were suspended 363.6 g (1120 mmol) of 4-(diphenylmethoxy)-1-piperidinepropaneamine, 200.0 g (747 mmol) of ethyl 2-(6-chloroimidazo[1,2-b]pyridazin-2-yl)-2-methylpropionate and 158.4 g (1490 mmol) of sodium carbonate, which were then heated in an oil bath (bath temperature 165–170° C.) under a nitrogen gas stream and stirred for 3.5 hours. After cooling to room temperature, 2000 mL of ethyl acetate and 2000 mL of water were added, followed by separation into two layers. The organic layer was washed with 1000 mL of water twice and concentrated under reduced pressure. To the residue was added 1000 mL of ethanol and concentrated under reduced pressure to yield 588 g of crude ethyl 2-[6-[3-[4-(diphenylmethoxy)piperidino]propylamino]imidazo[1,2-b]pyridazin-2-yl]-2-methylpropionate as an oily material. This oily material was dissolved in 1400 mL of ethanol, and 59.8 g (1490 mmol) of sodium hydroxide dissolved in 600 mL of water was added thereto. The reaction mixture was heated to 60° C. (inner temperature) and stirred for 1 hour. The reaction solution was concentrated under reduced pressure. To the residue were added 2000 mL of water and 2000 mL of ethyl acetate, followed by separation into two layers. The aqueous layer was washed with 1000 mL of ethyl acetate twice, and 2000 mL of ethanol was added to the aqueous layer. After the aqueous layer was adjusted to about pH 6 by the addition of 1000 mL of 1N hydrochloric acid, the crystals formed were collected by filtration, washed with 800 mL of water and 800 mL of ethanol:water (1:1), and dried to yield 353.6 g of the crude title compound. HPLC purity area percentage 97.7%, Yield 82.0%.

To 353.6 g of the crude title compound thus obtained was added 1240 mL of ethanol, and heated under reflux for 1 hour. The solution was stirred under ice-cooling. The crystals formed were collected by filtration, washed with 930 mL of cold ethanol and dried. The resulting crystals were suspended in 2000 mL of water and stirred for 1 hour while heating in a water bath (inner temperature 65–70° C.). After cooling to room temperature, the crystals formed were collected by filtration, washed with 1000 mL of water and dried to yield 276 g of the title compound.

Melting point 203–205° C. (The crystals began to soften at 110–120° C. and solidified again.); Elemental analysis: for $C_{31}H_{37}N_5O_3 \cdot 2H_2O$; Calculated (.%): C, 66.05 ; H, 7.33 ; N, 12.42; Found (%): C, 66.35 ; H, 7.29 ; N, 12.39.
Powder X-ray diffraction analysis result

| D-Space, angstrom | Intensity $I/I_0$ (%) |
|---|---|
| 6.94 | 84 |
| 12.88 | 41 |
| 15.10 | 53 |
| 17.56 | 84 |
| 18.70 | 39 |
| 19.24 | 62 |
| 20.66 | 60 |
| 21.06 | 100 |
| 21.76 | 54 |
| 26.42 | 43 |
| 28.24 | 37 |

EXAMPLE 136A

Method for Producing 2-[6-[3-[4-(Diphenylmethoxy)piperidino]propylamino]imidazo[1,2-b]pyridazin-2-yl]-2-methylpropionic Acid (Anhydride)

In 500 mL of ethanol, 3.20 g (5.67 mmol) of the 2-[6-[3-[4-(diphenylmethoxy)piperidino]propylamino]imidazo[1,2-b]pyridazin-2-yl]-2-methylpropionic acid dihydrate obtained in Example 135A was dissolved under heating, followed by concentrating at atmospheric pressure until the total volume became 250 mL. After standing at room temperature, the crystals formed were collected by filtration, washed with ethanol and dried to yield 2.67 g of the title compound.

Melting point 205–206° C. (decomposed); Elemental analysis: for $C_{31}H_{37}N_5O_3$; Calculated (%): C, 70.56 ; H, 7.07 ; N, 13.27; Found (%): C, 70.42 ; H, 6.89 ; N, 13.32.
Powder X-ray diffraction analysis result

| D-Space, angstrom | Intensity $I/I_0$ (%) |
|---|---|
| 3.20 | 32 |
| 3.48 | 100 |
| 15.46 | 33 |
| 16.60 | 37 |
| 18.46 | 72 |
| 19.26 | 33 |
| 20.12 | 30 |
| 20.58 | 38 |
| 23.38 | 32 |
| 23.40 | 33 |

EXAMPLE 137A

Method for Producing 2-[6-[3-[4-(Diphenylmethoxy)piperidino]propylamino]imidazo[1,2-b]pyridazin-2-yl]-2-methylpropionic Acid Dihydrate To 10 mL of water was suspended 0.250 g of the 2-[6-[3-[4-(diphenylmethoxy)piperidino]propylamino]imidazo[1,2-b]pyridazin-2-yl]-2-methylpropionic acid (anhydride) obtained in Example 136A and stirred for 3 hours in a water bath (bath temperature 80° C.). After cooling to room temperature, the crystals formed were collected by filtration, washed with water and dried to yield 0.233 g of the total compound. The resulting 2-[6-[3-[4-(diphenylmethoxy)piperidino]propylamino]imidazo[1,2-b]pyridazin-2-yl]-2-methylpropionic acid dihydrate was identical to the compound obtained in Example 135A on the basis of the agreement of their melting points, elemental analysis values, powder X-ray diffraction analysis data, etc.

EXAMPLE 138A

Production of 2-[6-[3-[4-(Diphenylmethoxy)piperidino]propylamino]-3-methylimidazo[1,2-b]pyridazin-2-yl]-2-methylpropionic Acid In 25 mL of N-methyl-2-pyrrolidinone were dissolved 17.0 g of 4-(diphenylmethoxy)-1-piperidinepropaneamine and 7.39 g of ethyl 2-(6-chloro-3-methylimidazo[1,2-b]pyridazin-2-yl)-=2-methylpropionate, and stirred at 160° C. for 8.5 hours. After cooling, a water was added and extracted with ethyl acetate. The extract was washed with a saturated brine solution and dried over magnesium sulfate. Following to concentration under reduced pressure. The residue was subjected to silica gel column chromatography to be eluted with ethyl acetate:methanol:triethylamine (50:5:1). The desired fraction was collected and concentrated to yield 10.4 g of ethyl 2-[6-[3-[4-(diphenylmethoxy)piperidino]propylamino]-3-methylimidazo[1,2-b]pyridazin-2-yl]-2-methylpropionate as an oily material. In 100 mL of ethanol was dissolved this oily material, and 18.3 mL of a 5N aqueous sodium hydroxide solution was added thereto and heated under reflux for 2 hours. After cooling, the mixture was concentrated under reduced pressure. The residue was diluted with water and washed with diisopropyl ether. The aqueous layer was adjusted to pH 5 by the addition of 5N hydrochloric acid. The crystals formed were collected by filtration, recrystallized from methanol-water (10:1), and dried to yield 4.09 g of the title compound.

Melting point 219–220° C.; Elemental analysis: for $C_{32}H_{39}N_5O_3$; Calculated (%): C, 70.95 ; H, 7.26 ; N, 12.93; Found (%): C, 70.85 ; H, 7.00; N, 13.20.

EXPERIMENTAL EXAMPLE 1A

Effect on Histamine-induced Skin Reactions in Guinea Pigs

Male Hartley guinea pigs weighing about 500 g were used. After the dorsal hair was shaved under ether anesthesia, 1 ml of a 2.5% pontamine sky blue solution was injected intravenously administered, and then 0.1 ml of histamine at 3 μg/ml was injected intradermally into 2 sites (left and right) in the back. Thirty minutes after the injection of histamine, animals were killed by bleeding and the skin was removed. Two perpendicular diameters (mm) of each blue spot on the inside of the skin were measured and multiplied; the mean for the two products was taken as the microvascular permeability index. Test compounds were suspended in a 5% gum arabic solution and orally administered in a volume of 0.2 ml/100 g body weight 1 hour before histamine administration. Animals in the control group received the same volume of a 5% gum arabic solution. The suppression rate of the sample for the title reaction was calculated using Equation 1.

Inhibition (%) of histamine-induced skin reactions=100×(1−vascular permeability index in the presence of drug/vascular permeability index in control group)   Equation 1

The results are given in Table 1.

TABLE 1

| Compound | Inhibition (%) of Histamine-induced Skin Reactions, 3 mg/kg Oral Administration |
|---|---|
| Example 6A | 91 |
| Example 12A | 91 |
| Example 18A | 91 |
| Example 20A | 92 |
| Example 21A | 91 |
| Example 37A | 92 |
| Example 41A | 92 |

TABLE 1-continued

| Compound | Inhibition (%) of Histamine-induced Skin Reactions, 3 mg/kg Oral Administration |
|---|---|
| Example 45A | 91 |
| Example 135A | 91 |

EXPERIMENTAL EXAMPLE 2A

1) Preparation of Guinea Pig Eosinophils

To male Hartley guinea pigs, 2 ml of equine serum (Bio-Whittaker, Inc.) was intraperitoneally administered once weekly for 8 consective weeks. At 48 hours after final administration, 75 ml of physiological saline was intraperitoneally injected, after which the saline was recovered and centrifuged at 400×g for 5 minutes. The resulting sediment was suspended in 5 ml of Percoll solution (density (d)=1.07) and layered on top of the multiple layers of different densities of Percoll solution (density(d)=1.112, 5 ml; d=1.095, 10 ml; d=1.090, 10 ml; d=1.085, 5 ml), followed by centrifugation at 1,000×g for 25 minutes (20° C.). The cell layer formed at the interface between densities 1.112 and 1.095 was collected. Erythrocytes present in the collected cell sediment were removed by hypotonic treatment (suspended in water for 30 seconds).

The cell sediment was washed 3 times with Hanks' solution containing 1 0mM Hepes (DojinKagaku) (Hanks-Hepes) and suspended in a Hanks-Hepes solution containing 2% human serum albumin (Wako Pure Chemical Industry or Sigma) (Hanks-Hepes-HSA) to a final concentration of $5.56 \times 10^6$ cells/ml. Eosinophil purity was 90%, viability being over 98%.

2) Determination of Chemotactic Reaction Suppression

To a 24-well petri dish, which serves as a lower chamber, 600 μl of Hanks-Hepes-HSA solution containing $LTB_4$ (final concentration $10^{-8}$ M, Cascade Biochemical Ltd.), was transferred, followed by incubation at 37° C. for 30 minutes in a carbon dioxide incubator. Separately, 200 μl of eosinophil suspension ($5 \times 10^6$ cells/ml), previously incubated at 37° C. for 15 minutes, was added to Chemotaxicell (polycarbonate membrane, pore size 3 μm, thickness 10 μm), which serves as an upper chamber, after the upper chamber was attached to the 24-well petri dish. After 2 hours of reaction in the $CO_2$ incubator, the Chemotaxicell was removed; 60 μl of a 2% (w/v) solution of EDTA in physiological saline was added to the liquid in the lower chamber. After the mixture was on cooled ice, the cells migrating into the lower chamber were counted using a blood cell counter [Coulter Counter (trade name)]. The test drug, dissolved in N,N-dimethyl formamide (DMF), was added to both the upper and lower chambers to a final concentration of $10^{-5}$ M.

Chemotactic reaction suppression rate=[1−(number of migrating cells in the presence of drug/number of migrating cells in the absence of drug)]×100   Equation 2

Suppression rates of $LTB_4$-induced chemotactic reaction by test substances ($1 \times 10^{-5}$ M) were calculated using the above equation. The results are shown in Table 2.

TABLE 2

| Compound | Suppression Rate (%) |
|---|---|
| Example 2A | 54 |
| Example 6A | 64 |
| Example 20A | 61 |
| Example 34A | 50 |
| Example 35A | 52 |
| Example 36A | 64 |
| Example 47A | 54 |
| Example 51A | 80 |
| Example 59A | 54 |
| Example 61A | 50 |
| Example 62A | 52 |

PREPARATION EXAMPLE 1A

| | | |
|---|---|---|
| (1) Compound of Example 6A | 10.0 | mg |
| (2) Lactose | 60.0 | mg |
| (3) Corn starch | 35.0 | mg |
| (4) Gelatin | 3.0 | mg |
| (5) Magnesium stearate | 2.0 | mg |

A mixture of 10.0 mg of the compound obtained in Example 6A, 60.0 mg of lactose and 35.0 mg of corn starch was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

PREPARATION EXAMPLE 2A

| | | |
|---|---|---|
| (1) Compound of Example 6A | 10.0 | mg |
| (2) Lactose | 70.0 | mg |
| (3) Corn starch | 50.0 | mg |
| (4) Soluble starch | 7.0 | mg |
| (5) Magnesium stearate | 3.0 | mg |

10.0 mg of the compound obtained in Example 6A and 3.0 mg of magnesium stearate were mixed and granulated, using 0.07 ml of an aqueous solution of soluble starch (containing 7.0 mg of soluble starch). The resulting granules were dried and mixed with 70.0 mg of lactose and 50.0 mg of corn starch, followed by compression, to yield tablets.

PREPARATION EXAMPLE 3A

| | | |
|---|---|---|
| (1) Compound of Example 6A | 5.0 | mg |
| (2) Sodium chloride | 20.0 | mg |
| (3) Distilled water was added to reach a total quantity of 2 ml. | | |

5.0 mg of the compound obtained in Example 6A and 20.0 mg of sodium chloride were dissolved in distilled water, and diluted with water to reach a total quantity of 2.0 ml. The resulting solution was filtered and aseptically packed in a 2 ml ampule, which was sterilized and sealed to yield a solution for injection.

PREPARATION EXAMPLE 4A

| | | |
|---|---|---|
| (1) Compound of Example 135A | 40.0 | mg |
| (2) Lactose | 60.0 | mg |
| (3) Corn starch | 35.0 | mg |
| (4) Gelatin | 3.0 | mg |
| (5) Magnesium stearate | 2.0 | mg |

A mixture of 10.0 mg of the compound obtained in Example 135A, 60.0 mg of lactose and 35.0 mg of corn starch was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

PREPARATION EXAMPLE 5A

| | | |
|---|---|---|
| (1) Compound of Example 135A | 10.0 | mg |
| (2) Lactose | 70.0 | mg |
| (3) Corn starch | 50.0 | mg |
| (4) Soluble starch | 7.0 | mg |
| (5) Magnesium stearate | 3.0 | mg |

10.0 mg of the compound obtained in Example 135A and 3.0 mg of magnesium stearate were mixed and granulated, using 0.07 ml of an aqueous solution of soluble starch (containing 7.0 mg of soluble starch). The resulting granules were dried and mixed with 70.0 mg of lactose and 50.0 mg of corn starch, followed by compression, to yield tablets.

PREPARATION EXAMPLE 6A

| | | |
|---|---|---|
| (1) Compound of Example 138A | 10.0 | mg |
| (2) Lactose | 60.0 | mg |
| (3) Corn starch | 35.0 | mg |
| (4) Gelatin | 3.0 | mg |
| (5) Magnesium stearate | 2.0 | mg |

A mixture of 10.0 mg of the compound obtained in Example 138A, 60.0 mg of lactose and 35.0 mg of corn starch was granulated through a sieve of 1 mm mesh, using 0.03 ml of a 10% aqueous solution of gelatin (containing 3.0 mg of gelatin), after which it was dried at 40° C. and again sieved. The resulting granules were mixed with 2.0 mg of magnesium stearate, followed by compression. The resulting core tablets were coated with a sugar coat, using an aqueous suspension of sucrose, titanium dioxide, talc and gum arabic. The coated tablets were polished with beeswax to yield finished coated tablets.

PREPARATION EXAMPLE 7A

| | | |
|---|---|---|
| (1) Compound of Example 138A | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 138A and 3.0 mg of magnesium stearate were mixed and granulated, using 0.07 ml of an aqueous solution of soluble starch (containing 7.0 mg of soluble starch). The resulting granules were dried and mixed with 70.0 mg of lactose and 50.0 mg of corn starch, followed by compression, to yield tablets.

PREPARATION EXAMPLE 8A

After uniformly mixing 1500 g of the compound disclosed in Example 135A, 2025 g of lactose and 556.5 g of corn starch in a fluidized bed granulator (FD-5 S, POWREX CO.), the mixture was granulated by spraying an aqueous solution of 126 g of hydroxypropyl cellulose in the granulator, and then dried in the fluidized bed granulator. The dried granules were milled by using a power mill with a punching screen of 1.5 mm$\phi$ to form milled granules. 3927 g of the uniform granules are taken and 210 g of croscarmellose sodium and 63 g of magnesium stearate are added thereto. These were mixed in a Tumbler mixer to provide granules for tabletting. The granules were tabletted by using a tabletting machine equipped with a die 6.5 mm in diameter to provide core tablets each weighing 300 mg. The core tablets were sprayed, in a Doria coater coating machine, with a liquid prepared by dissolving hydroxypropylmethylcellulose 2910 (TC-5) and macrogol 6000 and dispersing titanium oxide and ferric oxide to provide about 13500 film coated tablets of the following formulation containing 100 mg per tablet.

Tablet formulation:

| Composition | Amount (mg) |
|---|---|
| (1) Compound of Example 135A | 100.0 |
| (2) Lactose | 135.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
|---|---|
| (1) Core tablet | 300.0 |
| (Film ingredients) | |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 9A

About 13500 film coated tablets of the following formulation containing 25 mg of the compound disclosed in Example 135A per tablet was prepared in accordance with the method disclosed in Preparation Example 8A.

Tablet formulation:

| Composition | Amount (mg) |
|---|---|
| (1) Compound of Example 135A | 25.0 |
| (2) Lactose | 210.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
|---|---|
| (1) Core tablet | 300.0 |
| (Film ingredients) | |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 10A

About 13500 film coated tablets of the following formulation containing 5 mg of the compound disclosed in Example 135A per tablet was prepared in accordance with the method disclosed in Preparation Example 8A.

Tablet formulation:

| Composition | Amount (mg) |
|---|---|
| (1) Compound of Example 135A | 5.0 |
| (2) Lactose | 230.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
|---|---|
| (1) Core tablet | 300.0 |
| (Film ingredients) | |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 11A

About 13500 film coated tablets of the following formulation containing 1 mg of the compound disclosed in Example 135A per tablet was prepared in accordance with the method disclosed in Preparation Example 8A.

Tablet formulation:

| Composition | Amount (mg) |
| --- | --- |
| (1) Compound of Example 135A | 1.0 |
| (2) Lactose | 234.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
| --- | --- |
| (1) Core tablet (Film ingredients) | 300.0 |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 12A

| | |
| --- | --- |
| White vaseline | 40 g |
| Cetanol | 10 g |
| Bleached bees wax | 5 g |
| Sorbitan sesquioleate | 5 g |
| Lauromocrogold | 0.5 g |
| Methyl para-hydroxybenzoate | 0.1 g |
| Propyl para-hydroxybenzoate | 0.1 g |
| Purified water | adequate amount |

An official absorption ointment (100 g) of the above formulation was heated to 70° C. in advance, and to its solution was added a solution prepared by dissolving under heating 1 g of the compound prepared in Example 135A in 20 mL of methanol. After heating and mixing at that temperature for 10 minutes, the remaining methanol was removed and the residue was cooled to room temperature to provide an absorption ointment.

EXAMPLE B: COMPOUND (I')

REFERENCE EXAMPLE 1B

Production of Ethyl 2-(6-Chloroimidazo[1,2-b]pyridazin-2-yl)-2-methylpropionate

Method A

Step A:

Ethyl 6-Chloroimidazo[1,2-b]pyridazine-2-acetate

After 11.2 g of 3-amino-6-chloropyridazine was suspended in 150 mL of ethanol, 28.6 g of ethyl 4-chloroacetoacetate was added thereto and heated under reflux for 24 hours. After cooling, the mixture was concentrated under reduced pressure and the residue was adjusted to pH 7 by the addition of an aqueous sodium hydrogencarbonate solution and extracted with ethyl acetate. The extract was washed with a saline solution and dried over magnesium sulfate. After concentration under reduced pressure. The residue was subjected to silica gel chromatography to be eluted with hexane:ethyl acetate (2:3). The desired fraction was collected to provide 12.7 g of the title compound.

$^1$H-NMR (CDCl$_3$) δ ppm: 1.29 (3H, t, J=7 Hz), 3.89 (2H, s), 4.23 (2H, q, J=7 Hz), 7.05, 7.85 (1H each, d, J=9 Hz), 7.95 (1H, s).

Step B:

In 50 mL of N,N-dimethylformamide was dissolved 6.8 g of ethyl 6-chloroimidazo[1,2-b]pyridazine-2-acetate. While stirring in ice-cold water, 2.46 g of 60% oleaginous sodium hydride dispersion in mineral oil was added in small portions, and thereafter the mixture was brought to room temperature and stirred for 30 minutes. To the mixture was added 4.36 mL of methyl iodide while cooling in ice-cold water, and thereafter stirred at room temperature for 2 hours. To the mixture was poured ice-cold water, and then extracted with ethyl acetate. The extract is washed with a saline solution, dried over magnesium sulfate, and concentrated under reduced pressure. The residue was subjected to silica gel chromatography to be eluted with hexane:ethyl acetate (2:1). The desired fraction was collected and concentrated to provide 4.06 g of the title compound.

Melting point 64–65° C.; Elemental analysis: for C$_{12}$H$_{14}$N$_3$C$_2$Cl; Calculated (%): C, 53.84 ; H, 5.27 ; N, 15.70; Found (%): C, 53.85 ; H, 5.16; N, 15.80.

Method B

The title compound can also be synthesized by the following method.

A suspension of 3-amino-6-chloropyridazine (80.0 g), ethyl 4-bromo-2,2-dimethyl-3-oxobutanate (201 g) and disodium hydrogenphosphate (131 g) in ethanol (300 mL) was heated under reflux for 8 hours. To the reaction mixture was added water (300 mL) and extracted twice with ethyl acetate (300 mL). The combined organic layer was washed with water (600 mL) twice and with a saturated aqueous sodium chloride solution (300 mL), dried over magnesium sulfate, treated with active carbon, filtered, and concentrate under reduced pressure. To the residue was added diisopropyl ether (200 mL), and the resulting mixture was filtered to remove the insoluble material and concentrated under reduced pressure. The residue was subjected to silica gel chromatography (hexane:ethyl acetate 100:1; 2:1 and then 1:1), and crystallized from hexane to provide the title compound (99.3 g).

EXAMPLE 1B

Method for Producing Ethyl 2-[6-[3-[4-(Diphenylmethoxy)piperidino]propylamino]imidazo[1,2-b]pyridazin-2-yl]-2-methylpropionate A mixture of 12.12 g (37.4 mmol) of 4-(diphenylmethoxy)-1-piperidinepropaneamine, 10.00 g (37.4 mmol) of ethyl 2-(6-chloroimidazo[1,2-b]pyridazin-2-yl)-2-methylpropionate and 3.94 g (37.4 mmol) of sodium carbonate was heated to 192–195° C. and stirred for 3.5 hours. After cooling to room temperature, 100 mL of ethyl acetate was added and dissolved, and then washed with 100 mL and 50 mL of water. The organic layer was concentrated under reduced pressure. The residue was subjected to silica gel chromatography to be eluted with ethyl acetate:methanol:triethyl amine (100:5:1). The desired fraction was collected and concentrated to provide 10.22 g of the crude title compound. HPLC purity area percentage 90.9%, Yield 44.7%.

EXAMPLE 2B

Method for Producing Ethyl 2-[6-[3-[4-(Diphenylmethoxy)piperidino]propylamino]imidazo[1,2-b]pyridazin-2-yl]-2-methylpropionate In 13.4 mL of N-methyl-2-pyrrolidinone were dissolved 6.49 g (20 mmol) of 4-(diphenylmethoxy)-1-piperidinepropaneamine and 2.68 g (10.0 mmol) of ethyl 2-(6-chloroimidazo[1,2-b]pyridazin-2-yl)-2-methylpropionate, heated to 191–195° C. under a nitrogen atmosphere and stirred for 4.5 hours. After cooling to room temperature, 20 mL of water and 1.01 g (2 mmol) of sodium hydrogencarbonate were added and extracted twice with 30 mL of ethyl acetate. The extract was washed with 20 mL of water three times and the organic layer was concentrated under reduced pressure. The residue was subjected to silica gel chromatography to be eluted with ethyl acetate:methanol:triethylamine (100:5:1). The desired fraction was collected and concentrated to provide 5.14 g of the crude title compound. Purity 83%, yield 77%, determined from the integral values of the proton NMR.

EXAMPLE 3B

Method for Producing Ethyl 2-[6-[3-[4-(Diphenylmethoxy)piperidino]propylamino]imidazo[1,2-b]pyridazin-2-yl]-2-methylpropionate In 120 mL of dimethyl sulfoxide were suspended 54.54 g (168 mmol) of 4-(diphenylmethoxy)-1-piperidinepropaneamine, 30.00 g (112.2 mmol) of ethyl 2-(6-chloroimidazo[1,2-b]pyridazin-2-yl)-2-methylpropionate and 11.82 g (112.2 mmol) of sodium carbonate, heated to 160° C. and stirred for 2 hours. After cooling to room temperature, 300 mL of ethyl acetate and 300 mL of water were added and separated into two layers. The organic layer was washed twice with 150 mL of water and concentrated under reduced pressure. The residue was subjected to alumina chromatography to be eluted with ethyl acetate. The desired fraction was collected and concentrated to provide 75.96 g of the crude title compound. HPLC purity area percentage 70.5%, Yield 85%.

EXAMPLE 4B

Method for Producing 2-[6-[3-[4-(Diphenylmethoxy)piperidino]propylamino]imidazo[1,2-b]pyridazin-2-yl]-2-methylpropionic Acid Dihydrate In 300 mL of dimethyl sulfoxide were suspended 181.8 g (560 mmol) of 4-(diphenylmethoxy)-1-piperidinepropaneamine, 100.0 g (374 mmol) of ethyl 2-(6-chloroimidazo[1,2-b]pyridazin-2-yl)-2-methylpropionate and 79.18 g (747 mmol) of sodium carbonate, which were then heated to 160° C. under a nitrogen atmosphere and stirred for 2 hours. After cooling to room temperature, 1000 mL of ethyl acetate and 1000 mL of water were added, followed by separation into two layers. The organic layer was washed with 500 mL of water twice and concentrated under reduced pressure. To the residue was added 500 mL of ethanol and concentrated under reduced pressure to yield 293.3 g of crude ethyl 2-[6-[3-[4-(diphenylmethoxy)piperidino]propylamino]imidazo[1,2-b]pyridazin-2-yl]-2-methylpropionate as an oily material (HPLC purity area percentage 58.3%). This oily material was dissolved in 700 mL of ethanol, and 29.88 g of sodium hydroxide dissolved in 300 mL of water was added thereto. The reaction solution was heated to 60° C. and stirred for 1 hour. The reaction mixture was concentrated under reduced pressure. To the residue were added 1000 mL of water and 1000 mL of ethyl acetate, followed by separation into two layers. The aqueous layer was washed with 500 mL of ethyl acetate twice, and 1000 mL of ethanol was added to the aqueous layer. After the aqueous layer was adjusted to about pH 6 by the addition of 500 mL of 1N hydrochloric acid, the crystals formed were collected by filtration, washed with 400 mL of water and 400 mL of ethanol:water (1:1), and dried to yield 137.8 g of the title compound. HPLC purity area percentage 92.5%, Yield 60.6%.

Melting point 203–205° C. (The crystals began to soften at 110–120° C. and solidified again.); Elemental analysis: for $C_{31}H_{37}N_5O_3 \cdot 2H_2O$; Calculated (%): C, 66.05 ; H. 7.33 ; N, 12.42; Found (%): C, 66.06 ; H, 7.35 ; N, 12.46.

EXAMPLE 5B

Method for Producing 2-[6-[3-[4-(Diphenylmethoxy)piperidino]propylamino]imidazo[1,2-b]pyridazin-2-yl]-2-methylpropionic Acid Dihydrate In 30 mL of dimethyl sulfoxide were suspended 18.18 g (56 mmol) of 4-(diphenylmethoxy)-1-piperidinepropaneamine, 10.00 g (37.4 mmol) of ethyl 2-(6-chloroimidazo[1,2-b]pyridazin-2-yl)-2-methylpropionate and 7.92 g (74.7 mmol) of sodium carbonate, which were then heated to 130° C. under a nitrogen atmosphere and stirred for 9 hours. After cooling to room temperature, 100 mL of ethyl acetate and 100 mL of water were added, followed by separation into two layers. The organic layer was washed with 50 mL of water twice and concentrated under reduced pressure. To the residue was added 50 mL of ethanol and concentrated under reduced pressure to yield 30.3 g of crude ethyl 2-[6-[3-[4-(diphenylmethoxy)piperidino]propylamino]imidazo[1,2-b]pyridazin-2-yl]-2-methylpropionate as an oily material (HPLC purity area percentage 58.3%). This oily material was dissolved in 70 mL of ethanol, and 2.99 g of sodium hydroxide dissolved in 30 mL of water was added thereto. The reaction mixture was heated to 60° C. and stirred for 1 hour. The reaction solution was concentrated under reduced pressure. To the residue were added 100 mL of water and 100 mL of ethyl acetate, followed by separation into two layers. The aqueous layer was washed with 50 mL of ethyl acetate twice, and 100 mL of ethanol was added to the aqueous layer. After the aqueous layer was adjusted to about pH 6 by the addition of 50 mL of 1N hydrochloric acid, the crystals formed were collected by filtration, washed with 40 mL of water and 40 mL of ethanol:water (1:1), and dried to yield 15.56 g of the title compound. HPLC purity area percentage 98.0%, Yield 72.3%.

Melting point 203–205° C. (The crystals began to soften at 110–12° C. and solidified again.).

EXAMPLE 6B

Method for Producing 2-[6-[3-[4-(Diphenylmethoxy)piperidino]propylamino]imidazo[1,2-b]pyridazin-2-yl]-2-methylpropionic Acid Dihydrate In 300 mL of dimethyl sulfoxide were suspended 181.8 g (560 mmol) of 4-(diphenylmethoxy)-1-piperidinepropaneamine, 100.0 g (374 mmol) of ethyl 2-(6-chloroimidazo[1,2-b]pyridazin-2-yl)-2-methylpropionate and 79.18 g (747 mmol) of sodium carbonate, which were then heated to 110° C. while bubbling a nitrogen gas and stirred for 24 hours. After cooling to room temperature, 1000 mL of ethyl acetate and 1000 mL of water were added, followed by separation into two layers. The organic layer was washed with 500 mL of water twice and concentrated under reduced pressure. To the residue was added 500 mL of ethanol and concentrated under reduced pressure to yield 294.6 g of crude ethyl 2-[6-[3-[4-(diphenylmethoxy) piperidino]propylamino]imidazo[1,2-b]pyridazin-2-yl]-2-methylpropionate as an oily material (HPLC purity area percentage 76.6%). This oily material was dissolved in 700 mL of ethanol, and 29.88 g of sodium hydroxide dissolved in 300 mL of water was added thereto. The reaction solution was heated to 60° C. and stirred for 1 hour. The reaction solution was concentrated under reduced pressure. To the residue were added 1000 mL of water and 1000 mL of ethyl acetate, followed by separation into two layers. The aqueous layer was washed with 500 mL of ethyl acetate twice, and 1000 mL of ethanol was added to the aqueous layer. The aqueous layer was adjusted to about pH 6 by the addition of 500 mL of 1N hydrochloric acid and stirred at room temperature for 30 minutes and at 10° C. for 1 hour. The crystals formed were collected by filtration, washed with 400 mL of water and 400 mL of ethanol:water (1:1), and dried to yield 159.5 g of the title compound. HPLC purity area percentage 98.0%, Yield 74.1%.

EXAMPLE 7B

Method for Producing 2-[6-[3-[4-(Diphenylmethoxy)piperidino]propylamino]imidazo [1,2-b]pyridazin-2-yl]-2-methylpropionic Acid Dihydrate In 24 L of dimethyl sulfoxide were suspended 14.5 kg (44.68 mol) of 4-(diphenylmethoxy)-1-piperidinepropaneamine, 8.0 kg (29.88 mol) of ethyl 2-(6-chloroimidazo[1,2-b]pyridazin-2-yl)-2-methylpropionate, 6.3 kg (59.43 mol) of sodium carbonate and 300 g (2.92 mol) of sodium bromide, which were then heated to 145±5° C. under a nitrogen atmosphere and stirred for 7 hours. After cooling to room temperature, 80 L of ethyl acetate and 80 L of water were added, followed by separation into two layers. The organic layer was washed with 40 L of water twice and concentrated under reduced pressure. To the residue was added 60 L of ethanol and concentrated until the total volume became 40 L under reduced pressure to yield a solution of crude ethyl 2-[6-[3-[4-(diphenylmethoxy) piperidino]propylamino]imidazo[1,2-b]pyridazin-2-yl]-2-methylpropionate in ethanol. To the ethanol solution was added 2.4 kg of sodium hydroxide dissolved in 8 L of water. The reaction mixture was heated to 60±5° C. and stirred for 1 hour. The reaction mixture was cooled to 30±5° C. and adjusted to pH 10 or lower by the addition of 13 L of 3N hydrochloric acid, followed by the addition of 56 L of ethyl acetate. The mixture was adjusted to pH 6–7 by the addition of 13 L of 3N hydrochloric acid and 6 L of water was added thereto. The crystals formed were collected by filtration, washed with 40 L of a mixed solvent of water:ethanol:ethyl acetate (1:1:1), and dried to yield 13.5 kg of the title compound. HPLC purity area percentage 98.0%, Yield 80.1%.

Melting point 203–205° C. (The crystals began to soften at 110–1206° C. and solidified again.).

EXAMPLE C: COMPOUND (II"), COMPOUND (Ia), COMPOUND (Ib)

REFERENCE EXAMPLE 1C

Production of Ethyl 2-(6-Chloroimidazo[1,2-b] pyridazin-2-yl)-2-methylpropionate Method A Step A:

Ethyl 6-Chloroimidazo[1,2-b]pyridazine-2-acetate

After 11.2 g of 3-amino-6-chloropyridazine was suspended in 150 mL of ethanol, 28.6 g of ethyl 4-chloroacetoacetate was added thereto and heated under reflux for 24 hours. After cooling, the mixture was concentrated under reduced pressure and the residue was adjusted to pH 7 by the addition of an aqueous sodium hydrogencarbonate solution and extracted with ethyl acetate. The extract was washed with a brine solution and dried over magnesium sulfate. After concentration under reduced pressure. The residue was subjected to silica gel chromatography to be eluted with hexane:ethyl acetate (2:3). The desired fraction was collected to provide 12.7 g of the title compound.

$^1$H-NMR (CDCl$_3$) δ ppm: 1.29 (3H, t, J=7 Hz), 3.89 (2H, s), 4.23 (2H, q, J=7 Hz), 7.05, 7.85 (1H each, d, J=9 Hz), 7.95 (1H, s).

Step B:

In 50 mL of N,N-dimethylformamide was dissolved 6.8 g of ethyl 6-chloroimidazo[1,2-b]pyridazine-2-acetate. While stirring in ice-cold water, 2.46 g of 60% sodium hydride dispersion in mineral oil was added in small portions, and thereafter the mixture was brought to room temperature and stirred for 30 minutes. To the mixture was added 4.36 mL of methyl iodide while cooling in ice-cold water, and thereafter stirred at room temperature for 2 hours. To the mixture was poured ice-cold water, and then extracted with ethyl acetate. The extract was washed with a brine solution, dried over magnesium sulfate, and concentrated under reduced pressure. The residue was subjected to silica gel chromatography to be eluted with hexane:ethyl acetate (2:1). The desired fraction was collected and concentrated to provide 4.06 g of the title compound.

Melting point 64–65° C.; Elemental analysis: for C$_{12}$H$_{14}$N$_3$O$_2$Cl; Calculated (%): C, 53.84 ; H, 5.27 ; N, 15.70; Found (%): C, 53.85 ; H, 5.16; N, 15.80.

Method B

The title compound can also be synthesized by the following method.

A suspension of 3-amino-6-chloropyridazine (80.0 g), ethyl 4-bromo-2,2-dimethyl-3-oxobutanate (201 g) and disodium hydrogenphosphate (131 g) in ethanol (300 mL) was heated under reflux for 8 hours. To the reaction mixture was added water (300 mL) and extracted twice with ethyl acetate (300 mL). The combined organic layer was washed with water (600 mL) twice and with a saturated aqueous sodium chloride solution (300 mL), dried over magnesium sulfate, treated with active carbon, filtered, and concentrate under reduced pressure. To the residue was added diisopropyl ether (200 mL), and the resulting mixture was filtered to remove the insoluble material and concentrated under reduced pressure. The residue was subjected to silica gel chromatography (hexane:ethyl acetate 100:1, 2:1 and then 1:1), and crystallized from hexane to provide the title compound (99.3 g).

REFERENCE EXAMPLE 2C

Method for Producing Ethyl 2-[6-[3-[4-(Diphenylmethoxy)piperidino]propylamino]imidazo[1,2-b]pyridazin-2-yl]-2-methylpropionate Difumarate 4.2 g of 4-(diphenylmethoxy)-1-piperidinepropaneamine and 1.76 g of ethyl 2-(6-chloroimidazo[1,2-b]pyridazin-2-yl)-2-methylpropionate were stirred at 192–200° C. for 3.5 hours. After cooling, an aqueous sodium bicarbonate solution was added thereto and extracted with ethyl acetate. The extract was washed with a brine solution, dried over magnesium sulfate and concentrated under reduced pressure. The residue was subjected to silica gel chromatography to be eluted with ethyl acetate:methanol:triethyl amine (100:5:1). The desired fraction was collected and dissolved in 16 mL of ethyl acetate, and a solution prepared by dissolving 867 mg of fumaric acid in 16 mL of methanol was added thereto, followed by concentration. To the residue was added acetone and the crystals formed were collected by filtration, washed with acetone and dried to provide 2.30 g of the title compound.

Melting point 126–128° C.; Elemental analysis: for $C_{41}H_{49}N_5O_{11}$; Calculated (%): C, 62.50 ; H, 6.27 ; N, 8.89; Found (%): C, 62.28 ; H, 6.15; N, 8.97.

REFERENCE EXAMPLE 3C

Method for Producing 2-[6-[3-[4-(Diphenylmethoxy)piperidino]propylamino]imidazo[1,2-b]pyridazin-2-yl]-2-methylpropionic Acid (Anhydride)

In 500 mL of ethanol, 3.20 g (5.67 mmol) of the 2-[6-[3-4-(diphenylmethoxy)piperidino]propylamino]imidazo[1,2-b]pyridazin-2-yl]-2-methylpropionic acid dihydrate obtained in Example 3C was dissolved under heating, followed by concentrating under ordinary pressure until the total volume became 250 mL. After still standing at room temperature, the crystals formed were collected by filtration, washed with ethanol and dried to yield 2.67 g of the title compound.

Melting point 205–206° C. (decomposed); Elemental analysis: for $C_{31}H_{37}N_5O_3$; Calculated (%): C, 70.56 ; H, 7.07 ; N, 13.27; Found (%): C, 70.42; H, 6.89; N, 13.32.

Powder X-ray diffraction analysis result

| D-Space, angstrom | Intensity $I/I_0$ (%) |
| --- | --- |
| 3.20 | 32 |
| 3.48 | 100 |
| 11.62 | 30 |
| 15.46 | 35 |
| 16.60 | 37 |
| 17.56 | 33 |
| 18.46 | 72 |
| 19.26 | 33 |
| 20.12 | 30 |
| 20.58 | 38 |
| 23.38 | 32 |
| 23.40 | 33 |

EXAMPLE 1C

Production of Ethyl 2-[6-[3-[4-(Diphenylmethoxy)piperidino]propylamino]imidazo[1,2-b]pyridazin-2-yl]-2-methylpropionate Disuccinate In 1 mL of ethanol, 0.278 g of the ethyl 2-[6-[3-[4-(diphenylmethoxy)piperidino]propylamino]imidazo[1,2-b]pyridazin-2-yl]-2-methylpropionate synthesized in Reference Example 2C is dissolved, and 0.118 g of succinic acid is added thereto and dissolved, followed by concentration under reduced pressure. To the residue was added 0.5 mL of tetrahydrofuran and the residue was dissolved. After the addition of 2 mL of ethyl acetate, crystals formed were collected by filtration, washed with ethyl acetate and dried to yield 0.382 g of the title compound.

Melting point 98–101° C. (decomposed); Elemental analysis: for $C_{41}H_{53}N_5O_{11} \cdot \frac{1}{3}CH_3CO_2C_2H_5$; Calculated (%): C, 61.92 ; H, 6.83 ; N, 8.53; Found (%): C, 61.54; H, 6.83 ; N, 8.50.

EXAMPLE 2C

Production of Ethyl 2-[6-[3-[4-(Diphenylmethoxy)piperidino]propylamino]imidazo[1,2-b]pyridazin-2-yl]-2-methylpropionate Citrate (1:1)

In 8 mL of ethanol, 1.667 g of the ethyl 2-[6-[3-[4-(diphenylmethoxy)piperidino]propylamino]imidazo[1,2-b]pyridazin-2-yl]-2-methylpropionate synthesized in Reference Example 2C was dissolved, and 0.631 g of citric acid monohydrate was added thereto and dissolved under heating, followed by concentration under reduced pressure. To the residue was added 23 mL of ethyl acetate, and the crystals formed were collected by filtration and washed with 12 mL of ethyl acetate. To the crystals was added 30 mL of methanol and the crystals were dissolved under heating, followed by concentration under reduced pressure. To the residue was added 30 mL of ethanol and the residue was then dissolved. After still standing, the crystals formed were collected by filtration, washed with 10 mL of ethanol and dried to yield 2.007 g of the title compound.

Melting point 176° C. (decomposed); Elemental analysis: for $C_{39}H_{49}N_5O_{10}$; Calculated (%): C, 62.64 ; H, 6.60 ; N, 9.36; Found (%): C, 62.50 ; H, 6.56 ; N, 9.43.

EXAMPLE 3C

Method for Producing 2-[6-[3-[4-(Diphenylmethoxy)piperidino]propylamino]imidazo[1,2-b]pyridazin-2-yl]-2-methylpropionate Dihydrate In 600 mL of dimethyl sulfoxide were suspended 363.6 g (1120 mmol) of 4-(diphenylmethoxy)-1-piperidinepropaneamine, 200.0 g (747 mmol) of ethyl 2-(6-chloroimidazo[1,2-b]pyridazin-2-yl)-2-methylpropionate and 158.4 g (1490 mmol) of sodium carbonate, which were then heated in an oil bath (bath temperature 165–170° C.) under a nitrogen gas stream and stirred for 3.5 hours. After cooling to room temperature, 2000 mL of ethyl acetate and 2000 mL of water were added, followed by separation into two layers. The organic layer was washed with 1000 mL of water twice and concentrated under reduced pressure. To the residue was added 1000 mL of ethanol and concentrated under reduced pressure to yield 588 g of crude ethyl 2-[6-[3-[4-(diphenylmethoxy)piperidino]propylamino]imidazo[1,2-b]pyridazin-2-yl]-2-methylpropionate as an oily material. This oily material was dissolved in 1400 mL of ethanol, and 59.8 g (1490 mmol) of sodium hydroxide dissolved in 600 mL of water was added thereto. The reaction mixture was heated to 60° C. (inner temperature) and stirred for 1 hour. The reaction solution was concentrated under reduced pressure. To the residue were added 2000 mL of water and 2000 mL of ethyl acetate, followed by separation into two layers. The aqueous layer was washed with 1000 mL of ethyl acetate twice, and 2000 mL of ethanol was added to the aqueous layer. After the aqueous layer was adjusted to about pH 6 by the addition of 1000 mL of, 1N hydrochloric acid, the crystals formed were collected by filtration, washed with 800 mL of water and 800 mL of ethanol:water (1:1), and dried to yield 353.6 g of the crude title compound. HPLC purity area percentage 97.7%, Yield 82.0%.

To 353.6 g of the crude title compound thus obtained was added 1240 mL of ethanol, and heated under reflux for 1 hour. The mixture was stirred under ice-cooling. The crystals formed were collected by filtration, washed with 930 mL of cold ethanol and dried. The resulting crystals were suspended in 2000 mL of water and stirred for 1 hour while heating in a water bath (inner temperature 65–70° C.). After cooling to room temperature, the crystals formed were collected by filtration, washed with 1000 mL of water and dried to yield 276 g of the title compound.

Melting point 203–205° C. (The crystals began to soften at 110–120° C. and solidified again.); Elemental analysis: for $C_{31}H_{37}N_5O_3 \cdot 2H_2O$ ; Calculated (%): C, 66.05 ; H, 7.33 ; N, 12.42; Found (%): C, 66.35 ; H, 7.29 ; N, 12.39.
Powder X-ray diffraction analysis result

| D-Space, angstrom | Intensity $I/I_0$ (%) |
|---|---|
| 6.94 | 84 |
| 12.88 | 41 |
| 13.72 | 62 |
| 15.10 | 53 |
| 17.56 | 84 |
| 18.70 | 39 |
| 19.24 | 62 |
| 20.66 | 60 |
| 21.06 | 100 |
| 21.76 | 54 |
| 26.42 | 43 |
| 28.24 | 37 |

EXAMPLE 4C

Method for Producing 2-[6-[3-[4-(Diphenylmethoxy)piperidino]propylamino]imidazo[1,2-b]pyridazin-2-yl]-2-methylpropionic Acid Dihydrate To 10 mL of water was suspended 0.250 g of the 2-[6-[3-[4-(diphenylmethoxy)piperidino]propylamino]imidazo[1,2-b]pyridazin-2-yl]-2-methylpropionic acid (anhydride) obtained in Reference Example 3C and stirred for 3 hours in a water bath (bath temperature 80° C.). After cooling to room temperature, the crystals formed were collected by filtration, washed with water and dried to yield 0.233 g of the total compound. The resulting 2-[6-[3-[4-(diphenylmethoxy)piperidino]propylamino]imidazo[1,2-b]pyridazin-2-yl]-2-methylpropionic acid dihydrate was identical to the compound obtained in Example 3C on the basis of the agreement of their melting points, elemental analysis values, powder X-ray diffraction analysis data, etc.

EXAMPLE 5C

Production of 2-[6-[3-4-(Diphenylmethoxy)piperidino]propylamino]-3-methylimidazo[1,2-b]pyridazin-2-yl]-2-methylpropionic Acid In 25 mL of N-methyl-2-pyrrolidinone were dissolved 17.0 g of 4-(diphenylmethoxy)-1-piperidinepropaneamine and 7.39 g of ethyl 2-(6-chloro-3-methylimidazo[1,2-b]pyridazin-2-yl)-2-methylpropionate, and stirred at 160° C. for 8.5 hours. After cooling, a water was added and extracted with ethyl acetate. The extract was washed with a saturated brine solution and dried over magnesium sulfate. Following to concentration under reduced pressure. The residue was subjected to silica gel column chromatography to be eluted with ethyl acetate:methanol:triethylamine (50:5:1). The desired fraction was collected and concentrated to yield 10.4 g of ethyl 2-[6-[3-[4-(diphenylmethoxy)piperidino]propylamino]-3-methylimidazo[1,2-b]pyridazin-2-yl]-2-methylpropionate as an oily material. In 100 mL of ethanol was dissolved this oily material, and 18.3 mL of a 5N aqueous sodium hydroxide solution was added thereto and heated under reflux for 2 hours. After cooling, the mixture was concentrated under reduced pressure. The residue was diluted with water and washed with diisopropyl ether. The aqueous layer was adjusted to pH 5 by the addition of 5N hydrochloric acid. The crystals formed were collected by filtration, recrystallized from methanol-water (10:1), and dried to yield 4.09 g of the title compound.

Melting point 219–220° C.; Elemental analysis: for $C_{32}H_{39}N_5O_3$; Calculated (%): C, 70.95; H, 7.26; N, 12.93; Found (%): C, 70.85 ; H, 7.00; N, 13.20.

EXPERIMENTAL EXAMPLE 1C

Effect on Histamine-induced Skin Reactions in Guinea Pigs

Male Hartley guinea pigs weighing about 500 g were used. After the dorsal hair was shaved under ether anesthesia, 1 ml of a 2.5% pontamine sky blue solution was injected intravenously administered, and then 0.1 ml of histamine at 3 μg/ml was injected intradermally into 2 sites (left and right) in the back. Thirty minutes after the injection of histamine, animals were killed by bleeding and he skin was removed. Two perpendicular diameters (mm) of each blue spot on the inside of the skin were measured and multiplied, the mean for the two products was taken as the microvascular permeability index. Test compounds were suspended in a 5% gum arabic solution and orally administered in a volume of 0.2 ml/100 g body weight 1 hour before histamine administration. Animals in the control group received the same volume of a 5% gum arabic solution. The suppression rate of the sample for the title reaction was calculated using Equation 1.

Inhibition (%) of histamine-induced skin reactions=100×(1−vascular permeability index in the presence of drug/vascular permeability index in control group)    Equation 1

The results are given in Table 3.

TABLE 3

| Compound | Inhibition (%) of Histamine-induced Skin Reactions, 3 mg/kg Oral Administration |
|---|---|
| Example 3C | 91 |

PREPARATION EXAMPLE 1C (1) Compound of Example 3C 10.0 mg
(2) Lactose 60.0 mg
(3) Corn starch 35.0 mg
(4) Gelatin 3.0 mg
(5) Magnesium stearate 2.0 mg A mixture of 10.0 mg of the compound obtained in Example 3C, 60.0 mg of lactose and 35.0 mg of corn starch is granulated through a sieve of 1 mm mesh, using 0.03 ml of a 10% aqueous solution of gelatin (containing 3.0 mg of gelatin), after which it is dried at 40° C. and again sieved. The resulting granules are mixed with 2.0 mg of magnesium stearate, followed by compression. The resulting core tablets are coated with a sugar coat, using an aqueous suspension of sucrose, titanium dioxide, talc and gum arabic. The coated tablets are polished with beeswax to yield finished coated tablets.

PREPARATION EXAMPLE 2C

| (1) Compound of Example 3C | 10.0 mg |
|---|---|
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 3C and 3.0 mg of magnesium stearate are mixed and granulated, using 0.07 ml of an aqueous solution of soluble starch (containing 7.0 mg of soluble starch). The resulting granules are dried and mixed with 70.0 mg of lactose and 50.0 mg of corn starch, followed by compression, to yield tablets.

PREPARATION EXAMPLE 3C

| (1) Compound of Example 4C | 10.0 mg |
|---|---|
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 4C, 60.0 mg of lactose and 35.0 mg of corn starch is granulated through a sieve of 1 mm mesh, using 0.03 ml of a 10% aqueous solution of gelatin (containing 3.0 mg of gelatin), after which it is dried at 40° C. and again sieved. The resulting granules are mixed with 2.0 mg of magnesium stearate, followed by compression. The resulting core tablets are coated with a sugar coat, using an aqueous suspension of sucrose, titanium dioxide, talc and gum arabic. The coated tablets are polished with beeswax to yield finished coated tablets.

PREPARATION EXAMPLE 4C

| (1) Compound of Example 4C | 10.0 mg |
|---|---|
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 4C and 3.0 mg of magnesium stearate are mixed and granulated, using 0.07 ml of an aqueous solution of soluble starch (containing 7.0 mg of soluble starch). The resulting granules are dried and mixed with 70.0 mg of lactose and 50.0 mg of corn starch, followed by compression, to yield tablets.

PREPARATION EXAMPLE 5C

After uniformly mixing 1500 g of the compound disclosed in Example 3C, 2025 g of lactose and 556.5 g of corn starch in a fluidized bed granulator (FD-5 S, POWREX CO.), the mixture was granulated by spraying an aqueous solution of 126 g of hydroxypropylcellulose in the granulator, and then dried in the fluidized bed granulator. The dried granules were milled by using a power mill with a punching screen of 1.5 mm$\phi$ to form uniform granules. 3927 g of the uniform granules are taken and 210 g of croscarmellose sodium and 63 g of magnesium stearate are added thereto. These were mixed in a Tumbler mixer to provide granules for tabletting. The granules were tabletted by using a tabletting machine equipped with a die 6.5 mm in diameter to provide care tablets each weighing 300 mg. The core tablets were sprayed, in a Doria coater coating machine, with a liquid prepared by dissolving hydroxypropylmethylcellulose 2910 (TC-5) and macrogol 6000 and dispersing titanium oxide and ferric oxide to provide about 13500 film coated tablets of the following formulation containing 100 mg per tablet.

Tablet formulation:

| Composition | Amount (mg) |
|---|---|
| (1) Compound of Example 3C | 100.0 |
| (2) Lactose | 135.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| (1) Core tablet | 300.0 |
|---|---|
| (Film ingredients) | |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 6C

About 13500 film coated tablets of the following formulation containing 25 mg of the compound disclosed in Example 3C per tablet was prepared in accordance with the method disclosed in Preparation Example 5C.

Tablet formulation:

| Composition | Amount (mg) |
|---|---|
| (1) Compound of Example 3C | 25.0 |
| (2) Lactose | 210.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
|---|---|
| (1) Core tablet (Film ingredients) | 300.0 |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 7C

About 13500 film coated tablets of the following formulation containing 5 mg of the compound disclosed in Example 3C per tablet was prepared in accordance with the method disclosed in Preparation Example 5C.

Tablet formulation:

| Composition | Amount (mg) |
|---|---|
| (1) Compound of Example 3C | 5.0 |
| (2) Lactose | 230.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
|---|---|
| (1) Core tablet (Film ingredients) | 300.0 |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 8C

About 13500 film coated tablets of the following formulation containing 1 mg of the compound disclosed in Example 3C per tablet was prepared in accordance with the method disclosed in Preparation Example 5C.

Tablet formulation:

| Composition | Amount (mg) |
|---|---|
| (1) Compound of Example 3C | 1.0 |
| (2) Lactose | 234.0 |
| (3) Corn starch | 37.1 |
| (4) Croscarmellose sodium | 15.0 |
| (5) Hydroxypropylcellulose | 8.4 |
| (6) Magnesium stearate | 4.5 |
| Total (Core tablet) | 300.0 |

Film coated tablet formulation:

| | |
|---|---|
| (1) Core tablet (Film ingredients) | 300.0 |
| (2) Hydroxypropyl-methylcellulose 2910 | 7.485 |
| (3) Macrogol 6000 | 1.5 |
| (4) Titanium oxide | 1.0 |
| (5) Ferric oxide | 0.015 |
| Total | 310.0 |

PREPARATION EXAMPLE 9C

| | |
|---|---|
| White vaseline | 40 g |
| Cetanol | 10 g |
| Bleached bees wax | 5 g |
| Sorbitan sesquioleate | 5 g |
| Lauromocrogold | 0.5 g |
| Methyl para-hydroxybenzoate | 0.1 g |
| Propyl para-hydroxybenzoate | 0.1 g |
| Purified water | adequate amount |

An official absorption ointment (100 g) of the above formulation was heated to 70° C. in advance, and to its solution was added a solution prepared by dissolving under heating 1 g of the compound prepared in Example 3C in 20 mL of methanol. After heating and mixing at that temperature for 10 minutes, the remaining methanol was removed and the residue was cooled to room temperature to provide an absorption ointment.

INDUSTRIAL APPLICABILITY

The compound (I) or a salt thereof of the present invention exhibits excellent anti-allergic activity, anti-histaminic activity, anti-inflammatory activity, eosinophil chemotaxis-inhibiting activity and the like and is useful as an agent for preventing or treating allerdoderma such as contact dermatitis, pruritus, dried dermatitis, acute urticaria and prurigo.

According to the production process of the present invention, the compound (I') or a salt thereof, which exhibits excellent anti-allergic activity, anti-histaminic activity, anti-inflammatory activity, eosinophil chemotaxis-inhibiting activity and the like and is useful as an agent for preventing or treating asthma, allergic rhinitis, atopic dermatitis, allergic conjunctivitis, chronic urticaria and the like, can be produced in good efficiency and in a high yield.

The hydrate of the compound (I") or the succinate or citrate of the compound (I") of the present invention exhibits excellent anti-allergic activity, anti-histaminic activity, anti-inflammatory activity, eosinophil chemotaxis-inhibiting activity and the like and is useful as an agent for preventing or treating asthma, allergic rhinitis, atopic dermatitis, allergic conjunctivitis, chronic urticaria and the like. Moreover, these compounds have excellent stability.

What is claimed is:

1. A method for producing a compound represented by the formula:

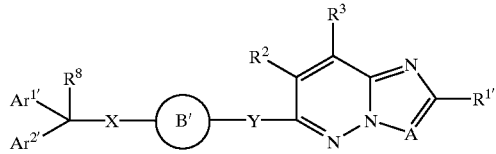
(I')

wherein $Ar^{1'}$ and $Ar^{2'}$ are independently an aromatic group optionally having a substituent, and $Ar^{1'}$ and $Ar^{2'}$ may form a condensed cyclic group with an adjacent carbon atom;

ring B' is

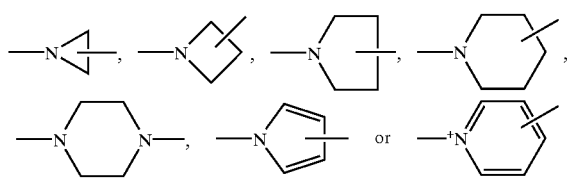

optionally having a substituent;

X and Y are the same or different and are independently
  a bond,
  an oxygen atom,
  S(O)p
    wherein p is an integer of 0 to 2,
  $NR^4$
    wherein $R^4$ is a hydrogen atom or a lower alkyl group, or a bivalent linear lower hydrocarbon group which may contain 1 to 3 hetero atoms and the bivalent linear lower hydrocarbon group may be substituted;

A is a nitrogen atom or $CR^7$ wherein $R^7$ is a hydrogen atom, a halogen atom, a hydrocarbon optionally having a substituent, an acyl group or a hydroxy group optionally having a substituent;

$R^{1'}$ is a hydrocarbon group substituted by an optionally esterified carboxyl group;

$R^2$ and $R^3$ are the same or different and are independently a hydrogen atom, a halogen atom, a hydrocarbon group optionally having a substituent, an acyl group or a hydroxy group optionally having a substituent;

$R^8$ is a hydrogen atom, a hydroxy group which may be substituted by a lower alkyl group or a carboxyl group, or a salt thereof, which comprises reacting a compound represented by the formula:

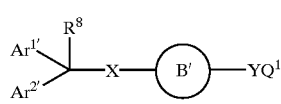
(II)

wherein $Q^1$ represents a leaving group;
the other symbols are same as defined in the above,
or a salt thereof, with a compound represented by the formula:

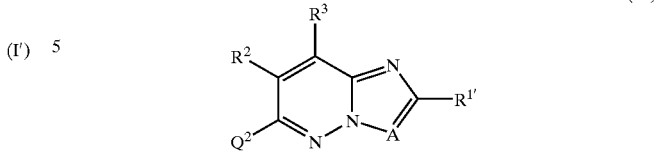
(III)

wherein $Q^2$ represents a leaving group;
the other symbols are same as defined above,
or a salt thereof in sulfoxide and in the presence of an alkali metal carbonate, and if necessary in an atmosphere of inert gas.

2. The method of claim 1 wherein said sulfoxide is dimethyl sulfoxide.

3. The method of claim 1 wherein said alkali metal carbonate is sodium carbonate.

4. A method as claimed in claim 1 wherein the reaction is further conducted in the presence of halogenated alkali metals.

5. A method as claimed in claim 4 wherein halogenated alkali metal is sodium bromide.

6. A method as claimed in claim 1 wherein $Ar^{1'}$ and $Ar^{2'}$ are a $C_{6-14}$ single cyclic or condensed cyclic aromatic hydrocarbon group which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy and (xxviii) $C_{7-16}$ aralkyloxy; and $Ar^{1'}$, $Ar^{2'}$ and the adjacent carbon atom may form a condensed cyclic group represented by the formula:

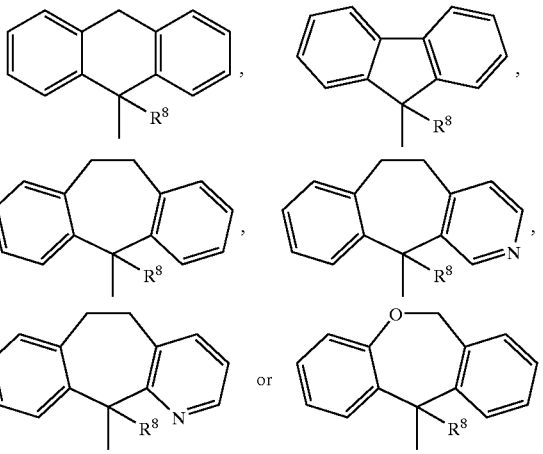

wherein $R^8$ is a hydrogen atom, a hydroxy group which may be substituted by $C_{1-6}$ alkyl or a carboxyl group, and the condensed cyclic group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

the ring B' is piperidine or piperazine which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

X and Y are same or different and are independently ① a bond, ② an oxygen atom, ③ S(O)p wherein p is an integer of 0 to 2, ④ $NR^4$ wherein $R^4$ is a hydrogen atom or a linear or branched $C_{1-6}$ alkyl group or ⑤ a bivalent linear $C_{1-6}$ hydrocarbon group which may contain 1 to 3 hetero atoms selected from an oxygen atom and a sulfur atom, and the bivalent linear $C_{1-6}$ hydrocarbon group may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

A is a nitrogen atom or $CR^7$ wherein $R^7$ is
(1) a hydrogen atom,
(2) a halogen atom,
(3) a $C_{1-6}$ alkyl group, a $C_{2-6}$ alkenyl group, a $C_{2-6}$ alkynyl group, a $C_{3-6}$ cycloalkyl group, condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkylcarbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, (4) an acyl group represented by the formula: —(C=O)—$R^9$, —$SO_2$—$R^9$, —SO—$R^9$, —(C=O)$NR^{10}R^9$, —(C=O)O—$R^9$, —(C=S)O—$R^9$ or —(C=S)$NR^{10}R^9$ wherein $R^9$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo or (c) a group represented by the formula: —$OR^{11}$ wherein $R^{11}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, $R^{10}$ is a hydrogen atom or a $C_{1-6}$ alkyl group, or (5) a group represented by the formula: —$OR^{12}$ wherein $R^{12}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

$R^{1'}$ is a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group which is substituted by a group represented by the formula: —$COOR^{11}$ wherein $R^{11}$ is (1) a hydrogen atom or (2) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkyl sulfonyl, (xxvi) $C_{6-10}$ aryl, (xxvii) $C_{6-10}$ aryloxy, (xxviii) $C_{7-16}$ aralkyloxy and (xxix) oxo;

$R^2$ and $R^3$ are the same or different and are independently (1) a hydrogen atom, (2) a halogen atom, (3) a $C_{1-6}$ alkyl group, a $C_{2-6}$ alkenyl group, a $C_{2-6}$ alkynyl group, a $C_{3-6}$ cycloalkyl group, condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxycarbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, (4) an acyl group represented by the formula: —(C=O)—$R^{13}$, —$SO_2$—$R^{13}$, —SO—$R^{13}$, —(C=O)$NR^{14}R^{13}$, —(C=O)O—$R^{13}$, —(C=S)O—$R^{13}$ or —(C=S)$NR^{14}R^{13}$ wherein $R^{13}$ is (a) a hydrogen atom, (b) a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo or (c) a group represented by the formula: —$OR^{15}$ wherein $R^{15}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ aikylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxy-carbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo, $R^{14}$ is a hydrogen atom or a $C_{1-6}$ alkyl group; or (4) a group represented by the formula: —$OR^{16}$ wherein $R^{16}$ is a hydrogen atom, or a $C_{1-6}$ alkyl group, a $C_{2-6}$ alkenyl group, a $C_{2-6}$ alkynyl group, a $C_{3-6}$ cycloalkyl group, a condensed group formed by a $C_{3-6}$ cycloalkyl group and a benzene ring optionally having 1 to 3 substituents selected from the group consisting of $C_{1-6}$ alkoxy, a $C_{6-14}$ aryl group and a $C_{7-16}$ aralkyl group, which may be substituted by a group selected from the group consisting of (i) a halogen atom, (ii) $C_{1-6}$ alkylenedioxy, (iii) nitro, (iv) cyano, (v) optionally halogenated $C_{1-6}$ alkyl, (vi) optionally halogenated $C_{2-6}$ alkenyl, (vii) optionally halogenated $C_{2-6}$ alkynyl, (viii) $C_{3-6}$ cycloalkyl, (ix) $C_{1-6}$ alkoxy optionally having 1 to 3 substituents selected from the group consisting of halogen atoms, mono- or di-$C_{1-6}$ alkylamino and $C_{1-6}$ alkoxy-carbonyl, (x) optionally halogenated $C_{1-6}$ alkylthio, (xi) hydroxy, (xii) amino, (xiii) mono-$C_{1-6}$ alkylamino, (xiv) di-$C_{1-6}$ alkylamino, (xv) 5 or 6 membered cyclic amino, (xvi) $C_{1-6}$ alkyl-carbonyl, (xvii) carboxyl, (xviii) $C_{1-6}$ alkoxycarbonyl, (xix) carbamoyl, (xx) thiocarbamoyl, (xxi) mono-$C_{1-6}$ alkyl-carbamoyl, (xxii) di-$C_{1-6}$ alkyl-carbamoyl, (xxiii) $C_{6-10}$ aryl-carbamoyl, (xxiv) sulfo, (xxv) $C_{1-6}$ alkylsulfonyl, (xxvi) $C_{6-10}$ aryl, (xxvii) $C_{6-10}$ aryloxy, (xxviii) $C_{7-16}$ aralkyloxy and (xxix) oxo;

$R^8$ is a hydrogen atom, a hydroxy group which may be substituted by a $C_{1-6}$ alkyl group or a carboxyl group.

7. A method for producing a compound as claimed in claim 1 wherein the leaving group represented by $Q^1$ is a hydrogen atom or an alkali metal.

8. A method for producing a compound as claimed in claim 1 wherein the leaving group represented by $Q^2$ is a halogen atom, $C_{6-10}$ arylsulfonyloxy group or a $C_{1-4}$ arylsulfonyloxy group.

9. A method for treating contact dermatitis, pruritus, dried dermatitis, acute urticaria or prurigo comprising administering to a mammal in need thereof a pharmaceutically effective amount of 2-[6-[3-[4-(diphenylmethoxy)piperidino]propylamino]imidazo[1,2-b]pyridazin-2-yl]-2-methylpropionic acid dihydrate.

10. 2-[6-[3-[4-(diphenylmethoxy)piperidino]propylamino]imidazo[1,2-b]pyridazin-2-yl]-2-methylpropionic acid dihydrate.

11. 2-[6-[3-[4-(diphenylmethoxy)piperidino]propylamino]-3-methylimidazo[1,2-b]pyridazin-2-yl]-2-methylpropionic acid or a salt thereof.

12. 2-[6-[3-[4-(diphenylmethoxy)piperidino]propylamino]imidazo[1,2-b]pyridazin-2-yl]-2-methylpropionic acid dihydrate;

ethyl 2-[6-[3-[4-(diphenylmethoxy)piperidino]propylamino]imidazo[1,2-b]pyridazin-2-yl]-2-methylpropionate disuccinate;

ethyl 2-[6-[3-[4-(diphenylmethoxy)piperidino]propylamino]imidazo[1,2-b]pyridazin-2-yl]-2-methylpropionate citrate;

2-[6-[3-[4-(diphenylmethoxy)piperidino]propylamino]-3-methylimidazo[1,2-b]pyridazin-2-yl]-2-methylpropionic acid;

and salts and prodrugs thereof.

13. A hydrate of a compound represented by the formula:

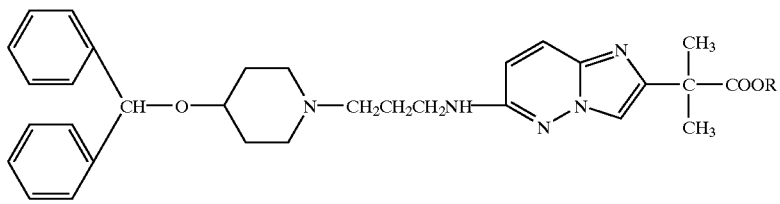

(I″)

wherein R is a hydrogen atom or an ethyl group, or a succinate or citrate of the compound (I″).

14. A compound, as claimed in claim 10 which shows the following Powder X-ray diffraction analysis result:

| D-Space, angstrom | Intensity $I/I_0$ (%) |
|---|---|
| 6.94 | 84 |
| 12.88 | 41 |
| 13.72 | 62 |
| 15.10 | 53 |
| 17.56 | 84 |
| 18.70 | 39 |
| 19.24 | 62 |
| 20.66 | 60 |
| 21.06 | 100 |
| 21.76 | 54 |
| 26.42 | 43 |
| 28.24 | 37. |

15. A method for producing a compound as claimed in claim 13 which comprises (1) contacting a compound which is obtained by reacting a compound represented by the formula:

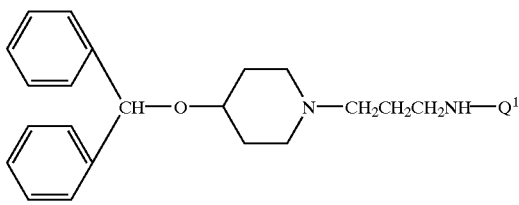

wherein $Q^1$ is a leaving group, or a salt thereof with a compound represented by the formula:

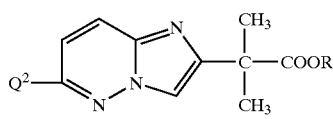

wherein $Q^2$ is a leaving group, R is same as defined in claim 13 or a salt thereof with water, or (2) reacting a free form of the compound (I″) as defined in claim 25 with succinic acid or citric acid.

16. A pharmaceutical composition which comprises a compound from any one of claims 13, 10, 14 and 11; and a pharmaceutically acceptable excipient, binder, disintegrating agent, solvent or carrier.

17. A method for suppressing a histamine and/or an eosinophil chemotaxis comprising administering an effective amount of claimed in a compound from any one of claims 13, 10, 14 and 11 or a pro-drug as claimed in claim 12 to mammals.

18. A method for treating allergic diseases comprising administering an effective amount of a compound from any one of claims 13, 10, 14 and 11 or a pro-drug as claimed in claim 12 to mammals.

19. A method for treating asthma, allergic conjunctivitis, allergic rhinitis, chronic urticaria or atopic dermatitis which comprises administering an effective amount of a compound from any one of claims 13, 10, 14 and 11 or a pro-drug as claimed in claim 12 to mammals.

20. A method for treating contact dermatitis, pruritus, dried dermatitis, acute urticaria or prurigo comprising administering to a mammal in need thereof a pharmaceutically effective amount of a compound from any one of claims 13, 10, 14 and 11 or a pro-drug as claimed in claim 12 to mammals.

* * * * *